United States Patent
Broo et al.

(10) Patent No.: US 7,723,333 B2
(45) Date of Patent: *May 25, 2010

(54) NON-ANILINIC DERIVATIVES OF ISOTHIAZOL-3(2H)-ONE 1,1-DIOXIDES AS LIVER X RECEPTOR MODULATORS

(75) Inventors: Anders Broo, Mölndal (SE); Robert Judkins, Mölndal (SE); Lanna Li, Mölndal (SE); Eva-Lotte Lindstedt-Alstermark, Mölndal (SE); Pernilla Sandberg, Mölndal (SE); Marianne Swanson, Mölndal (SE); Lars Weidolf, Mölndal (SE); Kay Brickmann, Mölndal (SE); Patrik Holm, Pargas (FI)

(73) Assignee: AstraZeneca AB, Sodertalje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 11/813,470

(22) PCT Filed: Jan. 9, 2006

(86) PCT No.: PCT/SE2006/000029

§ 371 (c)(1),
(2), (4) Date: May 8, 2008

(87) PCT Pub. No.: WO2006/073366

PCT Pub. Date: Jul. 13, 2006

(65) Prior Publication Data

US 2009/0005353 A1    Jan. 1, 2009

(30) Foreign Application Priority Data

Jan. 10, 2005   (SE) .................................. 0500055

(51) Int. Cl.
| | |
|---|---|
| *A61K 31/5355* | (2006.01) |
| *A61K 31/501* | (2006.01) |
| *A61K 31/4523* | (2006.01) |
| *A61K 31/4427* | (2006.01) |
| *A61K 31/427* | (2006.01) |
| *A61K 31/4155* | (2006.01) |
| *C07D 275/02* | (2006.01) |
| *C07D 233/54* | (2006.01) |
| *C07D 413/02* | (2006.01) |
| *C07D 401/02* | (2006.01) |
| *C07D 239/02* | (2006.01) |
| *C07D 211/00* | (2006.01) |
| *C07D 417/02* | (2006.01) |

(52) U.S. Cl. .............................. 514/236.8; 514/252.05; 514/256; 514/326; 514/342; 514/372; 514/397; 544/133; 544/238; 544/242; 546/184; 546/269.7; 548/213; 548/311.1

(58) Field of Classification Search ............... 514/236.8, 514/252.05, 256, 326, 342, 372, 397; 544/133, 544/238, 242; 546/184, 269.7; 548/213, 548/311.1

See application file for complete search history.

(56) References Cited

U.S. PATENT DOCUMENTS

2003/0195238 A1   10/2003   Gil et al.

FOREIGN PATENT DOCUMENTS

| EP | 1069110 | 1/2001 |
|---|---|---|
| JP | 2001163786 A | 6/2001 |
| WO | 9708143 | 3/1997 |
| WO | 0021927 | 4/2000 |
| WO | 0054759 | 9/2000 |
| WO | 0103705 | 1/2001 |
| WO | 0174771 | 10/2001 |
| WO | 0246183 | 6/2002 |
| WO | 03031440 | 4/2003 |
| WO | 2004111022 | 12/2004 |
| WO | 2005005416 | 1/2005 |
| WO | 2005005417 | 1/2005 |
| WO | 2005035551 | 4/2005 |

OTHER PUBLICATIONS

Office Action dated Dec. 22, 2008 received in copending U.S. Appl. No. 11/813,489.
Patani, George, A. Bioisosterism: A rational approach in drug design. Chem. Rev. 96 (1996) 3147-3176.
Atherosclerosis. Retrieved online via Internet [Dec. 13, 2008] http://www.nlm.nih.gov/medlineplus/ency/article/000171.htm.

(Continued)

*Primary Examiner*—Kamal A Saeed
*Assistant Examiner*—Samantha L Shterengarts
(74) *Attorney, Agent, or Firm*—Pepper Hamilton LLP

(57) ABSTRACT

The present invention relates to certain novel compounds of the formula (I)

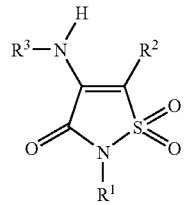

formula (I)

to processes for preparing such compounds, to their the utility in modulation of nuclear hormone receptors Liver X Receptor (LXR) α (NR1H3) and/or β (NR1H2) and in treating and/or preventing clinical conditions including cardiovascular diseases such as atherosclerosis; inflammatory diseases, Alzheimer's disease, lipid disorders (dyslipidemias) whether or not associated with insulin resistance, type 2 diabetes and other manifestations of the metabolic syndrome, to methods for their therapeutic use and to pharmaceutical compositions containing them.

26 Claims, No Drawings

OTHER PUBLICATIONS

Office Action dated Dec. 22, 2008 received in copending U.S. Appl. No. 11/813,458.

Notice of allowance dated Apr. 16, 2009 received in copending U.S. Appl. No. 11/813,481.

Notice of Co-Pending Applications: U.S. Appl. No. 11/813,489; U.S. Appl. No. 11/813,467; U.S. Appl. 11/813,481 and U.S. Appl. No. 11/813,458.

Laffitte et al., "Activation of liver X receptor improves glucose tolerance through coordinate regulation of glucose metabolism in liver and adipose tissue," PNAS (2003) 100 (9): 5419-5424.

SEQUENCE LISTING

<160> NUMBER OF SEQ ID NOS: 15

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: ABCA1
      forward primer

<400> SEQUENCE: 1
aagggtttct ttgctcagat tgtc                                          24

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: ABCA1
      reverse primer

<400> SEQUENCE: 2
tgccaaaggg tggcaca                                                  17

<210> SEQ ID NO 3
<211> LENGTH: 25
<212> TYPE: DNA
<213> ORGANISM: Artificial Sequence
<220> FEATURE:
<223> OTHER INFORMATION: Description of Artificial Sequence: ABCA1 probe

<400> SEQUENCE: 3
ccagctgtct ttgtttgcat tgccc                                         25

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: ABCG1
      forward primer

<400> SEQUENCE: 4
ccatgaatgc cagcagctac t                                             21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: ABCG1
      reverse primer

<400> SEQUENCE: 5
cactgacacg cacacggact                                               20

<210> SEQ ID NO 6
<211> LENGTH: 19
<212> TYPE: DNA
<213> ORGANISM: Artificial Sequence
<220> FEATURE:
<223> OTHER INFORMATION: Description of Artificial Sequence: ABCG1 probe

<400> SEQUENCE: 6
tgccgcaatg acggagccc                                                19

```
<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: FAS forward
      primer

<400> SEQUENCE: 7
ggcatcattg ggcactcctt                                                 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: FAS reverse
      primer

<400> SEQUENCE: 8
gctgcaagca cagcctctct                                                 20

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: FAS probe

<400> SEQUENCE: 9
ccatctgcat agccacaggc aacctc                                          26

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: SREBP Lc
      forward primer

<400> SEQUENCE: 10
ggagccatgg attgcacatt                                                 20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: SREBP Lc
      reverse primer

<400> SEQUENCE: 11
cctgtctcac ccccagcata                                                 20

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: SREBP Lc
      probe

<400> SEQUENCE: 12
cagctcatca acaaccaaga cagtgacttc c                                    31
```

-continued

```
<210> SEQ ID NO 13
<211> LENGTH: 24
<212> TYPE: DNA
<213> ORGANISM: Artificial Sequence
<220> FEATURE:
<223> OTHER INFORMATION: Description of Artificial Sequence: 36B4
      forward primer

<400> SEQUENCE: 13
gaggaatcag atgaggatat ggga                                          24

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: 36B4
      reverse primer

<400> SEQUENCE: 14
aagcaggctg acttggttcc                                               20

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: 36B4 probe

<400> SEQUENCE: 15
tcggtctctc gactaatccc gccaa                                         25
```

NON-ANILINIC DERIVATIVES OF ISOTHIAZOL-3(2H)-ONE 1,1-DIOXIDES AS LIVER X RECEPTOR MODULATORS

CROSS-REFERENCE TO RELATED APPLICATIONS

This application is the U.S. National Stage filing of International Application Serial No. PCT/SE2006/000029 filed Jan. 9, 2006, which claims priority to Swedish Application No. 0500055-9 filed Jan. 10, 2005, each of which is incorporated herein by reference in its entirety.

FIELD OF THE INVENTION

The present invention relates to certain novel 4-(amino) isothiazol-3(2H)-one 1,1-dioxides, to processes for preparing such compounds, to their the utility in modulation of nuclear hormone receptors Liver X Receptor (LXR) α (NR1H3) and/or β (NR1H2) and in treating and/or preventing clinical conditions including cardiovascular diseases such as atherosclerosis; inflammatory diseases, Alzheimer's disease, lipid disorders (dyslipidemias) whether or not associated with insulin resistance, type 2 diabetes and other manifestations of the metabolic syndrome, to methods for their therapeutic use and to pharmaceutical compositions containing them.

BACKGROUND OF THE INVENTION

Abnormalities of cholesterol and fatty acid homeostasis, that are reflected as diverse dyslipidemias, are causal of atherosclerosis and consequently cardiovascular disease (CVD). This disease is one of the major health problems in industrialized countries and is reaching the same prevalence in adults in developing nations. Most studies show that statins reduce low density lipoproteins (LDL) cholesterol by 25-30% and the relative risk of coronary events by approximately 30%. While this beneficial effect is significant, effectively 70% of the treated cohort remains with unchanged risk. This has prompted intense research in order to identify other common abnormalities of lipid metabolism that if efficiently treated could improve the results of current CVD therapy.

The nuclear hormone receptors LXR α and β use oxysterols as natural ligands. They appear to act as cholesterol sensors with target genes that are required for cholesterol efflux from macrophages, like ATP binding cassette transporter A1 (ABCA1) and apoE, as well as gene products, like cholesterol ester transferase protein (CETP) and phospholipid transport protein (PLTP), that are required for the function of high density lipoprotein (HDL) in the reverse cholesterol transport. In the liver, LXR ligands seem to stimulate the hepatobiliary secretion of cholesterol, a pathway controlled by the ABCG5 and ABCG8. The same cholesterol transporters appear to reduce cholesterol absorption in enterocytes, therefore influencing total body cholesterol balance. These effects of LXR stimulation could help to explain its remarkable anti-atherosclerotic properties observed in animal models.

Recently the synthetic LXR ligands GW3965 (Glaxo) and T-0901317 (Tularik) were reported to increase glucose tolerance in fat fed obese mouse, which was interpreted to result from reduced hepatic gluconeogenesis and increased glucose uptake in adipocytes Lafitte B A et al. (Proc Natl Acad Sci USA. 2003 Apr. 29; 100(9):5419-24). Activation of LXR's improves glucose tolerance through coordinated regulation of glucose metabolism in liver and adipose tissue.

JP2001163786A discloses the synthesis of certain novel 2-(substituted alkyl)-4-(substituent)-5-(substituent)isothiazol-3(2H)-one 1,1-dioxides wherein the 4- or 5-positions are substituted by e.g. H, lower alkyl or carboxyl. These compounds are reported to have matrixmetalloproteinase (MMP) inhibitory activity (especially matrixmetalloproteinase-13 (MMP-13) inhibitory activity) and aggrecanase inhibitory activity, and are useful in the prevention or treatment of arthritis (especially osteoarthritis) and for inhibiting metastasis, infiltration or proliferation of cancer (especially breast cancer).

EP1069110A1 discloses the synthesis of certain novel 2-(substituted alkyl)-4-(substituent)-5-(substituent)isothiazol-3(2H)-one 1,1-dioxides wherein the 4- or 5-positions are substituted by e.g. H, lower alkyl or carboxyl. These compounds are reported to have matrixmetalloproteinase-13 (MMP-13) inhibitory activity and aglycanase inhibitory activity, and are useful for treating arthritic disorders such as reumatoid arthritis.

WO9708143A1 discloses the synthesis of 2-(substituted alkyl)-4-(substituent)-5-(substituent)isothiazol-3(2H)-one 1,1-dioxides wherein the substituents in 4- or 5-positions are selectioned from nitro, cyano, trifluoromethyl, carbethoxy, carbomethoxy, carbopropoxy, acetyl, carbamoyl, carbamoyl substituted with an alkyl of 1 to 3 carbon atoms, acetoxy, carboxy, hydroxy, amino, amino substituted with an alkyl of 1 to 3 carbon atoms, alkyl of 1 to 4 carbon atoms, alkoxy of 1 to 4 carbon atoms or halo, or the 4 and/or 5 positions are unsubstituted, and their use for reducing levels of Tumor Necrosis Factor (TNF) in mammals.

In the application WO05/005417 it is disclosed that certain novel 1-(substituted alkyl)-3 amino-4 phenyl-1H-pyrrole-2, 5-dione derivatives have utility in the modulation of nuclear hormone receptors Liver X Receptor (LXR) α (NR1H3) and/or β (NR1H2) and in treating and/or preventing clinical conditions including cardiovascular diseases.

In the application WO05/005416 it is disclosed that certain novel 5-thioxo-1,5-dihydro-2H-pyrrol-2-one and 1H-pyrrole-2,5-dithione derivatives have utility in the modulation of nuclear hormone receptors Liver X Receptor (LXR) α (NR1H3) and/or β (NR1H2) and in treating and/or preventing clinical conditions including cardiovascular diseases.

WO05/035551 discloses certain novel 2-(substituent)-4-(substituent)-5-(substituent)isothiazol-3(2H)-one 1,1-dioxides. These compounds are reported to modulate the activity of a target protein such as a phosphatase.

The term "LXR modulator" as used herein more specifically means a compound with the ability to modulate the biological activity of LXRα and/or LXRβ via increase or decrease of the function and/or expression of LXRα and/or LXRβ, where LXRα and/or LXRβ function may include transcription regulatory activity and/or protein-binding. Modulation may occur in vitro or in vivo. Modulation, as described herein, includes antagonism, agonism, partial antagonism and/or partial agonism of a function or characteristic associated with LXRα and/or LXRβ, either directly or indirectly, and/or the upregulation or downregulation of LXRα and/or LXRβ expression, either directly or indirectly. More specifically, such an LXR modulator either enhances or inhibits the biological activities of LXR via the function and/or expression of LXR. If such a modulator partially or completely enhances the biological activities of LXR via the function and/or expression of LXR, it is a partial or full LXR agonist, respectively. It is the object of the present invention to provide LXR modulators. Another object of this invention is to provide LXR modulator compounds being LXR agonists.

It should be noted that to show activity in the specific Test Methods described herein, the LXR modulator compound must bind to the ligand binding domain of the LXR and recruit either the specific peptide derived from the co-activator protein, SRC1, to the modulator compound-bound LXR complex in the described Co-activator recruitment assay, or one or more of the nuclear hormone receptor co-factors present in for example the U2OS cell-based method described herein. The compounds of this invention that form an LXR-modulator compound-complex may recruit at least one or more of the other >80 known different nuclear hormone receptor cofactors in any other cell-based method prepared and assayed according to known procedures. Compounds according to formula (I), that do not recruit the SRC1-derived peptide or any of the co-factors present in the in cell-based method described herein, is however anticipated to bind to LXR and the LXR-modulator compound-complex so formed will recruit at least one or more of the other >80 known different nuclear receptor cofactors present in other cellular system. The LXR modulator compound-complex may also displace co-repressors, such as NcOR, with simultaneous recruitment of a co-activator or may only displace a co-repressor without co-activator recruitment, leading to partial activation of certain LXR regulated genes. Recruiter peptides derived from any of these other nuclear hormone receptor cofactors may be similarly prepared and assayed according to known procedures.

DESCRIPTION OF THE INVENTION

According to a first aspect of the invention there is provided a compound of formula I:

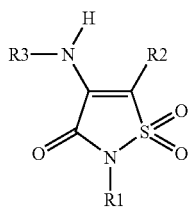

formula I or a pharmaceutically acceptable salt or solvate thereof, or a solvate of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

cycloalkyl or heterocyclyl each optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

cycloalkylY or heterocyclylY wherein cycloalkyl or heterocyclyl each optionally is substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenylY or heteroarylY wherein phenyl or heteroaryl each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

$R^2$ represents phenyl which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$R^3$ represents

X which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

MP or $Het^3$P wherein M and $Het^3$ each optionally is substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following: halogen (Cl, F, Br, I), OH, CN, $NR^aR^a$, $OR^b$, $SR^b$, $S(O)R^b$, $SO_2R^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

AP or Het$^5$P wherein A and Het$^5$ each optionally is substituted by one or more of the following: halogen (F, Cl, Br, I), OH, CN, NO$_2$, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

E or Het$^4$ each optionally substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following: halogen (F, Cl, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

The following definitions shall apply throughout the specification and the appended claims unless specifically stated otherwise:

The term "X" denotes a straight or branched, saturated or unsaturated alkyl group having 1 to 6 carbon atoms wherein said alkyl group may optionally be interrupted by O, S, SiR$^b$R$^b$, S(O), SO$_2$, C(O), NR$^a$, OC(O), C(O)O, NR$^a$C(O), C(O)NR$^a$, SO$_2$NR$^a$ or NR$^a$SO$_2$. It shall be understood that when X is present more than once in the same compound then the value may be the same or different. Examples of said "X" include, but are not limited to, methyl, ethyl, propyl, isopropyl, butyl, tert-butyl, isobutyl, pentyl, hexyl, vinyl, isopropenyl, allyl, but-2-enyl, ethynyl, 2-propynyl, 2-methoxyethyl, 3-methylpropyl, methylthiomethyl, 3-hydroxypropyl, 2-(2-methoxyethoxy)ethyl, 3-(2-methoxyethoxy)propyl, 2,2-dimethylpropyl, 2-hydroxyethyl, 2,2,2-trifluoroethyl, 2,3-dihydroxypropyl, 2-cyanoethyl and methyl ethanoylglycinate.

The term "Y" denotes a straight or branched, saturated or unsaturated alkylene group having 1 to 3 carbon atoms wherein said alkylene group binds to nitrogen in 2-position in the isothiazol-3(2H)-one 1,1-dioxide and may optionally be interrupted or ended by one of the following: O, S, SiR$^b$R$^b$, S(O), SO$_2$, C(O), OC(O), C(O)O, NR$^c$C(O), C(O)NR$^c$, NR$^c$ and/or Y is optionally substituted by one or more of the following independently selected from: OH, F, CN, NR$^a$R$^a$, C$_1$-C$_4$alkyl, OR$^b$, SR$^b$, SiR$^b$R$^b$R$^b$, S(O)R$^b$ or SO$_2$R$^b$. In the definition of "Y" the term "ended by O, S, SiR$^b$R$^b$, S(O), SO$_2$, C(O), OC(O), C(O)O, NR$^c$C(O), C(O)NR$^c$, NR$^c$" means that the alkylene group has as the last position O, S, SiR$^b$R$^b$, S(O), SO$_2$, C(O), OC(O), C(O)O, NR$^c$C(O), C(O)NR$^c$ or NR$^c$ before it binds further to phenyl, heteroaryl, cycloalkyl or heterocyclyl. Examples of said "Y" include, but are not limited to, methylene, ethylene, propylene, 2-methylethylene, and 1-methylethylene.

The term "Z" denotes a straight or branched, saturated or unsaturated alkylene group having 1 to 6 carbon atoms wherein said alkylene group binds to E or Het$^4$ and one of the following: Q, Het$^1$, R or Het$^2$, and may optionally be interrupted or ended by one of the following: O, S, SiR$^b$R$^b$, S(O), SO$_2$, C(O), OC(O), C(O)O, C(O)CR$^a$, NR$^a$C(O), C(O)NR$^a$, NR$^a$, SO$_2$NR$^a$, NR$^a$SO$_2$, or is one of the following: O, S, SiR$^b$R$^b$, S(O), SO$_2$, C(O), OC(O), C(O)O, NR$^a$C(O), C(O)NR$^a$, NR$^a$, SO$_2$NR$^a$, NR$^a$SO$_2$ and/or Z is optionally substituted by one or more of the following independently selected from: OH, F, CN, NR$^c$R$^c$, C(O)R$^c$, OR$^b$, SR$^c$, SiR$^b$R$^b$R$^b$, S(O)R$^c$, SO$_2$R$^c$, phenyl, phenylC$_1$-C$_3$alkyl, or C$_1$-C$_4$alkyl which is optionally substituted by one or more of the following independently selected from: F, OH, NR$^a$R$^a$, SR$^b$, SiR$^b$R$^b$R$^b$, S(O)R$^b$, SO$_2$R$^b$, OR$^b$. In the definition of "Z" the term "ended by O, S, SiR$^b$R$^b$, S(O), SO$_2$, C(O), OC(O), C(O)O, NR$^a$C(O), C(O)NR$^a$, NR$^a$, SO$_2$NR$^a$, NR$^a$SO$_2$," means that the alkylene group has as the last position O, S, SiR$^b$R$^b$, S(O), SO$_2$, C(O), OC(O), C(O)O, NR$^a$C(O), C(O)NR$^a$, NR$^a$, SO$_2$NR$^a$ or NR$^a$SO$_2$ before it binds further to E, Het$^4$, Q, Het$^1$, R or Het$^2$. Examples of said "Z" include, but are not limited to, methylene, ethylene, propylene, butylene, pentylene, hexylene, O, S, S(O), SO$_2$, C(O), OC(O), C(O)O, C(O)CH$_2$, CH$_2$C(O), C(O)(C$_1$-C$_4$alkyl), NHC(O), C(O)NH, NH, SO$_2$NH, NHSO$_2$, N(C$_1$-C$_4$alkyl)C(O), C(O)N(C$_1$-C$_4$alkyl), N(C$_1$-C$_4$alkyl), SO$_2$N(C$_1$-C$_4$alkyl), N(C$_1$-C$_4$alkyl)SO$_2$, 1-methylpropylene, 2-methylpropylene and 3-methylpropylene. In the definition of Z it is to be understood that specific values bind in the order written, i.e. from left to right. For example, when Z is C(O)CH$_2$ then C(O) in said C(O)CH$_2$ binds to E or Het$^4$ and CH$_2$ in said C(O)CH$_2$ binds to Q, Het$^1$, R or Het$^2$.

The term "M" denotes a saturated or unsaturated non-aromatic monocarbocyclic ring composed of 3, 4, 5, 6, 7 or 8 carbon atoms or a saturated or unsaturated non-aromatic or partly aromatic bicyclic ring system composed of 8, 9 or 10 carbon atoms. Examples of said "M" include, but are not limited to, cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl, cyclooctadienyl, decaline, hydrindane, indane, indene, and bicyclo[4.2.0]octa-1,3,5-triene.

The term "E" denotes a saturated or unsaturated non-aromatic monocarbocyclic ring composed of 3, 4, 5, 6, 7 or 8 carbon atoms or a saturated or unsaturated non-aromatic or partly aromatic bicyclic ring system composed of 8, 9 or 10 carbon atoms. The ring binds, unless otherwise specified, through its non-aromatic part to nitrogen in 4-position on the isothiazol-3(2H)-one 1,1-dioxide. Examples of said "E" include, but are not limited to, cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl, cyclooctadienyl, decaline, hydrindane, indane, indene and bicyclo[4.2.0]octa-1,3,5-triene.

The term "A" denotes an aromatic monocyclic ring composed of 6 carbon atoms or an aromatic bicyclic ring system composed of 10 carbon atoms. Examples of said "A" include, but are not limited to, phenyl, naphtalene and azulene.

The term "P" denotes a straight or branched, saturated or unsaturated alkylene group having 1 to 6 carbon atoms wherein the alkylene group binds to nitrogen in 4-position on the isothiazol-3(2H)-one 1,1-dioxide and is optionally interrupted or ended by one of the following: O, $NR^a$, S, $SiR^bR^b$, S(O), $SO_2$, C(O), OC(O), C(O)O, $NR^aC(O)$, $C(O)NR^a$, $SO_2NR^a$, $NR^aSO_2$ and/or P is optionally substituted by one or more of the following independently selected from: F, OH, CN, $NR^aR^a$, $C(O)R^c$, $OR^b$, $SR^b$, $SiR^bR^bR^b$, $S(O)R^b$, $SO_2R^b$, phenyl, phenyl$C_1$-$C_3$alkyl, or $C_1$-$C_4$alkyl which is optionally substituted by one or more of the following independently selected from: F, OH, $NR^aR^a$, $SR^b$, $SiR^bR^bR^b$, $S(O)R^b$, $SO_2R^b$ or $OR^b$. In the definition of "P" the term "ended by O, $NR^a$, S, $SiR^bR^b$, S(O), $SO_2$, C(O), OC(O), C(O)O, $NR^aC(O)$, $C(O)NR^a$, $SO_2NR^a$, $NR^aSO_2$" means that the alkylene group has as the last position O, $NR^a$, S, $SiR^bR^b$, S(O), $SO_2$, C(O), OC(O), C(O)O, $NR^aC(O)$, $C(O)NR^a$, $SO_2NR^a$ or $NR^aSO_2$" before it binds further to M, $Het^3$, A or $Het^5$. Examples of said "P" include, but are not limited to, methylene, ethylene, propylene, butylene, ethyleneoxy, propyleneoxy, butyleneoxy, ethyleneamino, ethylenethio, propylenethio, $CH_2C(O)NHCH_2$, $CH_2C(O)O$, $CH_2CH_2C(O)OCH_2CH_2CH_2C(O)O$, $CH_2C(O)OCH_2$, $CH_2C(O)OCH_2CH_2$, $CH_2CH_2OCOCH_2$, $CH_2C(O)OCH(CH_3)CH_2$, 1-methylpropylene, 2-methylpropylene and 3-methylpropylene. In the definition of P it is to be understood that the specific values bind in the order written, i.e. from left to right. For example, when P is ethyleneoxy then it is the oxygen that binds to M, $Het^3$, A or $Het^5$.

The term "Q" denotes a saturated or unsaturated non-aromatic monocyclic ring composed of 3, 4, 5, 6, 7 or 8 carbon atoms, which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$. Examples of said "Q" include, but are not limited to, cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "R" denotes a phenyl group which is optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

The term "T" denotes methylene or is one of the following: O, $NR^a$, S, $SiR^bR^b$, S(O), $SO_2$, C(O), OC(O), C(O)O, $NR^aC(O)$, $C(O)NR^a$, $SO_2NR^a$ or $NR^aSO_2$. T binds to M, $Het^3$, A or $Het^5$ and one of the following: Q, $Het^1$, R or $Het^2$. Examples of said "T" include, but are not limited to, methylene, O, $NR^a$, S, $SiR^bR^b$, S(O), $SO_2$, C(O), OC(O), C(O)O, $NR^aC(O)$, $C(O)NR^a$, $SO_2NR^a$ and $NR^aSO_2$.

The term "$C_1$alkyl" denotes an alkyl group having 1 carbon atom. An example of said alkyl includes, but is not limited to, methyl.

The term "$C_1$-$C_3$alkyl" denotes a straight or branched, saturated or unsaturated alkyl group having 1 to 3 carbon atoms. Examples of said alkyl include, but are not limited to, methyl, ethyl, propyl, isopropyl, vinyl, isopropenyl, allyl, ethynyl, and 2-propynyl.

The term "$C_1$-$C_4$alkyl" denotes a straight or branched, saturated or unsaturated alkyl group having 1 to 4 carbon atoms. Examples of said alkyl include, but are not limited to, methyl, ethyl, propyl, isopropyl, tert-butyl, vinyl, isopropenyl, allyl, but-2-enyl, ethynyl, 2-propynyl, and but-2-ynyl.

The term "halogen" denotes fluoro, chloro, bromo and iodo groups.

The term "cycloalkyl" denotes a saturated or unsaturated non-aromatic monocyclic ring composed of 3, 4, 5, 6, 7 or 8 carbon atoms. For example, $C_3$-$C_6$cycloalkyl denotes a saturated or unsaturated non-aromatic monocyclic ring composed of 3, 4, 5 or 6 carbon atoms, for example cyclopropyl, cyclobutyl, cyclopentyl or cyclohexyl. Further examples of said "cycloalkyl" include, but are not limited to, cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "heterocyclyl" denotes a saturated or unsaturated non-aromatic 3, 4, 5, 6, 7 or 8 membered monocyclic ring in which one or more of the atoms in the ring is an element other than carbon independently selected from one or more of for example nitrogen, oxygen or sulfur. The term "sulfur" shall be understood to include sulphoxide (S(O)) and sulphone ($SO_2$). The term "nitrogen" shall be understood to include nitrogen oxide (NO). Examples of said "heterocyclyl" include, but are not limited to, aziridine, azetidine, 2-pyrroline, 3-pyrroline, pyrrolidine, imidazoline, piperidine, piperazine, 2-pyrazoline, oxirane, oxetane, tetrahydrofuran, tetrahydropyran, 1,4-dioxane, 1,3-dioxolane, 1,2-oxathiolane, morpholine, 3-pyrazoline, pyrazolidine, 2H-pyrane, 4H-pyrane, 1,4-dithiane, 1,4-oxathiane and thiomorpholine.

The term "heteroaryl" denotes an aromatic 5 or 6 membered monocyclic ring in which one or more of the atoms in the ring is an element other than carbon independently selected from one or more of for example nitrogen, oxygen and sulfur. The term "sulfur" shall be understood to include sulphoxide (S(O)) and sulphone ($SO_2$). The term "nitrogen" shall be understood to include nitrogen oxide (NO). Examples of said "heteroaryl" include, but are not limited to, furan, pyrrole, pyrazine, pyrazole, imidazole, triazole, pyrimidine, pyridazine, pyridine, pyridine-1-oxide, isoxazole, oxazole, isothiazole, thiazole, thiophene, 1,2,4-triazole, furazane, 1,2,3-oxadiazole, 1,2,4-oxadiazole, 1,2,5-oxadiazole, 1,3,4-oxadiazole, 1,2,5-thiadiazole, 1,2,4-thiadiazole and 1,2,3-thiadiazole.

The term "$Het^1$" denotes a saturated or unsaturated non-aromatic 3, 4, 5, 6, 7, 8, 9, or 10 membered monocyclic ring in which one or more of the atoms in the ring is an element other than carbon independently selected from one or more of for example nitrogen, oxygen or sulfur, and wherein the ring optionally is substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$. The term "sulfur" shall be understood to include sulphoxide (S(O)) and sulphone ($SO_2$). The term "nitrogen" shall be understood to include nitrogen oxide (NO). Examples of said "$Het^1$" include, but are not limited to aziridine, azetidine, 2-pyrroline, 3-pyrroline, pyrrolidine, imidazoline, piperidine, piperazine, 2-pyrazoline, oxirane, oxetane, tetrahydrofuran, tetrahydropyran, 1,4-dioxane, 1,3-dioxolane, 1,2-oxathiolane, morpholine, 3-pyrazoline, pyrazolidine, 2H-pyrane, 4H-pyrane, 1,4-dithiane, 1,4-oxathiane and thiomorpholine.

The term "$Het^2$" denotes an aromatic 5 or 6 membered monocyclic ring in which one or more of the atoms in the ring is an element other than carbon independently selected from one or more of for example nitrogen, oxygen and sulfur, and which is substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following independently selected from: F, OH, CN, $NR^aR^a$, $OR^b$, $SR^b$, $SiR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$. The term "sulfur" shall be understood to include sulphoxide (S(O)) and sulphone ($SO_2$). The term "nitrogen" shall be understood to include nitrogen oxide (NO). Examples of said "$Het^2$" include, but are not limited to, furan, pyrrole, pyrazine, pyrazole, imidazole, triazole, pyrimidine, pyridazine, pyridine, pyridine-1-oxide, isoxazole, oxazole, isothiazole, thiazole, thiophene, 1,2,4-triazole, furazane, 1,2,3-oxadiazole, 1,2,4-oxadiazole, 1,2,5-oxadiazole, 1,3,4-oxadiazole, 1,2,5-thiadiazole, 1,2,4-thiadiazole and 1,2,3-thiadiazole.

The term "$Het^3$" denotes a saturated or unsaturated non-aromatic 3, 4, 5, 6, 7, 8, 9 or 10 membered monocyclic ring or a saturated or unsaturated non-aromatic or partly aromatic 9 or 10 membered bicyclic ring system in which one or more of the atoms in the monocyclic ring or bicyclic ring system is an element other than carbon independently selected from one or more of for example nitrogen, oxygen or sulfur. The term "sulfur" shall be understood to include sulphoxide (S(O)) and sulphone ($SO_2$). The term "nitrogen" shall be understood to include nitrogen oxide (NO). Examples of said "$Het^3$" include, but are not limited to aziridine, azetidine, 2-pyrroline, 3-pyrroline, pyrrolidine, imidazoline, piperidine, piperazine, 2-pyrazoline, oxirane, oxetane, tetrahydrofuran, tetrahydropyran, 1,4-dioxane, 1,3-dioxolane, 1,2-oxathiolane, morpholine, 3-pyrazoline, pyrazolidine, 2H-pyrane, 4H-pyrane, 1,4-dithiane, 1,4-oxathiane, thiomorpholine, indoline, 1,3-dihydro-2-benzofuran, 2,3-dihydro-1-benzofuran, 1,3-benzodioxole, 2,3-dihydro-1,4-benzodioxine, chroman and isochroman.

The term "$Het^4$" denotes a saturated or unsaturated non-aromatic 3, 4, 5, 6, 7, 8, 9 or 10 membered monocyclic ring or a saturated or unsaturated non-aromatic or partly aromatic 9 or 10 membered bicyclic ring system in which one or more of the atoms in the monocyclic ring or bicyclic ring system is an element other than carbon independently selected from one or more of for example nitrogen, oxygen or sulfur. The term "sulfur" shall be understood to include sulphoxide (S(O)) and sulphone ($SO_2$). The term "nitrogen" shall be understood to include nitrogen oxide (NO). The ring binds, unless otherwise specified, through its non-aromatic part to nitrogen in 4-position on the isothiazol-3(2H)-one 1,1-dioxide. Examples of said "$Het^4$" include, but are not limited to, aziridine, azetidine, 2-pyrroline, 3-pyrroline, pyrrolidine, imidazoline, piperidine, piperazine, 2-pyrazoline, oxirane, oxetane, tetrahydrofuran, furan, tetrahydropyran, 1,4-dioxane 1,3-dioxolane, 1,2-oxathiolane, morpholine, 3-pyrazoline, pyrazolidine, isoxazole, 2H-pyrane, 4H-pyrane, 1,4-dithiane, 1,4-oxathiane, thiomorpholine, indoline, 1,3-dihydro-2-benzofuran, 2,3-dihydro-1-benzofuran, 1,3-benzodioxole, 2,3-dihydro-1,4-benzodioxine, chroman and isochroman.

The term "$Het^5$" denotes an aromatic 5 or 6 membered monocyclic ring or an aromatic 9 or 10 membered bicyclic ring in which one or more of the atoms in the monocyclic ring or bicyclic ring system is an element other than carbon independently selected from one or more of for example nitrogen, oxygen or sulfur. The term "sulfur" shall be understood to include sulphoxide (S(O)) and sulphone ($SO_2$). The term "nitrogen" shall be understood to include nitrogen oxide (NO). Examples of said "$Het^5$" include, but are not limited to, furan, pyrrole, pyrazine, pyrazole, imidazole, triazole, pyrimidine, pyridazine, pyridine, pyridine-1-oxide, isoxazole, oxazole, isothiazole, thiazole, thiophene, 1,2,4-triazole, furazane, 1,2,3-oxadiazole, 1,2,4-oxadiazole, 1,2,5-oxadiazole, 1,3,4-oxadiazole, 1,2,5-thiadiazole, 1,2,4-thiadiazole 1,2,3-thiadiazole, benzofuran, isobenzofuran, indole, isoindole, benzothiophene, benzo[c]thiophene, benzimidazole, purine, indazole, benzoxazole, benzisoxazole, benzthiazole, quinoline, quinoxaline, quinazoline, cinnoline and isoquinoline.

$R^a$ independently represents H or a straight or branched, saturated or unsaturated $C_1$-$C_4$alkyl chain optionally substituted by one or more F.

$R^b$ independently represents a straight or branched, saturated or unsaturated $C_1$-$C_4$alkyl chain optionally substituted by one or more F.

$R^c$ independently represents H or a straight or branched, saturated or unsaturated $C_1$-$C_3$alkyl chain optionally substituted by one or more F.

It shall be understood that when a substitutent bears more than one of $R^a$, $R^b$ or $R^c$ then each of these may be the same or different. For example, $NR^aR^a$ includes amino, alkylamino and dialkylamino. Furthermore, it shall be understood that when different substituents in the same compound bear more than one of $R^a$, $R^b$ or $R^c$ then each of these may be the same or different.

Further values of $R^1$, $R^2$ and $R^3$ in compounds of formula I now will follow. It will be understood that such values may be used where appropriate with any of the definitions, claims or embodiments defined hereinbefore or hereinafter.

In a first group of compounds of formula I $R^1$ represents

X which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

cycloalkyl or heterocyclyl each optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenyl or heteroaryl each optionally substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

cycloallylY or heterocyclylY wherein cycloalkyl or heterocyclyl each optionally is substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenylY or heteroarylY wherein phenyl or heteroaryl each optionally is substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

R$^2$ represents phenyl which is optionally substituted by one or more of the following: halogen (Cl, F, I, Br), OH, CN, NO$_2$, NR$^a$R$^a$, OR$^b$, SR$^b$S(O)R$^b$SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R$^3$ represents

X which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$ or NR$^a$C(O)NR$^a$R$^a$;

MP or Het$^3$P wherein M and Het$^3$ each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het$^3$ each optionally is substituted on the aromatic ring by one or more of the following: halogen (Cl, F, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

AP or Het$^5$P wherein A and Het$^5$ each optionally is substituted by one or more of the following: halogen (F, Cl, Br, I), OH, CN, NO$_2$, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

E or Het$^4$ each optionally substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following: halogen (F, Cl, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

In a second group of compounds of formula I

R$^1$ represents

X which is optionally substituted by one or more of the following: F, OH, CN, NR$^a$R$^a$, OR$^b$, SR$^b$, S(O)R$^b$, SO$_2$R$^b$, C(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$ or C(O)R$^b$;

cycloalkyl or heterocyclyl each optionally substituted by one or more of the following: F, OH, CN, NR$^a$R$^a$, OR$^b$, SR$^b$, S(O)R$^b$, SO$_2$R$^b$, C(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$ or C(O)R$^b$;

phenyl or heteroaryl each optionally substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, or C$_1$-C$_4$alkyl optionally substituted by one or more of the following: F, OH, CN, NR$^a$R$^a$, OR$^b$, SR$^b$, S(O)R$^b$, SO$_2$R$^b$, C(O)R$^b$;

cycloalkylY or heterocyclylY wherein cycloalkyl or heterocyclyl each optionally is substituted by one or more of the following: F, OH, CN, NR$^a$R$^a$, OR$^b$, SR$^b$, S(O)R$^b$, SO$_2$R$^b$, C(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$;

phenylY or heteroarylY wherein phenyl or heteroaryl each optionally is substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$;

R$^2$ represents phenyl which is optionally substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, R$^3$ is the same as in the first group of compounds of formula I.

In a third group of compounds of formula I

R$^1$ represents

X which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$ or NR$^a$C(O)NR$^a$R$^a$ R$^2$ is the same as in the second group of compounds of formula I, R$^3$ is the same as in the first group of compounds of formula I.

In a fourth group of compounds of formula I

R$^1$ represents

X which is optionally substituted by one or more of the following: F, OH, CN, NR$^a$R$^a$, OR$^b$, SR$^b$, S(O)R$^b$, SO$_2$R$^b$, C(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$ or C(O)R$^b$, R$^2$ is the same as in the second group of compounds of formula I, R$^3$ is the same as in the first group of compounds of formula I.

In a fifth group of compounds of formula I

R$^1$ is the same as in the first group of compounds of formula I,

R$^2$ is the same as in the first group of compounds of formula I, and

R$^3$ represents

X which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$ or NR$^a$C(O)NR$^a$R$^a$.

In a sixth group of compounds of formula I

R$^1$ is the same as in the first group of compounds of formula I,

R$^2$ is the same as in the first group of compounds of formula I, and

R$^3$ represents

MP or Het$^3$P wherein M and Het$^3$ each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O) OR$^b$, OC(O)NR$^a$R$^a$ or NR$^a$C(O)NR$^a$R$^a$, and wherein M or Het$^3$ each optionally is substituted on the aromatic ring by one or more of the following: halogen (Cl, F, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$ Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

AP or Het$^5$P wherein A and Het$^5$ each optionally is substituted by one or more of the following: halogen (F, Cl, Br, I), OH, CN, NO$_2$, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

In a seventh group of compounds of formula I

R$^1$ is the same as in the first group of compounds of formula I,

R$^2$ is the same as in the first group of compounds of formula I, and

R$^3$ represents

E or Het$^4$ each optionally substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$ C(O)NR$^a$R$^a$, OC(O)R$^b$, C(O)OR$^a$SO$_2$NR$^a$R$^a$NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following: halogen (F, Cl, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

In an 8$^{th}$ group of compounds of formula I

R$^1$ is the same as in the second group of compounds of formula I,

R$^2$ is the same as in the second group of compounds of formula I, and

R$^3$ represents

X which is optionally substituted by one or more of the following: F, OH, CN, NR$^a$R$^a$, OR$^b$, SR$^b$, S(O)R$^b$, SO$_2$R$^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$ In a 9$^{th}$ group of compounds of formula I $R^1$ is the same as in the second group of compounds of formula I, $R^2$ is the same as in the second group of compounds of formula I, and $R^3$ represents MP or Het$^3$P wherein M and Het$^3$ each optionally is substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, Het$^1$, Het$^1$T, R, RT, Het$^2$, Het$^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^a$, $C(O)OR^a$, $SO_2NR^aR^aNR^aSO_2R^b$, $NR^aC(O)OR^b$, $OC(O)NR^aR^a$ or $NR^aC(O)NR^aR^a$, and wherein M or Het$^3$ each optionally is substituted on the aromatic ring by one or more of the following: halogen (Cl, F, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, Het$^1$, Het$^1$T, R, RT, Het$^2$, Het$^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

AP or Het$^5$P wherein A and Het$^5$ each optionally is substituted by one or more of the following: halogen (F, Cl, Br, I), OH, CN, $NO_2$, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, Het$^1$, Het$^1$T, R, RT, Het$^2$, Het$^5$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

In an 10$^{th}$ group of compounds of formula I $R^1$ is the same as in the second group of compounds of formula I, $R^2$ is the same as in the second group of compounds of formula I, and $R^3$ represents E or Het$^4$ each optionally substituted on the non-aromatic ring by one or more of the following: F, OH, CN, $NR^aR^a$, $OR^b$, $SR^bS(O)R^b$, $SO_2R^b$, $C(O)R^a$, $NR^aC(O)R^b$, $C(O)NR^aR^aOC(O)R^bC(O)OR^a$, $SO_2NR^aR^a$, $NR^aSO_2R^b$, $OC(O)NR^aR^a$, $NR^aC(O)OR^a$, $NR^aC(O)R^a$, Q, QZ, Het$^1$, Het$^1$Z, R, RZ, Het$^2$, Het$^2$Z, or $C_1$-$C_4$alkyl which is optionally substituted by one or more of the following: F, OH, CN, $NR^aR^a$, $OR^b$, $SR^bS(O)R^b$, $SO_2R^b$, $C(O)R^b$, $NR^aC(O)R^bC(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and E or Het$^4$ each optionally is substituted on the aromatic ring by one or more of the following: halogen (F, Cl, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, Het$^1$, Het$^1$Z, R, RZ, Het$^2$, Het$^2$Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

In an 11$^{th}$ group of compounds of formula I $R^1$ is the same as in the third group of compounds of formula I, $R^2$ is the same as in the third group of compounds of formula I, and $R^3$ represents X which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$ $C(O)R^b$ or $NR^aC(O)NR^aR^a$.

In a 12$^{th}$ group of compounds of formula I $R^1$ is the same as in the third group of compounds of formula I, $R^2$ is the same as in the third group of compounds of formula I, and $R^3$ represents MP or Het$^3$P wherein M and Het$^3$ each optionally is substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, Het$^1$, Het$^1$T, R, RT, Het$^2$, Het$^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^bNR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or Het$^3$ each optionally is substituted on the aromatic ring by one or more of the following: halogen (Cl, F, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, Het$^1$, Het$^1$T, R, RT, Het$^2$, Het$^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

AP or Het$^5$P wherein A and Het$^5$ each optionally is substituted by one or more of the following: halogen (F, Cl, Br, I), OH, CN, $NO_2$, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, Het$^1$, Het$^1$T, R, RT, Het$^2$, Het$^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

In a 13$^{th}$ group of compounds of formula I $R^1$ is the same as in the third group of compounds of formula I, $R^2$ is the same as in the third group of compounds of formula I, and $R^3$ represents E or $Het^4$ each optionally substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QZ, $Het^1$, $Het^1Z$, R, RZ, $Het^2$, $Het^2Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and E or $Het^4$ each optionally is substituted on the aromatic ring by one or more of the following: halogen (F, Cl, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1Z$, R, RZ, $Het^2$, $Het^2Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $S_2NR^aR^a$, $NR^aSO_2R^b$, $NR^aC(O)OR^b$, $OC(O)NR^aR^a$ or $NR^aC(O)NR^aR^a$;

In a 14th group of compounds of formula I $R^1$ is the same as in the fourth group of compounds of formula I, $R^2$ is the same as in the fourth group of compounds of formula I, and $R^3$ represents X which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$.

In a 15th group of compounds of formula I $R^1$ is the same as in the fourth group of compounds of formula I, $R^2$ is the same as in the fourth group of compounds of formula I, and $R^3$ represents MP or $Het^3P$ wherein M and $Het^3$ each optionally is substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following: halogen (Cl, F, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, $Het^1$, $Het^1T$, R, RT, $Het^2$, $Het^2T$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC$ $(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

AP or $Het^5P$ wherein A and $Het^5$ each optionally is substituted by one or more of the following: halogen (F, Cl, Br, I), OH, CN, $NO_2$, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

In a 16th group of compounds of formula I $R^1$ is the same as in the fourth group of compounds of formula I, $R^2$ is the same as in the fourth group of compounds of formula I, and $R^3$ represents E or $Het^4$ each optionally substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QZ, $Het^1$, $Het^1Z$, R, RZ, $Het^2$, $Het^2Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and E or $Het^4$ each optionally is substituted on the aromatic ring by one or more of the following: halogen (F, Cl, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1Z$, R, RZ, $Het^2$, $Het^2Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

The compounds of formula I have activity as medicaments. In particular the compounds of formula (I) are LXR agonists.

In another aspect of the invention, there is provided a compound according to formula (V) in which $R^1$ is selected from ethyl, isopropyl, n-butyl, tertbutyl, cyclopentyl, hexyl, benzyl, 2-methoxyethyl, pyridin-2-ylmethyl, pyridin-3-ylmethyl, pyridin-4-ylmethyl, tetrahydrofuran-2-ylmethyl or 2-(3-fluorophenyl)ethyl; and $R^2$ is phenyl.

In another aspect of the invention, there is provided a compound according to formula (VI) in which $R^1$ is selected from ethyl, isopropyl, n-butyl, tertbutyl, cyclopentyl, hexyl, benzyl, 2-methoxyethyl, pyridin-2-ylmethyl, pyridin-3-ylmethyl, pyridin-4-ylmethyl, tetrahydrofuran-2-ylmethyl or 2-(3-fluorophenyl)ethyl, $R^2$ is phenyl and L is a leaving group such as for instance Cl, Br, I, methanesulfonate (MsO) or trifluoromethanesulfonate (OTf).

In one aspect of the invention there is provided a compound of formula (I) in which $R^1$ is selected from ethyl, isopropyl, n-butyl, tertbutyl, cyclopentyl, hexyl, benzyl, 2-methoxyethyl, pyridin-2-ylmethyl, pyridin-3-ylmethyl, pyridin-4-ylmethyl, tetrahydrofuran-2-ylmethyl or 2-(3-fluorophenyl)ethyl;

$R^2$ is phenyl; and $R^3$ is selected from butyl, hexyl, benzyl, 3-[3-(hydroxymethyl)phenoxy]propyl, 4-phenylbutyl, 3-(2-methoxyphenoxy)propyl, 3-[4-(hydroxymethyl)phenoxy]propyl, 3-(2-fluorophenoxy)propyl, 3-(2-chlorophenoxy)propyl, 3-(3-methoxyphenoxy)propyl, 3-(pyridin-3-yloxy)propyl, 3-(pyridin-4-yloxy)propyl, 1-[3-chloro-5-(trifluoromethyl)pyridin-2-yl]piperidin-4-yl, 3-(phenylthio)propyl, 3-phenoxypropyl, 3-(3-chlorophenoxy)propyl, 3-(3-fluorophenoxy)propyl, 3-(4-fluorophenoxy)propyl, 1-[4-(trifluoromethyl)pyrimidin-2-yl]piperidin-4-yl, cis-4-hydroxycyclohexyl, 4-phenoxybutyl, 3-[(1-oxidopyridin-3-yl)oxy]propyl, 3-(4-methoxyphenoxy)propyl, 4,4-difluorocyclohexyl, 2-phenoxyethyl, 2-phenylethyl, 4-(difluoromethoxy)benzyl, trans-4-hydroxycyclohexyl, 3-hydroxypropyl, 2,3-dihydro-1,4-benzodioxin-2-ylmethyl, 4-hydroxycyclohexyl, 3-(4-chlorophenoxy)propyl, 1,3-benzodioxol-5-ylmethyl, 2,3-dihydro-1H-inden-2-yl, 2-(morpholin-4-yl)ethyl, 3-(4-isopropylphenoxy)propyl, 3-[benzyl(butyl)amino]propyl, 3-(3,5-dipropoxyphenoxy)propyl, 2,2-diphenylethyl, 2-(1H-imidazol-4-yl)ethyl 4-morpholin-4-ylbenzyl, 3-(2-methoxyethoxy)propyl, 3-morpholin-4-ylpropyl, 2-methoxyethyl, tetrahydro-2H-pyran-4-yl, 4-hydroxycyclohexyl, 4-methoxybenzyl, 3-(3-hydroxyphenoxy)propyl, 3-(3-acetamidophenoxy)propyl, 3-(4-N,N-dimethylaminocarbonylmethylphenoxy)propyl, 3-(3-carboxymethylphenoxy)propyl, 3-(3-methoxycarbonylmethylphenoxy)propyl, 3-(3-methoxycarbonylphenoxy)propyl, 3-(4-carboxymethylphenoxy)propyl, 3-(4-methoxycarbonylmethylphenoxy)propyl, 3-(3-acetylaminophenoxy)propyl, 3-(4-hydroxyphenylcarboxy)propyl, 3-(4-carboxyphenoxy)propyl or 1-(2-nitriloethyl)piperidin-4-yl.

FURTHER EMBODIMENTS OF THE INVENTION

According to another embodiment of the invention there is provided a compound of general formula (I)

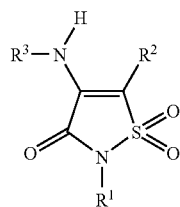

formula (I)

or a pharmaceutically acceptable salt thereof, wherein $R^1$ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$;

or $R^1$ is cycloalkyl or heterocyclyl each optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)OR^a$, $C(O)NR^aR^a$, $NR^aC(O)R^b$, $C(O)OR^a$, $OC(O)R^b$, $SO_2$ $NR^aR^a$, $NR^aSO_2R^b$, $NR^aC(O)OR^b$, $OC(O)NR^a$ or $NR^aC(O)NR^aR^a$;

or $R^1$ is phenyl or heteroaryl each optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

or $R^1$ is cycloalkylY or heterocyclylY wherein cycloalkyl or heterocyclyl each optionally is substituted by one or more of the following independently selected from: F, OH, CN, $NR^aR^a$, $OR^b$, $SR^b$, $SiR^bR^bR^b$, $S(O)R^b$, $SO_2R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

or $R^1$ is phenylY or heteroarylY wherein phenyl or heteroaryl each optionally is substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2$ $NR^aR^a$, $NR^aSO_2R^b$, $NR^aC(O)OR^b$, $OC(O)NR^aR^a$ or $NR^aC(O)NR^aR^a$;

$R^2$ represents phenyl which is optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$; $SO_2R^b$, $C(O)R^b$, $C(O)NR^aR^a$, $NR^aC(d)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$R^3$ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$;

or $R^3$ is MP or $Het^3P$ wherein M and $Het^3$ each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following independently selected from: halogen (Cl, F, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

or $R^3$ is AP or $Het^5P$ wherein A and $Het^5$ each optionally is substituted by one or more of the following independently selected from: halogen (F, Cl, Br, I), OH, CN, $NO_2$, $NR^aR^a$, $OR^b$, $SR^b$, $SiR^bR^bR^bS(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^aNR^aSO_2R^b$, $NR^aC(O)OR^b$, $OC(O)NR^aR^a$ or $NR^aC(O)NR^aR^a$;

or $R^3$ is E or $Het^4$ each optionally substituted on the non-aromatic ring by one or more of the following independently selected from: F. OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QZ, $Het^1$, $Het^1Z$, R, RZ, $Het^2$, $Het^2Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and E or $Het^4$ each optionally is substituted on the aromatic ring by one or more of the following independently selected from: halogen (F, Cl, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1Z$, R, RZ, $Het^2$, $Het^2Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

Further values of $R^1$, $R^2$ and $R^3$ will now follow. It will be understood that such values may be used where appropriate with any of the definitions, claims or embodiments defined hereinbefore or hereinafter.

In a first embodiment of the invention there is provided a class of compounds of formula I wherein $R^1$ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$;

or $R^1$ is cycloalkyl or heterocyclyl each optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

or $R^1$ is phenyl or heteroaryl each optionally substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

or $R^1$ is cycloalkylY or heterocyclylY wherein cycloalkyl or heterocyclyl each optionally is substituted by one or more of the following independently selected from: F, OH, CN, $NR^aR^a$, $OR^b$, $SR^b$, $SiR^bR^bR^b$, $S(O)R^b$, $SO_2R^b$, $C(O)R^bC(O)NR^aR^a$, $NR^aC(O)R^b$, $C(O)OR^a$, $OC(O)R^b$, $SO_2NR^aR^a$. $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

or $R^1$ is phenylY or heteroarylY wherein phenyl or heteroaryl each optionally is substituted by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^1$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^aNR^aSO_2R^b$, $NR^aC(O)OR^b$, $OC(O)NR^aR^a$ or $NR^aC(O)NR^aR^a$;

$R^2$ represents phenyl which is optionally substituted by one or more of the following independently selected from: halogen (Cl, F, I, Br), OH, CN, $NO_2$, $NR^aR^a$, $OR^b$, $SR^b$, $SiR^bR^bR^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R$^3$ represents
  X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, SR$^b$, SiR$^b$R$^b$R$^b$, S(O)R$^b$, SO$_2$R$^b$, C(O)R$^b$ or NR$^a$C(O)NR$^a$R$^a$;

or R$^3$ is MP or Het$^3$P wherein M and Het$^3$ each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^B$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$,
    and wherein M or Het$^3$ each optionally is substituted on the aromatic ring by one or more of the following independently selected from: halogen (Cl, F, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

or R$^3$ is AP or Het$^5$P wherein A and Het$^5$ each optionally is substituted by one or more of the following independently selected from: halogen (F, Cl, Br, I), OH, CN, NO$_2$, NR$^a$R$^a$, OR$^b$, SR$^b$, SiR$^b$R$^b$R$^b$S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$ C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

or R$^3$ is E or Het$^4$ each optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following independently selected from: halogen (F, Cl, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$ NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$NR$^a$SO$_2$R$^b$, NR$^a$C(O)OR$^b$, OC(O)NR$^a$R$^a$ or NR$^a$C(O)NR$^a$R$^a$.

In a second embodiment of the invention there is provided a class of compounds of formula (I) wherein
R$^1$ represents
  X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$ or C(O)R$^b$;

or R$^1$ is cycloalkyl or heterocyclyl each optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$ or C(O)R$^b$;

or R$^1$ is phenyl or heteroaryl each optionally substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$;

or R$^1$ is cycloalkylY or heterocyclylY wherein cycloalkyl or heterocyclyl each optionally is substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$;

or R$^1$ is phenylY or heteroarylY wherein phenyl or heteroaryl each optionally is substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$SO$_2$R$^b$, C(O)R$^b$;

R$^2$ represents
  phenyl which is optionally substituted by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, R$^3$ is the same as for the first embodiment.

In a third embodiment of the invention there is provided a class of compounds of formula (I) wherein $R^1$ represents
- X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$, $R^2$ is the same as for the second embodiment, and
$R^3$ is the same as for the first embodiment.

In a fourth embodiment of the invention there is provided a class of compounds of formula (I) wherein
$R^1$ represents
- X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$ or $C(O)R^b$, $R^2$ is the same as for the second embodiment, and
$R^3$ is the same as for the first embodiment.

In a fifth embodiment of the invention there is provided a class of compounds of formula (I) wherein
$R^1$ is the same for the first embodiment,
$R^2$ is the same as for the first embodiment, and
$R^3$ represents
- X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$.

In a sixth embodiment of the invention there is provided a class of compounds of formula (I) wherein
$R^1$ is the same as for the first embodiment,
$R^2$ is the same as for the first embodiment, and
$R^3$ represents
- MP or $Het^3P$ wherein M and $Het^3$ each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following independently selected from: halogen (Cl, F, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

or $R^3$ is AP or $Het^5P$ wherein A and $Het^5$ each optionally is substituted by one or more of the following independently selected from: halogen (F, Cl, Br, I), OH, CN, $NO_2$, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2 NR^aR^a$, $NR^aSO_2R^b$, $NR^aC(O)OR^b$, $OC(O)NR^aR^a$ or $NR^aC(O)NR^aR^a$.

In a seventh embodiment of the invention there is provided a class of compounds of formula (I) wherein
$R^1$ is the same as for the first embodiment,
$R^2$ is the same as for the first embodiment, and
$R^3$ represents
- E or $Het^4$ each optionally substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q. QZ, $Het^1$, $Het^1Z$, R, RZ, $Het^2$, $Het^2Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and E or $Het^4$ each optionally is substituted on the aromatic ring by one or more of the following independently selected from: halogen (F, Cl, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1Z$, R, RZ, $Het^2$, $Het^1Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

In an 8' embodiment of the invention there is provided a class of compounds of formula (I) wherein
$R^1$ is the same as for the second embodiment,
$R^2$ is the same as for the second embodiment, and
$R^3$ represents
- X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$.

In a $9^{th}$ embodiment of the invention there is provided a class of compounds of formula (I) wherein
$R^1$ is the same as for the second embodiment,
$R^2$ is the same as for the second embodiment, and
$R^3$ represents MP or Het³P wherein M and Het³ each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het³ each optionally is substituted on the aromatic ring by one or more of the following independently selected from: halogen (Cl, F, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

or R³ is AP or Het⁵P wherein A and Het⁵ each optionally is substituted by one or more of the following independently selected from: halogen (F, Cl, Br, I), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

In a 10$^{th}$ embodiment of the invention there is provided a class of compounds of formula (I) wherein
R¹ is the same as for the second embodiment,
R² is the same as for the second embodiment, and
R³ represents
E or Het⁴ each optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het¹, Het¹Z, R, RZ, Het², Het²Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het⁴ each optionally is substituted on the aromatic ring by one or more of the following independently selected from: halogen (F, Cl, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het¹, Het¹Z, R, RZ, Het², Het²Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

In an 11$^{th}$ embodiment of the invention there is provided a class of compounds of formula (I) wherein
R¹ is the same as for the third embodiment,
R² is the same as for the third embodiment, and
R³ represents
X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$.

In a 12$^{th}$ embodiment of the invention there is provided a class of compounds of formula (I) wherein
R¹ is the same as for the third embodiment,
R² is the same as for the third embodiment, and
R³ represents
MP or Het³P wherein M and Het³ each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het³ each optionally is substituted on the aromatic ring by one or more of the following independently selected from: halogen (Cl, F, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

or R³ is AP or Het⁵P wherein A and Het⁵ each optionally is substituted by one or more of the following independently selected from: halogen (F, Cl, Br, I), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

In a 13$^{th}$ embodiment of the invention there is provided a class of compounds of formula (I) wherein
R¹ is the same as for the third embodiment,
R² is the same as for the third embodiment, and R³ represents
E or Het⁴ each optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het¹, Het¹Z, R, RZ, Het², Het²Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het⁴ each optionally is substituted on the aromatic ring by one or more of the following independently selected from: halogen (F, Cl, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het¹, Het¹Z, R, RZ, Het², Het²Z, or C$_1$-C$_4$alkyl which is optionally substituted by one or more of the following independently selected from: F, OH, CN, NR$^a$R$^a$OR$^b$, SR$^b$, SiR$^b$R$^b$R$^b$S(O)R$^b$, SO$_2$R$^b$, C(O)R$^b$, NR$^a$C(O)R$^b$, C(O)NR$^a$R$^b$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

In a 14$^{th}$ embodiment of the invention there is provided a class of compounds of formula (I) wherein
R¹ is the same as for the fourth embodiment,
R² is the same as for the fourth embodiment, and
R³ represents
X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$.

In a 15$^{th}$ embodiment of the invention there is provided a class of compounds of formula (I) wherein
R¹ is the same as for the fourth embodiment,
R² is the same as for the fourth embodiment, and
R³ represents
MP or Het³P wherein M and Het³ each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het³ each optionally is substituted on the aromatic ring by one or more of the following independently selected from: halogen (Cl, F, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O) NR$^a$R$^a$;

or R³ is AP or Het⁵P wherein A and Het⁵ each optionally is substituted by one or more of the following independently selected from: halogen (F, Cl, Br, I), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het¹, Het¹T, R, RT, Het², Het²T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O) OR$^b$, OC(O)NR$^a$R$^a$ or NR$^a$C(O)NR$^a$R$^a$.

In a 16$^{th}$ embodiment of the invention there is provided a class of compounds of formula (I) wherein
R¹ is the same as for the fourth embodiment,
R² is the same as for the fourth embodiment, and
R³ represents
E or Het⁴ each optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O) NR$^a$R$^a$, NR$^a$C(O)OR$^b$, NR$^a$C(O)NR$^a$R$^a$, Q, QZ, Het¹, Het¹Z, R, RZ, Het², Het²Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het⁴ each optionally is substituted on the aromatic ring by one or more of the following independently selected from: halogen (F, Cl, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het¹, Het¹Z, R, RZ, Het², Het²Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O) NR$^a$R$^a$, OC(O)R$^b$, C(O)OR$^a$, SO$_2$NR$^a$R$^a$, NR$^a$SO$_2$, NR$^a$C(O)OR$^b$, OC(O)NR$^a$R$^a$ or NR$^a$C(O)NR$^a$R$^a$.

The compounds of formula (I) have activity as medicaments. In particular, the compounds of formula (I) are LXR agonists.

Specific compounds of the invention are one or more of the following:
2-tert-butyl-4-({3-[3-(hydroxymethyl)phenoxy]propyl}amino)-5-phenylisothiazol-3(2H)-one 1,1-dioxide
2-tert-butyl-5-phenyl-4-[(4-phenylbutyl)amino]isothiazol-3(2H)-one 1,1-dioxide
2-tert-butyl-4-{[3-(2-methoxyphenoxy)propyl]amino}-5-phenylisothiazol-3(2H)-one 1,1-dioxide
2-tert-butyl-4-({3-[4-(hydroxymethyl)phenoxy]propyl}amino)-5-phenylisothiazol-3(2H)-one 1,1-dioxide
N-(3-{3-[(2-tert-butyl-1,1-dioxido-3-oxo-5-phenyl-2,3-dihydroisothiazol-4-yl)amino]propoxy}phenyl)acetamide
2-tert-butyl-4-{[3-(2-fluorophenoxy)propyl]amino}-5-phenylisothiazol-3(2H)-one 1,1-dioxide 2-isopropyl-5-phenyl-4-[(4-phenylbutyl)amino]isothiazol-3(2H)-one 1,1-dioxide
2-(4-{3-[(2-tert-butyl-1,1-dioxido-3-oxo-5-phenyl-2,3-dihydroisothiazol-4-yl)amino]propoxy}phenyl)-N,N-dimethylacetamide
2-tert-butyl-4-{[3-(2-chlorophenoxy)propyl]amino}-5-phenylisothiazol-3(2H)-one 1,1-dioxide
2-tert-butyl-4-{[3-(3-methoxyphenoxy)propyl]amino}-5-phenylisothiazol-3(2H)-one 1,1-dioxide
(3-{3-[(2-tert-butyl-1,1-dioxido-3-oxo-5-phenyl-2,3-dihydroisothiazol-4-yl)amino]propoxy}phenyl)acetic acid
2-tert-butyl-5-phenyl-4-{[3-(pyridin-3-yloxy)propyl]amino isothiazol-3(2H)-one 1,1-dioxide methyl (3-{3-[(2-tert-butyl-1,1-dioxido-3-oxo-5-phenyl-2,3-dihydroisothiazol-4-yl)amino]propoxy}phenyl)acetate
2-tert-butyl-5-phenyl-4-{[3-(pyridin-4-yloxy)propyl]amino}isothiazol-3(2H)-one 1,1-dioxide
4-(benzylamino)-2-tert-butyl-5-phenylisothiazol-3(2H)-one 1,1-dioxide
4-({1-[3-chloro-5-(trifluoromethyl)pyridin-2-yl]piperidin-4-yl}amino)-2-isopropyl-5-phenylisothiazol-3(2H)-one 1,1-dioxide
2-tert-butyl-5-phenyl-4-[(2-phenylethyl)amino]isothiazol-3(2H)-one 1,1-dioxide
2-cyclopentyl-5-phenyl-4-[(4-phenylbutyl)amino]isothiazol-3(2H)-one 1,1-dioxide
2-tert-butyl-5-phenyl-4-{[3-(phenylthio)propyl]amino}isothiazol-3(2H)-one 1,1-dioxide
2-tert-butyl-4-[(3-phenoxypropyl)amino]-5-phenylisothiazol-3(2H1)-one 1,1-dioxide
2-tert-butyl-4-{[3-(3-chlorophenoxy)propyl]amino}-5-phenylisothiazol-3(2H)-one 1,1-dioxide
methyl 3-{3-[(2-tert-butyl-1,1-dioxido-3-oxo-5-phenyl-2,3-dihydroisothiazol-4-yl)amino]propoxy}benzoate
2-benzyl-5-phenyl-4-[(4-phenylbutyl)amino]isothiazol-3(2H)-one 1,1-dioxide
(4-{3-[(2-tert-butyl-1,1-dioxido-3-oxo-5-phenyl-2,3-dihydroisothiazol-4-yl)amino]propoxy}phenyl)acetic acid
2-tert-butyl-4-{[3-(3-fluorophenoxy)propyl]amino}-5-phenylisothiazol-3(2H)-one 1,1-dioxide
methyl (4-{3-[(2-tert-butyl-1,1-dioxido-3-oxo-5-phenyl-2,3-dihydroisothiazol-4-yl)amino]propoxy}phenyl)acetate
2-tert-butyl-4-{[3-(4-fluorophenoxy)propyl]amino}-5-phenylisothiazol-3(2H)-one 1,1-dioxide
2-isopropyl-5-phenyl-4-({1-[4-(trifluoromethyl)pyrimidin-2-yl]piperidin-4-yl}amino)isothiazol-3(2H)-one 1,1-dioxide
N-(3-{3-[(2-butyl-1,1-dioxido-3-oxo-5-phenyl-2,3-dihydroisothiazol-4-yl)amino]propoxy}phenyl)acetamide
3-[(2-tert-butyl-1,1-dioxido-3-oxo-5-phenyl-2,3-dihydroisothiazol-4-yl)amino]propyl 4-hydroxybenzoate
4-(benzylamino)-2-isopropyl-5-phenylisothiazol-3(2H)-one 1,1-dioxide
2-[2-(3-fluorophenyl)ethyl]-5-phenyl-4-[(4-phenylbutyl)amino]isothiazol-3(2H)-one 1,1-dioxide
4-[(cis-4-hydroxycyclohexyl)amino]-2-isopropyl-5-phenyl-isothiazol-3(2H)-one 1,1-dioxide
2-tert-butyl-4-[(4-phenoxybutyl)amino]-5-phenylisothiazol-3(2H)-one 1,1-dioxide
2-tert-butyl-4-({3-[(1-oxidopyridin-3-yl)oxy]propyl}amino)-5-phenylisothiazol-3(2H)-one 1,1-dioxide
2-tert-butyl-4-[(2-phenoxyethyl)amino]-5-phenylisothiazol-3(2H)-one 1,1-dioxide
4-(benzylamino)-2-cyclopentyl-5-phenylisothiazol-3(2H)-one 1,1-dioxide
2-tert-butyl-4-{[3-(4-methoxyphenoxy)propyl]amino}-5-phenylisothiazol-3(2H)-one 1,1-dioxide
4-[(4,4-difluorocyclohexyl)amino]-2-isopropyl-5-phenyl-isothiazol-3(2H)-one 1,1-dioxide
2-isopropyl-4-[(2-phenoxyethyl)amino]-5-phenylisothiazol-3(2H)-one 1,1-dioxide
5-phenyl-4-[(4-phenylbutyl)amino]-2-(tetrahydrofuran-2-ylmethyl)isothiazol-3(2H)-one 1,1-dioxide
4-(benzylamino)-2-butyl-5-phenylisothiazol-3(2H)-one 1,1-dioxide
2-butyl-4-(hexylamino)-5-phenylisothiazol-3(2H)-one 1,1-dioxide
2-butyl-5-phenyl-4-[(2-phenyl-ethyl)amino]isothiazol-3(2H)-one 1,1-dioxide
2-butyl-4-{[4-(difluoromethoxy)benzyl]amino}-5-phenyl-isothiazol-3(2H)-one 1,1-dioxide
4-[(trans-4-hydroxycyclohexyl)amino]-2-isopropyl-5-phenylisothiazol-3(2H)-one 1,1-dioxide
2-tert-butyl-4-[(3-hydroxypropyl)amino]-5-phenylisothiazol-3(2H)-one 1,1-dioxide
5-phenyl-4-[(4-phenylbutyl)amino]-2-(pyridin-3-ylmethyl)isothiazol-3(2H1)-one 1,1-dioxide
2-tert-butyl-4-[(2,3-dihydro-1,4-benzodioxin-2-ylmethyl)amino]-5-phenylisothiazol-3(2H)-one 1,1-dioxide
2-butyl-4-[(4-hydroxycyclohexyl)amino]-5-phenylisothiazol-3(2H)-one 1,1-dioxide
4-{3-[(2-tert-butyl-1,1-dioxido-3-oxo-5-phenyl-2,3-dihydroisothiazol-4-yl)amino]propoxy}benzoic acid
3-{4-[(2-isopropyl-3-dioxido-3-oxo-5-phenyl-2,3-dihydroisothiazol-4-yl)amino]piperidin-1-yl}propanenitrile
2-tert-butyl-4-{[3-(4-chlorophenoxy)propyl]amino}-5-phenylisothiazol-3(2H)-one 1,1-dioxide
5-phenyl-4-[(4-phenylbutyl)amino]-2-(pyridin-4-ylmethyl)isothiazol-3(2H)-one 1,1-dioxide
4-[(1,3-benzodioxol-5-ylmethyl)amino]-2-butyl-5-phenyl-isothiazol-3(2H)-one 1,1-dioxide
4-(2,3-dihydro-1H-inden-2-ylamino)-2-(2-methoxyethyl)-S-phenylisothiazol-3(2H)-one 1,1-dioxide
2-butyl-4-[(2-morpholin-4-ylethyl)amino]-5-phenylisothiazol-3(2H)-one 1,1-dioxide
2-tert-butyl-4-{[3-(4-isopropylphenoxy)propyl]amino}-5-phenylisothiazol-3(2H)-one 1,1-dioxide
4-({3-[benzyl(butyl)amino]propyl}amino)-2-tert-butyl-5-phenylisothiazol-3(2H)-one 1,1-dioxide
2-tert-butyl-4-{[3-(3,5-dipropoxyphenoxy)propyl]amino}-5-phenylisothiazol-3(2H)-one 1,1-dioxide
2-tert-butyl-4-[(2,2-diphenylethyl)amino]-5-phenylisothiazol-3(2H)-one 1,1-dioxide
2-ethyl-4-{[2-(1H-imidazol-4-yl)ethyl]amino}-5-phenyl-isothiazol-3(2H)-one 1,1-dioxide
2-butyl-4-[(4-morpholin-4-ylbenzyl)amino]-5-phenyl-isothiazol-3(2H)-one 1,1-dioxide
2-butyl-4-{[3-(2-methoxyethoxy)propyl]amino}-5-phenyl-isothiazol-3(2H)-one 1,1-dioxide
2-butyl-4-[(3-morpholin-4-ylpropyl)amino]-5-phenyl-isothiazol-3(2H)-one 1,1-dioxide
2-butyl-4-[(2-methoxyethyl)amino]-5-phenylisothiazol-3(21)-one 1,1-dioxide
2-(2-methoxyethyl)-5-phenyl-4-(tetrahydro-2H-pyran-4-ylamino)isothiazol-3(2H)-one 1,1-dioxide
4-(hexylamino)-2-(2-methoxyethyl)-5-phenylisothiazol-3(2H)-one 1,1-dioxide
4-[(4-hydroxycyclohexyl)amino]-2-(2-methoxyethyl)-5-phenylisothiazol-3(2H)-one 1,1-dioxide
4-[(1,3-benzodioxol-5-ylmethyl)amino]-2-(2-methoxyethyl)-5-phenylisothiazol-3(2H)-one 1,1-dioxide
2-butyl-4-[(4-methoxybenzyl)amino]-5-phenylisothiazol-3(2H)-one 1,1-dioxide 5-phenyl-4-[(4-phenylbutyl)amino]-2-(pyridin-2-ylmethyl) isothiazol-3(2H)-one 1,1-dioxide
2-tert-butyl-4-{[3-(3-hydroxyphenoxy)propyl]amino}-5-phenylisothiazol-3(2H)-one 1,1-dioxide
3-{3-[(2-tert-butyl-1,1-dioxido-3-oxo-5-phenyl-2,3-dihydroisothiazol-4-yl)amino]propoxy}benzoic acid
4-{2-[(2-tert-butyl-1,1-dioxido-3-oxo-5-phenyl-2,3-dihydroisothiazol-4-yl)amino]ethyl}phenyl methanesulfonate
4-{2-[(2-tert-butyl-1,1-dioxido-3-oxo-5-phenyl-2,3-dihydroisothiazol-4-yl)amino]ethyl}benzenesulfonamide
2-tert-butyl-4-({1-[3-chloro-5-(trifluoromethyl)pyridin-2-yl]piperidin-4-yl}amino)-5-phenylisothiazol-3(2H)-one 1,1-dioxide
tert-butyl 3-{2-[(2-tert-butyl-1,1-dioxido-3-oxo-5-phenyl-2,3-dihydroisothiazol-4-yl)amino]ethyl}azetidine-1-carboxylate
2-{2-[(2-tert-butyl-1,1-dioxido-3-oxo-5-phenyl-2,3-dihydroisothiazol-4-yl)amino]ethoxy}phenyl methanesulfonate
4-{2-[(2-tert-butyl-1,1-dioxido-3-oxo-5-phenyl-2,3-dihydroisothiazol-4-yl)amino]ethyl}benzonitrile
4-({4-[(2-tert-butyl-1,1-dioxido-3-oxo-5-phenyl-2,3-dihydroisothiazol-4-yl)amino]piperidin-1-yl}methyl)benzonitrile
2-tert-butyl-4-(isopropylamino)-5-phenylisothiazol-3(2H)-one 1,1-dioxide
4-{2-[(2-isopropyl-1,1-dioxido-3-oxo-5-phenyl-2,3-dihydroisothiazol-4-yl)amino]ethyl}phenyl methanesulfonate
tert-butyl 3-({2-[(2-tert-butyl-1,1-dioxido-3-oxo-5-phenyl-2,3-dihydroisothiazol-4-yl)amino]ethyl}thio)pyrrolidine-1-carboxylate
2-tert-butyl-5-phenyl-4-{[3-(pyridin-2-yloxy)propyl]amino}isothiazol-3(2H)-one 1,1-dioxide
2-tert-butyl-4-[(2-{[3-chloro-5-(trifluoromethyl)pyridin-2-yl]amino}ethyl)amino]-5-phenylisothiazol-3(2H)-one 1,1-dioxide
2-tert-butyl-5-phenyl-4-({1-[2-(trifluoromethyl)benzoyl]piperidin-4-yl}amino)isothiazol-3(2H)-one 1,1-dioxide
2-tert-butyl-4-{[1-(5-methylpyridin-2-yl)piperidin-4-yl]amino}-5-phenylisothiazol-3(2H)-one 1,1-dioxide
2-tert-butyl-4-{[1-(6-chloropyridazin-3-yl)piperidin-4-yl]amino}-5-phenylisothiazol-3(2H)-one 1,1-dioxide
tert-butyl 4-[(2-tert-butyl-1,1-dioxido-3-oxo-5-phenyl-2,3-dihydroisothiazol-4-yl)amino]piperidine-1-carboxylate
methyl 2-{2-[(2-tert-butyl-1,1-dioxido-3-oxo-5-phenyl-2,3-dihydroisothiazol-4-yl)amino]ethoxy}benzoate
methyl 3-({4-[(2-tert-butyl-1,1-dioxido-3-oxo-5-phenyl-2,3-dihydroisothiazol-4-yl)amino]piperidin-1-yl}methyl)benzoate
2-tert-butyl-4-{[1-(6-methoxypyridazin-3-yl)piperidin-4-yl]amino}-5-phenylisothiazol-3(2H)-one 1,1-dioxide
2-tert-butyl-4-({1-[(2-chloropyridin-3-yl)carbonyl]piperidin-4-yl}amino)-5-phenylisothiazol-3(2H)-one 1,1-dioxide
2-{2-[(2-isopropyl-1,1-dioxido-3-oxo-5-phenyl-2,3-dihydroisothiazol-4-yl)amino]ethoxy}phenyl methanesulfonate
2-tert-butyl-4-{[1-(6-chloropyridin-3-yl)piperidin-4-yl]amino}-5-phenylisothiazol-3(2H)-one 1,1-dioxide
4-[(1-benzylpiperidin-4-yl)amino]-2-tert-butyl-5-phenylisothiazol-3(2H)-one 1,1-dioxide
4-{2-[(2-isopropyl-1,1-dioxido-3-oxo-5-phenyl-2,3-dihydroisothiazol-4-yl)amino]ethyl}benzenesulfonamide
4-{2-[(2-isopropyl-1,1-dioxido-3-oxo-5-phenyl-2,3-dihydroisothiazol-4-yl)amino]ethyl}benzonitrile
2-tert-butyl-4-(ethylamino)-5-phenylisothiazol-3(2H)-one 1,1-dioxide
2-tert-butyl-4-({1-[(5-methylisoxazol-3-yl)methyl]piperidin-4-yl}amino)-5-phenylisothiazol-3(2H)-one 1,1-dioxide
$N^2$-(2-tert-butyl-1,1-dioxido-3-oxo-5-phenyl-2,3-dihydroisothiazol-4-yl)-$N^2$-[3-(difluoromethoxy)benzyl]glycinamide
4-[(1-benzoylpiperidin-4-yl)amino]-2-tert-butyl-5-phenylisothiazol-3(2H)-one 1,1-dioxide
2-tert-butyl-5-phenyl-4-{[1-(phenylacetyl)piperidin-4-yl]amino}isothiazol-3(2H)-one 1,1-dioxide
2-tert-butyl-5-phenyl-4-[(1-pyridin-2-ylpiperidin-4-yl)amino]isothiazol-3(2H)-one 1,1-dioxide
2-tert-butyl-5-phenyl-4-[(1-pyridazin-3-ylpiperidin-4-yl)amino]isothiazol-3(2H)-one 1,1-dioxide
2-tert-butyl-5-phenyl-4-{[2-(pyridin-3-yloxy)ethyl]amino}isothiazol-3(2H)-one 1,1-dioxide
2-tert-butyl-4-{[1-(5-fluoropyridin-2-yl)piperidin-4-yl]amino}-5-phenylisothiazol-3(2H)-one 1,1-dioxide
2-tert-butyl-4-{[3-(3,5-dimethyl-1H-pyrazol-1-yl)propyl]amino}-5-phenylisothiazol-3(2H)-one 1,1-dioxide
2-tert-butyl-4-{[1-(2-chloro-6-methylisonicotinoyl)piperidin-4-yl]amino}-5-phenylisothiazol-3(2H)-one 1,1-dioxide
2-tert-butyl-4-{[1-(5-chloropyridin-2-yl)piperidin-4-yl]amino}-5-phenylisothiazol-3(2H)-one 1,1-dioxide
2-tert-butyl-5-phenyl-4-({1-[4-(trifluoromethyl)pyridin-2-yl]piperidin-4-yl}amino)isothiazol-3(2H)-one 1,1-dioxide
4-({4-[(2-tert-butyl-1,1-dioxido-3-oxo-5-phenyl-2,3-dihydroisothiazol-4-yl)amino]piperidin-1-yl}carbonyl)benzonitrile
2-tert-butyl-4-{[1-(3,4-difluorobenzoyl)piperidin-4-yl]amino}-5-phenylisothiazol-3(2H)-one 1,1-dioxide
4-[(1-acetylpiperidin-4-yl)amino]-2-tert-butyl-5-phenylisothiazol-3(2H)-one 1,1-dioxide
3-{2-[(2-isopropyl-1,1-dioxido-3-oxo-5-phenyl-2,3-dihydroisothiazol-4-yl)amino]ethyl}benzonitrile
2-tert-butyl-5-phenyl-4-({2-[2-(trifluoromethoxy)phenyl]ethyl}amino)isothiazol-3(2H)-one 1,1-dioxide
4-{2-[(2-tert-butyl-1,1-dioxido-3-oxo-5-phenyl-2,3-dihydroisothiazol-4-yl)amino]ethoxy}phenyl methanesulfonate
4-[(1-benzylpyrrolidin-3-yl)amino]-2-tert-butyl-5-phenylisothiazol-3(2H)-one 1,1-dioxide
4-({1-[3-chloro-5-(trifluoromethyl)pyridin-2-yl]azetidin-3-yl}amino)-2-isopropyl-5-phenylisothiazol-3(2H)-one 1,1-dioxide
N-benzyl-$N^2$-(2-tert-butyl-1,1-dioxido-3-oxo-5-phenyl-2,3-dihydroisothiazol-4-yl)glycinamide
2-tert-butyl-4-[(1-isobutyrylpiperidin-4-yl)amino]-5-phenylisothiazol-3(2H)-one 1,1-dioxide
2-tert-butyl-5-phenyl-4-[(2-pyridin-2-ylethyl)amino] isothiazol-3(2H)-one 1,1-dioxide
2-tert-butyl-4-{[2-(2-chlorophenyl)ethyl]amino}-5-phenylisothiazol-3(2H)-one 1,1-dioxide
2-tert-butyl-5-phenyl-4-{[1-(2-phenylethyl)piperidin-4-yl]amino}isothiazol-3(2H)-one 1,1-dioxide
2-tert-butyl-5-phenyl-4-({2-[3-(trifluoromethyl)phenyl]ethyl}amino)isothiazol-3(2H)-one 1,1-dioxide
2-tert-butyl-5-phenyl-4-[(4-{[4-(trifluoromethyl)phenyl]thio}cyclohexyl)amino]isothiazol-3(2H)-one 1,1-dioxide
2-tert-butyl-5-phenyl-4-[(2-{[3-(trifluoromethoxy)phenyl]thio}ethyl)amino]isothiazol-3(2H)-one 1,1-dioxide
2-tert-butyl-4-{[2-(4-chlorophenoxy)ethyl]amino}-5-phenylisothiazol-3(2H)-one 1,1-dioxide 2-tert-butyl-5-phenyl-4-({1-[5-(trifluoromethyl)pyridin-2-yl]piperidin-4-yl}amino)isothiazol-3(2H)-one 1,1-dioxide 2-tert-butyl-5-phenyl-4-({2-[3-(trifluoromethoxy)phenoxy]ethyl}amino)isothiazol-3(2H)-one 1,1-dioxide tert-butyl 3-{2-[(2-tert-butyl-1,1-dioxido-3-oxo-5-phenyl-2,3-dihydroisothiazol-4-yl)amino]ethoxy}azetidine-1-carboxylate 2-tert-butyl-4-[(2,2-dimethylpropyl)amino]-5-phenyl-isothiazol-3(2H)-one 1,1-dioxide 2-tert-butyl-4-(tert-butylamino)-5-phenylisothiazol-3(2H)-one 1,1-dioxide methyl ({[(2-tert-butyl-1,1-dioxido-3-oxo-5-phenyl-2,3-dihydroisothiazol-4-yl)amino]acetyl}amino)acetate 2-tert-butyl-5-phenyl-4-(piperidin-4-ylamino)isothiazol-3(2H)-one 1,1-dioxide 2-tert-butyl-4-[(1-methylpiperidin-4-yl)amino]-5-phenyl-isothiazol-3(2H)-one 1,1-dioxide 2-tert-butyl-4-[(2-hydroxyethyl)amino]-5-phenylisothiazol-3(2H)-one 1,1-dioxide 4-{[2-(biphenyl-2-ylthio)ethyl]amino}-2-tert-butyl-5-phenylisothiazol-3(2H)-one, 1,1-dioxide 2-tert-butyl-5-phenyl-4-{[2-(pyrrolidin-3-ylthio)ethyl]amino}isothiazol-3(2H)-one 1,1-dioxide 2-tert-butyl-4-{[(5-methyl-3-phenylisoxazol-4-yl)methyl]amino}-5-phenylisothiazol-3(2H)-one 1,1-dioxide 2-tert-butyl-5-phenyl-4-{[(1,3,5-trimethyl-1H-pyrazol-4-yl)methyl]amino}isothiazol-3(2H)-one 1,1-dioxide 2-tert-butyl-5-phenyl-4-[(2-{[5-(trifluoromethyl)pyridin-2-yl]oxy}ethyl)amino]isothiazol-3(2H)-one 1,1-dioxide 2-tert-butyl-5-phenyl-4-({2-[4-(trifluoromethoxy)phenyl]ethyl}amino)isothiazol-3(2H)-one 1,1-dioxide 2-tert-butyl-5-phenyl-4-[(2,2,2-trifluoroethyl)amino]isothiazol-3(2H)-one 1,1-dioxide 2-tert-butyl-4-[(2,3-dihydroxypropyl)amino]-1-phenyl-isothiazol-3(2H)-one 1,1-dioxide 3-[(2-tert-butyl-1,1-dioxido-3-oxo-phenyl-2,3-dihydroisothiazol-4-yl)amino]propanenitrile 4-{[2-(3,4-dimethoxyphenyl)ethyl]amino}-2-isopropyl-5-phenylisothiazol-3(2H)-one 1,1-dioxide 4-{[2-(3-chloro-4-methoxyphenyl)ethyl]amino}-2-isopropyl-5-phenylisothiazol-3(2H)-one 1,1-dioxide 4-{2-[(2-isobutyl-1,1-dioxido-3-oxo-5-phenyl-2,3-dihydroisothiazol-4-yl)amino]ethyl}phenyl methanesulfonate 2-isopropyl-5-phenyl-4-[(1-pyridin-2-ylpiperidin-4-yl)amino]isothiazol-3(2H)-one 1,1-dioxide 4-(2-{[2-(4-fluorobenzyl)-1,1-dioxido-3-oxo-5-phenyl-2,3-dihydroisothiazol-4-yl]amino}ethyl)phenyl methanesulfonate 2-isopropyl-4-(isopropylamino)-5-phenylisothiazol-3(2H)-one 1,1-dioxide 2-isopropyl-5-phenyl-4-[(1-pyridin-2-ylazetidin-3-yl)amino]isothiazol-3(2H)-one 1,1-dioxide 2-tert-butyl-4-{[(5-methylisoxazol-3-yl)methyl]amino}-5-phenylisothiazol-3(2H)-one 1,1-dioxide 4-{[2-(4-hydroxy-3,5-dimethoxyphenyl)ethyl]amino}-2-isopropyl-5-phenylisothiazol-3(2H)-one 1,1-dioxide 4-{[2-(2-aminopyridin-4-yl)ethyl]amino}-2-isopropyl-5-phenylisothiazol-3(2H)-one 1,1-dioxide 2-isopropyl-5-phenyl-4-[(2-pyridin-4-ylethyl)amino]isothiazol-3(2H)-one 1,1-dioxide 2-isopropyl-5-phenyl-4-[(2-pyridin-3-ylethyl)amino]isothiazol-3(2H)-one 1,1-dioxide 4-{[2-(3,5-dimethylisoxazol-4-yl)ethyl]amino}-2-isopropyl-5-phenylisothiazol-3(2H)-one 1,1-dioxide 4-[2-({2-[(5-methylisoxazol-3-yl)methyl]-1,1-dioxido-3-oxo-5-phenyl-2,3-dihydroisothiazol-4-yl}amino)ethyl]phenyl methanesulfonate 4-{[2-(3,5-dimethyl-1H-pyrazol-4-yl)ethyl]amino}-2-isopropyl-5-phenylisothiazol-3(2H)-one 1,1-dioxide 4-[2-({2-[(methylthio)methyl]-1,1-dioxido-3-oxo-5-phenyl-2,3-dihydroisothiazol-4-yl}amino)ethyl]phenyl methanesulfonate 2,6-Dimethylphenyl 4-[(2-tert-butyl-1,1-dioxido-3-oxo-5-phenyl-2,3-dihydroisothiazol-4-yl)amino]butanoate 2-Mesitylethyl N-(2-tert-butyl-1,1-dioxido-3-oxo-5-phenyl-2,3-dihydroisothiazol-4-yl)glycinate 2-[(2-tert-butyl-1,1-dioxido-3-oxo-5-phenyl-2,3-dihydroisothiazol-4-yl)amino]ethyl (2,6-dimethylphenyl)acetate Phenyl N-(2-tert-butyl-1,1-dioxido-3-oxo-5-phenyl-2,3-dihydroisothiazol-4-yl)-beta-alaninate 4-(Trifluoromethoxy)phenyl N-(2-tert-butyl-1,1-dioxido-3-oxo-5-phenyl-2,3-dihydroisothiazol-4-yl)-beta-alaninate 1-Methylpiperidin-4-yl N-(2-tert-butyl-1,1-dioxido-3-oxo-5-phenyl-2,3-dihydroisothiazol-4-yl)-beta-alaninate 2-Mesityl-1-methylethyl[(2-tert-butyl-1,1-dioxido-3-oxo-5-phenyl-2,3-dihydroisothiazol-4-yl)amino]acetate 4-Methoxybenzyl N-(2-tert-butyl-1,1-dioxido-3-oxo-5-phenyl-2,3-dihydroisothiazol-4-yl)glycinate 4-Methoxyphenyl N-(2-tert-butyl-1,1-dioxido-3-oxo-5-phenyl-2,3-dihydroisothiazol-4-yl)glycinate or a pharmaceutically acceptable salt thereof.

In one aspect of the invention, there is provided a compound of formula (I) in which $R^1$ is selected from ethyl, isopropyl, n-butyl, tertbutyl, cyclopentyl, hexyl, benzyl, 2-methoxyethyl, pyridin-2-ylmethyl, pyridin-3-ylmethyl, pyridin-4-ylmethyl, tetrahydrofuran-2-ylmethyl or 2-(3-fluorophenyl)ethyl;

$R^2$ is phenyl; and $R^3$ is selected from n-butyl, n-hexyl, benzyl, 3-[3-(hydroxymethyl)phenoxy]propyl, 4-phenylbutyl, 3-(2-methoxyphenoxy)propyl, 3-[4-(hydroxymethyl)phenoxy]propyl, 3-(2-fluorophenoxy)propyl, 3-(2-chlorophenoxy)propyl, 3-(3-methoxyphenoxy)propyl, 3-(pyridin-3-yloxy)propyl, 3-(pyridin-4-yloxy)propyl, 1-[3-chloro-5-(trifluoromethyl)pyridin-2-yl]piperidin-4-yl, 3-(phenylthio)propyl, 3-phenoxypropyl, 3-(3-chlorophenoxy)propyl, 3-(3-fluorophenoxy)propyl, 3-(4-fluorophenoxy)propyl, 1-[4-(trifluoromethyl)pyrimidin-2-yl]piperidin-4-yl, cis-4-hydroxycyclohexyl, 4-phenoxybutyl, 3-[(1-oxidopyridin-3-yl)oxy]propyl, 3-(4-methoxyphenoxy)propyl, 4,4-difluorocyclohexyl, 2-phenoxyethyl, 2-phenylethyl, 4-(difluoromethoxy)benzyl, trans-4-hydroxycyclohexyl, 3-hydroxypropyl, 2,3-dihydro-1,4-benzodioxin-2-ylmethyl, 4-hydroxycyclohexyl, 3-(4-chlorophenoxy)propyl, 1,3-benzodioxol-5-ylmethyl, 2,3-dihydro-1H-inden-2-yl, 2-(morpholin-4-yl)ethyl, 3-(4-isopropylphenoxy)propyl, 3-[benzyl(butyl)amino]propyl, 3-(3,5-dipropoxyphenoxy)propyl, 2,2-diphenylethyl, 2-(1H-imidazol-4-yl)ethyl, 4-morpholin-4-ylbenzyl, 3-(2-methoxyethoxy)propyl, 3-morpholin-4-ylpropyl, 2-methoxyethyl, tetrahydro-2H-pyran-4-yl, 4-hydroxycyclohexyl, 4-methoxybenzyl, 3-(3-hydroxyphenoxy)propyl, 3-(3-acetamidophenoxy)propyl, 3-(4-N,N-dimethylaminocarbonylmethylphenoxy)propyl, 3-(3-carboxymethylphenoxy)propyl, 3-(3-methoxycarbonylmethylphenoxy)propyl, 3-(3-methoxycarbonylphenoxy)propyl, 3-(4-carboxymethylphenoxy)propyl, 3-(4-methoxycarbonylmethylphenoxy)propyl, 3-(3-acetylaminophenoxy)propyl, 3-(4-hydroxyphenylcarboxy)propyl, 3-(4-carboxyphenoxy)propyl, 1-(2-nitriloethyl)piperidin-4-yl, isopropyl, ethyl, 2,2-dimethylpropyl, tertbutyl, 2-(2-methoxyethoxy)ethyl, 2-hydroxyethyl, 2,2,2-trifluoroethyl, methyl ethanoylglycinate, 2,3-dihydro-1,4-benzodioxin-6-ylmethyl, 1,3,5-trimethyl-1H-pyrazol-4-ylmethyl, 3-(3,5-dimethyl-1H-pyrazol-1-yl)propyl, 2-(pyrrolidin-2-ylthio)ethyl, 2-[1-(tertbutoxycarbonyl)pyrrolidin-3-yl]ethyl, 2-[1-(tert-butoxycarbonyl)pyrrolidin-3-yl]ethyl, 2-{[1-(tert-butoxycarbonyl)pyrrolidin-3-yl]thio}ethyl, 2-pyridin-2-ylethyl, 2-{[3-chloro-5-(trifluoromethyl)pyridin-2-yl]amino}ethyl, 2-{[5-(trifluoromethyl)pyridin-2-yl]oxy}ethyl, 3-(pyridin-2-yloxy)propyl, 1-(tert-butoxycarbonyl)piperidin-4-yl, 1-acetylpiperidin-4-yl, piperidin-4-yl, 1-methylpiperidin-4-yl, 1-isobutyrylpiperidin-4-yl, 1-pyridin-2-ylpiperidin-4-yl, 1-(5-fluoropyridin-2-yl)piperidin-4-yl, 1-(5-chloropyridin-2-yl)piperidin-4-yl, 1-(5-methylpyridin-2-yl)piperidin-4-yl, 1-[4-(trifluoromethyl)pyridin-2-yl]piperidin-4-yl, 1-[5-(trifluoromethyl)pyridin-2-yl]piperidin-4-yl, 1-(6-chloropyridin-3-yl)piperidin-4-yl, 1-pyridazin-3-ylpiperidin-chlorophenyl)ethyl, 3-(3-carboxyphenoxy) propyl, 3-[3-(2-methoxy-2-oxoethyl)phenoxy]propyl, 3-[4-(2-methoxy-2-oxoethyl)phenoxy]propyl, 3-{4-[2-(dimethylamino)-2-oxoethyl]phenoxy}propyl, 3-[(4-hydroxybenzoyl)oxy]propyl, 2-{2-[(methylsulfonyl)oxy]phenoxy}ethyl, 2-{4-[(methylsulfonyl)oxy]phenoxy}ethyl, 2-[2-(methoxycarbonyl)phenoxy]ethyl, 2-(4-chlorophenoxy)ethyl, 2-[3-(trifluoromethoxy)phenoxy]ethyl, 2-{[3-(trifluoromethoxy)phenyl]thio}ethyl, 2-(benzylamino)-2-oxoethyl, 2-{[3-(difluoromethoxy)benzyl]amino}-2-oxoethyl.4-yl, 1-(6-chloropyridazin-3-yl)piperidin-4-yl, 1-(6-methoxypyridazin-3-yl)piperidin-4-yl, 1-(4-cyanobenzyl)piperidin-4-yl, 1-[2-(trifluoromethyl)benzoyl]piperidin-4-yl, 1-[3-(methoxycarbonyl)benzyl]piperidin-4-yl, 1-benzylpiperidin-4-yl, 1-benzoylpiperidin-4-yl, 1-(phenylacetyl)piperidin-4-yl, 1-(4-cyanobenzoyl)piperidin-4-yl, 1-(3,4-difluorobenzoyl)piperidin-4-yl, 1-(2-phenylethyl)piperidin-4-yl, 1-(2-phenylethyl)piperidin-4-yl, 1-benzylpyrrolidin-3-yl, 4-{[4-(trifluoromethyl)phenyl]thio}cyclohexyl, 1-[(5-methylisoxazol-3-yl)methyl]piperidin-4-yl, 1-(2-chloro-6-methylisonicotinoyl)piperidin-4-yl, 1-[(2-chloropyridin-3-yl)carbonyl]piperidin-4-yl, 2-{4-[(methylsulfonyl)oxy]phenyl}ethyl, 2-[4-(aminosulfonyl)phenyl]ethyl, 2-(4-cyanophenyl)ethyl, 2-(3-cyanophenyl)ethyl, 2-[2-(trifluoromethoxy)phenyl]ethyl or 2-[3-(trifluoromethoxy)phenyl]ethyl.

According to a further aspect of the invention $R^1$ and $R^3$ are the same as for any of the embodiments 1 to 16, and $R^2$ is unsubstituted phenyl.

According to a further aspect of the invention $R^1$ and $R^3$ are the same as for any claims, aspects or embodiments hereinbefore or hereinafter, and $R^2$ is unsubstituted phenyl.

According to a further aspect of the invention $R^1$ and $R^2$ are the same as for the first embodiment of the invention, and $R^3$ is the same as for the first embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ and $R^2$ are the same as for the first embodiment of the invention, and $R^3$ is the same as for the first embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SOR^b$, $C(O)R^b$ $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to a further aspect of the invention $R^1$ and $R^2$ are the same as for the second embodiment of the invention, and $R^3$ is the same as for the second embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ and $R^2$ are the same as for the second embodiment of the invention, and $R^3$ is the same as for the second embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$.

According to a further aspect of the invention $R^1$ and $R^2$ are the same as for the third embodiment of the invention, and $R^3$ is the same as for the third embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ and $R^2$ are the same as for the third embodiment of the invention, and $R^3$ is the same as for the third embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$.

According to a further aspect of the invention $R^1$ and $R^2$ are the same as for the fourth embodiment of the invention, and $R^3$ is the same as for the fourth embodiment of the invention except that MP is excluded; $Het^3$, A and $Het^5$ are not substituted by Q, QT, $Het^1$, $Het^1T$, R, RT, $Het^2$ or Het T; E is not substituted by Q, QZ, $Het^1$, $Het^1Z$, R, RZ, Het or $Het^2Z$; and $Het^4$ is not substituted by Q, QZ, $Het^1$, $Het^1Z$, R or $Het^2Z$.

According to a further aspect of the invention $R^1$ and $R^2$ are the same as for the fourth embodiment of the invention, and $R^3$ is the same as for the fourth embodiment of the invention except that MP is excluded; $Het^3$, A and $Het^5$ are not substituted by Q, QT, $Het^1$, $Het^1T$, R, RT, $Het^2$ or Het T; E is not substituted by Q, QZ, $Het^1$, $Het^1Z$, R, RZ, Het or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$.

According to a further aspect of the invention $R^1$ and $R^2$ are the same as for the sixth embodiment of the invention, and $R^3$ is the same as for the sixth embodiment of the invention except that MP is excluded; and $Het^3$, A and $Het^5$ are not substituted by Q, QT, $Het^1$, $Het^1T$, R, RT, $Het^2$ or $Het^2T$.

According to one aspect of the invention $R^1$ and $R^2$ are the same as for the seventh embodiment of the invention, and $R^3$ is the same as for the seventh embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to one aspect of the invention $R^1$ and $R^2$ are the same as for the seventh embodiment of the invention, and $R^3$ is the same as for the seventh embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F, or $R^1$ is $C_3$-$C_6$cycloalkyl; $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to a further aspect of the invention $R^1$ and $R^2$ are the same as for the 9$^{th}$ embodiment of the invention, and $R^3$ is the same as for the 9$^{th}$ embodiment of the invention s except that MP is excluded; and $Het^3$, A and $Het^5$ are not substituted by Q, QT, $Het^1$, $Het^1T$, R, RT, $Het^2$ or $Het^2T$.

According to a further aspect of the invention $R^1$ and $R^2$ are the same as for the 10$^{th}$ embodiment of the invention, and $R^3$ is the same as for the 10$^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ and $R^2$ are the same as for the 10$^{th}$ embodiment of the invention, and $R^3$ is the same as for the 10$^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F, or $R^1$ is $C_3$-$C_6$cycloalkyl; $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$.

According to a further aspect of the invention $R^1$ and $R^2$ are the same as for the 12$^{th}$ embodiment of the invention, and $R^3$ is the same as for the 12$^{th}$ embodiment of the invention except that MP is excluded; and $Het^3$, A and $Het^5$ are not substituted by Q, QT, $Het^1$, $Het^1T$, R, RT, $Het^2$ or $Het^2T$.

According to a further aspect of the invention $R^1$ and $R^2$ are the same as for the 13$^{th}$ embodiment of the invention, and $R^3$ is the same as for the 13$^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ and $R^2$ are the same as for the 13$^{th}$ embodiment of the invention, and $R^3$ is the same as for the 13$^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F; $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$.

According to a further aspect of the invention $R^1$ and $R^2$ are the same as for the 15$^{th}$ embodiment of the invention, and $R^3$ is the same as for the 15$^{th}$ embodiment of the invention except that MP is excluded; and $Het^3$, A and $Het^5$ are not substituted by Q, QT, $Het^1$, $Het^1T$, R, RT, $Het^2$ or $Het^2T$.

According to a further aspect of the invention $R^1$ and $R^2$ are the same as for the 16$^{th}$ embodiment of the invention, and $R^3$ is the same as for the 16 h embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ and $R^2$ are the same as for the 16$^{th}$ embodiment of the invention, and $R^3$ is the same as for the 16$^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$, with the proviso that when $R^1$ is $C_1$-$C_4$alkyl which is optionally substituted by one or more of F; $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $R^b$, $SiR^bR^bR^b$, $S(O)R^b$, $SO_2R^b$, $C(O)R^b$.

According to a further aspect of the invention $R^1$ is the same as for the first embodiment of the invention, $R^2$ is unsubstituted phenyl, and $R^3$ is the same as for the first embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to one aspect of the invention $R^1$ is the same as for the second embodiment of the invention, $R^2$ is unsubstituted phenyl, and $R^3$ is the same as for the second embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ is the same as for the third embodiment of the invention, $R^2$ is unsubstituted phenyl, and $R^3$ is the same as for the third embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to one aspect of the invention $R^1$ is the same as for the fourth embodiment of the invention, $R^2$ is unsubstituted phenyl, and $R^3$ is the same as for the fourth embodiment of the invention except that MP is excluded; $Het^3$, A and $Het^5$ are not substituted by Q, QT, $Het^1$, $Het^1T$, R, RT, $Het^2$ or $Het^2T$; E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ is the same as for the sixth embodiment of the invention, $R^2$ is unsubstituted phenyl, and $R^3$ is the same as for the sixth embodiment of the invention except that MP is excluded; and $Het^3$, A and $Het^5$ are not substituted by Q, QT, $Het^1$, $Het^1T$, R, RT, $Het^2$ or $Het^2T$.

According to one aspect of the invention $R^1$ is the same as for the seventh embodiment of the invention, $R^2$ is unsubstituted phenyl, and $R^3$ is the same as for the seventh embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ is the same as for the $9^{th}$ embodiment of the invention, $R^2$ is unsubstituted phenyl, and $R^3$ is the same as for the $9^{th}$ embodiment of the invention except that MP is excluded; and $Het^3$, A and $Het^5$ are not substituted by Q, QT, $Het^1$, $Het^1T$, R, RT, $Het^2$ or $Het^2T$.

According to one aspect of the invention $R^1$ is the same as for the $10^{th}$ embodiment of the invention, $R^2$ is unsubstituted phenyl, and $R^3$ is the same as for the $10^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ is the same as for the $12^{th}$ embodiment of the invention, $R^2$ is unsubstituted phenyl, and $R^3$ is the same as for the $12^{th}$ embodiment of the invention except that MP is excluded; and $Het^3$, A and $Het^5$ are not substituted by Q, QT, $Het^1$, $Het^1T$, R, RT, $Het^2$ or $Het^2T$.

According to one aspect of the invention $R^1$ is the same as for the $13^{th}$ embodiment of the invention, $R^2$ is unsubstituted phenyl, and $R^3$ is the same as for the $13^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ is the same as for the $15^{th}$ embodiment of the invention, $R^2$ is unsubstituted phenyl, and $R^3$ is the same as for the $15^{th}$ embodiment of the invention except that MP is excluded; and $Het^3$, A and $Het^5$ are not substituted by Q, QT, $Het^1$, $Het^1T$, R, RT, $Het^2$ or $Het^2T$.

According to one aspect of the invention $R^1$ is the same as for the $16^{th}$ embodiment of the invention, $R^2$ is unsubstituted phenyl, and $R^3$ is the same as for the $16^{th}$ embodiment of the invention except that E is not substituted by Q, QZ, $Het^1$, $Het^1Z$, R, RZ, $Het^2$ or $Het^2Z$; and $Het^4$ is not substituted by Q, QZ, $Het^1$, $Het^1Z$, R or $Het^2Z$.

According to a further aspect of the invention $R^1$ and $R^2$ are the same as for the first embodiment of the invention, and $R^3$ is the same as for the first embodiment of the invention except that MP is excluded; $Het^5$ is not substituted by Q, QT, $Het^1$, $Het^1T$, R, RT, $Het^2$ or $Het^2T$; $Het^3$ and A are not substituted by Q, QT, $Het^1$, $Het^1T$, RT, $Het^2$ or $Het^2T$; E is not substituted by Q, QZ, $Het^1$, $Het^1Z$, R, $Het^2$ or $Het^2Z$; and $Het^4$ is not substituted by Q, QZ, $Het^1$ or R.

According to a further aspect of the invention $R^1$ and $R^2$ are the same as for the first embodiment of the invention, and $R^3$ is the same as for the first embodiment of the invention except that MP is excluded; $Het^5$ is not substituted by Q, QT, $Het^1$, $Het^1T$, R, RT, $Het^2$ or $Het^2T$; $Het^3$ and A are not substituted by Q, QT, $Het^1$, $Het^1T$, RT, $Het^2$ or $Het^2T$; E is not substituted by Q, QZ, $Het^1$, $Het^1Z$, R, $Het^2$ or $Het^2Z$; and $Het^4$ is not substituted by Q, QZ, $Het^1$ or R, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

According to one aspect of the invention $R^1$ and $R^2$ are the same as for the second embodiment of the invention, and $R^3$ is the same as for the second embodiment of the invention except that MP is excluded, $Het^5$ is not substituted by Q, QT, $Het^1$, $Het^1T$, R, RT, $Het^2$ or $Het^2T$; $Het^3$ and A are not substituted by Q, QT, $Het^1$, $Het^1T$, RT, $Het^1$ or $Het^2T$; E is not substituted by Q, QZ, $Het^1$, $Het^1Z$, R, $Het^2$ or $Het^2Z$; and $Het^4$ is not substituted by Q, QZ, $Het^1$ or R.

According to one aspect of the invention $R^1$ and $R^2$ are the same as for the second embodiment of the invention, and $R^3$ is the same as for the second embodiment of the invention except that MP is excluded, $Het^5$ is not substituted by Q, QT, $Het^1$, $Het^1T$, R, RT, $Het^2$ or $Het^2T$; $Het^3$ and A are not substituted by Q, QT, $Het^1$, $Het^1T$, RT, $Het^2$ or $Het^2T$; E is not substituted by Q, QZ, $Het^1$, $Het^1Z$, R, $Het^2$ or $Het^2Z$; and $Het^4$ is not substituted by Q, QZ, $Het^1$ or R, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$.

According to a further aspect of the invention R$^1$ and R$^2$ are the same as for the third embodiment of the invention, and R$^3$ is the same as for the third embodiment of the invention except that MP is excluded; Het$^5$ is not substituted by Q, QT, Het$^1$, Het$^1$T, R, RT, Het$^2$ or Het$^2$T; Het$^3$ and A are not substituted by Q, QT, Het$^1$, Het$^1$T, RT, Het$^2$ or Het$^1$T; E is not substituted by Q, QZ, Het$^1$, Het$^1$Z, R, Het$^2$ or Het$^2$Z; and Het$^4$ is not substituted by Q, QZ, Het$^1$ or R.

According to a further aspect of the invention R$^1$ and R$^2$ are the same as for the third embodiment of the invention, and R$^3$ is the same as for the third embodiment of the invention except that MP is excluded; Het$^5$ is not substituted by Q, QT, Het$^1$, Het$^1$T, R, RT, Het$^2$ or Het$^2$T; Het$^3$ and A are not substituted by Q, QT, Het$^1$, Het$^1$T, RT, Het$^2$ or Het$^2$T; E is not substituted by Q, QZ, Het$^1$, Het$^1$Z, R, Het$^2$ or Het$^2$Z; and Het$^4$ is not substituted by Q, QZ, Het$^1$ or R, with the proviso that when R$^1$ is C$_1$-C$_4$alkyl which is optionally substituted by one or more of F; R$^3$ is C$_1$-C$_4$alkyl or C$_3$-C$_6$cycloalkyl, then R$^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$.

According to one aspect of the invention R$^1$ and R$^2$ are the same as for the fourth embodiment of the invention, and R$^3$ is the same as for the fourth embodiment of the invention except that MP is excluded; Het$^5$ is not substituted by Q, QT, Het$^1$, Het$^1$T, R, RT, Het$^2$ or Het$^2$T; Het$^3$ and A are not substituted by Q, QT, Het$^1$, Het$^1$T, RT, Het$^2$ or Het$^2$T; E is not substituted by Q, QZ, Het$^1$, Het$^1$Z, R, Het$^2$ or Het$^2$Z; and Het$^4$ is not substituted by Q, QZ, Het$^1$ or R.

According to one aspect of the invention R$^1$ and R$^2$ are the same as for the fourth embodiment of the invention, and R$^3$ is the same as for the fourth embodiment of the invention except that MP is excluded; Het$^5$ is not substituted by Q, QT, Het$^1$, Het$^1$T, R, RT, Het$^2$ or Het$^2$T; Het$^3$ and A are not substituted by Q, QT, Het$^1$, Het$^1$T, RT, Het$^2$ or Het$^2$T; E is not substituted by Q, QZ, Het$^1$, Het$^1$Z, R, Het$^2$ or Het$^2$Z; and Het$^4$ is not substituted by Q, QZ, Het$^1$ or R, with the proviso that when R$^1$ is C$_1$-C$_4$alkyl which is optionally substituted by one or more of F; R$^3$ is C$_1$-C$_4$alkyl or C$_3$-C$_6$cycloalkyl, then R$^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$.

According to a further aspect of the invention R$^1$ and R$^2$ are the same as for the sixth embodiment of the invention, and R$^3$ is the same as for the sixth embodiment of the invention except that MP is excluded; Het$^5$ is not substituted by Q, QT, Het$^1$, Het$^1$T, R, RT, Het$^2$ or Het$^2$T; Het$^3$ and A are not substituted by Q, QT, Het$^1$, Het$^1$T, RT, Het$^2$ or Het$^2$T.

According to one aspect of the invention R$^1$ and R$^2$ are the same as for the seventh embodiment of the invention, and R$^3$ is the same as for the seventh embodiment of the invention except that E is not substituted by Q, QZ, Het$^1$, Het$^1$Z, R, Het$^2$ or Het$^2$Z; and Het$^4$ is not substituted by Q, QZ, Het$^1$ or R.

According to one aspect of the invention R$^1$ and R$^2$ are the same as for the seventh embodiment of the invention, and R$^3$ is the same as for the seventh embodiment of the invention except that E is not substituted by Q, QZ, Het$^1$, Het$^1$Z, R, Het$^2$ or Het$^2$Z; and Het$^4$ is not substituted by Q, QZ, Het$^1$ or R, with the proviso that when R$^1$ is C$_1$-C$_4$alkyl which is optionally substituted by one or more of F, or R$^1$ is C$_3$-C$_6$cycloalkyl; R$^3$ is C$_3$-C$_6$cycloalkyl, then R$^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$.

According to a further aspect of the invention R$^1$ and R$^2$ are the same as for the 9$^{th}$ embodiment of the invention, and R$^3$ is the same as for the 9$^{th}$ embodiment of the invention except that MP is excluded; Het$^5$ is not substituted by Q, QT, Het$^1$, Het$^1$T, R, RT, Het$^2$ or Het$^2$T; and Het$^3$ and A are not substituted by Q, QT, Het$^1$, Het$^1$T, RT, Het$^2$ or Het$^2$T.

According to one aspect of the invention R$^1$ and R$^2$ are the same as for the 10$^{th}$ embodiment of the invention, and R$^3$ is the same as for the 10$^{th}$ embodiment of the invention except that E is not substituted by Q, QZ, Het$^1$, Het$^1$Z, R, Het$^2$ or Het$^2$Z; and Het$^4$ is not substituted by Q, QZ, Het$^1$ or R.

According to one aspect of the invention R$^1$ and R$^2$ are the same as for the 10$^{th}$ embodiment of the invention, and R$^3$ is the same as for the 10$^{th}$ embodiment of the invention except that E is not substituted by Q, QZ, Het$^1$, Het$^1$Z, R, Het$^2$ or Het$^2$Z; and Het$^4$ is not substituted by Q, QZ, Het$^1$ or R, with the proviso that when R$^1$ is C$_1$-C$_4$alkyl which is optionally substituted by one or more of F, or R$^1$ is C$_3$-C$_6$cycloalkyl; R$^3$ is C$_3$-C$_6$cycloalkyl, then R$^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$.

According to a further aspect of the invention R$^1$ and R$^2$ are the same as for the 12$^{th}$ embodiment of the invention, and R$^3$ is the same as for the 12$^{th}$ embodiment of the invention except that MP is excluded; Het$^5$ is not substituted by Q, QT, Het$^1$, Het$^1$T, R, RT, Het$^2$ or Het$^2$T; and Het$^3$ and A are not substituted by Q, QT, Het$^1$, Het$^1$T, RT, Het$^2$ or Het$^2$T.

According to one aspect of the invention R$^1$ and R$^2$ are the same as for the 13$^{th}$ embodiment of the invention, and R$^3$ is the same as for the 13$^{th}$ embodiment of the invention except that E is not substituted by Q, QZ, Het$^1$, Het$^1$Z, R, Het$^2$ or Het$^2$Z; and Het$^4$ is not substituted by Q, QZ, Het$^1$ or R.

According to one aspect of the invention R$^1$ and R$^2$ are the same as for the 13$^{th}$ embodiment of the invention, and R$^3$ is the same as for the 13$^{th}$ embodiment of the invention except that E is not substituted by Q, QZ, Het¹, Het¹Z, R, Het² or Het²Z; and Het⁴ is not substituted by Q, QZ, Het¹ or R, with the proviso that when R¹ is $C_1$-$C_4$alkyl which is optionally substituted by one or more of F; R³ is $C_3$-$C_6$cycloalkyl, then R² is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$ $SiR^bR^bR^b$ $S(O)R^b$ $SOR^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$.

According to a further aspect of the invention R¹ and R² are the same as for the 15$^{th}$ embodiment of the invention, and R³ is the same as for the 15$^{th}$ embodiment of the invention except that MP is excluded; Het⁵ is not substituted by Q, QT, Het¹, Het¹T, R, RT, Het² or Het²T; and Het³ and A are not substituted by Q, QT, Het¹, Het¹T, RT, Het² or Het²T.

According to one aspect of the invention R¹ and R² are the same as for the 16$^{th}$ embodiment of the invention, and R³ is the same as for the 16$^{th}$ embodiment of the invention except that E is not substituted by Q, QZ, Het¹, Het¹Z, R, Het² or Het²Z; and Het⁴ is not substituted by Q, QZ, Het¹ or R.

According to one aspect of the invention R¹ and R² are the same as for the 16$^{th}$ embodiment of the invention, and R³ is the same as for the 16$^{th}$ embodiment of the invention except that E is not substituted by Q, QZ, Het¹, Het¹Z, R, Het² or Het²Z; and Het⁴ is not substituted by Q, QZ, Het¹ or R, with the proviso that when R¹ is $C_1$-$C_4$alkyl which is optionally substituted by one or more of F; R³ is $C_3$-$C_6$cycloalkyl, then R² is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$.

According to a further aspect of the invention R¹ is the same as for the first embodiment of the invention, R² is unsubstituted phenyl, and R³ is the same as for the first embodiment of the invention except that MP is excluded; Het⁵ is not substituted by Q, QT, Het¹, Het¹T, R, RT, Het² or Het²T; Het³ and A are not substituted by Q, QT, Het¹, Het¹T, RT, Het² or Het²T; and E is not substituted by Q, QZ, Het¹, Het¹Z, R, Het² or Het²Z; and Het⁴ is not substituted by Q, QZ, Het¹ or R.

According to one aspect of the invention R¹ is the same as for the second embodiment of the invention, R² is unsubstituted phenyl, and R³ is the same as for the second embodiment of the invention except that MP is excluded; Het⁵ is not substituted by Q, QT, Het¹, Het¹T, R, RT, Het² or Het²T; Het³ and A are not substituted by Q, QT, Het¹, Het¹T, RT, Het² or Het²T; and E is not substituted by Q, QZ, Het¹, Het¹Z, R. Het² or Het²Z; and Het⁴ is not substituted by Q, QZ, Het¹ or R.

According to a further aspect of the invention R¹ is the same as for the third embodiment of the invention, R² is unsubstituted phenyl, and R³ is the same as for the third embodiment of the invention except that MP is excluded; Het⁵ is not substituted by Q, QT, Het¹, Het¹T, R, RT, Het² or Het²T; Het³ and A are not substituted by Q, QT, Het¹, Het¹T, RT, Het² or Het²T; and E is not substituted by Q, QZ, Het¹, Het¹Z, R, Het² or Het²Z; and Het⁴ is not substituted by Q, QZ, Het¹ or R.

According to one aspect of the invention R¹ is the same as for the fourth embodiment of the invention, R² is unsubstituted phenyl, and R³ is the same as for the fourth embodiment of the invention except that MP is excluded; Het⁵ is not substituted by Q, QT, Het¹, Het¹T, R, RT, Het² or Het²T; Het³ and A are not substituted by Q, QT, Het¹, Het¹T, RT, Het² or Het²T; and E is not substituted by Q, QZ, Het¹, Het¹Z, R, Het² or Het²Z; and Het⁴ is not substituted by Q, QZ, Het¹ or R.

According to a further aspect of the invention R¹ is the same as for the sixth embodiment of the invention, R² is unsubstituted phenyl, and R³ is the same as for the sixth embodiment of the invention except that MP is excluded; Het⁵ is not substituted by Q, QT, Het¹, Het¹T, R, RT, Het² or Het²T; Het³ and A are not substituted by Q, QT, Het¹, Het¹T, RT, Het² or Het²T.

According to one aspect of the invention R¹ is the same as for the seventh embodiment of the invention, R² is unsubstituted phenyl, and R³ is the same as for the seventh embodiment of the invention except that E is not substituted by Q, QZ, Het¹, Het¹Z, R, Het² or Het²Z; and Het⁴ is not substituted by Q, QZ, Het¹ or R.

According to a further aspect of the invention R¹ is the same as for the 9$^{th}$ embodiment of the invention, R² is unsubstituted phenyl, and R³ is the same as for the 9$^{th}$ embodiment of the invention except that MP is excluded; Het⁵ is not substituted by Q, QT, Het¹, Het¹T, R, RT, Het² or Het²T; Het³ and A are not substituted by Q, QT, Het¹, Het¹T, RT, Het² or Het²T.

According to one aspect of the invention R¹ is the same as for the 10$^{th}$ embodiment of the invention, R² is unsubstituted phenyl, and R³ is the same as for the 10$^{th}$ embodiment of the invention except that E is not substituted by Q, QZ, Het¹, Het¹Z, R, Het² or Het²Z; and Het⁴ is not substituted by Q, QZ, Het¹ or R.

According to a further aspect of the invention R¹ is the same as for the 12$^{th}$ embodiment of the invention, R² is unsubstituted phenyl, and R³ is the same as for the 12$^{th}$ embodiment of the invention except that MP is excluded; Het⁵ is not substituted by Q, QT, Het¹, Het¹T, R, RT, Het² or Het²T; Het³ and A are not substituted by Q, QT, Het¹, Het¹T, RT, Het² or Het²T.

According to one aspect of the invention R¹ is the same as for the 13$^{th}$ embodiment of the invention, R² is unsubstituted phenyl, and R³ is the same as for the 13$^{th}$ embodiment of the invention except that E is not substituted by Q, QZ, Het¹, Het¹Z, R, Het² or Het²Z; and Het⁴ is not substituted by Q, QZ, Het¹ or R.

According to a further aspect of the invention R¹ is the same as for the 15$^{th}$ embodiment of the invention, R² is unsubstituted phenyl, and R³ is the same as for the 15$^{th}$ embodiment of the invention except that MP is excluded; and Het⁵ is not substituted by Q, QT, Het¹, Het¹T, R, RT, Het² or Het²T; Het³ and A are not substituted by Q, QT, Het¹, Het¹T, RT, Het² or Het²T.

According to a further aspect of the invention R¹ is the same as for the 16$^{th}$ embodiment of the invention, R² is unsubstituted phenyl, and R³ is the same as for the 16$^{th}$ embodiment of the invention except that E is not substituted by Q, QZ, Het¹, Het¹Z, R, Het² or Het²Z; and Het⁴ is not substituted by Q, QZ, Het¹ or R.

According to an alternative aspect of the invention R¹ is the same as for the fourth embodiment of the invention, R² is unsubstituted phenyl, and R³ represents X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$.

According to an alternative aspect of the invention $R^1$ is the same as for the fourth embodiment of the invention, $R^2$ is unsubstituted phenyl, and $R^3$ represents $Het^3P$ wherein $Het^3$ optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein $Het^3$ optionally is substituted on the aromatic ring by one or more of the following independently selected from: halogen (Cl, F, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^a$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

According to an alternative aspect of the invention $R^1$ is the same as for the fourth embodiment of the invention, $R^2$ is unsubstituted phenyl, and $R^3$ represents AP wherein A optionally is substituted by one or more of the following independently selected from: halogen (F, Cl, Br, I), OH, CN, $NO_2$, $NR^aR^a$, $OR^b$, $SR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

According to an alternative aspect of the invention $R^1$ is the same as for the fourth embodiment of the invention, $R^2$ is unsubstituted phenyl, and $R^3$ represents $Het^5P$ wherein $Het^5$ optionally is substituted by one or more of the following independently selected from: halogen (F, Cl, Br, I), OH, CN, $NO_2$, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

According to an alternative aspect of the invention $R^1$ is the same as for the fourth embodiment of the invention, $R^2$ is unsubstituted phenyl, and $R^3$ represents E which is optionally substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and E optionally is substituted on the aromatic ring by one or more of the following independently selected from: halogen (F, Cl, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

According to an alternative aspect of the invention $R^1$ is the same as for the fourth embodiment of the invention, $R^2$ is unsubstituted phenyl, and $R^3$ is $Het^4$ which is optionally substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and $Het^4$ optionally is substituted on the aromatic ring by one or more of the following independently selected from: halogen (F, Cl, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

According to an alternative aspect of the invention $R^1$ is the same as for the fourth embodiment of the invention, $R^2$ is unsubstituted phenyl, and $R^3$ represents $Het^4$ which is optionally substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $Het^2$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and $Het^4$ optionally is substituted on the aromatic ring by one or more of the following independently selected from: halogen (F, Cl, Br, I), OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, $Het^2$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

According to an alternative aspect of the invention R$^1$ is the same as for the fourth embodiment of the invention. R$^2$ is unsubstituted phenyl, and R$^3$ represents Het$^4$ which is optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, RZ, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and Het$^4$ optionally is substituted on the aromatic ring by one or more of the following independently selected from: halogen (F, Cl, Br, I), OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, RZ, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

All of the preceding aspects may also be used with any claims, aspects or embodiments of the invention hereinbefore or hereinafter.

According to an alternative aspect of the invention R$^1$ is selected from n-butyl, tert-butyl or 2-methoxyethyl, R$^2$ is unsubstituted phenyl, and R$^3$ is selected from ethyl, 2,2,2-trifluoroethyl, isopropyl, tert-butyl, 2,2-dimethylpropyl, n-hexyl, 2-hydroxyethyl, 2-methoxyethyl, 3-hydroxypropyl, 2-(2-methoxyethoxy)ethyl, 3-(2-methoxyethoxy)propyl, methyl ethanoylglycinate or 2,3-dihydroxypropyl.

According to an alternative aspect of the invention R$^1$ is selected from n-butyl, tert-butyl, ethyl, 2-methoxyethyl, R$^2$ is unsubstituted phenyl, and R$^3$ is selected from 2,3-dihydro-1,4-benzodioxin-2-ylmethyl, 2,3-dihydro-1,4-benzodioxin-6-ylmethyl, 2-morpholin-4-ylethyl, 2-[1-(tert-butoxycarbonyl)azetidin-3-yl]ethyl, 3-morpholin-4-ylpropyl, 3-(3,5-dimethyl-1H-pyrazol-1-yl)propyl, 2-(pyrrolidin-3-ylthio)ethyl, 2-{1-(tert-butoxycarbonyl)pyrrolidin-3-yl]thio}ethyl or 3-[(1-methylpiperidin-4-yl)oxy]-3-oxopropyl.

According to an alternative aspect of the invention R$^1$ is selected from ethyl, tert-butyl, n-butyl, isopropyl, 2-methoxyethyl, (3-fluorophenyl)ethyl, cyclopentyl, benzyl, pyridin-2-ylmethyl, pyridin-3-ylmethyl, pyridin-4-ylmethyl, tetrahydrofuran-2-ylmethyl. isobutyl, 4-fluorobenzyl, (5-methylisoxazol-3-yl)methyl or (methylthio)methyl, R$^2$ is unsubstituted phenyl, and R$^3$ is selected from 4-(difluoromethoxy)benzyl, 4-methoxybenzyl, 2,2-diphenylethyl, 2-phenylethyl, 2-{4-[(methylsulfonyl)oxy]phenyl}ethyl, 2-[4-(aminosulfonyl)phenyl]ethyl, 2-(4-cyanophenyl)ethyl, 2-(3-cyanophenyl)ethyl, 2-[2-(trifluoromethoxy)phenyl]ethyl, 2-[3-(trifluoromethoxy)phenyl]ethyl, 2-(2-chlorophenyl)ethyl, 3-[benzyl(butyl)amino]propyl, 4-phenylbutyl, 3-phenoxypropyl, 3-(2-fluorophenoxy)propyl, 3-(3-fluorophenoxy)propyl, 3-(4-fluorophenoxy)propyl, 3-(2-chlorophenoxy)propyl, 3-(3-chlorophenoxy)propyl, 3-(4-chlorophenoxy)propyl, 3-(2-methoxyphenoxy)propyl, 3-(3-methoxyphenoxy)propyl, 3-(4-methoxyphenoxy)propyl, 3-(3-carboxyphenoxy)propyl, 3-(4-carboxyphenoxy)propyl, 3-(3-hydroxyphenoxy)propyl, 3-[3-(hydroxymethyl)phenoxy]propyl, 3-[4-(hydroxymethyl)phenoxy]propyl, 3-[3-(2-methoxy-2-oxoethyl)phenoxy]propyl, 3-[4-(2-methoxy-2-oxoethyl)phenoxy]propyl, 3-[3-(acetylamino)phenoxy]propyl, 3-[3-(carboxymethyl)phenoxy]propyl, 3-[3-(methoxycarbonyl)phenoxy]propyl, 3-(4-isopropylphenoxy)propyl, 3-[(1-oxidopyridin-3-yl)oxy]propyl, 3-{4-[2-(dimethylamino)-2-oxoethyl]phenoxy}propyl, 3-[(4-hydroxybenzoyl)oxy]propyl, 2-phenoxyethyl, 2-{2-[(methylsulfonyl)oxy]phenoxy}ethyl, 2-{4-[(methylsulfonyl)oxy]phenoxy}ethyl, 2-[2-(methoxycarbonyl)phenoxy]ethyl, 2-(4-chlorophenoxy)ethyl, 2-[3-(trifluoromethoxy)phenoxy]ethyl, 4-phenoxybutyl, 2-{[3-(trifluoromethoxy)phenyl]thio}ethyl, 3-(phenylthio)propyl, 2-(benzylamino)-2-oxoethyl, 2-{[3-(difluoromethoxy)benzyl]amino}-2-oxoethyl, 2-(3,4-dimethoxyphenyl)ethyl, 2-(3-chloro-4-methoxyphenyl)ethyl, 2-(4-hydroxy-3,5-dimethoxyphenyl)ethyl, 2-(4-methoxyphenyl)-2-oxoethyl, 2-[(4-methoxybenzyl)oxy]-2-oxoethyl, 2-(2-mesitylethoxy)-2-oxoethyl, 2-(2-mesityl-1-methylethoxy)-2-oxoethyl, 3-oxo-3-phenoxypropyl, 3-oxo-3-[4-(trifluoromethoxy)phenoxy]propyl, 2-{[(2,6-dimethylphenyl)acetyl]oxy}ethyl or 4-(2,6-dimethylphenoxy)-4-oxobutyl.

According to an alternative aspect of the invention R$^1$ is selected from tert-butyl, ethyl or isopropyl, R$^2$ is unsubstituted phenyl, and R$^3$ is selected from 2-(1H-imidazol-4-yl)ethyl, 2-pyridin-2-ylethyl, 2-{[3-chloro-5-(trifluoromethyl)pyridin-2-yl]amino}ethyl, 2-{[5-(trifluoromethyl)pyridin-2-yl]oxy}ethyl, 3-(pyridin-2-yloxy)propyl, 3-(pyridin-3-yloxy)propyl, 3-(pyridin-4-yloxy)propyl, (1,3,5-trimethyl-1H-pyrazol-4-yl)methyl, 3-[(1-oxidopyridin-3-yl)oxy]propyl or (5-methylisoxazol-3-yl)methyl, 2-(2-aminopyridin-4-yl)ethyl, 2-pyridin-4-ylethyl, 2-pyridin-3-ylethyl, 2-(3,5-dimethylisoxazol-4-yl)ethyl or 2-(3,5-dimethyl-1H-pyrazol-4-yl)ethyl.

According to an alternative aspect of the invention R$^1$ is selected from n-butyl, isopropyl or 2-methoxymethyl, R$^2$ is unsubstituted phenyl, and R$^3$ is selected from trans-4-hydroxycyclohexyl, cis-4-hydroxycyclohexyl, 4-hydroxycyclohexyl, 4,4-difluorocyclohexyl or 2,3-dihydro-1H-inden-2-yl.

According to an alternative aspect of the invention R$^1$ is selected from tert-butyl, isopropyl or 2-methoxyethyl, R$^2$ is unsubstituted phenyl, and R$^3$ is selected from 1-(2-cyanoethyl)piperidin-4-yl, 1-(tert-butoxycarbonyl)piperidin-4-yl, 1-acetylpiperidin-4-yl, piperidin-4-yl, 1-methylpiperidin-4-yl, 1-isobutyrylpiperidin-4-yl or tetrahydro-2H-pyran-4-yl.

According to an alternative aspect of the invention R$^1$ is selected from isopropyl or tert-butyl, R$^2$ is unsubstituted phenyl, and R$^3$ is selected from 1-[3-chloro-5-(trifluoromethyl)pyridin-2-yl]piperidin-4-yl, 1-pyridin-2-ylpiperidin-4-yl, 1-(5-fluoropyridin-2-yl)piperidin-4-yl, 1-(5-chloropyridin-2-yl)piperidin-4-yl, 1-(5-methylpyridin-2-yl)piperidin-4-yl, 1-[4-(trifluoromethyl)pyridin-2-yl]piperidin-4-yl, 1-[5-(trifluoromethyl)pyridin-2-yl]piperidin-4-yl, 1-(6-chloropyridin-3-yl)piperidin-4-yl, 1-pyridazin-3-ylpiperidin-4-yl, 1-(6-chloropyridazin-3-yl)piperidin-4-yl, 1-(6-methoxypyridazin-3-yl)piperidin-4-yl, 1-[4-(trifluoromethyl)pyrimidin-2-yl]piperidin-4-yl, 1-[3-chloro-5-(trifluoromethyl)pyridin-2-yl]azetidin-3-yl or 1-pyridin-2-ylazetidin-3-yl.

All of the preceding aspects may also be used with any claims, aspects or embodiments of the invention hereinbefore or hereinafter.

In an alternative embodiment there is provided a compound of general formula (I), or a pharmaceutically acceptable salt thereof, wherein $R^1$ and $R^3$ are as defined in any claim, aspect or embodiment of the invention hereinbefore or hereinafter, and wherein $R^2$ is unsubstituted phenyl.

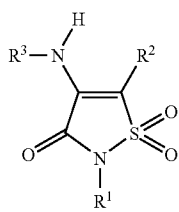

formula (I)

In another alternative embodiment there is provided a compound of general formula I, or a pharmaceutically acceptable salt thereof, wherein $R^1$ and $R^3$ are as defined in any claim, aspect or embodiment of the invention hereinbefore or hereinafter, and wherein $R^2$ is phenyl which is optionally substituted in the ortho position by any of the suitable substituents described hereinbefore or hereinafter.

In another alternative embodiment there is provided a compound of general Formula I, or a pharmaceutically acceptable salt thereof, wherein $R^1$ and $R^3$ are as defined in any claim, aspect or embodiment of the invention hereinbefore or hereinafter, and wherein $R^2$ is phenyl which is optionally substituted by halogen (F, Cl, Br, I).

The above embodiments may be combined with any other embodiment, aspect or claim of the invention described hereinbefore or hereinafter.

In an alternative embodiment of the invention there is provided a compound of general formula I wherein $R^1$, $R^2$ and $R^3$ are defined as for the first embodiment of the invention, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In an alternative embodiment of the invention there is provided a compound of general formula I wherein $R^1$, $R^2$ and $R^3$ are defined as for the second embodiment of the invention, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the third embodiment of the invention, with the proviso that when $R^1$ is $C_1$-$C_4$alkyl which is optionally substituted by one or more of F; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the fourth embodiment of the invention, with the proviso that when $R^1$ is $C_1$-$C_4$alkyl which is optionally substituted by one or more of F; $R^3$ is $C_1$-$C_4$alkyl or $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the fifth embodiment of the invention, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In an alternative embodiment of the invention there is provided a compound of general formula I wherein $R^1$, $R^2$ and $R^3$ are defined as for the seventh embodiment of the invention, with the proviso that when $R^1$ is $C_1$-$C_4$alkyl which is optionally substituted by one or more of F, or $R^1$ is $C_3$-$C_6$cycloalkyl; $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

In an alternative embodiment of the invention there is provided a compound of general formula I wherein $R^1$, $R^2$ and $R^3$ are defined as for the 8$^{th}$ embodiment of the invention, with the proviso that when $R^1$ is $C_1$-$C_4$alkyl which is optionally substituted by one or more of F, or $R^1$ is $C_3$-$C_6$cycloalkyl; $R^3$ is $C_1$-$C_4$alkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the 10$^{th}$ embodiment of the invention, with the proviso that when $R^1$ is $C_1$-$C_4$alkyl which is optionally substituted by one or more of F, or $R^1$ is $C_3$-$C_6$cycloalkyl; $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the 11$^{th}$ embodiment of the invention, with the proviso that when $R^1$ is $C_1$-$C_4$alkyl which is optionally substituted by one or more of F; $R^3$ is $C_1$-$C_4$alkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the 13$^{th}$ embodiment of the invention, with the proviso that when $R^1$ is $C_1$-$C_4$alkyl which is optionally substituted by one or more of F; $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the 14$^{th}$ embodiment of the invention, with the proviso that when $R^1$ is $C_1$-$C_4$alkyl which is optionally substituted by one or more of F; $R^3$ is $C_1$-$C_4$alkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

In an alternative embodiment of the invention there is provided a compound of general formula I wherein $R^1$, $R^2$ and $R^3$ are defined as for the 16$^{th}$ embodiment of the invention, with the proviso that when $R^1$ is $C_1$-$C_4$alkyl which is optionally substituted by one or more of F, $R^3$ is $C_3$-$C_6$cycloalkyl, then $R^2$ is phenyl which is optionally substituted in the meta and/or para position by halogen (F, Cl, Br, I) and/or optionally substituted in the ortho position by position by one or more of the following independently selected from: halogen (Cl, F, I, Br), OH, CN, $NO_2$, $NR^aR^a$, $OR^b$, $SR^b$, $SiR^bR^bR^b$, $S(O)R^b$, $SO_2R^b$, or $C(O)R^b$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, or $C(O)R^b$.

The above embodiments may be combined with any other embodiment, aspect or claim of the invention described hereinbefore or hereinafter.

In an alternative embodiment of the invention there is provided a compound of general formula (I) wherein $R^1$, $R^2$, and $R^3$ are as defined for any aspect, claim or embodiment hereinbefore or hereinafter, with the proviso that when $R^1$ is $C_1$-$C_4$alkyl optionally substituted by one or more F, or $R^1$ is $C_3$-$C_6$cycloalkyl; $R^3$ is $C_1$-$C_4$alkyl or $C_3$-$C_6$cycloalkyl, then $R^2$ is not phenyl substituted in the para position by a $C_1$alkyl that bears one substituent selected from: $NR^aR^a$, $NR^aSO_2R^b$, $NR^aC(O)R^b$, $NR^aC(O)OR^b$ or $NR^aC(O)NR^aR^a$, and one substituent selected from: $C(O)R^b$, $C(O)OR^a$ or $C(O)NR^aR^a$; and $R^2$ is not phenyl substituted in the para position by a straight or branched $C_2$-$C_4$alkyl chain in which the terminal carbon atom (i.e. that carbon not connected to the phenyl) bears one substituent selected from: $NR^aR^a$, $NR^aSO_2R^b$, $NR^aC(O)R^b$, $NR^aC(O)OR^b$ or $NR^aC(O)NR^aR^a$, and one substituent selected from: $C(O)R^b$, $C(O)OR^a$ or $C(O)NR^aR^a$; wherein $R^a$ and $R^b$ are as defined for any aspect, claim or embodiment hereinbefore or hereinafter.

In an alternative embodiment of the invention there is provided a compound of general formula (I) wherein $R^1$, $R^2$, and $R^3$ are as defined for any aspect, claim or embodiment hereinbefore or hereinafter, with the proviso that when $R^1$ is $C_1$-$C_4$alkyl optionally substituted by one or more F, or $R^1$ is $C_3$-$C_6$cycloalkyl; $R^3$ is $C_1$-$C_4$alkyl or $C_3$-$C_6$cycloalkyl, then $R^2$ is not phenyl substituted in the para position by a $C_1$alkyl that bears one substituent selected from: $NR^aR^a$, $NR^aSO_2R^b$, $NR^aC(O)R^b$, $NR^aC(O)OR^b$ or $NR^aC(O)NR^aR^a$, and one substituent selected from: $C(O)R^b$, $C(O)OR^a$ or $C(O)NR^aR^a$; and $R^2$ is not phenyl substituted in the para position by a straight or branched $C_2$-$C_4$alkyl chain in which the terminal carbon atom (i.e. that carbon not connected to the phenyl) bears one substituent selected from: $NR^aR^a$, $NR^aSO_2R^b$, $NR^aC(O)R^b$, $NR^aC(O)OR^b$ or $NR^aC(O)NR^aR^a$, and one substituent selected from: $C(O)R^b$, $C(O)OR^a$ or $C(O)NR^aR^a$; wherein $R^a$ and $R^b$ are as defined for any aspect, claim or embodiment hereinbefore or hereinafter, and $R^2$ is not phenyl which is further substituted in the ortho or meta positions by H, halogen, $C_1$-$C_4$alkyl, OH, $OR^b$, $SR^b$, $NO_2$, CN, $S(O)R^b$, $SO_2R^b$, $C(O)R^b$, $C(O)NR^aR^a$, $C(O)OR^a$, $NR^aR^a$, $NR^aSO_2R^b$, $NR^aC(O)R^b$ or $NR^aC(O)NR^aR^a$.

In an alternative embodiment of the invention there is provided a compound of general formula (I) wherein $R^1$, $R^2$, and $R^3$ are as defined for any aspect, claim or embodiment hereinbefore or hereinafter, with the proviso that when $R^1$ is $C_1$-$C_4$alkyl optionally substituted by one or more F, or $R^1$ is $C_3$-$C_6$cycloalkyl; $R^3$ is $C_1$-$C_4$alkyl or $C_3$-$C_6$cycloalkyl, then $R^2$ is not phenyl substituted in the meta position by $NR^aR^a$, $OR^b$, $SR^b$, $S(O)R^b$, $SO_2R^b$, $C(O)R^b$, $C(O)NR^aR^a$, $C(O)OR^a$, $SO_2NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $S(O)R^b$, $SO_2R^b$, $C(O)R^b$, $C(O)OR^a$, $C(O)NR^aR^a$ or $OC(O)R^b$; wherein $R^a$ and $R^b$ are as defined for any aspect, claim or embodiment hereinbefore or hereinafter, with the proviso that when $R^2$ is phenyl substituted in the meta position by $C(O)OR^a$ then $R^a$ can be H.

In an alternative embodiment of the invention there is provided a compound of general formula (I) wherein $R^1$, $R^2$, and $R^3$ are as defined for any aspect, claim or embodiment hereinbefore or hereinafter, with the proviso that when $R^1$ is $C_1$-$C_4$alkyl optionally substituted by one or more F, or $R^1$ is $C_3$-$C_6$cycloalkyl; $R^3$ is $C_1$-$C_4$alkyl or $C_3$-$C_6$cycloalkyl, then $R^2$ is not phenyl substituted in one of the meta positions by $NR^aR^a$, $OR^b$, $SR^b$, $S(O)R^b$, $SO_2R^b$, $C(O)R^b$, $C(O)NR^aR^a$, $C(O)OR^a$, $SO_2NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $S(O)R^b$, $SO_2R^b$, $C(O)R^b$, $C(O)OR^a$, $C(O)NR^aR^a$ or $OC(O)R^b$; wherein $R^a$ and $R^b$ are as defined for any aspect, claim or embodiment hereinbefore or hereinafter, with the proviso that when $R^2$ is phenyl substituted in the meta position by $C(O)OR^a$ then $R^a$ can be H, and $R^2$ is not phenyl which is further substituted in the ortho, para or other meta position by H, halogen, $C_1$-$C_4$alkyl, OH, $OR^b$, $SR^b$, $NO_2$, CN, $S(O)R^b$, $SO_2R^b$, $C(O)R^b$, $C(O)NR^aR^a$, $C(O)OR^a$, $NR^aR^a$, $NR^aSO_2R^b$, $NR^aC(O)R^b$ or $NR^aC(O)NR^aR^a$.

In a further aspect of the invention there is provided a compound of general formula (V), (VI), (IX), (X), (XII) or (XIII)

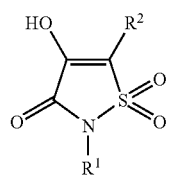
(V)

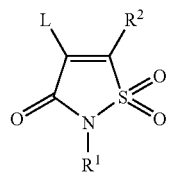
(VI)

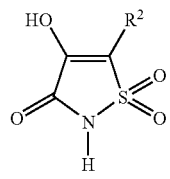
(IX)

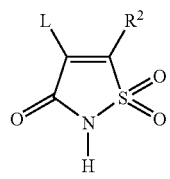
(X)

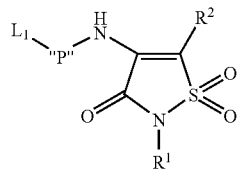
(XII)

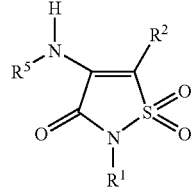
(XIII)

or a pharmaceutically acceptable salt thereof, wherein $R^1$ is as defined for any aspects, embodiments or claims hereinbefore or hereinafter, $R^2$ is as defined for any aspects, embodiments or claims hereinbefore or hereinafter, L is a suitable leaving group such as Cl, Br, I, p-toluensulfonate, methanesulfonate or trifluoromethanesulfonate, "P" is as defined for P in any aspects, embodiments or claims hereinbefore or hereinafter, $L_1$ is OH, $NH_2$, SH or a suitable leaving group such as Cl, Br, I, p-toluensulfonate, methanesulfonate or trifluoromethanesulfonate, and $R^5$ is $Het^4$ or E wherein $Het^4$ and E are as defined for any aspects, embodiments or claims hereinbefore or hereinafter, with the proviso that the following compounds are excluded: 4-hydroxy-5-phenylisothiazol-3(2H)-one 1,1-dioxide, 5-(4-aminophenyl)-4-hydroxy-2-methylisothiazol-3(2H)-one 1,1-dioxide, 4-hydroxy-2-methyl-5-(4-nitrophenyl)isothiazol-3(2H)-one 1,1-dioxide, 4-hydroxy-2-methyl-5-phenylisothiazol-3(2H)-one 1,1-dioxide, 5-(3,4-dichlorophenyl)-4-hydroxyisothiazol-3(2H)-one 1,1-dioxide, 2-benzyl-4-hydroxy-5-phenylisothiazol-3(2H)-one 1,1-dioxide, and 4-hydroxy-2-(4-methylphenyl)-5-phenylisothiazol-3(2H)-one 1,1-dioxide. It shall be understood that protecting groups can be used when $L_1$ is OH, $NH_2$ or SH.

Certain compounds of the present invention may exist as tautomers or stereoisomers (e.g. racemate, enantiomer, diastereomer or E- or Z-isomer). It is to be understood that the present invention encompasses all such tautomers or stereoisomers.

Certain compounds of the present invention may exist as solvates or hydrates. It is to be understood that the present invention encompasses all such solvates or hydrates.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

A suitable pharmaceutically acceptable salt of a compound of the invention is, for example, an acid-addition salt of a compound of the invention which is sufficiently basic, for example, an acid-addition salt with, for example, an inorganic or organic acid, for example hydrochloric, hydrobromic, nitric, methansulphonic, sulphuric, phosphoric, trifluoroacetic, para-toluene sulphonic, 2-mesitylen sulphonic, citric, acetic, tartaric, fumaric, lactic, succinic, malic, malonic, maleic, 1,2-ethanedisulphonic, adipic, aspartic, benzenesulphonic, benzoic, ethanesulphonic or nicotinic acid. In addition a suitable pharmaceutically acceptable salt of a compound of the invention, is, for example, a base-addition salt of a compound of the invention which is sufficiently acidic, for example, a metal salt, for example, sodium, potassium, calcium, magnesium, zinc or aluminum, an ammonium salt, a salt with an organic base which affords a physiologically acceptable cation, which includes quaternary ammonium hydroxides, for example methylamine, ethylamine, diethylamine, trimethylamine, tert-butylamine, triethylamine, dibenzylamine, N,N-dibenzylethylamine, cyclohexylethylamine, tris-(2-hydroxyethyl)amine, hydroxyethyl diethylamine, (1R,2S)-2-hydroxyinden-1-amine, morpholine, N-methylpiperidine, N-ethylpiperidine, piperazine, methylpiperazine, adamantylamine, choline hydroxide, tetrabutylammonium hydroxide, tris-(hydroxymethyl)methylamine hydroxide, L-arginine, N-methyl D-glucamine, lysine or arginine.

The compound of the formula (I), or other compounds disclosed herein, may be administered in the form of a prodrug which is broken down in the human or animal body to give a compound of the formula (I). Examples of pro-drugs include in vivo hydrolysable esters and in vivo hydrolysable amides of a compound of the formula (I).

Methods of Preparation

The compounds of the invention may be prepared as outlined in the Schemes below. However, the invention is not limited to these methods. The compounds may also be prepared as described for structurally related compounds in the prior art. The reactions can be carried out according to standard procedures or as described in the experimental section.

In the Schemes below the term "reagent" means a reagent that can transform a hydroxy group into a leaving group L. Examples of such leaving groups are for instance Cl, Br, I, methanesulfonate (OMs), p-toluensulfonate or trifluoromethanesulfonate (OTf). Furthermore, in all Schemes below $R^1$, $R^2$ and $R^3$ are as defined for any aspects, embodiments or claims hereinbefore or hereinafter.

Schemes I-IX illustrate different processes for synthesizing compounds of formula (I).

Scheme I

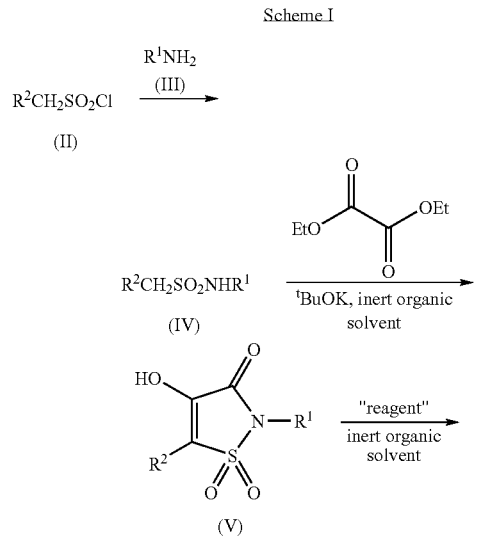

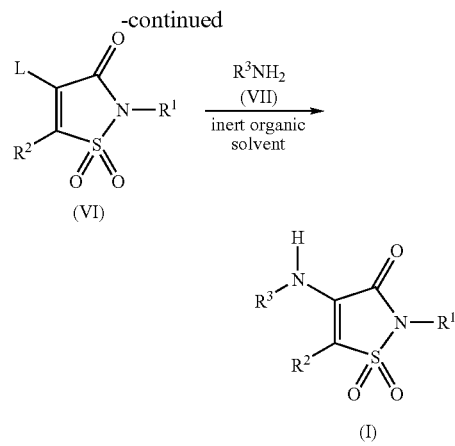

Scheme I describes a method of preparation of compounds according to formula (I), wherein $R^1$, $R^2$ and $R^3$ are as defined for any aspects or embodiments hereinbefore or hereinafter, and L is a leaving group such as for instance Cl, Br, I, p-toluensulfonate, methanesulfonate or trifluoromethanesulfonate, comprising the following steps:

a) A process for the preparation of a compound according to formula (I) comprising the step of reacting a compound of formula (VI)

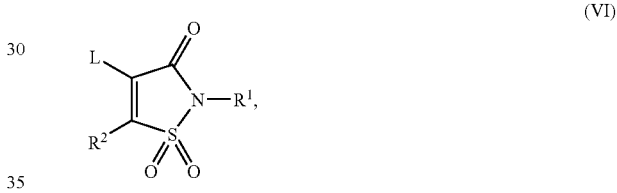

with a compound of formula (VII)

optionally in the presence of an inert organic solvent such as dimethylformamide.

b) A process for the preparation of a compound according to formula (VI)

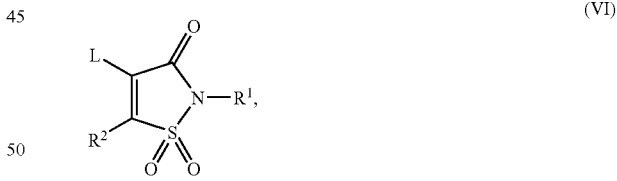

comprising the step of reacting a compound of formula (V)

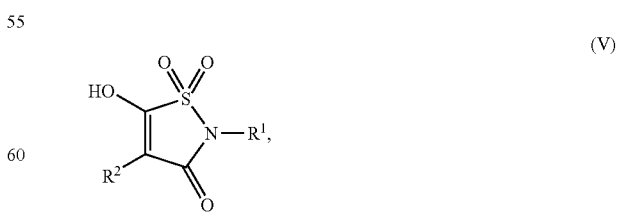

with a reagent that can transform the hydroxy group in the compound of formula (V) into a leaving group L, optionally in the presence of an inert organic solvent.

c) A process for the preparation of a compound according to formula (V)

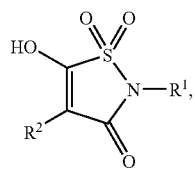
(V)

comprising the step of reacting a compound of formula (IV)

$R^2CH_2SO_2NHR^1$ (IV)

with diethyl oxalate, or a suitable equivalent thereof, in the presence of a base such as for instance potassium tert-butoxide, optionally in the presence of an inert organic solvent such as THF.

d) A process for the preparation of a compound according to formula (IV)

$R^2CH_2SO_2NHR^1$ (IV), comprising the step of reacting a compound of formula (II)

$R^2CH_2SO_2Cl$ (II)

with a compound of formula (III)

$R^1NH_2$ (III), optionally in the presence of a base and an inert organic solvent.

Scheme II describes a method of preparation of compounds according to formula (I), wherein $R^1$, $R^2$ and $R^3$ are as defined for any aspects or embodiments hereinbefore or hereinafter, and L is a leaving group such as for example Cl, Br, I, p-toluensulfonate, methanesulfonate or trifluoromethanesulfonate, comprising the following steps:

a) A process for the preparation of a compound according to formula (I) comprising the step of reacting (i) a compound of formula (VI)

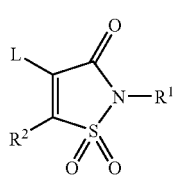
(VI)

with a compound of formula (VII)

$R^3NH_2$ (VII)

optionally in the presence of an inert organic solvent such as dimethylformamide; or Scheme II

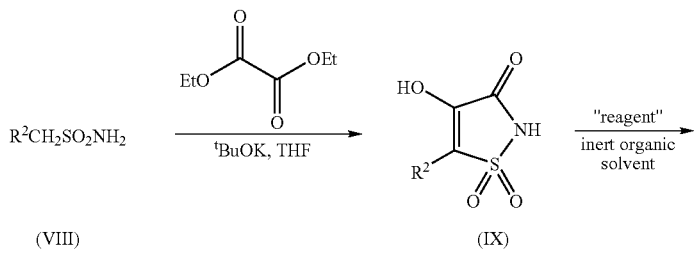

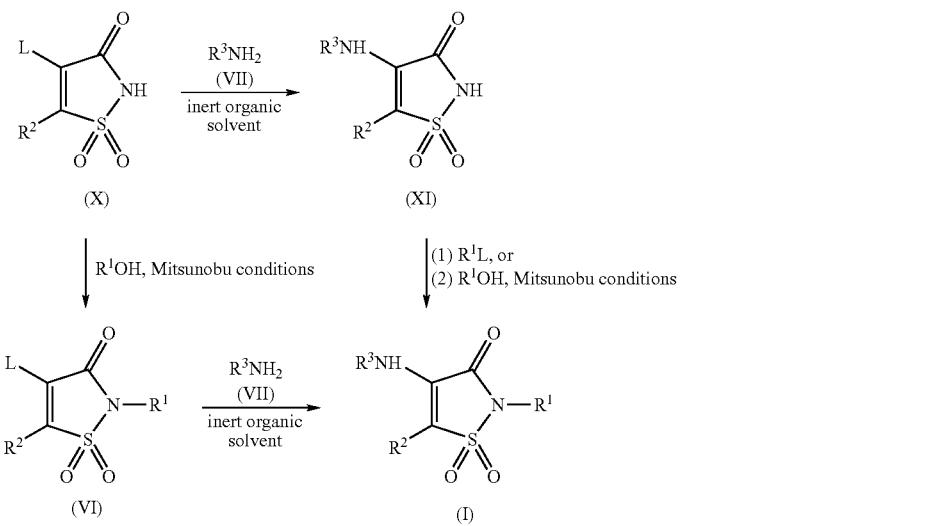

(ii) a compound of formula (XI)

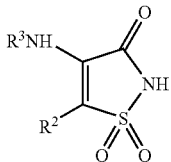
(XI)

either with R¹OH using Mitsunobu conditions or with an alkylating agent such as R¹L.

b) A process for the preparation of a compound according to formula (VI)

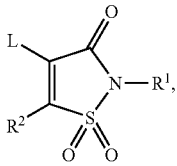
(VI)

comprising the step of reacting a compound of formula (X)

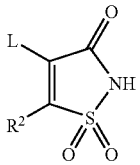
(X)

with R¹OH using Mitsunobu conditions.

c) A process for the preparation of a compound according to formula (XI)

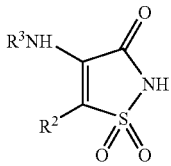
(XI)

comprising the step of reacting a compound of formula (X)

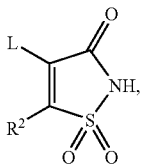
(X)

with a compound of formula (VII)

R³NH₂ (VII), optionally in the presence of an inert organic solvent.

d) A process for the preparation of a compound according to formula (X)

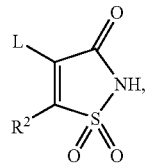
(X)

comprising the step of reacting a compound of formula (IX)

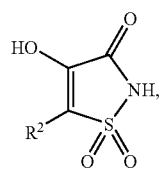
(IX)

with a reagent that transforms the hydroxy group in the compound of formula (IX) into a leaving group L.

e) A process for the preparation of a compound of formula (IX)

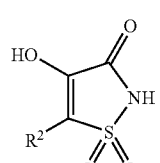
(IX)

comprising the step of reacting a compound of formula (VIII)

R²CH₂SO₂NH₂ (VIII)

with diethyl oxalate, or a suitable equivalent thereof, in the presence of a base such as for instance potassium tert-butoxide, optionally in the presence of an inert organic solvent such as THF.

Scheme III
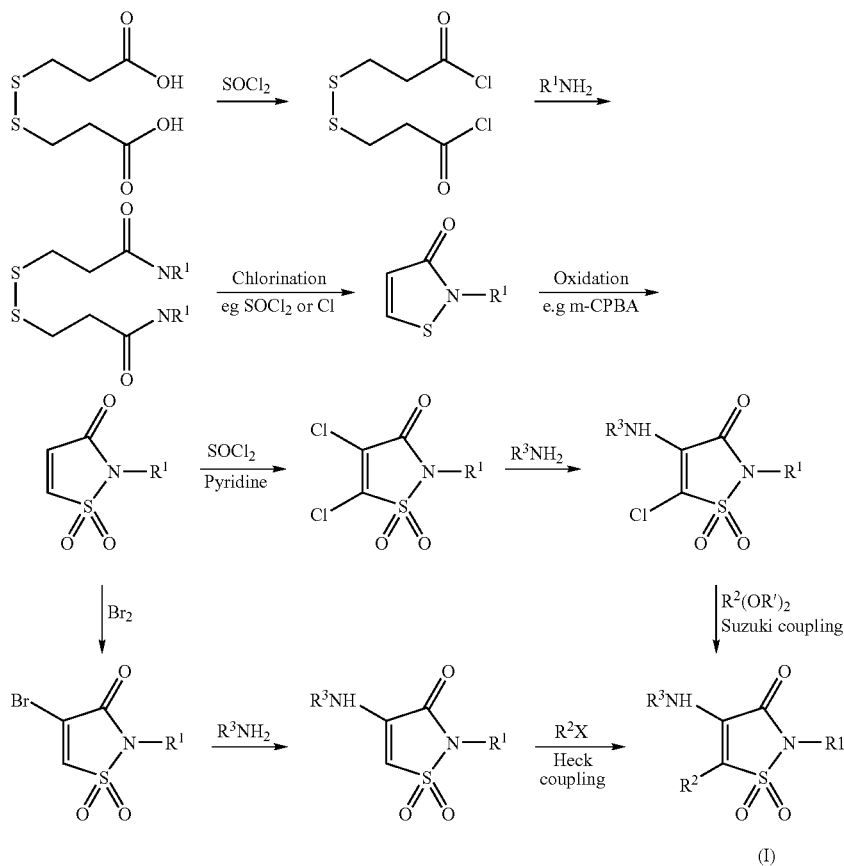
In Scheme III R²X is an aryl halide, wherein R² is defined as for any aspects, embodiments or claims hereinbefore or hereinafter. Furthermore, in Schemes III, IV and V R²(OR')₂ is a reagent wherein R² is defined as for any aspects, embodiments or claims hereinbefore or hereinafter and R' is a hydrocarbon.
Scheme IV
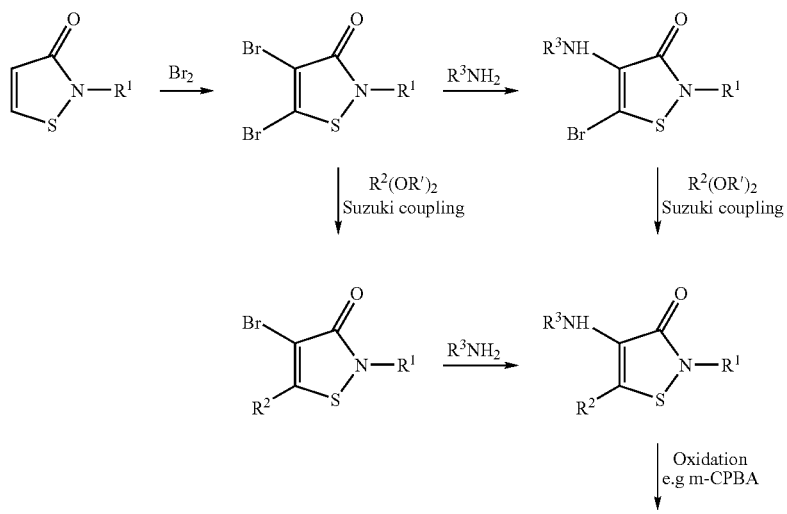

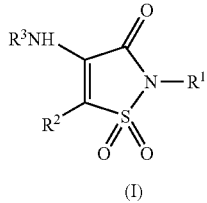

(I)

Scheme V

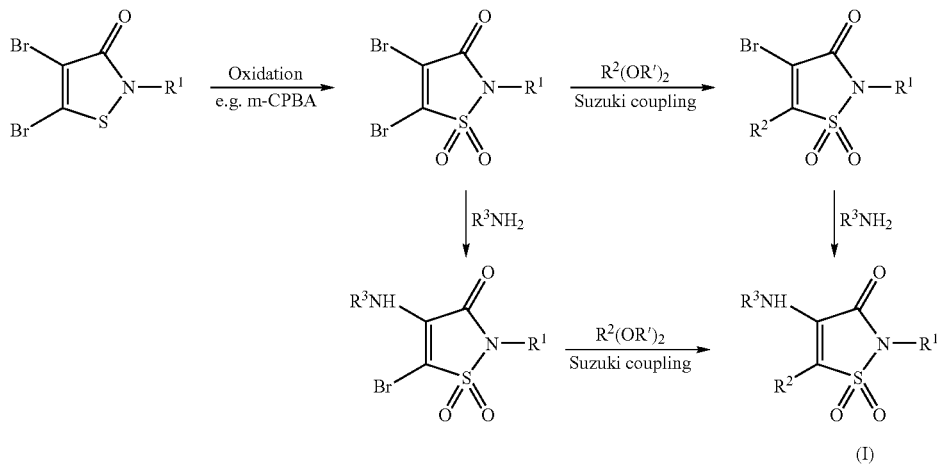

Scheme VI further illustrates the synthesis of some of the compounds of the invention. In Scheme VI "P" is defined as for P in any aspects, embodiments or claims hereinbefore or hereinafter, $R^{4'}$ is a suitable derivative of M, $Het^3$, A or $Het^5$, which are optionally substituted by one or more of the following independently selected from: Q, QT, $Het^1$, $Het^1T$, R, RT, $Het^2$ or $Het^2T$. $R^{4'}$ reacts with the tosylate to yield a compound of formula (I). It is appreciated that in Scheme VI other leaving groups than tosylates may be used. Furthermore, in Scheme VI the tosylate, or another suitable leaving group, can be transformed into a nucleophile such as for instance amino, hydroxy or thio. The coupling with the reagent $R^{4'}$ is performed using appropriate reaction conditions known to a person skilled in the art, and examples of this coupling can be found in the experimental part of this application. $R^4$—"P"—NH is equal to $R^3NH$. $R^4$ is M, $Het^3$, A or $Het^5$, which are optionally substituted by one or more of the following independently selected from: Q, QT, $Het^1$, $Het^1T$, R, RT, $Het^2$ or $Het^2T$. M, $Het^3$, A, $Het^5$, Q, T, $Het^1$, R and $Het^2$ are defined as for any aspects, embodiments or claims hereinbefore or hereinafter.

Scheme VI

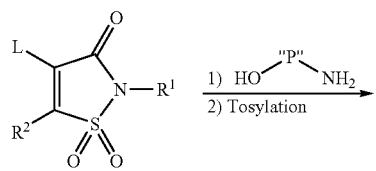

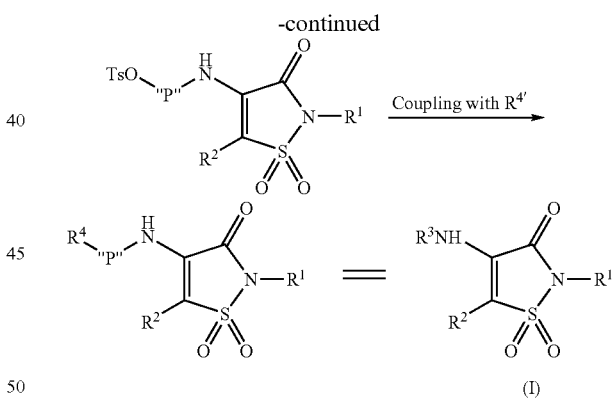

Scheme VII further illustrates the synthesis of some of the compounds of the invention. In Scheme VII "P" is defined as for P in any aspects, embodiments or claims hereinbefore or hereinafter, $R^{4'}$ is a suitable derivative of M, $Het^3$, A or $Het^5$, which are optionally substituted by one or more of the following independently selected from: Q, QT, $Het^1$, $Het^1T$, R, RT, $Het^2$ or $Het^2T$. $R^{4'}$ reacts with the hydroxy group to yield a compound of formula (I). The coupling with the reagent $R^{4'}$ is performed using appropriate reaction conditions known to a person skilled in the art, and examples of this coupling can be found in the experimental part of this application. $R^4O$—"P"—NH is equal to $R^3NH$. $R^4$ is M, $Het^3$, A or $Het^5$, which are optionally substituted by one or more of the following independently selected from: Q, QT, $Het^1$, $Het^1T$, R, RT, $Het^2$ or $Het^2T$. M, $Het^3$, A, $Het^5$, Q, T, $Het^1$, R and $Het^2$ are defined as for any aspects, embodiments or claims hereinbefore or hereinafter. It is appreciated that in Scheme VII other nucleophiles than hydroxy may be used such as for instance thio and amino.

Scheme VII

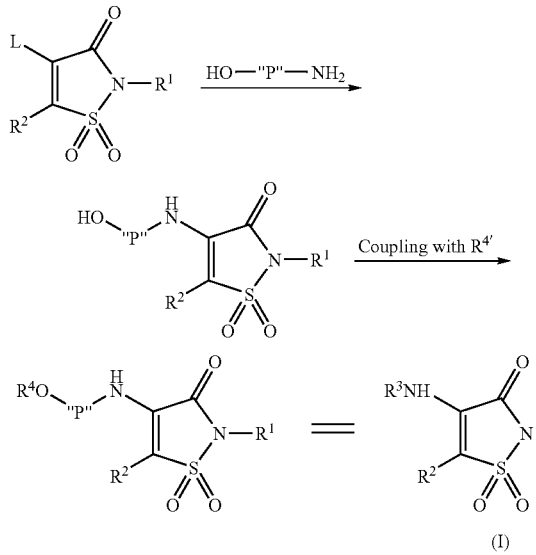

Scheme VIII further illustrates the synthesis of some of the compounds of the invention. In Scheme VIII $R^5NH_2$ is $Het^4NH_2$ or $E-NH_2$. $Het^4$ and E are as defined for any aspects, embodiments or claims hereinbefore or hereinafter. $R^6L$ is a reagent in which $R^6$ is Q, QZ, $Het^1$, $Het^1Z$, R, RZ, $Het^2$ or $Het^2Z$, and L is a leaving group such as for example Cl, Br, I, p-toluensulfonate, methanesulfonate or trifluoromethanesulfonate. Q, Z, $Het^1$, R, and $Het^2$ are as defined for any aspects, embodiments or claims hereinbefore or hereinafter. $R^6$—$R^5$—NH is equal to $R^3NH$. The coupling with $R^6L$ is performed using appropriate reaction conditions known to a person skilled in the art, and examples of this coupling can be found in the experimental part of this application.

Scheme VIII

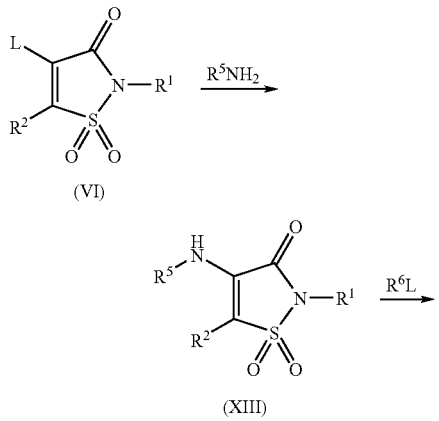

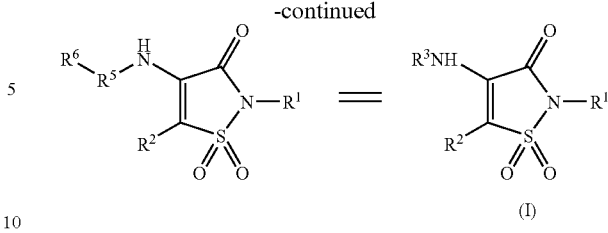

The expression "inert organic solvent" refers to a solvent which does not react with the starting materials, reagents, intermediates or products in a manner which adversely affects the yield of the desired product. Examples of such solvents are for instance dimethylformamide, methylene chloride and acetonitrile.

The individual reactions steps in Schemes I-VIII may be performed while heating either using conventional means such as heating the reaction mixture on an oil bath, or heating the reaction mixture in a microwave oven.

Furthermore, it shall be understood that the $R^1$ group in a compound of formula (I) can be replaced by another $R^1$ group, e.g. cyclopentyl. For example, when $R^1$ is tert-butyl it can be removed by deprotection with trifluoroacetic acid, and the resulting compound can subsequently be reacted with an alkylating agent containing the new $R^1$ group. This is illustrated in Scheme IX, where PG denotes a protecting group.

Scheme IX

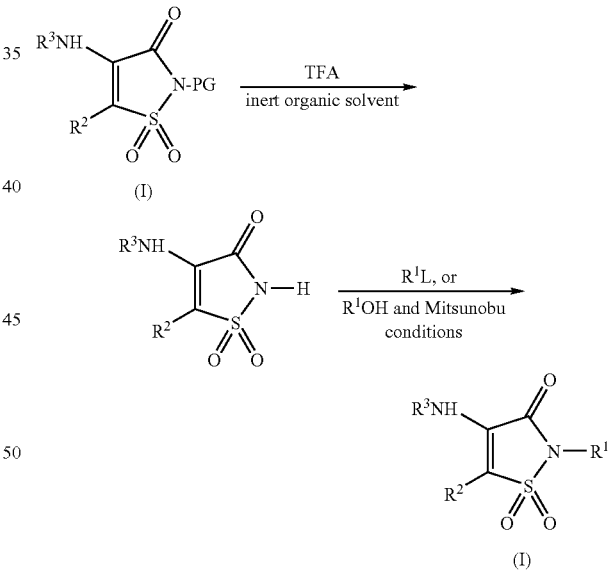

It shall be understood that in some of the reactions in this application it may be necessary to use protecting group for functionalities such as for example hydroxyl groups, amino groups, and carboxyl groups. Further representative protecting groups can be found in T. W. Green and P. G. M. Wuts, Protective Groups in Organic Synthesis, 3$^{rd}$ Ed., Wiley and Sons, Inc., New York (1999), which is incorporated hereby by reference in its entirety.

It shall be understood that the diethyl oxalate used in the Schemes above can be exchanged for equivalent reagents such as e.g. methyl oxalyl chloride.

It shall be understood that the potassium tert-butoxide used in the Schemes above can be exchanged for equivalent reagents such as e.g. lithium tert-butoxide.

Compounds of formula (II) and (IV) are commercially available or may be prepared as described in the experimental part in this patent application or by methods known by those skilled in the art.

Compounds of formula (VII) are commercially available or may be prepared as described in the experimental part in this patent application or by methods known by those skilled in the art. Furthermore, compounds of formula (VII) may be prepared in an analogous way to the procedures described in the experimental part in this patent application. Certain compounds of formula (V), (VI), (IX), (X), (XII) and (XIII) are believed to be novel and are claimed herein as useful intermediates in the preparation of compounds of formula (I). All intermediates are commercially available or may be prepared as described in the experimental part in this patent application or by methods known by those skilled in the art. Furthermore, the intermediates may be prepared in an analogous way to the procedures described in the experimental part in this patent application.

It is to be understood that when $R^1$ or $R^3$ represent nitrogen oxides in compounds of formula (I) these are prepared from the corresponding amines and an oxidizing agent such as metachloroperbenzoic acid (MCPBA) optionally in the presence of an inert organic solvent such as dichloromethane.

Persons skilled in the art will appreciate that, in order to obtain compounds of the invention in an alternative and in some occasions, more convenient manner, the individual process steps mentioned hereinbefore may be performed in a different order, and/or the individual reactions may be performed at different stage in the overall route (i.e. chemical transformations may be performed upon different intermediates to those associated hereinbefore with a particular reaction).

Pharmaceutical Preparations

The compounds of the invention will normally be administered via the oral, parenteral, intravenous, intramuscular, subcutaneous or in other injectable ways, buccal, rectal, vaginal, transdermal and/or nasal route and/or via inhalation, in the form of pharmaceutical preparations comprising the active ingredient or a pharmaceutically acceptable salt or solvate thereof, or a solvate of such a salt, in a pharmaceutically acceptable dosage form. Depending upon the disorder and patient to be treated and the route of administration, the compositions may be administered at varying doses.

Suitable daily doses of the compounds of the invention in therapeutical treatment of humans are about 0.0001-100 mg/kg body weight, preferably 0.01-10 mg/kg body weight.

Oral formulations are preferred particularly tablets or capsules which may be formulated by methods known to those skilled in the art to provide doses of the active compound in the range of 0.007 mg to 700 mg for example 1 mg, 3 mg, 5 mg, 10 mg, 25 mg, 50 mg, 100 mg and 250 mg.

According to a further aspect of the invention there is thus provided a pharmaceutical formulation including any of the compounds of the invention, or pharmaceutically acceptable derivatives thereof, in admixture with pharmaceutically acceptable excipients, oils which may be glycerides, diluents and/or carriers.

Pharmacological Properties

The compounds of formula I are useful for normalization of cholesterol homeostasis, decreasing intestinal cholesterol absorption, improving reverse cholesterol transport, improving HDL functionality, increasing HDL-cholesterol levels, decreasing LDL-cholesterol levels, decreasing cholesterol content of apoB-containing lipoproteins, stimulating cholesterol efflux from vascular cells and/or decreasing the inflammatory response of vascular cells. As a consequence of these properties the compounds of formula I are expected to have anti-atherosclerotic effects.

The compounds of formula I are useful in the prevention or treatment of cardiovascular disease in a mammal, particularly a human. The compounds of formula I are useful in the prevention or treatment of atherosclerosis in a mammal, particularly a human. Cardiovascular disease includes but is not limited to conditions associated with atherosclerosis, arteriosclerosis, hypercholesterolemia, and other kinds of dyslipidemia that increase the risk for cardiovascular disease. In particular the compounds of formula I are useful in the treatment or prevention of cardiovascular disease, especially those involving atherosclerosis, hypercholesterolemia and dyslipidemia.

The compounds of formula I also serve to prevent lipid accumulation in, or remove lipids from, tissue deposits such as atherosclerotic plaques or xanthomas in a patient with atherosclerotic disease manifest by clinical signs such as angina, claudication, bruits, one that has suffered a mycardial infarction, stroke or transient ischemic attack, or one diagnosed by angiography, sonography or MRI.

The compounds of formula I also serve to prevent or reduce the risk of developing atherosclerosis, as well as for halting or slowing the progression of atherosclerotic disease once it has become clinically evident, comprising the administration of a prophylactically or therapeutically effective amount, as appropriate, of a compound of formula I to a mammal, including a human, who is at risk of developing atherosclerosis or who already has atherosclerotic disease.

Atherosclerosis encompasses vascular diseases and conditions that are recognized and understood by physicians practicing in the relevant fields of medicine. Atherosclerotic cardiovascular disease including restenosis following revascularization procedures, coronary heart disease (also known as coronary artery disease or ischemic heart disease), cerebrovascular disease including multi-infarct dementia, and peripheral vessel disease including erectile dysfunction are all clinical manifestations of atherosclerosis and are therefore encompassed by the terms "atherosclerosis" and "atherosclerotic disease".

The present compounds of formula I are also useful for the prophylaxis and/or treatment of clinical conditions associated with atherosclerosis such as inherited or induced hypercholesterolemia as well as inherited or induced reduced sensitivity to insulin (insulin resistance syndrome also known as metabolic syndrome) and associated metabolic disorders. These clinical conditions will include, but will not be limited to, general obesity, abdominal obesity, arterial hypertension, hyperinsulinaemia, type 2 diabetes, type 1 diabetes and other more rare forms of diabetes mellitus and the dyslipidaemia characteristically appearing with insulin resistance. This dyslipidaemia, also known as the atherogenic lipoprotein profile, is characterised by moderately elevated non-esterified fatty acids, elevated VLDL triglyceride rich particles, high ApoB levels, low BDL levels associated with low apoAI levels in the presence of small, dense, LDL particles, phenotype B.

The compounds of formula I are expected to be useful in treating patients with combined or mixed hyperlipidemias and dyslipidemias, especially low HDL levels with or without other manifestations of the metabolic syndrome.

The compounds of formula I are expected to be useful in treating patients with low HDL levels of other reasons than metabolic syndrome or type 2 diabetes.

Treatment with the compounds of formula I are expected to lower the cardiovascular morbidity and mortality associated with atherosclerosis due to their antidyslipidaemic as well as antiinflammatory properties. The cardiovascular disease conditions include macro-angiopathies of various internal organs causing myocardial infarction, congestive heart failure, cerebrovascular disease and peripheral arterial insufficiency. The insulin sensitizing effect of the compounds of formula I is also expected to prevent or delay the development of type 2 diabetes from the metabolic syndrome and diabetes of pregnancy. Therefore the development of long-term complications associated with chronic hyperglycaemia in diabetes mellitus such as the micro-angiopathies causing renal disease, retinal damage and peripheral vascular disease of the lower limbs are expected to be delayed.

The compounds of formula I may also be useful for the prevention or treatment of inflammation and neurodegenerative diseases or neurological disorders. Accordingly, this invention also provides a method for preventing or treating inflammation in the CNS, reducing amyloid pathology and a method for preventing or treating neurodegenerative diseases or disorders characterized by neuron degeneration, neuron injury or impaired plasticity or inflammation in the CNS. The neurodegenerative diseases or conditions characterized by neuron degeneration and inflammation will include but will not be limited to stroke, Alzheimer's disease, fronto-temporal dementias (taupathies), peripheral neuropathy, Parkinson's disease, dementia with Lewy bodies, Huntington's disease, amyotrophic lateral sclerosis and multiple sclerosis.

The compounds of formula I are useful in preventing or treating inflammatory conditions or diseases. These diseases or conditions will include but will not be limited to atherosclerotic diseases such as angina pectoris and myocardial infarction but also rheumatoid arthritis, juvenile rheumatoid arthritis, systemic lupus erythematosus, osteoarthritis, degenerative joint disease, one or more connective tissue diseases, ankylosing spondolytis, bursitis, Sjogren's syndrome, psoriasis, psoriatic arthritis, neuralgia, synovitis, glomerulonephritis, vasculitis or sarcoidosis as well as inflammatory bowel diseases such as Coeliac disease, proctitis, eosinopilic gastro-enteritis, mastocytosis, Crohn's disease, ulcerative colitis, microscopic colitis, indeterminant colitis, irritable bowel disorder, irritable bowel syndrome and distal proctitis. Compounds of formula I may also be used in other inflammatory conditions of the lung including asthma, adult respiratory distress syndrome, chronic obstructive pulmonary disease and pneumonia bronchitis.

Furthermore the compounds of formula I may be useful in treatment of various conditions outside the cardiovascular system whether or not associated with insulin resistance, like polycystic ovarian syndrome, obesity and cancer.

The present invention provides a method of treating and/or preventing rheumatoid arthritis comprising the administration of an effective amount of a compound of formula (I) to a mammal (particularly a human) in need thereof.

The present invention provides a method of treating and/or preventing juvenile rheumatoid arthritis comprising the administration of an effective amount of a compound of formula (I) to a mammal (particularly a human) in need thereof.

The present invention provides a method of treating and/or preventing systemic lupus erythematosus comprising the administration of an effective amount of a compound of formula (I) to a mammal (particularly a human) in need thereof.

The present invention provides a method of treating and/or preventing osteoarthritis comprising the administration of an effective amount of a compound of formula (I) to a mammal (particularly a human) in need thereof.

The present invention provides a method of treating and/or preventing degenerative joint disease comprising the administration of an effective amount of a compound of formula (I) to a mammal (particularly a human) in need thereof.

The present invention provides a method of treating and/or preventing one or more connective tissue diseases comprising the administration of an effective amount of a compound of formula (I) to a mammal (particularly a human) in need thereof.

The present invention provides a method of treating and/or preventing ankylosing spondolytis comprising the administration of an effective amount of a compound of formula (I) to a mammal (particularly a human) in need thereof.

The present invention provides a method of treating and/or preventing bursitis comprising the administration of an effective amount of a compound of formula (I) to a mammal (particularly a human) in need thereof.

The present invention provides a method of treating and/or preventing Sjogren's syndrome comprising the administration of an effective amount of a compound of formula (I) to a mammal (particularly a human) in need thereof.

The present invention provides a method of treating and/or preventing psoriasis comprising the administration of an effective amount of a compound of formula (I) to a mammal (particularly a human) in need thereof.

The present invention provides a method of treating and/or preventing psoriatic arthritis comprising the administration of an effective amount of a compound of formula (I) to a mammal (particularly a human) in need thereof.

The present invention provides a method of treating and/or preventing neuralgia comprising the administration of an effective amount of a compound of formula (I) to a mammal (particularly a human) in need thereof.

The present invention provides a method of treating and/or preventing synovitis comprising the administration of an effective amount of a compound of formula (I) to a mammal (particularly a human) in need thereof.

The present invention provides a method of treating and/or preventing glomerulonephritis comprising the administration of an effective amount of a compound of formula (I) to a mammal (particularly a human) in need thereof.

The present invention provides a method of treating and/or preventing vasculitis or sarcoidosis comprising the administration of an effective amount of a compound of formula (I) to a mammal (particularly a human) in need thereof.

The present invention provides a method of treating and/or preventing Coeliac disease comprising the administration of an effective amount of a compound of formula (I) to a mammal (particularly a human) in need thereof.

The present invention provides a method of treating and/or preventing proctitis comprising the administration of an effective amount of a compound of formula (I) to a mammal (particularly a human) in need thereof.

The present invention provides a method of treating and/or preventing eosinopilic gastro-enteritis comprising the administration of an effective amount of a compound of formula (I) to a mammal (particularly a human) in need thereof.

The present invention provides a method of treating and/or preventing mastocytosis comprising the administration of an effective amount of a compound of formula (I) to a mammal (particularly a human) in need thereof.

The present invention provides a method of treating and/or preventing microscopic colitis comprising the administration of an effective amount of a compound of formula (I) to a mammal (particularly a human) in need thereof.

The present invention provides a method of treating and/or preventing indeterminant colitis comprising the administration of an effective amount of a compound of formula (I) to a mammal (particularly a human) in need thereof.

The present invention provides a method of treating and/or preventing irritable bowel disorder comprising the administration of an effective amount of a compound of formula (I) to a mammal (particularly a human) in need thereof.

The present invention provides a method of treating and/or preventing inflammatory bowel disease comprising the administration of an effective amount of a compound of formula (I) to a mammal (particularly a human) in need thereof.

The present invention provides a method of treating and/or preventing Crohn's disease comprising the administration of an effective amount of a compound of formula (I) to a mammal (particularly a human) in need thereof.

The present invention provides a method of treating and/or preventing ulcerative colitis comprising the administration of an effective amount of a compound of formula (I) to a mammal (particularly a human) in need thereof.

The present invention provides a method of treating and/or preventing irritable bowel syndrome comprising the administration of an effective amount of a compound of formula (I) to a mammal (particularly a human) in need thereof.

The present invention provides a method of treating and/or preventing the insulin resistance syndrome and/or metabolic disorders (as defined above) comprising the administration of a compound of formula (I) to a mammal (particularly a human) in need thereof.

The present invention provides a method of treating and/or preventing type 2 diabetes comprising the administration of an effective amount of a compound of formula (I) to a mammal (particularly a human) in need thereof.

The present invention provides a method of treating and/or preventing cardiovascular disease comprising the administration of an effective amount of a compound of formula (I) to a mammal (particularly a human) in need thereof.

The present invention provides a method of treating and/or preventing atherosclerosis comprising the administration of an effective amount of a compound of formula (I) to a mammal (particularly a human) in need thereof.

The present invention provides a method of treating and/or preventing hypercholesterolemia comprising the administration of an effective amount of a compound of formula (I) to a mammal (particularly a human) in need thereof.

The present invention provides a method of treating and/or preventing conditions associated with a need for improving reverse cholesterol transport comprising the administration of an effective amount of a compound of formula (I) to a mammal (particularly a human) in need thereof.

The present invention provides a method of treating and/or preventing conditions associated with a need for decreasing intestinal cholesterol absorption comprising the administration of an effective amount of a compound of formula (I) to a mammal (particularly a human) in need thereof.

The present invention provides a method of treating and/or preventing conditions associated with a need for increasing HDL-cholesterol levels comprising the administration of an effective amount of a compound of formula (I) to a mammal (particularly a human) in need thereof.

The present invention provides a method of treating and/or preventing conditions associated with a need for decreasing LDL-cholesterol levels comprising the administration of an effective amount of a compound of formula (I) to a mammal (particularly a human) in need thereof.

The present invention provides a method of treating and/or preventing inflammatory conditions comprising the administration of an effective amount of a compound of formula (I) to a mammal (particularly a human) in need thereof.

The present invention provides a method of treating and/or preventing Alzheimer's disease comprising the administration of an effective amount of a compound of formula (I) to a mammal (particularly a human) in need thereof.

The present invention provides a method of treating and/or preventing arteriosclerosis comprising the administration of an effective amount of a compound of formula (I) to a mammal (particularly a human) in need thereof.

The present invention provides a method of treating and/or preventing conditions associated with a need for improving HDL function comprising the administration of an effective amount of a compound of formula (I) to a mammal (particularly a human) in need thereof.

The present invention provides a method of treating and/or preventing hyperlipidemic conditions comprising the administration of an effective amount of a compound of formula (I) to a mammal (particularly a human) in need thereof.

The present invention provides a method of treating and/or preventing dyslipidemic conditions comprising the administration of an effective amount of a compound of formula (I) to a mammal (particularly a human) in need thereof.

The present invention provides a method of treating and/or preventing dyslipidemia comprising the administration of an effective amount of a compound of formula (I) to a mammal (particularly a human) in need thereof.

In a further aspect the present invention provides the use of a compound of formula (I) as a medicament.

In a further aspect the present invention provides the use of a compound of formula (I) in the manufacture of a medicament for the treatment and/or prophylaxis of rheumatoid arthritis.

In a further aspect the present invention provides the use of a compound of formula (I) in the manufacture of a medicament for the treatment and/or prophylaxis of juvenile rheumatoid arthritis.

In a further aspect the present invention provides the use of a compound of formula (I) in the manufacture of a medicament for the treatment and/or prophylaxis of systemic lupus erythematosus.

In a further aspect the present invention provides the use of a compound of formula (I) in the manufacture of a medicament for the treatment and/or prophylaxis of osteoarthritis.

In a further aspect the present invention provides the use of a compound of formula (I) in the manufacture of a medicament for the treatment and/or prophylaxis of degenerative joint disease.

In a further aspect the present invention provides the use of a compound of formula (I) in the manufacture of a medicament for the treatment and/or prophylaxis of one or more connective tissue diseases.

In a further aspect the present invention provides the use of a compound of formula (I) in the manufacture of a medicament for the treatment and/or prophylaxis of ankylosing spondolytis.

In a further aspect the present invention provides the use of a compound of formula (I) in the manufacture of a medicament for the treatment and/or prophylaxis of bursitis.

In a further aspect the present invention provides the use of a compound of formula (I) in the manufacture of a medicament for the treatment and/or prophylaxis of Sjogren's syndrome.

In a further aspect the present invention provides the use of a compound of formula (I) in the manufacture of a medicament for the treatment and/or prophylaxis of psoriasis. In a further aspect the present invention provides the use of a compound of formula (I) in the manufacture of a medicament for the treatment and/or prophylaxis of psoriatic arthritis.

In a further aspect the present invention provides the use of a compound of formula (I) in the manufacture of a medicament for the treatment and/or prophylaxis of neuralgia.

In a further aspect the present invention provides the use of a compound of formula (I) in the manufacture of a medicament for the treatment and/or prophylaxis of synovitis.

In a further aspect the present invention provides the use of a compound of formula (I) in the manufacture of a medicament for the treatment and/or prophylaxis of glomerulonephritis.

In a further aspect the present invention provides the use of a compound of formula (I) in the manufacture of a medicament for the treatment and/or prophylaxis of vasculitis or sarcoidosis.

In a further aspect the present invention provides the use of a compound of formula (I) in the manufacture of a medicament for the treatment and/or prophylaxis of Coeliac disease.

In a further aspect the present invention provides the use of a compound of formula (I) in the manufacture of a medicament for the treatment and/or prophylaxis of proctitis.

In a further aspect the present invention provides the use of a compound of formula (I) in the manufacture of a medicament for the treatment and/or prophylaxis of eosinopilic gastro-enteritis.

In a further aspect the present invention provides the use of a compound of formula (I) in the manufacture of a medicament for the treatment and/or prophylaxis of mastocytosis.

In a further aspect the present invention provides the use of a compound of formula (I) in the manufacture of a medicament for the treatment and/or prophylaxis of microscopic colitis.

In a further aspect the present invention provides the use of a compound of formula (I) in the manufacture of a medicament for the treatment and/or prophylaxis of indeterminant colitis.

In a further aspect the present invention provides the use of a compound of formula (I) in the manufacture of a medicament for the treatment and/or prophylaxis of irritable bowel disorder.

In a further aspect the present invention provides the use of a compound of formula (I) in the manufacture of a medicament for the treatment and/or prophylaxis of inflammatory bowel disease.

In a further aspect the present invention provides the use of a compound of formula (I) in the manufacture of a medicament for the treatment and/or prophylaxis of Crohn's disease.

In a further aspect the present invention provides the use of a compound of formula (I) in the manufacture of a medicament for the treatment and/or prophylaxis of ulcerative colitis.

In a further aspect the present invention provides the use of a compound of formula (I) in the manufacture of a medicament for the treatment and/or prophylaxis of irritable bowel syndrome.

In a further aspect the present invention provides the use of a compound of formula (I) in the manufacture of a medicament for the treatment and/or prophylaxis of dyslipidemic conditions.

In a further aspect the present invention provides the use of a compound of formula (I) in the manufacture of a medicament for the treatment and/or prophylaxis of insulin resistance and/or metabolic disorders.

In a further aspect the present invention provides the use of a compound of formula (I) in the manufacture of a medicament for the treatment and/or prophylaxis of cardiovascular disease.

In a further aspect the present invention provides the use of a compound of formula (I) in the manufacture of a medicament for the treatment and/or prophylaxis of atherosclerosis.

In a further aspect the present invention provides the use of a compound of formula (I) in the manufacture of a medicament for the treatment and/or prophylaxis of hypercholesterolemia.

In a further aspect the present invention provides the use of a compound of formula (I) in the manufacture of a medicament for the treatment and/or prophylaxis of conditions associated with a need for improving reverse cholesterol transport.

In a further aspect the present invention provides the use of a compound of formula (I) in the manufacture of a medicament for the treatment and/or prophylaxis of conditions associated with a need for decreasing intestinal cholesterol absorption.

In a further aspect the present invention provides the use of a compound of formula (I) in the manufacture of a medicament for the treatment and/or prophylaxis of conditions associated with a need for increasing HDL-cholesterol levels.

In a further aspect the present invention provides the use of a compound of formula (I) in the manufacture of a medicament for the treatment and/or prophylaxis of conditions associated with a need for decreasing LDL-cholesterol levels.

In a further aspect the present invention provides the use of a compound of formula (I) in the manufacture of a medicament for the treatment and/or prophylaxis of inflammatory conditions.

In a further aspect the present invention provides the use of a compound of formula (I) in the manufacture of a medicament for the treatment and/or prophylaxis of Alzheimer's disease.

In a further aspect the present invention provides the use of a compound of formula (I) in the manufacture of a medicament for the treatment and/or prophylaxis of arteriosclerosis.

In a further aspect the present invention provides the use of a compound of formula (I) in the manufacture of a medicament for the treatment and/or prophylaxis of type 2 diabetes.

In a further aspect the present invention provides the use of a compound of formula (I) in the manufacture of a medicament for the treatment and/or prophylaxis of conditions associated with a need for improving HDL function.

In a further aspect the present invention provides the use of a compound of formula (I) in the manufacture of a medicament for the treatment and/or prophylaxis of hyperlipidemic conditions.

In a further aspect the present invention provides the use of a compound of formula (I) in the manufacture of a medicament for the treatment and/or prophylaxis of dyslipidemia.

Combination Therapy

The compounds of the invention may be combined with another therapeutic agent that is useful in the treatment of disorders associated with the development and progress of atherosclerosis such as hypertension, hyperlipidaemias, dyslipidaemias, diabetes, inflammation and obesity. The compounds of the invention may be combined with another therapeutic agent that decreases the ratio of LDL:HDL or apoB:apoA-1 an agent that causes a decrease in circulating levels of LDL-cholesterol or apoB or triglycerides. In patients with diabetes mellitus the compounds of the invention may also be combined with therapeutic agents used to correct carbohydrate metabolism treat complications related to micro-angiopathies.

In another aspect of the present invention, the compound of formula (I), or a pharmaceutically acceptable salt or solvate thereof, or a solvate of such a salt, may be administered in association with cholesterol biosynthesis inhibitors, or pharmaceutically acceptable salts, solvates, solvates of such salts or prodrugs thereof. Suitable cholesterol biosynthesis inhibitors include HMG CoA reductase inhibitors, squalene synthesis inhibitors and squalene epoxidase inhibitors. Suitable squalene synthesis inhibitor are squalestatin 1, TAK-475, compounds described in WO2005012284 and a suitable squalene epoxidase inhibitor is NB-598.

In this aspect of the invention, the compound of formula (I), or a pharmaceutically acceptable salt or solvate thereof, or a solvate of such a salt, may be administered in association with an HMG CoA reductase inhibitor, or pharmaceutically acceptable salts, solvates, solvates of such salts or prodrugs thereof. Suitably the HMG CoA reductase inhibitor, or pharmaceutically acceptable salts, solvates, solvates of such salts or prodrugs thereof are statins well known in the art. Particular statins are selected from the group consisting of atorvastatin, fluvastatin, pitavastatin, lovastatin, mevastatin, nicostatin, nivastatin, pravastatin and simvastatin, or a pharmaceutically acceptable salt, especially sodium or calcium, solvate, solvate of such a salt or a prodrug thereof. A particular statin is atorvastatin, or a pharmaceutically acceptable salt, solvate, solvate of such a salt or a prodrug thereof. A more particular statin is atorvastatin calcium salt. A particularly preferred statin is, however, rosuvastatin, or a pharmaceutically acceptable salt, solvate, solvate of such a salt or a prodrug thereof. A preferable particular statin is rosuvastatin calcium salt.

In the present application, the term "cholesterol biosynthesis inhibitors" also includes chemical modifications of the UMG CoA reductase inhibitors, squalene synthesis inhibitors and squalene epoxidase inhibitors, such as esters, prodrugs and metabolites, whether active or inactive.

In another aspect of the present invention, the compound of formula (I), or a pharmaceutically acceptable salt or solvate thereof, or a solvate of such a salt, may be administered in association with an inhibitor of the ileal bile acid transport system (IBAT inhibitor), or pharmaceutically acceptable salts, solvates, solvates of such salts or prodrugs thereof. Suitable compounds possessing IBAT inhibitory activity have been described, see for instance the compounds described in WO 93/16055, WO 94/18183, WO 94/18184, WO 96/05188, WO 96/08484, WO 96/16051, WO 97/33882, WO 98/07449, WO 98/03818, WO 98/38182, WO 00/01687, WO 00/47568, WO 00/61568, WO 00/62810, WO 01/68906, DE 19825804, WO 00/38725, WO 00/38726, WO 00/38727, WO 00/38728, WO 00/38729, WO 01/68906, WO 01/66533, WO 02/32428, WO 02/50051, WO 03/040124, WO 03/040127, WO03/043992, WO03/061604, WO 04/020421, WO 04/076430, EP 864 582, EP 489 423, EP 549 967, EP 573 848, EP 624 593, EP 624 594, EP 624 595 and EP 624 596 and the contents of these patent applications are incorporated herein by reference.

Further suitable compounds possessing IBAT inhibitory activity have been described in WO 94/24087, WO 98/56757, WO 00/20392, WO 00/20393, WO 00/20410, WO 00/20437, WO 01/34570, WO 00/35889, WO 01/68637, WO 02/08211, WO 03/020710, WO 03/022825, WO 03/022830, WO 03/022286, WO 03/091232, WO 03/106482, JP 10072371, U.S. Pat. No. 5,070,103, EP 251 315, EP 417 725, EP 869 121, EP 1 070 703 and EP 597 107 and the contents of these patent applications are incorporated herein by reference.

Particular classes of IBAT inhibitors suitable for use in the present invention are benzothiazepines, and the compounds described in the claims, particularly claim 1, of WO 00/01687, WO 96/08484 and WO 97/33882 are incorporated herein by reference. Other suitable classes of IBAT inhibitors are the 1,2-benzothiazepines, 1,4-benzothiazepines and 1,5-benzothiazepines. A further suitable class of IBAT inhibitors is the 1,2,5-benzothiadiazepines.

One particular suitable compound possessing IBAT inhibitory activity is (3R,5R)-3-butyl-3-ethyl-1,1-dioxido-5-phenyl-2,3,4,5-tetrahydro-1,4-benzothiazepin-8-yl β-D-glucopyranosiduronic acid (EP 864 582). A further suitable compound possessing IBAT inhibitory activity is S-8921 (EP 597 107).

In another aspect of the present invention, the compound of formula (I), or a pharmaceutically acceptable salt or solvate thereof, or a solvate of such a salt, may be administered in association with a cholesterol absorption antagonist, or pharmaceutically acceptable salts, solvates, solvates of such salts or prodrugs thereof, for example AVE-5530 or for example azetidinones such as ezetrol (zetia, ezetimibe) and those described in U.S. Pat. No. 5,767,115 which are incorporated herein by reference. Suitable compounds possessing cholesterol absorption antagonist activity have been described, see for instance the compounds described in WO 02/50027, WO 02/66464, WO 04/005247, WO 04/000803, WO 04/000804, WO 04/000805, WO05021495, WO05021497 and WO05033100 which are incorporated herein by reference.

In another aspect of the present invention, the compound of formula (I), or a pharmaceutically acceptable salt or solvate thereof, or a solvate of such a salt, may be administered in association with a bile acid sequestrant or pharmaceutically acceptable salts, solvates, solvates of such salts or prodrugs thereof. Suitable bile acid sequestrants include HBS-107, cholestyramine (Questran®, LoCholest®), cholestemide (Cholebine®), colesevelam (Welcholo®), cholestipol (Colestid®) and cosevelam hydrochloride.

In another aspect of the present invention, the compound of formula (I), or a pharmaceutically acceptable salt or solvate thereof, or a solvate of such a salt, may be administered in association with other agents that increase reverse cholesterol transport by other means than increasing expression of ABC-transporters, e.g. ApoA-1 mimetica. See for instance the compounds described in WO-2004094471 which are incorporated herein by reference. Suitable apoA-1 mimetica include D-F4, ETC 216, ETC 642, RTC 588, ETC 1001, Apo A1 Milano, D-4F and AVP-26452.

In another aspect of the invention, the compound of formula (I), or a pharmaceutically acceptable salt or solvate thereof, or a solvate of such a salt, may be administered in association with a peroxisome proliferator-activated receptor (PPAR) modulating agent. PPAR modulating agents include a PPAR alpha and/or gamma and/or delta agonist, or pharmaceutically acceptable salts, solvates, solvates of such salts or prodrugs thereof. Suitable PPAR alpha and/or gamma and/or delta agonists, pharmaceutically acceptable salts, solvates, solvates of such salts or prodrugs thereof are well known in the art. These include the compounds described in WO 01/12187, WO 01/12612, WO 99/62870, WO 99/62872, WO 99/62871, WO 98/57941, WO 01/40170, WO 04/000790, WO 04/000295, WO 04/000294, WO 03/051822, WO 03/051821, WO 02/096863, WO 04/056748, WO 03/051826, WO 02/085844, WO 01/40172, J Med Chem, 1996, 39, 665, Expert Opinion on Therapeutic Patents, 10 (5), 623-634 (in particular the compounds described in the patent applications listed on page 634) and J Med Chem, 2000, 43, 527 which are all incorporated herein by reference. Particularly a PPAR alpha and/or gamma and/or delta agonist refers to muraglitazar (BMS 298585), rivoglitazone (CS-011), netoglitazone (MCC-555), balaglitazone (DRF-2593, NN-2344), clofibrate (Atromid-S®), fenofibrate, bezafibrate (Oralipin®), gemfibrozil (Lopido™), ciprofibrate (Ciprol®), pioglitazone (Actos®), rosiglitazone (Avandia®), AVE-0847, AVE-8134, CLX-0921, DRF-10945, DRF-4832, E-3030, K-111, KRP-101, LBM-642 (oxeglitazar), LY-518674, LY-674, naveglitazar (LY-818), LY-929, 641597, GW-590735, GW-677954, GW-501516, metaglidasan (MBX-102), MBX-2044, ONO-5129, PLX-204, R-483 (BM131258), R-119702, T-131 (AMG-131), TAK-559 or TAK-654. Particularly a PPAR alpha and/or gamma and/or delta agonist refers to tesaglitazar ((S)-2-ethoxy-3-[4-(2-{4-methanesulphonyl-oxyphenyl}ethoxy)phenyl]propanoic acid) and pharmaceutically acceptable salts thereof.

In yet another aspect of the invention, the compound of formula (I), or a pharmaceutically acceptable salt or solvate thereof, or a solvate of such a salt, may be administered in association with a pyruvate dehydrogenase kinase (PDK) inhibitor, or a pharmaceutically acceptable salt, solvate, solvate of such a salt or a prodrug thereof.

In another aspect of the invention, the compound of formula (I), or a pharmaceutically acceptable salt or solvate thereof, or a solvate of such a salt, may be administered in association with a cholesteryl ester transfer protein (CETP) inhibitor, or pharmaceutically acceptable salts, solvates, solvates of such salts or prodrugs thereof, for example JTT-705, torcetrapib (CP-529414) and those referenced and described in WO 00/38725 page 7 line 22-page 10, line 17 which are incorporated herein by reference.

In another aspect of the invention, the compound of formula (I), or a pharmaceutically acceptable salt or solvate thereof, or a solvate of such a salt, may be administered in association with a microsomal-triglyceride transfer protein (MTP) inhibitor, or pharmaceutically acceptable salts, solvates, solvates of such salts or prodrugs thereof, for example implipatide, CP-346086, JTT-130 and those described in WO 03/004020, WO 03/002533, WO 02/083658 and WO 00/242291, and the contents of these patent applications are incorporated herein by reference, or those described in Science, 282, 751-54, 1998 which are incorporated herein by reference.

In another aspect of the invention, the compound of formula (I), or a pharmaceutically acceptable salt or solvate thereof, or a solvate of such a salt, may be administered in association with an agonist to the receptor HM74A (nicotinic acid receptor). Examples of HM74A agonists are e.g. compounds described in WO2005011677, WO2004032928, WO2004033431 or a nicotinic acid derivative, or pharmaceutically acceptable salts, solvates, solvates of such salts or prodrugs thereof, including slow release and combination products, for example, nicotinic acid (niacin), acipimox, nicofuranose, NIASPAN® and niceritrol.

In another aspect of the invention, the compound of formula (I), or a pharmaceutically acceptable salt or solvate thereof, or a solvate of such a salt, may be administered in association with a acyl coenzymA: cholesterol O-acyltransferase (ACAT) inhibitor, or ACAT2 or pharmaceutically acceptable salts, solvates, solvates of such salts or prodrugs thereof, for example CS-505, eflucimibe (F-12511), K-604 and SMP-797.

In yet another aspect of the invention, the compound of formula (I) or a pharmaceutically acceptable salt or solvate thereof, or a solvate of such a salt, may be administered in association with modulators of nuclear hormone receptors such as farnesoid X receptor (FXR), or pharmaceutically acceptable salt, solvate, solvate of such a salt or a prodrug thereof for example INT-747, or modulators of nuclear receptors such as retenoid X receptor (RXR), or a pharmaceutically acceptable salt, solvate, solvate of such a salt or a prodrug thereof.

In another aspect of the invention, the compound of formula (I), or a pharmaceutically acceptable salt or solvate thereof, or a solvate of such a salt, may be administered in association with a phytosterol compound, or pharmaceutically acceptable salts, solvates, solvates of such salts or prodrugs thereof, for example stanols and FM-VP4.

In another aspect of the invention, the compound of formula (I), or a pharmaceutically acceptable salt or solvate thereof, or a solvate of such a salt, may be administered in association with other therapies for the treatment of metabolic syndrome or type 2 diabetes and its associated complications, these include biguanide drugs, for example metformin, phenformin and buformin, insulin (synthetic insulin analogues, amylin) and oral antihyperglycemics (these are divided into prandial glucose regulators and alpha-glucosidase inhibitors). An example of an alpha-glucosidase inhibitor is acarbose or voglibose or miglitol. An example of a prandial glucose regulator is repaglinide or nateglinide.

In another aspect of the invention, the compound of formula (I), or a pharmaceutically acceptable salt or solvate thereof, or a solvate of such a salt, may be administered in association with a sulfonylurea for example: glimepiride, glibenclamide (glyburide), gliclazide, glipizide, gliquidone, chloropropamide, tolbutamide, acetohexamide, glycopyramide, carbutamide, glibonuride, glisoxepid, glybuthiazole, glibuzole, glyhexamide, glymiidine, glypinamide, phenbutamide, tolcylamide and tolazamide. Preferably the sulfonylurea is glimepiride or glibenclamide (glyburide). More preferably the sulfonylurea is glimepiride. Therefore the present invention includes administration of a compound of the present invention in conjunction with one, two or more existing therapies described in this paragraph. The doses of the other existing therapies for the treatment of type 2 diabetes and its associated complications will be those known in the art and approved for use by regulatory bodies for example the FDA and may be found in the Orange Book published by the FDA. Alternatively smaller doses may be used as a result of the benefits derived from the combination.

In another aspect of the invention, the compound of formula (I), or a pharmaceutically acceptable salt or solvate thereof, or a solvate of such a salt, may be administered in association with an antihypertensive compound for example althiazide, benzthiazide, captopril, carvedilol, chlorothiazide sodium, clonidine hydrochloride, cyclothiazide, delapril hydrochloride, dilevalol hydrochloride, doxazosin mesylate, fosinopril sodium, guanfacine hydrochloride, methyldopa, metoprolol succinate, moexipril hydrochloride, monatepil maleate, pelanserin hydrochloride, phenoxybenzemine hydrochloride, prazosin hydrochloride, primidolol, quinapril hydrochloride, quinaprilat, ramipril, terazosin hydrochloride, candesartan, candesartan cilexetil, telmisartan, amlodipine besylate, amlodipine maleate and bevantolol hydrochloride, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an angiotensin converting enzyme (ACE) inhibitor. Particular ACE inhibitors or pharmaceutically acceptable salts, solvates, solvate of such salts or prodrugs thereof, including active metabolites, which can be used in combination with a compound of formula (I) include but are not limited to, the following compounds: alacepril, alatriopril, ancovenin, benazepril, benazepril hydrochloride, benazeprilat, benzoylcaptopril, captopril, captopril-cysteine, captopril-glutathione, ceranopril, cilazapril, cilazaprilat, delapril, delapril-diacid, enalapril, enalaprilat, enapril, epicaptopril, foroxymithine, fosfenopril, fosenopril, fosenopril sodium, fosinopril, fosinopril sodium, fosinoprilat, fosinoprilic acid, hemorphin-4, imidapril, indolapril, indolaprilat, lisinopril, lyciumin A, lyciumin B, moexipril, moexiprilat, muracein A, muracein B, muracein C, pentopril, perindopril, perindoprilat, pivalopril, pivopril, quinapril, quinapril hydrochloride, quinaprilat, ramipril, ramiprilat, spirapril, spirapril hydrochloride, spiraprilat, spiropril, spiropril hydrochloride, temocapril, temocaptil hydrochloride, teprotide, trandolapril, trandolaprilat, zofenopril and zofenoprilat. Preferred ACE inhibitors are ramipril, ramiprilat, lisinopril, enalapril and enalaprilat. More preferred ACE inhibitors are ramipril and ramiprilat.

In another aspect of the invention, the compound of formula (I), or a pharmaceutically acceptable salt or solvate thereof, or a solvate of such a salt, may be administered in association with an angiotensin II receptor antagonist. Preferred angiotensin II receptor antagonists, pharmaceutically acceptable salts, solvates, solvate of such salts or a prodrugs thereof for use in combination with a compound of formula (I) include, but are not limited to, compounds: candesartan, candesartan cilexetil, losartan, valsartan, irbesartan, telmisartan and eprosartan. Particularly preferred angiotensin II receptor antagonists or pharmaceutically acceptable derivatives thereof are candesartan and candesartan cilexetil, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an andrenergic blocker. Andrenergic blocker include an alpha andrenergic blocker, or a beta andrenergic blocker, or a mixed alpha/beta andrenergic blocker or pharmaceutically acceptable salts, solvates, solvates of such salts or prodrugs thereof. Examples of andrenergic blockers are bretylium tosylate, dihydroergotamine so mesylate, phentolamine mesylate, solypertine tartrate, zolertine hydrochloride, carvedilol, labetalol hydrochloride, fenspiride hydrochloride, labetalol hydrochloride, proroxan, alfuzosin hydrochloride, acebutolol, acebutolol hydrochloride, alprenolol hydrochloride, atenolol, bunolol hydrochloride, carteolol hydrochloride, celiprolol hydrochloride, cetamolol hydrochloride, cicloprolol hydrochloride, dexpropranolol hydrochloride, diacetolol hydrochloride, dilevalol hydrochloride, esmolol hydrochloride, exaprolol hydrochloride, flestolol sulfate, labetalol hydrochloride, levobetaxolol hydrochloride, levobunolol hydrochloride, metalol hydrochloride, metoprolol, metoprolol tartrate, nadolol, pamatolol sulfate, penbutolol sulfate, practolol, propranolol hydrochloride, sotalol hydrochloride, timolol, timolol maleate, tiprenolol hydrochloride, tolamolol, bisoprolol, bisoprolol fumarate and nebivolol or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an andrenergic stimulant for example combination product of chlorothiazide and methyldopa, the combination product of methyldopa hydrochlorothiazide and methyldopa, clonidine hydrochloride, clonidine, the combination product of chlorthalidone and clonidine hydrochloride and guanfacine hydrochloride, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with calcium channel blocker for example clentiazem maleate, amlodipine besylate, isradipine, nimodipine, felodipine, nilvadipine, nifedipine, teludipine hydrochloride, diltiazem hydrochloride, belfosdil, verapamil hydrochloride or fostedil, or an AT-1 blocker, or a saluretic, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a diuretic for example the combination product of hydrochlorothiazide and spironolactone and the combination product of hydrochlorothiazide and triamterene, or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a vasodilator for example coronary vasodilators (for example fostedil, azaclorzine hydrochloride, chromonar hydrochloride, clonitrate, diltiazem hydrochloride, dipyridamole, droprenilamine, erythrityl tetranitrate, isosorbide dinitrate, isosorbide mononitrate, lidoflazine, mioflazine hydrochloride, mixidine, molsidomine, nicorandil, nifedipine, nisoldipine, nitroglycerine, oxprenolol hydrochloride, pentrinitrol, perhexyline maleate, prenylamine, propatyl nitrate, terodiline hydrochloride, tolamolol and verapamil), or pharmaceutically acceptable salts, solvates, solvates of such salts or prodrugs thereof. In another aspect of the invention, the compound of formula (I), or a pharmaceutically acceptable salt or solvate thereof, or a solvate of such a salt, may be administered in association with a anti-anginal agents for example amlodipine besylate, amlodipine maleate, betaxolol hydrochloride, bevantolol hydrochloride, butoprozine hydrochloride, carvedilol, cinepazet maleate, metoprolol succinate, molsidomine, monatepil maleate, primidolol, ranolazine hydrochloride, tosifen or verapamil hydrochloride or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an anti-coagulants selected from argatroban, bivalirudin, dalteparin sodium, desirudin, dicumarol, lyapolate sodium, nafamostat mesylate, phenprocoumon, tinzaparin sodium and warfarin sodium or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an antithrombotic agents for example anagrelide hydrochloride, bivalirudin, cilostazol, dalteparin sodium, danaparoid sodium, dazoxiben hydrochloride, efegatran sulfate, enoxaparin sodium, fluretofen, ifetroban, ifetroban sodium, lamifiban, lotrafiban hydrochloride, napsagatran, orbofiban acetate, roxifiban acetate, sibrafiban, tinzaparin sodium, trifenagrel, abciximab and zolimomab alitox or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with other agents that act as or deliver a Factor IIa agonist for example 3DP-4815, AZD-0837, melagatran, ximelagatran, ART-123, lepirudin, AVE-5026, bivaluridin, dabigatran etexilate, E-4444, odiparcil, ardeparin sodium, pegmusirudin, LB-30870, dermatan sulfate, argatroban, MCC-977, desirudin, deligoparin sodium, PGX-100, idraparinux sodium, SR-123781, SSR-182289A, SCH-530348, TRIB50, TGN-167, TGN-255, and compounds described in WO94/29336, WO97/23499 and WO02/44145, which are incorporated hereby by reference.

In another aspect of the invention, the compound of formula (I), or a pharmaceutically acceptable salt or solvate thereof, or a solvate of such a salt, may be administered in association with a fibrinogen receptor antagonists for example roxifiban acetate, fradafiban, orbofiban, lotrafiban hydrochloride, tirofiban, xemilofiban, monoclonal antibody 7E3 and sibrafiban or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a platelet inhibitors for example cilostezol, clopidogrel bisulfate, epoprostenol, epoprostenol sodium, ticlopidine hydrochloride, aspirin, ibuprofen, naproxen, sulindae, indomethacin, mefenamate, droxicam, diclofenac, sulfinpyrazone and piroxicam, dipyridamole or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a platelet aggregation inhibitors for example acadesine, beraprost, beraprost sodium, ciprostene calcium, itezigrel, lifarizine, lotrafiban hydrochloride, orbofiban acetate, oxagrelate, fradafiban, orbofiban, tirofiban and xemilofiban or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a hemorrheologic agents for example pentoxifylline or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with lipoprotein associated coagulation inhibitors; or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a Factor VIIa inhibitor or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a Factor Xa inhibitor or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with a low molecular weight heparin for example enoxaparin, nardroparin, dalteparin, certroparin, parnaparin, reviparin and tinzaparin or pharmaceutically acceptable salts, solvates, solvates of such salts or prodrugs thereof.

In another aspect of the invention, the compound of formula (I), or a pharmaceutically acceptable salt or solvate thereof, or a solvate of such a salt, may be administered in association with an anti-obesity compound, or pharmaceutically acceptable salts, solvates, solvates of such salts or prodrugs thereof, for example a pancreatic lipase inhibitor e.g. orlistat (EP 129,748), ATL-962, GT-389255 or an appetite (satiety) controlling substance for example sibutramine (Meridia®, Reductil®, GB 2,184,122 and U.S. Pat. No. 4,929,629), PYY 3-36 (amylin), APD-356, 1426, Axokine, T-71, a cannabinoid 1 (CB1) antagonist or inverse agonist, or pharmaceutically acceptable salts, solvates, solvates of such salts or prodrugs thereof, for example rimonabant (EP 656354), AVE-1625, CP945598, SR-147778, SLV-319, and as described in WO01/70700, or a Fatty Acid Synthesis (FAS) inhibitor, or pharmaceutically acceptable salts, solvates, solvates of such salts or prodrugs thereof or a melanin concentrating hormone (MCH) antagonist, or pharmaceutically acceptable salts, solvates, solvates of such salts or prodrugs thereof, for example 856464 and as described in WO 04/004726.

In another aspect of the invention, the compounds of formula (I), or a pharmaceutically acceptable salt or solvate thereof, or a solvate of such a salt, may be administrated in association with an anti-inflammatory agent such as glucocorticoids, non-steroidal anti-inflammatory agents (NSAID) or intestinal anti-inflammatory agents, or pharmaceutically acceptable salts, solvates, solvates of such salts or prodrugs thereof. Suitable glucocorticoids will include, but will not be limited to betametason, dexametason, methyl prednisolon, prednisolon, prednison, triamcinolon, hydrocortison, cortison and budesonid. Suitable non-steroidal anti-inflammatory agents will include, but will not be limited to indometacin, diclofenac, ibuprofen as well as acetylsalicylic acid. Suitable intestinal anti-inflammatory agents will include, but will not be limited to amino salicylates such as sulfasalazin, mesalazin, olsalazin and balsalazid.

In another aspect of the invention, the compounds of formula (I), or a pharmaceutically acceptable salt or solvate thereof, or a solvate of such a salt, may be administrated in association with a cholinesterase inhibitor or an N-methyl-D-aspartate (NMDA) receptor antagonist, or pharmaceutically acceptable salts, solvates, solvates of such salts or prodrugs thereof, such as donepezil, rivastigmin or galantamin or memantin.

Therefore in an additional feature of the invention, there is provided a method of treating and/or preventing metabolic disorders in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section or a pharmaceutically acceptable salt, solvate, solvate of such a salt or a prodrug thereof.

Therefore in an additional feature of the invention, there is provided a method for the treatment and/or prophylaxis of type 2 diabetes and its associated complications in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

Therefore in an additional feature of the invention, there is provided a method of treating and/or preventing hyperlipidemic conditions in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section or a pharmaceutically acceptable salt, solvate, solvate of such a salt or a prodrug thereof.

In an additional feature of the invention, there is provided a method for the treatment and/or prophylaxis of dyslipidemia in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of the insulin resistance syndrome in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of cardiovascular disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of atherosclerosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of hypercholesterolemia in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for improving reverse cholesterol transport in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for decreasing intestinal cholesterol absorption in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for increasing HDL-cholesterol levels in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for decreasing LDL-cholesterol levels in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of inflammatory conditions in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of Alzheimer's disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of arteriosclerosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for treating and/or preventing conditions associated with a need for improving HDL function in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of rheumatoid arthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of juvenile rheumatoid arthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of systemic lupus erythematosus in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of osteoarthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of degenerative joint disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of one or more connective tissue diseases in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of ankylosing spondolytis in a warm-blooded animal, such as man, in need of such treatment which comprises administering to said animal an effective amount of a compound of formula (V), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of bursitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of Sjogren's syndrome in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of psoriasis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of psoriatic arthritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of neuralgia in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of synovitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of glomerulonephritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of vasculitis or sarcoidosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of Coeliac disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of proctitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of eosinopilic gastro-enteritis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of mastocytosis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of microscopic colitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of indeterminant colitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of irritable bowel disorder in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of inflammatory bowel disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of Crohn's disease in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of ulcerative colitis in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of irritable bowel syndrome in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

In an additional feature of the invention, there is provided a method for the treatment and/or prophylaxis of dyslipidemic conditions in a warm-blooded animal, such as man, in need of such treatment which comprises administering to said animal an effective amount of a compound of formula (I), or a pharmaceutically acceptable salt or solvate thereof, or a solvate of such a salt, in simultaneous, sequential or separate administration with an effective amount of one of the other compounds described in this combination section, or a pharmaceutically acceptable salt, solvate, solvate of such a salt or a prodrug thereof.

According to a further aspect of the invention there is provided a pharmaceutical composition which comprises a compound of formula (I), or a pharmaceutically acceptable salt or solvate thereof, or a solvate of such a salt, and one of the other compounds described in this combination section or a pharmaceutically acceptable salt, solvate, solvate of such a salt or a prodrug thereof, in association with a pharmaceutically acceptable diluent or carrier.

According to a further aspect of the present invention there is provided a kit comprising a compound of formula (I), or a pharmaceutically acceptable salt or solvate thereof, or a solvate of such a salt, and one of the other compounds described in this combination section or a pharmaceutically acceptable salt, solvate, solvate of such a salt or a prodrug thereof.

According to a further aspect of the present invention there is provided a kit comprising:
a) a compound of formula (I), or a pharmaceutically acceptable salt or solvate thereof, or a solvate of such a salt, in a first unit dosage form;
b) one of the other compounds described in this combination section or a pharmaceutically acceptable salt, solvate, solvate of such a salt or a prodrug thereof; in a second unit dosage form; and
c) container means for containing said first and second dosage forms.

According to a further aspect of the present invention there is provided a kit comprising:
a) a compound of formula (I), or a pharmaceutically acceptable salt or solvate thereof, or a solvate of such a salt, together with a pharmaceutically acceptable diluent or carrier, in a first unit dosage form;
b) one of the other compounds described in this combination section or a pharmaceutically acceptable salt, solvate, solvate of such a salt or a prodrug thereof, in a second unit dosage form; and
c) container means for containing said first and second dosage forms.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of metabolic disorders and its associated complications in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of metabolic syndrome or type 2 diabetes and its associated complications in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of dyslipidemia in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of hyperlipidaemic conditions in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of cardiovascular disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of atherosclerosis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of hypercholesterolemia in a warm-blooded animal, such as man.

According to another feature of the invention there is provided the use of a compound of the formula (a), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for improving reverse cholesterol transport in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for decreasing intestinal cholesterol absorption in a warm-blooded animal, such as man.

According to another feature of the invention there is provided the use of a compound of the formula (I), of such or a pharmaceutically acceptable salt or solvate thereof, or a solvate a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for increasing HDL-cholesterol levels in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for decreasing LDL-cholesterol levels in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of inflammatory conditions in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Alzheimer's disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of arteriosclerosis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of a conditions associated with a need for improving HDL function in a warm-blooded animal, such as man.

According to another feature of the invention there is provided the use of a compound of the formula (a), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of rheumatoid arthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of juvenile rheumatoid arthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of systemic lupus erythematosus in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of osteoarthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis degenerative joint disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of one or more connective tissue diseases in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of ankylosing spondolytis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of bursitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Sjogren's syndrome in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of psoriasis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of psoriatic arthritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of neuralgia in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of synovitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of glomerulonephritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of vasculitis or sarcoidosis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Coeliac disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of proctitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of eosinopilic gastro-enteritis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of mastocytosis in a warm-blooded animal, such as man.

According to another feature of the invention there is provided the use of a compound of the formula (V), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of microscopic colitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of indeterminant colitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of irritable bowel disorder in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of inflammatory bowel disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of Crohn's disease in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of ulcerative colitis in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of irritable bowel syndrome in a warm-blooded animal, such as man.

According to another feature of the invention there is provided the use of a compound of the formula (I), or a pharmaceutically acceptable salt or solvate thereof, or a solvate of such a salt, and one of the other compounds described in this combination section, or a pharmaceutically acceptable salt, solvate, solvate of such a salt or a prodrug thereof, in the manufacture of a medicament for use in the treatment and/or prophylaxis of dyslipidemic conditions in a warm-blooded animal, such as man.

According to a further aspect of the present invention there is provided a combination treatment comprising the administration of an effective amount of a compound of the formula (I), or a pharmaceutically acceptable salt or solvate thereof, or a solvate of such a salt, optionally together with a pharmaceutically acceptable diluent or carrier, with the simultaneous, sequential or separate administration of an effective amount of one of the other compounds described in this combination section, or a pharmaceutically acceptable salt, solvate, solvate of such a salt or a prodrug thereof, optionally together with a pharmaceutically acceptable diluent or carrier to a warm-blooded animal, such as man in need of such therapeutic treatment.

Further Aspects of the Invention

Further aspect 1. A compound of general formula I

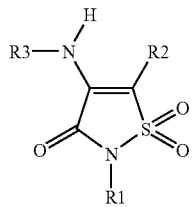

or a pharmaceutically acceptable salt or solvate thereof, or a solvate of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$;

cycloalkyl or heterocyclyl each optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$ or $NR^aC(O)NR^aR^a$;

phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

cycloalkylY or heterocyclylY wherein cycloalkyl or heterocyclyl each optionally is substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

phenylY or heteroarylY wherein phenyl or heteroaryl each optionally is substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$; C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

R$^2$ represents phenyl which is optionally substituted by one or more of the following: halogen (Cl, F, I, Br), OH, CN, NO$_2$, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R$^3$ represents

X which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$ or NR$^a$C(O)NR$^a$R$^a$;

MP or Het$^3$P wherein M and Het$^3$ each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het$^3$ each optionally is substituted on the aromatic ring by one or more of the following: halogen (Cl, F, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

AP or Het$^5$P wherein A and Het$^5$ each optionally is substituted by one or more of the following: halogen (F, Cl, Br, I), OH, CN, NO$_2$, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

E or Het$^4$ each optionally substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following: halogen (F, Cl, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

and in the above definitions

X represents a straight or branched, saturated or unsaturated alkyl group having 1 to 6 carbon atoms wherein said alkyl group may optionally be interrupted by O, S, S(O), SO$_2$, C(O), NR$^a$, OC(O), C(O)O, NR$^a$C(O), C(O)NR$^a$, SO$_2$NR$^a$ or NR$^a$SO$_2$;

Y binds to nitrogen in 2-position in the isothiazol-3(2H)-one 1,1-dioxide and represents a straight or branched, saturated or unsaturated alkyl group having 1 to 3 carbon atoms wherein said alkyl group may optionally be interrupted or ended by O, S, S(O), SO$_2$, C(O), OC(O), C(O)O, NR$^c$C(O), C(O)NR$^c$, NR$^c$ and/or Y is optionally substituted by one or more of the following: OH, F, CN, NR$^a$R$^a$, C$_1$-C$_4$alkyl, OR$^b$, SR$^b$, S(O)R$^b$ or SO$_2$R$^b$;

Z binds to E or Het$^4$ and one of the following: Q, Het$^1$, R or Het$^2$, and represents a straight or branched, saturated or unsaturated alkyl group having 1 to 6 carbon atoms wherein said alkyl group may optionally be interrupted or ended by O, S, S(O), SO$_2$, C(O), OC(O), C(O)O, NR$^a$C(O), C(O)NR$^a$, NR$^a$, SO$_2$NR$^a$, NR$^a$SO$_2$, optionally consists only of one of the following: O, S, S(O), SO$_2$, C(O), OC(O), C(O)O, NR$^a$C(O), C(O)NR$^a$, NR$^a$, SO$_2$NR$^a$, NR$^a$SO$_2$ and/or Z is optionally substituted by one or more of the following: OH, F, CN, NR$^c$R$^c$, C(O)R$^c$, OR$^b$, SR$^c$, S(O)R$^c$, SO$_2$R$^c$, phenyl, phenylC$_1$-C$_3$alkyl, or C$_1$-C$_4$alkyl which is optionally substituted by one or more of the following: F, OH, NR$^a$R$^a$, SR$^b$, S(O)R$^b$, SO$_2$R$^b$, OR$^b$;

M represents a saturated or unsaturated non-aromatic monocyclic ring composed of 3, 4, 5, 6, 7 or 8 carbon atoms or a saturated or unsaturated non-aromatic or partly aromatic bicyclic ring composed of 4, 5, 6, 7, 8, 9 or 10 carbon atoms;

E represents a saturated or unsaturated non-aromatic monocyclic ring composed of 3, 4, 5, 6, 7 or 8 carbon atoms or a saturated or unsaturated non-aromatic or partly aromatic bicyclic ring composed of 4, 5, 6, 7, 8, 9 or 10 carbon atoms, and the ring binds, unless otherwise specified, through its non-aromatic part to nitrogen in 4-position on the isothiazol-3(2H)-one 1,1-dioxide;

A represents an aromatic monocyclic ring composed of 3, 4, 5, 6, 7 or 8 carbon atoms or an aromatic bicyclic ring composed of 4, 5, 6, 7, 8, 9 or 10 carbon atoms;

P binds to nitrogen in 4-position on the isothiazol-3(2H)-one 1,1-dioxide and represents a straight or branched, saturated or unsaturated alkyl group having 1 to 6 carbon atoms wherein the alkyl group is optionally interrupted or ended by O, $NR^a$, S, S(O), $SO_2$, C(O), OC(O), C(O)O, $NR^aC(O)$, $C(O)NR^a$, $SO_2NR^a$, $NR^aSO_2$ and/or P is optionally substituted by one or more of the following: F, OH, CN, $NR^aR^a$, $C(O)R^c$, $OR^b$, $SR^b$, $S(O)R^b$, $SO_2R^b$, phenyl, phenyl$C_1$-$C_3$alkyl, or $C_1$-$C_4$alkyl which is optionally substituted by one or more of the following: F, OH, $NR^aR^a$, $SR^b$, $S(O)R^b$, $SO_2R^b$ or $OR^b$;

Q represents a saturated or unsaturated non-aromatic monocyclic ring composed of 3, 4, 5, 6, 7, 8 carbon atoms, which is optionally substituted by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

R represents a phenyl group which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)$—$OR^b$, $OC(O)NR^aR^a$ or $NR^aC(O)NR^aR^a$;

T binds to M, $Het^3$, A or $Het^5$ and represents an alkyl group having 1 carbon atom or optionally consists of one or more of the following: O, $NR^a$, S, S(O), $SO_2$, C(O), OC(O), C(O)O, $NR^aC(O)$, $C(O)NR^a$, $SO_2NR^a$ or $NR^aSO_2$;

$Het^1$ represents a saturated or unsaturated non-aromatic 3-10 membered monocyclic ring in which one or more of the atoms in the ring is an element other than carbon, for example nitrogen, oxygen or sulfur, and wherein the ring optionally is substituted by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(d)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$Het^2$ represents an aromatic 3-10 membered monocyclic ring in which one or more of the atoms in the ring is an element other than carbon, for example nitrogen, oxygen and sulfur, and which is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$;

$Het^3$ represents a saturated or unsaturated non-aromatic 3-10 membered monocyclic ring or a saturated or unsaturated non-aromatic or partly aromatic 4-10 membered bicyclic ring in which one or more of the atoms in the monocyclic or bicyclic ring is an element other than carbon, for example nitrogen, oxygen or sulfur;

$Het^4$ represents a saturated or unsaturated non-aromatic 3-10 membered monocyclic ring or a saturated or unsaturated non-aromatic or partly aromatic 4-10 membered bicyclic ring in which one or more of the atoms in the monocyclic or bicyclic ring is an element other than carbon, for example nitrogen, oxygen or sulfur, and the ring binds, unless otherwise specified, through its non-aromatic part to nitrogen in 4-position on the isothiazol-3(2H)-one 1,1-dioxide;

$Het^5$ represents an aromatic 3-10 membered monocyclic ring or an aromatic 4-10 membered bicyclic ring in which one or more of the atoms in the monocyclic or bicyclic ring is an element other than carbon, for example nitrogen, oxygen or sulfur;

$R^a$ independently represents H or a straight or branched, saturated or unsaturated $C_1$-$C_4$alkyl chain optionally substituted by one or more F;

$R^b$ independently represents a straight or branched, saturated or unsaturated $C_1$-$C_4$alkyl chain optionally substituted by one or more F; and $R^c$ independently represents H or a straight or branched, saturated or unsaturated $C_1$-$C_3$alkyl chain optionally substituted by one or more F.

Further aspect 2. A compound according to further aspect 1 or a pharmaceutically acceptable salt or solvate thereof, or a solvate of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$;

cycloalkyl or heterocyclyl each optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$; phenyl or heteroaryl each optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl optionally substituted by one or more of the following: F, OH, CN, $NR^aR^a$, $OR^b$, $SR^b$, $S(O)R^b$, $SO_2R^b$, $C(O)R^b$;

cycloalkylY or heterocyclylY wherein cycloalkyl or heterocyclyl each optionally is substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$;

phenylY or heteroarylY wherein phenyl or heteroaryl each optionally is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$;

$R^2$ represents phenyl which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$.

Further aspect 3. A compound according to further aspect 2 or a pharmaceutically acceptable salt or solvate thereof, or a solvate of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$.

Further aspect 4. A compound according to further aspect 3 or a pharmaceutically acceptable salt or solvate thereof, or a solvate of such a salt, wherein $R^1$ represents X which is optionally substituted by one or more of the following: F, OH, CN, $NR^aR^a$, $OR^b$, $SR^b$, $S(O)R^b$, $SO_2R^b$, $C(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$ or $C(O)R^b$.

Further aspect 5. A compound according to further aspect 1 or a pharmaceutically acceptable salt or solvate thereof, or a solvate of such a salt, wherein $R^3$ represents X which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$.

Further aspect 6. A compound according to further aspect 1 or a pharmaceutically acceptable salt or solvate thereof, or a solvate of such a salt, wherein $R^3$ represents MP or $Het^3P$ wherein M and $Het^3$ each optionally is substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following: halogen (Cl, F, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, $Het^1$, $Het^1T$, R, RT, $Het^2$, $Het^2T$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

AP or $Het^5P$ wherein A and $Het^5$ each optionally is substituted by one or more of the following: halogen (F, Cl, Br, I), OH, CN, $NO_2$, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^b$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

Further aspect 7. A compound according to further aspect 1 or a pharmaceutically acceptable salt or solvate thereof, or a solvate of such a salt, wherein $R^3$ represents E or $Het^4$ each optionally substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QZ, $Het^1$, $Het^1Z$, R, RZ, $Het^2$, $Het^2Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)R^a$, $SO_2NR^aR^a$, $NR^aSO_2R^b$, $NR^aC(O)OR^b$, a $NR^aC(O)NR^aR^a$, and E or $Het^4$ each optionally is substituted on the aromatic ring by one or more of the following: halogen (F, Cl, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1Z$, R, RZ, $Het^2$, $Het^2Z$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

Further aspect 8. A compound according to further aspect 2 or a pharmaceutically acceptable salt or solvate thereof, or a solvate of such a salt, wherein $R^3$ represents X which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$.

Further aspect 9. A compound according to further aspect 2 or a pharmaceutically acceptable salt or solvate thereof, or a solvate of such a salt, wherein $R^3$ represents MP or $Het^3$P wherein M and $Het^3$ each optionally is substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, $Het^1$T, R, RT, $Het^2$, $Het^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following: halogen (Cl, F, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)O$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, $Het^1$, $Het^1$T, R, RT, $Het^2$, $Het^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

AP or $Het^5$P wherein A and $Het^5$ each optionally is substituted by one or more of the following: halogen (F, Cl, Br, I), OH, CN, $NO_2$, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, $Het^1$, $Het^1$T, R, RT, $Het^2$, $Het^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

Further aspect 10. A compound according to further aspect 2 or a pharmaceutically acceptable salt or solvate thereof, or a solvate of such a salt, wherein $R^3$ represents E or $Het^4$ each optionally substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QZ, $Het^1$, $Het^1$Z, R, RZ, $Het^2$, $Het^2$Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2 NR^aR^a$, $NR^aSO_2R^b$, $NR^aC(O)OR^b$, $OC(O)NR^aR^a$ or $NR^aC(O)NR^aR^a$, and E or $Het^4$ each optionally is substituted on the aromatic ring by one or more of the following: halogen (F, Cl, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1$Z, R, RZ, $Het^2$, $Het^2$Z, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC$ $(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

Further aspect 11. A compound according to further aspect 3 or a pharmaceutically acceptable salt or solvate thereof, or a solvate of such a salt, wherein $R^3$ represents X which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$ or $NR^aC(O)NR^aR^a$.

Further aspect 12. A compound according to further aspect 3 or a pharmaceutically acceptable salt or solvate thereof, or a solvate of such a salt, wherein $R^3$ represents MP or $Het^3$P wherein M and $Het^3$ each optionally is substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, $Het^1$T, R, RT, $Het^2$, $Het^1$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aPa$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following: halogen (Cl, F, Br, I), OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, $Het^1$, $Het^1$T, R, RT, $Het^2$, $Het^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$;

AP or $Het^5$P wherein A and $Het^5$ each optionally is substituted by one or more of the following: halogen (F, Cl, Br, I), OH, CN, $NO_2$, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, $Het^1$, $Het^1$T, R, RT, $Het^2$, $Het^2$T, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$; $OC(O)NR^aR^a$ or $NR^aC(O)NR^aR^a$.

Further aspect 13. A compound according to further aspect 3 or a pharmaceutically acceptable salt or solvate thereof, or a solvate of such a salt, wherein $R^3$ represents E or $Het^4$ each optionally substituted on the non-aromatic ring by one or more of the following: F, OH, CN, $NR^aR^a$, $OR^b$, $SR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)N-$ R$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)$_b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following: halogen (F, Cl, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

Further aspect 14. A compound according to further aspect 4 or a pharmaceutically acceptable salt or solvate thereof, or a solvate of such a salt, wherein R$^3$ represents X which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$ or NR$^a$C(O)NR$^a$R$^a$.

Further aspect 15. A compound according to further aspect 4 or a pharmaceutically acceptable salt or solvate thereof, or a solvate of such a salt, wherein R$^3$ represents MP or Het$^3$P wherein M and Het$^3$ each optionally is substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het$^3$ each optionally is substituted on the aromatic ring by one or more of the following: halogen (Cl, F, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

AP or Het$^5$P wherein A and Het$^5$ each optionally is substituted by one or more of the following: halogen (F, Cl, Br, I), OH, CN, NO$_2$, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

Further aspect 16. A compound according to further aspect 4 or a pharmaceutically acceptable salt or solvate thereof, or a solvate of such a salt, wherein R$^3$ represents E or Het$^4$ each optionally substituted on the non-aromatic ring by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$C(O)R$^b$, NR$^a$C(O)R$^b$, C(O)NR$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following: halogen (F, Cl, Br, I), OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following: F, OH, CN, NR$^a$R$^a$, OR$^b$, SR$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$.

Further aspect 17. A compound according to further aspect 1 in which R$^1$ is selected from ethyl, isopropyl, n-butyl, tert-butyl, cyclopentyl, hexyl, benzyl, 2-methoxyethyl, pyridin-2-ylmethyl, pyridin-3-ylmethyl, pyridin-4-ylmethyl, tetrahydrofuran-2-ylmethyl or 2-(3-fluorophenyl)ethyl;

R$^2$ is phenyl; and

R$^3$ is selected from butyl, hexyl, benzyl, 3-[3-(hydroxymethyl)phenoxy]propyl, 4-phenylbutyl, 3-(2-methoxyphenoxy)propyl, 3-[4-(hydroxymethyl)phenoxy]propyl, 3-(2-fluorophenoxy)propyl, 3-(2-chlorophenoxy)propyl, 3-(3-methoxyphenoxy)propyl, 3-(pyridin-3-yloxy)propyl, 3-(pyridin-4-yloxy)propyl, 1-[3-chloro-5-(trifluoromethyl)pyridin-2-yl]piperidin-4-yl, 3-(phenylthio)propyl, 3-phenoxypropyl, 3-(3-chlorophenoxy)propyl, 3-(3-fluorophenoxy)propyl, 3-(4-fluorophenoxy)propyl, 1-[4-(trifluoromethyl)pyrimidin-2-yl]piperidin-4-yl, cis-4-hydroxycyclohexyl, 4-phenoxybutyl, 3-[(1-oxidopyridin-3-yl)oxy]propyl, 3-(4-methoxyphenoxy)propyl, 4,4-difluorocyclohexyl, 2-phenoxyethyl, 2-phenylethyl, 4-(difluoromethoxy)benzyl, trans-4-hydroxycyclohexyl, 3-hydroxypropyl, 2,3-dihydro-1,4-benzodioxin-2-ylmethyl, 4-hydroxycyclohexyl, 3-(4-chlorophenoxy)propyl, 1,3-benzodioxol-5-ylmethyl, 2,3-dihydro-1H-inden-2-yl, 2-(morpholin-4-yl)ethyl, 3-(4-isopropylphenoxy)propyl, 3-[benzyl(butyl)amino]propyl, 3-(3,5-dipropoxyphenoxy) propyl, 2,2-diphenylethyl, 2-(1H-imidazol-4-yl)ethyl 4-morpholin-4-ylbenzyl, 3-(2-methoxyethoxy)propyl, 3-morpholin-4-ylpropyl, 2-methoxyethyl, tetrahydro-2H-pyran-4-yl, 4-hydroxycyclohexyl, 4-methoxybenzyl, 3-(3-hydroxyphenoxy)propyl, 3-(3-acetamidophenoxy)propyl, 3-(4-N,N-dimethylaminocarbonylmethylphenoxy)propyl, 3-(3-carboxymethylphenoxy)propyl, 3-(3-methoxycarbonylmethylphenoxy)propyl, 3-(3-methoxycarbonylphenoxy)propyl, 3-(4-carboxymethylphenoxy)propyl, 3-(4-methoxycarbonylmethylphenoxy)propyl, 3-(3-acetylaminophenoxy)propyl, 3-(4-hydroxyphenylcarboxy)propyl, 3-(4-carboxyphenoxy) propyl or 1-(2-nitriloethyl)piperidin-4-yl.

Further aspect 18. A compound selected from one or more of the following:

2-tert-butyl-4-({3-[3-(hydroxymethyl)phenoxy]propyl}amino)-5-phenylisothiazol-3(2H)-one 1,1-dioxide
2-tert-butyl-5-phenyl-4-[(4-phenylbutyl)amino]isothiazol-3(2H)-one 1,1-dioxide
2-tert-butyl-4-{[3-(2-methoxyphenoxy)propyl]amino}-5-phenylisothiazol-3(2H)-one 1,1-dioxide
2-tert-butyl-4-({3-[4-(hydroxymethyl)phenoxy]propyl}amino)-5-phenylisothiazol-3(2H)-one 1,1-dioxide
N-(3-{3-[(2-tert-butyl-1,1-dioxido-3-oxo-5-phenyl-2,3-dihydroisothiazol-4-yl)amino]propoxy}phenyl)acetamide
2-tert-butyl-4-{[3-(2-fluorophenoxy)propyl]amino}-5-phenylisothiazol-3(2H)-one 1,1-dioxide
2-isopropyl-5-phenyl-4-[(4-phenylbutyl)amino]isothiazol-3(2H)-one 1,1-dioxide
2-(4-{3-[(2-tert-butyl-1,1-dioxido-3-oxo-5-phenyl-2,3-dihydroisothiazol-4-yl)amino]propoxy}phenyl)-N,N-dimethylacetamide
2-tert-butyl-4-{[3-(2-chlorophenoxy)propyl]amino}-5-phenylisothiazol-3(2H)-one 1,1-dioxide
2-tert-butyl-4-{[3-(3-methoxyphenoxy)propyl]amino}-5-phenylisothiazol-3(2H)-one 1,1-dioxide
(3-{3-[(2-tert-butyl-1,1-dioxido-3-oxo-5-phenyl-2,3-dihydroisothiazol-4-yl)amino]propoxy}phenyl)acetic acid
2-tert-butyl-5-phenyl-4-{[3-(pyridin-3-yloxy)propyl]amino}isothiazol-3(2H)-one 1,1-dioxide methyl (3-{3-[(2-tert-butyl-1,1-dioxido-3-oxo-5-phenyl-2,3-dihydroisothiazol-4-yl)amino]propoxy}phenyl)acetate
2-tert-butyl-5-phenyl-4-{[3-(pyridin-4-yloxy)propyl]amino}isothiazol-3(2H)-one 1,1-dioxide
4-(benzylamino)-2-tert-butyl-5-phenylisothiazol-3(2H)-one 1,1-dioxide
4-({1-[3-chloro-5-(trifluoromethyl)pyridin-2-yl]piperidin-4-yl}amino)-2-isopropyl-5-phenylisothiazol-3(2H)-one 1,1-dioxide
2-tert-butyl-5-phenyl-4-[(2-phenylethyl)amino]isothiazol-3(2H)-one 1,1-dioxide
2-cyclopentyl-5-phenyl-4-[(4-phenylbutyl)amino]isothiazol-3(2H)-one 1,1-dioxide
2-tert-butyl-5-phenyl-4-{[3-(phenylthio)propyl]amino}isothiazol-3(2H)-one 1,1-dioxide
2-tert-butyl-4-[(3-phenoxypropyl)amino]-5-phenylisothiazol-3(2H)-one 1,1-dioxide
2-tert-butyl-4-{[3-(3-chlorophenoxy)propyl]amino}-5-phenylisothiazol-3(2H)-one 1,1-dioxide
methyl 3-{3-[(2-tert-butyl-1,1-dioxido-3-oxo-5-phenyl-2,3-dihydroisothiazol-4-yl)amino]propoxy}benzoate
2-benzyl-5-phenyl-4-[(4-phenylbutyl)amino]isothiazol-3(2H)-one 1,1-dioxide
(4-{3-[(2-tert-butyl-1,1-dioxido-3-oxo-5-phenyl-2,3-dihydroisothiazol-4-yl)amino]propoxy}phenyl)acetic acid
2-tert-butyl-4-{[3-(3-fluorophenoxy)propyl]amino}-5-phenylisothiazol-3 (21)-one 1,1-dioxide
methyl (4-{3-[(2-tert-butyl-1,1-dioxido-3-oxo-5-phenyl-2,3-dihydroisothiazol-4-yl)amino]propoxy}phenyl)acetate
2-tert-butyl-4-{[3-(4-fluorophenoxy)propyl]amino}-5-phenylisothiazol-3(2H)-one 1,1-dioxide
2-isopropyl-5-phenyl-4-({1-[4-(trifluoromethyl)pyrimidin-2-yl]piperidin-4-yl}amino)isothiazol-3(2H)-one 1,1-dioxide N-(3-{3-[(2-butyl-1,1-dioxido-3-oxo-5-phenyl-2,3-dihydroisothiazol-4-yl)amino]propoxy}phenyl)acetamide
3-[(2-tert-butyl-1,1-dioxido-3-oxo-5-phenyl-2,3-dihydroisothiazol-4-yl)amino]propyl 4-hydroxybenzoate
4-(benzylamino)-2-isopropyl-5-phenylisothiazol-3(2H)-one 1,1-dioxide
2-[2-(3-fluorophenyl)ethyl]-5-phenyl-4-[(4-phenylbutyl)amino]isothiazol-3(2H)-one 1,1-dioxide
4-[(cis-4-hydroxycyclohexyl)amino]-2-isopropyl-5-phenylisothiazol-3(2H)-one 1,1-dioxide
2-tert-butyl-4-[(4-phenoxybutyl)amino]-5-phenylisothiazol-3(2H)-one 1,1-dioxide
2-tert-butyl-4-({3-[(1-oxidopyridin-3-yl)oxy]propyl}amino)-5-phenylisothiazol-3(2H)-one 1,1-dioxide
2-tert-butyl-4-[(2-phenoxyethyl)amino]-5-phenylisothiazol-3(2H)-one 1,1-dioxide
4-(benzylamino)-2-cyclopentyl-5-phenylisothiazol-3(2H)-one 1,1-dioxide
2-tert-butyl-4-{[3-(4-methoxyphenoxy)propyl]amino}-5-phenylisothiazol-3(2H)-one 1,1-dioxide
4-[(4,4-difluorocyclohexyl)amino]-2-isopropyl-5-phenylisothiazol-3(2H)-one 1,1-dioxide
2-isopropyl-4-[(2-phenoxyethyl)amino]-5-phenylisothiazol-3(2H)-one 1,1-dioxide
5-phenyl-4-[(4-phenylbutyl)amino]-2-(tetrahydrofuran-2-ylmethyl)isothiazol-3(2H)-one 1,1-dioxide
4-(benzylamino)-2-butyl-5-phenylisothiazol-3(2H)-one 1,1-dioxide
2-butyl-4-(hexylamino)-5-phenylisothiazol-3(2H)-one 1,1-dioxide
2-butyl-5-phenyl-4-[(2-phenylethyl)amino]isothiazol-3(2H)-one 1,1-dioxide
2-butyl-4-{[4-(difluoromethoxy)benzyl]amino}-5-phenylisothiazol-3(2H)-one 1,1-dioxide
4-[(trans-4-hydroxycyclohexyl)amino]-2-isopropyl-5-phenylisothiazol-3(2H)-one 1,1-dioxide
2-tert-butyl-4-[(3-hydroxypropyl)amino]-5-phenylisothiazol-3(2H)-one 1,1-dioxide
5-phenyl-4-[(4-phenylbutyl)amino]-2-(pyridin-3-ylmethyl)isothiazol-3(2H)-one 1,1-dioxide
2-tert-butyl-4-[(2,3-dihydro-1,4-benzodioxin-2-ylmethyl)amino]-5-phenylisothiazol-3(2H)-one 1,1-dioxide
2-butyl-4-[(4-hydroxycyclohexyl)amino]-5-phenylisothiazol-3(2H)-one 1,1-dioxide
4-{3-[(2-tert-butyl-1,1-dioxido-3-oxo-5-phenyl-2,3-dihydroisothiazol-4-yl)amino]propoxy}benzoic acid
3-{4-[(2-isopropyl-1,1-dioxido-3-oxo-5-phenyl-2,3-dihydroisothiazol-4-yl)amino]piperidin-1-yl}propanenitrile
2-tert-butyl-4-{[3-(4-chlorophenoxy)propyl]amino}-5-phenylisothiazol-3(2H)-one 1,1-dioxide
5-phenyl-4-[(4-phenylbutyl)amino]-2-(pyridin-4-ylmethyl)isothiazol-3(2H)-one 1,1-dioxide
4-[(1,3-benzodioxol-5-ylmethyl)amino]-2-butyl-5-phenylisothiazol-3(2H)-one 1,1-dioxide
4-(2,3-dihydro-1H-inden-2-ylamino)-2-(2-methoxyethyl)-5-phenylisothiazol-3(2H)-one 1,1-dioxide
2-butyl-4-[(2-morpholin-4-ylethyl)amino]-5-phenylisothiazol-3(2H)-one 1,1-dioxide
2-tert-butyl-4-{[3-(4-isopropylphenoxy)propyl]amino}-5-phenylisothiazol-3(2H)-one 1,1-dioxide
4-({3-[benzyl(butyl)amino]propyl}amino)-2-tert-butyl-5-phenylisothiazol-3(2H)-one 1,1-dioxide
2-tert-butyl-4-{[3-(3,5-dipropoxyphenoxy)propyl]amino}-5-phenylisothiazol-3(2H)-one 1,1-dioxide
2-tert-butyl-4-[(2,2-diphenylethyl)amino]-5-phenylisothiazol-3(2H)-one 1,1-dioxide 2-ethyl-4-{[2-(1H-imidazol-4-yl)ethyl]amino}-5-phenyl-isothiazol-3(2H)-one 1,1-dioxide
2-butyl-4-[(4-morpholin-4-ylbenzyl)amino]-5-phenyl-isothiazol-3(2H)-one 1,1-dioxide
2-butyl-4-{[3-(2-methoxyethoxy)propyl]amino}-5-phenyl-isothiazol-3(2H)-one 1,1-dioxide
2-butyl-4-[(3-morpholin-4-ylpropyl)amino]-5-phenyl-isothiazol-3(2H)-one 1,1-dioxide
2-butyl-4-[(2-methoxyethyl)amino]-5-phenylisothiazol-3(2H)-one 1,1-dioxide
2-(2-methoxyethyl)-5-phenyl-4-(tetrahydro-2H-pyran-4-ylamino)isothiazol-3(2H)-one 1,1-dioxide
4-(hexylamino)-2-(2-methoxyethyl)-5-phenylisothiazol-3(2H)-one 1,1-dioxide
4-[(4-hydroxycyclohexyl)amino]-2-(2-methoxyethyl)-5-phenylisothiazol-3(2H)-one 1,1-dioxide
4-[(1,3-benzodioxol-5-ylmethyl)amino]-2-(2-methoxyethyl)-5-phenylisothiazol-3(2H)-one 1,1-dioxide
2-butyl-4-[(4-methoxybenzyl)amino]-5-phenylisothiazol-3(2H)-one 1,1-dioxide
5-phenyl-4-[(4-phenylbutyl)amino]-2-(pyridin-2-ylmethyl)isothiazol-3(2H)-one 1,1-dioxide
2-tert-butyl-4-{[3-(3-hydroxyphenoxy)propyl]amino}-5-phenylisothiazol-3(2H)-one 1,1-dioxide
3-{3-[(2-tert-butyl-1,1-dioxido-3-oxo-5-phenyl-2,3-dihydroisothiazol-4-yl)amino]propoxy}benzoic acid or a pharmaceutically acceptable salt or solvate thereof, or a solvate of such a salt.

Further aspect 19. A process for the preparation of a compound according to any one of further aspect 1-18, wherein $R^1$, $R^2$ or $R^3$ are as defined in claim 1, comprising the step of reacting a compound of formula VI,

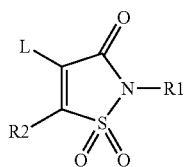

VI wherein $R^1$ and $R^2$ are as defined in claim 1 and L is a leaving group such as Cl, Br, I, methanesulfonate or trifluoromethanesulfonate, with a compound of formula VII, $R^3NH_2$　　VII wherein $R^3$ is as defined in claim 1, optionally in the presence of an inert organic solvent such as dimethylformamide.

Further aspect 20. A pharmaceutical formulation comprising a compound according to any one of further aspects 1-18 in admixture with pharmaceutically acceptable adjuvants, diluents and/or carriers.

Further aspect 21. The use of a compound according to any one of further aspects 1-18 in therapy.

Further aspect 22. The use of a compound according to any of further aspects 1-18 for the manufacture of a medicament for the modulation of the nuclear hormone receptors LXR α and/or β.

Further aspect 23. The use of a compound according to any one of further aspects 1-18 in the manufacture of a medicament for the treatment and/or prophylaxis of cardiovascular disease.

Further aspect 24. The use of a compound according to any one of further aspects 1-18 in the manufacture of a medicament for the treatment and/or prophylaxis of atherosclerosis.

Further aspect 25. The use of a compound according to any one of further aspects 1-18 in the manufacture of a medicament for the treatment and/or prophylaxis of hypercholesterolemia.

Further aspect 26. The use of a compound according to any one of further aspects 1-18 in the manufacture of a medicament for the treatment and/or prophylaxis of conditions associated with a need for improving reverse cholesterol transport.

Further aspect 27. The use of a compound according to any one of further aspects 1-18 in the manufacture of a medicament for the treatment and/or prophylaxis of conditions associated with a need for decreasing intestinal cholesterol absorption.

Further aspect 28. The use of a compound according to any one of further aspects 1-18 in the manufacture of a medicament for the treatment and/or prophylaxis of conditions associated with a need for increasing HDL-cholesterol levels.

Further aspect 29. The use of a compound according to any one of further aspects 1-18 in the manufacture of a medicament for the treatment and/or prophylaxis of conditions associated with a need for decreasing LDL-cholesterol levels.

Further aspect 30. The use of a compound according to any one of further aspects 1-18 in the manufacture of a medicament for the treatment and/or prophylaxis of inflammatory conditions.

Further aspect 31. The use of a compound according to any one of further aspects 1-18 in the manufacture of a medicament for the treatment and/or prophylaxis of Alzheimer's disease.

Further aspect 32. The use of a compound according to any one of further aspects 1-18 in the manufacture of a medicament for the treatment and/or prophylaxis of arteriosclerosis.

Further aspect 33. The use of a compound according to any one of further aspects 1-18 in the manufacture of a medicament for the treatment and/or prophylaxis of type 2 diabetes.

Further aspect 34. The use of a compound according to any one of further aspects 1-18 in the manufacture of a medicament the treatment and/or prophylaxis of conditions associated with a need for improving HDL function.

Further aspect 35. The use of a compound according to any one of further aspects 1-18 in the manufacture of a medicament for the treatment and/or prophylaxis of lipid disorders (dyslipidemia) whether or not associated with insulin resistance.

Further aspect 36. A method of treating and/or preventing lipid disorders (dyslipidemia) whether or not associated with insulin resistance comprising the administration of a compound according to any one of further aspects 1-18 to a mammal in need thereof.

Further aspect 37. A method for treatment and/or prophylaxis of cardiovascular disease comprising administering to a mammal, including man, in need of such a treatment an effective amount of a compound as defined in any of further aspects 1-18.

Further aspect 38. A method of treating and/or preventing atherosclerosis comprising the administration of an effective amount of a compound of formula I according to any one of further aspects 1-18 to a mammal in need thereof.

Further aspect 39. A method for treatment and/or prophylaxis of hypercholesterolemia comprising administering to a mammal, including man, in need of such a treatment an effective amount of a compound as defined in any of further aspects 1-18.

Further aspect 40. A method for treatment and/or prophylaxis of conditions associated with a need for improving reverse cholesterol transport comprising administering to a mammal, including man, in need of such a treatment an effective amount of a compound as defined in any of further aspects 1-18.

Further aspect 41. A method for treatment and/or prophylaxis of conditions associated with a need for decreasing intestinal cholesterol absorption comprising administering to a mammal, including man, in need of such a treatment an effective amount of a compound as defined in any of further aspects 1-18.

Further aspect 42. A method for treatment and/or prophylaxis of conditions associated with a need for increasing HDL-cholesterol levels comprising administering to a mammal, including man, in need of such a treatment an effective amount of a compound as defined in any of further aspects 1-18.

Further aspect 43. A method for treatment and/or prophylaxis of conditions associated with a need for decreasing LDL-cholesterol levels comprising administering to a mammal, including man, in need of such a treatment an effective amount of a compound as defined in any of further aspects 1-18.

Further aspect 44. A method for treatment and/or prophylaxis of inflammatory conditions comprising administering to a mammal, including man, in need of such a treatment an effective amount of a compound as defined in any of further aspects 1-18.

Further aspect 45. A method for treatment and/or prophylaxis of Alzheimer's disease comprising administering to a mammal, including man, in need of such a treatment an effective amount of a compound as defined in any of further aspects 1-18.

Further aspect 46. A method for treatment and/or prophylaxis of arteriosclerosis comprising administering to a mammal, including man, in need of such a treatment an effective amount of a compound as defined in any of further aspects 1-18.

Further aspect 47. A method for treatment and/or prophylaxis of type 2 diabetes comprising administering to a mammal, including man, in need of such a treatment an effective amount of a compound as defined in any of further aspects 1-18.

Further aspect 48. A method for treatment and/or prophylaxis of conditions associated with a need for improving HDL function comprising administering to a mammal, including man, in need of such a treatment an effective amount of a compound as defined in any of further aspects 1-18.

For the further aspects 1-48 above the definitions mentioned hereinbefore or the following definitions shall apply:

The term "X" denotes a straight or branched, saturated or unsaturated alkyl group having 1 to 6 carbon atoms wherein said alkyl group may optionally be interrupted by O, S, S(O), $SO_2$, C(O), $NR^a$, OC(O), C(O)O, $NR^aC(O)$, $C(O)NR^a$, $SO_2NR^a$ or $NR^aSO_2$.

The term "Y" denotes a straight or branched, saturated or unsaturated alkyl group having 1 to 3 carbon atoms wherein said alkyl group binds to nitrogen in 2-position in the isothiazol-3(2H)-one 1,1-dioxide and may optionally be interrupted or ended by O, S, S(O), $SO_2$, C(O), OC(O), C(O)O, $NR^cC(O)$, $C(O)NR^c$, $NR^c$ and/or Y is optionally substituted by one or more of the following: OH, F, CN, $NR^aR^a$, $C_1$-$C_4$alkyl, $OR^b$, $SR^b$, $S(O)R^b$ or $SO_2R^b$. In the definition of "Y" the term "ended by O, S, S(O), $SO_2$, C(O), OC(O), C(O)O, $NR^cC(O)$, $C(O)NR^c$, $NR^c$" means that the alkyl group has as the last position O, S, S(O), $SO_2$, C(O), OC(O), C(O)O, $NR^cC(O)$, $C(O)NR^c$ or $NR^c$ before it binds further to phenyl, heteroaryl, cycloalkyl or heterocyclyl.

The term "Z" denotes a straight or branched, saturated or unsaturated alkyl group having 1 to 6 carbon atoms wherein said alkyl group binds to E or $Het^4$ and one of the following: Q, $Het^1$, R or $Het^2$, and may optionally be interrupted or ended by O, S, S(O), $SO_2$, C(O), OC(O), C(O)O, $NR^aC(O)$, $C(O)NR^a$, $NR^a$, $SO_2NR^a$, $NR^aSO_2$, optionally consists only of one of the following: O, S, S(O), $SO_2$, C(O), OC(O), C(O)O, $NR^aC(O)$, $C(O)NR^a$, $NR^a$, $SO_2NR^a$, $NR^aSO_2$ and/or Z is optionally substituted by one or more of the following: OH, F, CN, $NR^cR^c$, $C(O)R^c$, $OR^b$, $SR^c$, $S(O)R^c$, $SO_2R^c$, phenyl, phenyl$C_1$-$C_3$alkyl, or $C_1$-$C_4$alkyl which is optionally substituted by one or more of the following: F, OH, $NR^aR^a$, $SR^b$, $S(O)R^b$, $SO_2R^b$, $OR^b$. In the definition of "Z" the term "ended by O, S, S(O), $SO_2$, C(O), OC(O), C(O)O, $NR^aC(O)$, $C(O)NR^a$, $NR^a$, $SO_2NR^a$, $NR^aSO_2$" means that the alkyl group has as the last position O, S, S(O), $SO_2$, C(O), OC(O), C(O)O, $NR^aC(O)$, $C(O)NR^a$, $NR^a$, $SO_2NR^a$ or $NR^aSO_2$ before it binds further to E, $Het^4$, Q, $Het^1$, R or $Het^2$.

The term "M" denotes a saturated or unsaturated non-aromatic monocyclic ring composed of 3, 4, 5, 6, 7 or 8 carbon-atoms or a saturated or unsaturated non-aromatic or partly aromatic bicyclic ring composed of 4, 5, 6, 7, 8, 9 or 10 carbon atoms.

The term "E" denotes a saturated or unsaturated non-aromatic monocyclic ring composed of 3, 4, 5, 6, 7 or 8 carbon atoms or a saturated or unsaturated non-aromatic or partly aromatic bicyclic ring composed of 4, 5, 6, 7, 8, 9 or 10 carbon atoms. The ring binds, unless otherwise specified, through its non-aromatic part to nitrogen in 4-position on the isothiazol-3(2H)-one 1,1-dioxide.

The term "A" denotes an aromatic monocyclic ring composed of 3, 4, 5, 6, 7 or 8 carbon atoms or an aromatic bicyclic ring composed of 4, 5, 6, 7, 8, 9 or 10 carbon atoms.

The term "P" denotes a straight or branched, saturated or unsaturated alkyl group having 1 to 6 carbon atoms wherein the alkyl group binds to nitrogen in 4-position on the isothiazol-3(2H)-one 1,1-dioxide and is optionally interrupted or ended by O, $NR^a$, S, S(O), $SO_2$, C(O), OC(O), C(O)O, $NR^aC(O)$, $C(O)NR^a$, $SO_2NR^a$, $NR^aSO_2$ and/or P is optionally substituted by one or more of the following: F, OH, CN, $NR^aR^a$, $C(O)R^c$, $OR^b$, $SR^b$, $S(O)R^b$, $SO_2R^b$, phenyl, phenyl$C_1$-$C_3$alkyl, or $C_1$-$C_4$alkyl which is optionally substituted by one or more of the following: F, OH, $NR^aR^a$, $SR^b$, $S(O)R^b$, $SO_2R^b$ or $OR^b$. In the definition of "P" the term "ended by O, $NR^a$, S, S(O), $SO_2$, C(O), OC(O), C(O)O, $NR^aC(O)$, $C(O)NR^a$, $SO_2NR^a$, $NR^aSO_2$" means that the alkyl group has as the last position O, $NR^a$, S, S(O), $SO_2$, C(O), OC(O), C(O)O, $NR^aC(O)$, $C(O)NR^a$, $SO_2NR^a$ or $NR^aSO_2$" before it binds further to M, $Het^3$, A or $Het^5$.

The term "Q" denotes a saturated or unsaturated non-aromatic monocyclic ring composed of 3, 4, 5, 6, 7, 8 carbon atoms, which is optionally substituted by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$. Examples of such Q include but are not limited to cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "R" denotes a phenyl group which is optionally substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$.

The term "T" denotes an alkyl group having 1 carbon atom or optionally consists of one or more of the following: O, $NR^a$, S, S(O), $SO_2$, C(O), OC(O), C(O)O, $NR^aC(O)$, $C(O)NR^a$, $SO_2NR^a$ or $NR^aSO_2$. T binds to M, $Het^3$, A or $Het^5$.

The term "$C_1$alkyl" denotes an alkyl group having 1 carbon atom. An example of said alkyl includes, but is not limited to, methyl.

The term "$C_1$-$C_3$alkyl" denotes a straight or branched, saturated or unsaturated alkyl group having 1 to 3 carbon atoms.

The term "$C_1$-$C_4$alkyl" denotes a straight or branched, saturated or unsaturated alkyl group having 1 to 4 carbon atoms.

The term "cycloalkyl" denotes a saturated or unsaturated non-aromatic monocyclic ring composed of 3, 4, 5, 6, 7, 8 carbon atoms, and includes but is not limited to cyclopropyl, cyclobutyl, cyclopentyl, cyclohexyl, cycloheptyl, cyclooctanyl, cyclobutenyl, cyclopentenyl, cyclohexenyl, cycloheptenyl, cyclooctenyl, cyclopentadienyl, cyclohexadienyl and cyclooctadienyl.

The term "heterocyclyl" denotes a saturated or unsaturated non-aromatic 3-8 membered monocyclic ring in which one or more of the atoms in the ring is an element other than carbon, for example nitrogen, oxygen or sulfur. The term "sulfur" shall be understood to include sulphoxide (S(O)) and sulphone ($SO_2$). The term "nitrogen" shall be understood to include nitrogen oxide (NO).

The term "heteroaryl" denotes an aromatic 3-8 membered monocyclic ring in which one or more of the atoms in the ring is an element other than carbon, for example nitrogen, oxygen and sulfur. The term "sulfur" shall be understood to include sulphoxide (S(O)) and sulphone ($SO_2$). The term "nitrogen" shall be understood to include nitrogen oxide (NO).

The term "$Het^1$" denotes a saturated or unsaturated non-aromatic 3-10 membered monocyclic ring in which one or more of the atoms in the ring is an element other than carbon, for example nitrogen, oxygen or sulfur, and wherein the ring optionally is substituted by one or more of the following: F, OH, CN, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2NR^aR^a$, $NR^aC(O)OR^b$, $OC(O)NR^aR^a$ or $NR^aC(O)NR^aR^a$. The term "sulfur" shall be understood to include sulphoxide (S(O)) and sulphone ($SO_2$). The term "nitrogen" shall be understood to include nitrogen oxide (NO).

The term "$Het^2$" denotes an aromatic 3-10 membered monocyclic ring in which one or more of the atoms in the ring is an element other than carbon, for example nitrogen, oxygen and sulfur, and which is substituted by one or more of the following: halogen (Cl, F, I, Br), OH, CN, $NO_2$, $NR^aR^a$, $OR^b$, $SR^b$, $S(O)R^b$, $SO_2R^b$, $C(O)R^b$, phenyl$C_1$alkyl, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following: F, OH, CN, $NR^aR^a$, $OR^b$, $SR^b$, $S(O)R^b$, $SO_2R^b$, $C(O)R^b$, $C(O)NR^aR^a$, $NR^aC(O)R^b$, $C(O)OR^a$, $OC(O)R^b$, $NR^aSO_2R^b$, $SO_2$ $NR^aR^a$, $NR^aC(O)OR^b$, $OC(O)NR^aR^a$ or $NR^aC(O)NR^aR^a$. The term "sulfur" shall be understood to include sulphoxide (S(O)) and sulphone ($SO_2$). The term "nitrogen" shall be understood to include nitrogen oxide (NO).

The term "$Het^3$" denotes a saturated or unsaturated non-aromatic 3-10 membered monocyclic ring or a saturated or unsaturated non-aromatic or partly aromatic 4-10 membered bicyclic ring in which one or more of the atoms in the monocyclic or bicyclic ring is an element other than carbon, for example nitrogen, oxygen or sulfur. The term "sulfur" shall be understood to include sulphoxide (S(O)) and sulphone ($SO_2$). The term "nitrogen" shall be understood to include nitrogen oxide (NO).

The term "$Het^4$" denotes a saturated or unsaturated non-aromatic 3-10 membered monocyclic ring or a saturated or unsaturated non-aromatic or partly aromatic 4-10 membered bicyclic ring in which one or more of the atoms in the monocyclic or bicyclic ring is an element other than carbon, for example nitrogen, oxygen or sulfur. The term "sulfur" shall be understood to include sulphoxide (S(O)) and sulphone ($SO_2$). The term "nitrogen" shall be understood to include nitrogen oxide (NO). The ring binds, unless otherwise specified, through its non-aromatic part to nitrogen in 4-position on the isothiazol-3(2H)-one 1,1-dioxide.

The term "$Het^5$" denotes an aromatic 3-10 membered monocyclic ring or an aromatic 4-10 membered bicyclic ring in which one or more of the atoms in the monocyclic or bicyclic ring is an element other than carbon, for example nitrogen, oxygen or sulfur. The term "sulfur" shall be understood to include sulphoxide (S(O)) and sulphone ($SO_2$). The term "nitrogen" shall be understood to include nitrogen oxide (NO).

$R^a$ independently represents H or a straight or branched, saturated or unsaturated $C_1$-$C_4$alkyl chain optionally substituted by one or more F.

$R^b$ independently represents a straight or branched, saturated or unsaturated $C_1$-$C_4$alkyl chain optionally substituted by one or more F.

$R^c$ independently represents H or a straight or branched, saturated or unsaturated $C_1$-$C_3$alkyl chain optionally substituted by one or more F.

The invention is illustrated, but not limited, by the following Examples.

The naming of the compounds in this patent application was made either using a program from ACD Labs (version 6.0/Name, 6.0 Name Batch or labs 8.0/Name) or using the function Autonom 2000 Name in the program Isis Draw.

EXAMPLES

Abbreviations

AcOH acetic acid
Atm atmosphere
DBU 2,3,4,6,7,8,9,10-octahydropyrimido[1,2-α]azepine
DCM dichloromethane
DIPEA N,N-diisopropylethylamine
DMAP 4-dimethylaminopyridine
DMF N,N-dimethylformamide DMSO dimethylsulfoxide
EDC 1-ethyl-3-(3-dimethylaminopropyl)carbodiimide hydrochloride
Et$_2$O diethyl ether
EtOAc ethyl acetate
EtOH ethanol
HOAt 1-Hydroxy-7-azabenzotriazole
HOBt 1H-1,2,3-benzotriazole-1-ol
HPFC high performance flash chromatography
HPLC high performance liquid chromatography
LC-MS liquid chromatography mass spectroscopy
MeCN acetonitrile
MCPBA metachloroperbenzoic acid
MeOH methanol
MTBE methyl tert-butyl ether
NMR nuclear magnetic resonance
PyBOP Benzotriazol-1-yl-oxytripyrrolidinophosphonium hexafluorophosphate
TEA triethylamine
TFA trifluoroacetic acid
THF tetrahydrofuran
UV ultra violet
rt room temperature
h hour(s)
mins minutes
b broad
bs broad singlet
d doublet
dd double doublet
m multiplet
qt quintet
singlet
t triplet
hep heptett
ds double singlett
sep septett

GENERAL EXAMPLE EXPERIMENTAL PROCEDURES

Phase Separator from IST was used. ISOLUTE SCX-2 were used as cation exchange columns. Flash column chromatography employed normal phase silica gel 60 (0.040-0.063 mm, Merck) or IST Isolute®SPE columns normal phase silica gel or Biotage Horizon HPFC System or a Horizon TM flash system using silica FLASH+EPFC Cartridges. TPLC purifications were performed on either a Gilson preparative HPLC system with a LW triggered fraction collector, equipped with an ACE C8 5 µm 250 mm×20 mm column, or a Kromasil C18 column, or on a Waters preparative HPLC system equipped with a Kromasil C8 10 µm 250 mm×21.2 mm column, or on a Waters preparative HPLC system equipped with an ACE C8 5 µm 250 mm×50 mm column or an ACE C8 5 µm 250 mm×20 mm column, or on a Waters FractionLynx HPLC system with a mass triggered fraction collector, equipped with a ACE C8 5 µm 100 mm×21.2 mm column; using MeCN/NH$_4$OAc buffer system with a gradient from 100% mobilphase A (5% MeCN+95% 0.1 M NH$_4$OAc) to 100% mobilphase B (100% MeCN) unless otherwise stated. $^1$H NMR and $^{13}$C NMR measurements were performed on a BRUKER ACP 300 or on a Varian Unity Plus 400, 500 or 600 spectrometer, operating at $^1$H frequencies of 300, 400, 500, 600 MHz, respectively, and $^{13}$C frequencies of 75, 100, 125 and 150 MHz, respectively. Chemical shifts are given in δ values (ppm) with the solvents used as internal standard, unless otherwise stated. Microwave heating was performed using single node heating in a Smith Creator or Emrys Optimizer from Personal Chemistry, Uppsala, Sweden. Mass spectral data were obtained using a Micromass LCT or Waters Q-T of micro system and, where appropriate, either positive ion data or negative ion data were collected.

Pyridine N-oxides were prepared by oxidizing the corresponding pyridine compounds with an oxidizing agent such as metachloroperbenzoic acid (MCPBA) in an inert organic solvent such as DCM at rt for 2-24 h.

Synthesis

Starting Material and Intermediates

N-(tert-Butyl)-1-phenylmethanesulfonamide

The title compound was prepared as described in the reference below:
Org. Biomol. Chem., 2003, 19, 3390-3395

2-tert-Butyl-4-hydroxy-5-phenylisothiazol-3(2H)-one 1,1-dioxide

Potassium tert-butoxide (0.845 g, 10.56 mmol) was added to a solution of N-(tert-butyl)-1-phenylmethanesulfonamide (1.2 g, 5.28 mmol) and diethyl oxalate (0.85 mL, 6.33 mmol) in THF (8 mL) and the mixture was heated at 150° C. for 15 mins in a microwave reactor. The reaction mixture was acidified with 1M HCl, the THF was evaporated and the residue was Example tracted with DCM. Evaporation and trituration of the residue with petroleum ether gave the title compound (7 g, 63%) as a solid; $^1$H NMR (500 MHz, CDCl$_3$): δ 7.44-7.32 (m, 5H), 3.90 (br s, 1H), 1.36 (s, 9H); Mass Spectrum: M–H$^+$ 280

2-tert-Butyl-4-chloro-5-phenylisothiazol-3(2H)-one 1,1-dioxide

Oxalyl chloride (3.39 g, 2.71 mmol) was added dropwise to a solution of 2-tert-butyl-4-hydroxy-5-phenylisothiazol-3 (2H)-one 1,1-dioxide (5 g, 17.77 mol) and DMF (15 mL) in DCM (220 mL) at 0° C. The reaction mixture was heated at 50° C. for 4 h, concentrated and the residue was diluted with EtOAc and washed with water, then brine and evaporated. The residue was purified by silica gel column chromatography, using a 98:2 mixture of petroleum ether and EtOAc as eluant. The product containing fractions were evaporated, the residue was triturated in petroleum ether and the solvent was decanted to give the title compound (3.9 g, 74%) as a solid; $^1$H NMR (500 MHz, CDCl$_3$): δ 7.97-7.92 (m, 2H), 7.61-7.51 (m, 3H), 1.75 (s, 9H); $^{13}$C NMR (125 MHz, CDCl$_3$): δ 156.5, 142.8, 132.3, 129.3, 128.8, 123.4, 63.0, 27.7.

4-[(3-Bromopropyl)amino]-2-tert-butyl-5-phenylisothiazol-3(2H)-one 1,1-dioxide A solution of TEA (0.18 mL, 1.33 mmol) in MeCN (5 mL) was added dropwise to a mixture of 2-tert-butyl-4-chloro-5-phenylisothiazol-3(2H)-one 1,1-dioxide (0.20 g, 0.67 mmol) and (3-bromopropyl)amine hydrobromide (0.146 g, 0.67 mmol) in MeCN (3 mL). After 45 mins a solution of (3-bromopropyl)amine hydrobromide (0.073 g, 0.33 mmol) and TEA (0.093 mL, 0.66 mmol) in MeCN (5 mL) was added dropwise to the reaction mixture. After 3 h, (3-bromopropyl) amine hydrobromide (0.073 g, 0.33 mmol) and TEA (0.093 mL, 0.66 mmol) was added to the reaction mixture. After 17 h the solvent was evaporated and the residue was purified by silica gel column chromatography using 10-20% EtOAc in petroleum ether mixture as eluant, to yield the title compound (0.112 g, 42%) as a solid; $^1$H NMR (500 MHz, CDCl3): δ 7.69-7.50 (m, 2H), 7.50-7.44 (m, 3H), 5.32 (t, 1H), 3.18 (t, 3H), 3.10-3.04 (m, 2H), 1.90-1.78 (m, 2H), 1.76 (s, 9H); Mass Spectrum M+H$^+$ 403.

N-Butyl-1-phenylmethanesulfonamide

The title compound can be prepared as described in the reference below:
Heterocycles, 1993, 36(4), 733-742

2-Butyl-4-hydroxy-5-phenylisothiazol-3(2H)-one 1,1-dioxide

N-Butyl-1-phenylmethanesulfonamide (2.0 g, 8.80 mmol) was dissolved in dry DMF (113 mL) under an atmosphere of nitrogen. Diethyl oxalate (1.44 g, 9.83 mmol) was added and the reaction mixture was cooled to 0° C. using an ice-bath. Potassium tert-butoxide (1.25 g, 11.14 mmol) was added in one portion and the reaction mixture was stirred for 5 mins at 0° C., followed by 19 h at rt. The mixture was cooled in an ice-bath and HCl (2M) was carefully added to give a pH~1 of the mixture. Most of the solvents were evaporated and the residue was partitioned between HCl (2M) and EtOAc. The combined organic layers were washed with water several times, dried with MgSO$_4$ and evaporated to dryness. The residue was purified using preparative HPLC (ACE C8, 0.1M NH$_4$OAc/MeCN, gradient) to give the title compound (0.96 g, 39%); $^1$H NMR (400 MHz, DMSO-d$_6$): δ 7.88-7.83 (m, 2H), 7.22-7.29 (m, 3H), 7.14 (bs, 1H), 6.98-7.15 (m, 2H), 3.48 (t, 2H), 1.59-1.67 (m, 2H), 1.27-1.37 (m, 2H), 0.88 (t, 3H); $^{13}$C NMR (100 MHz, DMSO-d$_6$): δ 163.1, 158.4, 132.3, 128.7, 124.2, 123.2, 37.8, 30.9, 20.2, 14.1; Mass Spectrum: M−H' 280.

2-Butyl-4-chloro-5-phenylisothiazol-3(2H)-one 1,1-dioxide

2-Butyl-4-hydroxy-5-phenylisothiazol-3(2H)-one 1,1-dioxide (444 mg, 1.58 mmol) was dissolved in dry DCM (15 mL) at rt and under an atmosphere of nitrogen. Oxalyl chloride (0.15 mL, 1.73 mmol) was added dropwise and the reaction mixture was refluxed for 1.5 h. DMF (0.08 mL) was added followed by the addition of oxalyl chloride (0.15 mL, 1.73 mmol) in 2 portions and the reaction mixture was refluxed for another 6 h. The solvents were evaporated and the residue was partitioned between water and DCM. The combined organic layers were washed with water and the two phases were separated using a phase separator. Evaporation of the organic phase gave the title compound (440 mg, 88%) as a brown oil with approximately 95% purity according to $^1$H-NMR and was used without further purification; $^1$H-NMR (400 MHz, CDCl$_3$): δ 7.96-8.00 (m, 2H), 7.53-7.62 (m, 3H), 3.74-3.80 (t, 2H), 1.78-1.87 (m, 2H), 1.39-1-50 (m, 2H), 0.98 (t, 3H); $^{13}$C-NMR (100 MHz, CDCl$_3$): δ 156.3, 137.1, 132.7, 129.6, 129.2, 127.6, 123.7, 40.9, 30.1, 20.1, 13.7.

N-Isopropyl-1-phenylmethanesulfonamide

The title compound can be prepared as described in the reference below:
Orazi, Orfeo O.; Corral, Renee A.; Bravo, Rodolfo; J. Heterocycl. Chem.; 23; 1986; 1701-1708.

4-Chloro-2-isopropyl-5-phenylisothiazol-3(2H)-one 1,1-dioxide

Step A. Methyl[(benzylsulfonyl)(isopropyl)amino](oxo)acetate

A mixture of N-isopropyl-1-phenylmethanesulfonamide (1.0 g, 4.7 mmol) and methyl oxalyl chloride (2.0 mL, 21.6 mmol) was heated at 120° C. for 1 h. Evaporation gave methyl [(benzylsulfonyl)(isopropyl)amino](oxo)acetate which was used directly in the next reaction without any purification.

Step B
4-Hydroxy-2-isopropyl-5-phenylisothiazol-3(2H)-one 1,1-dioxide

Potassium tert-butoxide (1.5 g, 13.4 mmol) was added to a solution of crude methyl[(benzylsulfonyl)(isopropyl)amino](oxo)acetate (2.0 g, 21.6 mmol) in DMF (15 mL).
After 17 h the mixture was evaporated and the residue was purified by silica gel column chromatography using a 4:1 mixture of EtOAc and MeOH as eluant, to give the title compound (0.5 g, 40%) as a solid.

Step C
4-Chloro-2-isopropyl-5-phenylisothiazol-3(2H)-one 1,1-dioxide

DMF (25 mL) and oxalyl chloride (0.2 mL, 2.29 mmol) were added separately to a solution of 4-hydroxy-2-isopropyl-5-phenylisothiazol-3(2H)-one 1,1-dioxide (0.5 g, 1.87 mmol) in DCM (25 mL) at 0° C. The reaction mixture was then heated at 50° C. for 4 h, water was added and the resulting mixture was extracted with EtOAc. The combined organic layers were washed with water, then brine and evaporated. The residue was purified by silica gel column chromatography using a 4:1 mixture of hexane and EtOAc as eluant to give the title compound (0.25 g, 46%) as a solid; $^1$H NMR (200 MHz, CDCl$_3$): δ 8.10-7.94 (m, 2H), 7.61-7.50 (m, 3H), 4.50 (sep, 1H), 1.61 (s, 3H), 1.65 (s, 6H).

2-[(2-tert-Butyl-1,1-dioxido-3-oxo-5-phenyl-2,3-dihydroisothiazol-4-yl)amino]ethyl 4-methylbenzenesulfonate The title compound was prepared as described for 3-[(2-tert-butyl-1,1-dioxido-3-oxo-5-phenyl-2,3-dihydroisothiazol-4-yl)amino]propyl 4-methylbenzenesulfonate from 2-tert-butyl-4-[(2-hydroxyethyl)amino]-5-phenylisothiazol-3(2H)-one 1,1-dioxide (Example 76) and 4-methylbenzenesulfonyl chloride with a reaction time of 17 h. The reaction mixture was purified by silica gel column chromatography (Horizons Biotage) using 50-100% DCM in petroleum ether 40-60° C. as eluent to give the title compound (1.93 g, 76%) as a solid; $^1$H NMR (500 MHz, CDCl$_3$): δ 7.76 (d, 1H), 7.46-7.35 (m, 7H), 5.44 (t, 1H), 3.85 (t, 2H), 3.18-3.12 (m, 2H), 2.49 (s, 3H), 1.74 (s, 9H); Mass Spectrum M+H$^+$ 479.

2-tert-Butyl-4-[(3-chloropropyl)amino]-5-phenylisothiazol-3(2H)-one 1,1-dioxide

A mixture of 2-tert-butyl-4-[(3-hydroxypropyl)amino]-5-phenylisothiazol-3(2H)-one 1,1-dioxide (Example 49) (0.14 g, 0.42 mmol 4-methylbenzenesulfonyl chloride (0.089 mg, 0.46 mmol) and TEA (0.065 ml, 0.46 mmol) in DCM (2 ml) was stirred at rt for 2 h, after which more TEA (0.065 ml, 0.46 mmol) and cat. DMAP were added. After a further 18 h more 4-methylbenzenesulfonyl chloride (0.16 mg, 0.84 mmol), TEA (0.059 ml, 0.42 mmol) and DMAP (0.052 g, 0.42 mmol) were added. After 5 h the reaction mixture was warmed to reflux for 18 h and evaporated to dryness. The residue was purified by silica gel column chromatography (Horizons Biotage) using 10% EtOAc in hexane as eluent to give the title compound (0.097 g, 64%). $^1$H NMR (500 MHz, CDCl$_3$): δ 7.56-7.50 (m, 2H), 7.50-7.44 (m, 3H), 5.32 (t, 1H), 3.35 (t, 2H), 3.08 (q, 2H), 1.80-1.72 (m, 11H); $^{13}$C NMR (125 MHz, CDCl$_3$): δ 159.8, 135.0, 131.8, 130.0, 128.9, 124.9, 107.8, 61.8, 41.7, 41.3, 32.0, 27.8; Mass Spectrum: M+H$^+$ 357.

3-[(2-tert-Butyl-1,1-dioxido-3-oxo-5-phenyl-2,3-dihydroisothiazol-4-yl)amino]propyl 4-methylbenzenesulfonate A mixture of 2-tert-butyl-4-[(3-hydroxypropyl)amino]-5-phenylisothiazol-3(2H)-one 1,1-dioxide (Example 49) (2.75 g, 8.12 mmol), 4-methylbenzenesulfonyl chloride (1.86 g, 9.74 mmol), DMAP (0.99 g, 8.12 mmol) and Na$_2$CO$_3$ (2.58 g, 24.35 mmol) in DCM (50 ml) was stirred at rt. After 2 h the mixture was filtered, evaporated and the residue purified by silica gel column chromatography (Horizons Biotage) using 5:1 DCM/petroleum ether 40-60° C. as eluent to give the title compound (2.34 g, 58%) as a solid; $^1$H NMR (500 MHz, CDCl$_3$): δ 7.74 (d, 2H), 7.50-7.39 (m, 3H), 7.36 (d, 2H), 5.30 (t, 1H), 3.85 (t, 2H), 2.98 (q, 2H), 2.48 (s, 3H), 1.73 (s, 9H), 1.62 (qt, 2H); $^{13}$C NMR (125 MHz, CDCl$_3$): δ 159.8, 145.4, 134.9, 132.9, 131.8, 130.2, 130.1, 129.0, 128.1, 124.9, 107.9, 67.2, 61.6, 40.3, 28.8, 27.8, 21.9; Mass Spectrum M+H+ 493.

4-[(2-Hydroxyethyl)amino]-2-isopropyl-5-phenyl-isothiazol-3(2H)-one 1,1-dioxide 4-Chloro-2-isopropyl-5-phenylisothiazol-3(2H)-one 1,1-dioxide (1.10 g, 3.85 mmol) was dissolved in dry DMF (10 mL) under nitrogen atmosphere. 2-Aminoethanol (0.28 g, 4.62 mmol) was added followed by TEA (0.58 g, 5.77 mmol). The reaction mixture was heated in a microwave reactor at 120° C. for 15 mins. The mixture was diluted with EtOAc, washed with saturated aqueous NaHCO$_3$, dried with Na$_2$SO$_4$, filtered and evaporated. The residue was purified on a Biotage Horizon HPFC system using Heptane and EtOAc as eluant and TEA as additive affording the title compound (1.18 g, 99.1%). $^1$H NMR (500 MHz, CDCl$_3$): δ 1.59 (d, 6H), 3.02 (q, 2H), 3.57 (t, 2H), 4.38-4.46 (m, 1H), 5.71 (bs, 1H), 7.43-7.46 (m, 3H), 7.50-7.53 (m, 2H); $^{13}$C NMR (125 MHz, CDCl$_3$): δ 20.38, 46.11, 47.76, 60.78, 107.46, 125.22, 128.96, 129.89, 131.70, 135.84, 158.67; Mass Spectrum: M+H$^+$ 311.

2-[(2-Isopropyl-4,4-dioxido-3-oxo-5-phenyl-2,3-dihydroisothiazol-4-yl)amino]ethyl 4-methylbenzenesulfonate A mixture of 4-[(2-hydroxyethyl)amino]-2-isopropyl-5-phenylisothiazol-3(2H)-one 1,1-dioxide (1.10 g, 3.54 mmol), 4-toluenesulfonyl chloride (0.81 g, 4.25 mmol), DMAP (0.43 g, 3.54 mmol) and Na$_2$CO$_3$ (1.13 g, 10.63 mmol) in dry DCM (20 mL) was stirred at rt for 4 h. The mixture was filtered and concentrated. The crude product was purified on a Horizon TM flash system using Heptane and EtOAc as eluant and TEA as additive affording the title compound (1.17 g, 71.1%). $^1$H NMR (500 MHz, CDCl$_3$): δ 1.59 (d, 6H), 2.48 (s, 3H), 3.18 (q, 2H), 3.85 (t, 2H), 4.37-4.45 (m, 1H), 5.47 (t, 1H), 7.37 (d, 2H), 7.40-7.46 (m, 5H), 7.76 (d, 2H); $^{13}$C NMR (125 MHz, CDCl$_3$): δ 20.37, 21.95, 42.80, 47.91, 67.46, 108.77, 124.61, 128.17, 129.19, 130.27, 130.32, 131.54, 132.48, 135.00, 145.74, 158.21; Mass Spectrum: M+H$^+$ 465.

4-[(2-Aminoethyl)amino]-2-tert-butyl-5-phenyl-isothiazol-3(2H)-one 1,1-dioxide Ethylenediamine (0.60 g, 10.0 mmol) was dissolved in dry DMF (50 ml) and heated to 60° C. 2-tert-Butyl-4-chloro-5-phenylisothiazol-3(2H)-one 1,1-dioxide (1.00 g, 3.34 mmol) dissolved in DMF (10 ml) was added dropwise over 30 mins and stirred at 60° C. for 10 mins. The reaction mixture was diluted with EtOAc (300 ml) and washed with water (400 ml and 2×200 ml), dried (Na$_2$SO$_4$), filtered and evaporated to give the title compound (0.97 g, 90%). $^1$H-NMR (500 MHz, CDCl$_3$): δ 7.50-7.45 (m, 2H), 7.42-7.37 (m, 3H), 5.83-5.76 (m, 1H), 2.84-2.78 (m, 2H), 2.67-2.62 (m, 2H), 1.71 (s, 9H); $^{13}$C-NMR (125 MHz, CDCl$_3$): δ 159.7, 135.4, 131.6, 129.5, 128.6, 125.2, 106.9, 61.5, 46.2, 40.8, 27.7; Mass Spectrum: M+H$^+$ 324.

4-[(4-Hydroxycyclohexyl)amino]-2-isopropyl-5-phenylisothiazol-3(2H)-one 1,1-dioxide 2-tert-Butyl-4-chloro-5-phenylisothiazol-3(2H)-one 1,1-dioxide (0.15 g, 0.53 mmol), 4-aminocyclohexanol (0.092 g, 0.80 mmol) and TEA (0.081 g, 0.80 mmol) was dissolved in dry MeCN (3 ml). The reaction was heated in a microwave reactor at 120° C. for 10 mins. A few extra drops of 4-aminocyclohexanol was added and the reaction was heated in a microwave reactor at 140° C. for 20 mins. The residue was purified by silica gel column chromatography using a 25:75 mixture of hexane and EtOAc, to give a 50:50 mixture of cis and trans isomers (0.130 g, 67%). The mixture was separated by HPLC (C8, 0.05M NH4OAc (pH=4.1):MeCN 1:1) to give cis (Example 38) and trans (Example 48) isomers.

N-(2-Methoxyethyl)-1-phenylmethanesulfonamide

Phenylmethanesulfonyl chloride (3.0 g, 15.7 mmol) was dissolved in dry THF (15 mL) and it was added dropwise to a solution of 2-methoxyethylamine (2.36 g, 31.5 mmol) in dry THF (50 mL) at 0° C. After addition the ice-bath was removed and the reaction was stirred at rt for 2.5 h. The solvent was removed in vacuo and the residue was dissolved in DCM. The mixture was washed with one portion of 5% aqueous HCl, several portions of water, dried through a phase separator and evaporated to give the title compound (3.58 g, 94%); $^1$H NMR (400 MHz, CDCl$_3$): δ 7.43-7.35 (m, 5H), 4.52 (br s, 1H), 4.26 (s, 2H), 3.40 (t, 2H), 3.32 (s, 3H), 3.14-3.09 (m, 2H); Mass Spectrum: M−H$^+$ 228.

4-Hydroxy-2-(2-methoxyethyl)-5-phenylisothiazol-3(2H)-one 1,1-dioxide

A solution of N-(2-methoxyethyl)-1-phenylmethanesulfonamide (3.5 g, 14.5 mmol) and diethyl oxalate (2.33 g, 16.0 mmol) in dry DMF was cooled in an ice-bath. Potassium tert-butoxide (2.17 g, 18.4 mmol) was added and after 5 mins the ice-bath was removed and the reaction was stirred at rt for 22 h. 2M HCl (45 mL) was added to the mixture and the acidic solution was extracted 3 times with dichloromethane. The combined organic layers were washed 4 times with water, dried through a phase separator and evaporated. The residue was purified by preparative HPLC [0.1M NH$_4$OAc/MeCN, (9:1 to 1:9)] to give the title compound (0.250 g, 6%) as a solid; $^1$H NMR (500 MHz, CD$_3$OD): δ 7.90-7.94 (m, 2H), 7.28-7.33 (m, 2H), 7.10-7.15 (m, 1H), 3.79 (t, 2H), 3.68 (t, 2H), 3.34 (s, 3H); Mass Spectrum: M−H$^+$ 282.

4-Chloro-2-(2-methoxyethyl)-5-phenylisothiazol-3(2H)-one 1,1-dioxide

Oxalyl chloride (0.185 g, 1.46 mmol) was added dropwise to a solution of 4-hydroxy-2-(2-methoxyethyl)-5-phenyl-isothiazol-3(2H)-one 1,1-dioxide (0.250 g, 0.88 mmol) in DCM (15 mL). The mixture was refluxed for 2 days and then evaporated. The residue was dissolved in water and extracted 3 times with dichloromethane. The combined organic layers were washed 2 times with water, dried through a phase separator and evaporated to give the title compound (0.245 g, 92%) as a solid; $^1$H NMR (500 MHz, CD$_3$OD): δ 7.94-7.97 (m, 2H), 7.58-7.67 (m, 3H), 3.94 (t, 2H), 3.70 (t, 2H), 3.38 (s, 3H).

N-Ethyl-1-phenylmethanesulfonamide

The title compound was prepared as described in the reference below:

Orazi, Orfeo O.; Corral, Renee A.; Bravo, Rodolfo; J. Heterocycl. Chem.; 23; 1986; 1701-1708.

2-Ethyl-4-hydroxy-5-phenylisothiazol-3(2H)-one 1,1-dioxide

N-Ethyl-1-phenylmethanesulfonamide (20 g) was divided into batches of 0.5 g each and taken in an 8 mL vial. To each vial was added potassium tert-butoxide (0.426 g, 3.8 mmol), ethyl oxalate (0.408 mL, 3.01 mmol) and dry THF (4 mL). Each vial was heated in a microwave reactor at 145° C. for 20 mins. Reaction mixture from all the vials were combined and treated with 1.5 N HCl (75 mL) and extracted with EtOAc. The organic layers were washed with water (3×25 mL) and brine, dried over Na$_2$SO$_4$ and evaporated. A small amount of the DCM was added to the solid residue and stirred well. Filtration gave nearly pure title compound (21 g, 82.6%) as off-white solid; $^1$H NMR (300 MHz, CDCl$_3$) δ 1.47 (t, 3H, J=7.2 Hz), 3.8 (q, 2H, J=7.2 Hz), 7.3-7.5 (m, 3H), 7.9-8.0 (m, 2H).

4-Chloro-2-ethyl-5-phenylisothiazol-3(2H)-one 1,1-dioxide

2-Ethyl-4-hydroxy-5-phenylisothiazol-3(2H)-one 1,1-dioxide (5 g, 19.76 mmol) was dissolved in dry DCM (250 mL) and cooled to 0° C. under N$_2$. Dry DMF (15 mL) was added, followed by oxalyl chloride (3 mL, 34.4 mmol). The ice-bath was removed and the mixture was refluxed at 50° C. under N$_2$ for 4 h. The reaction mixture was evaporated and the residue was diluted with EtOAc, washed with water (3×25 mL) and brine, dried over Na$_2$SO$_4$ and evaporated. Another (16 g, 63.24 mmol) of 2-ethyl-4-hydroxy-5-phenylisothiazol-3(2H)-one 1,1-dioxide was dissolved in dry DCM (500 mL) and cooled to 0° C. under N$_2$. Dry DMF (20 mL) was added followed by oxalyl chloride (9 mL, 103.2 mmol). The ice-bath was removed and the mixture was refluxed at 50° C. under N$_2$ for 4 h. The reaction mixture was evaporated and the residue was diluted with EtOAc, washed with water (3×50 mL) and brine, dried over Na$_2$SO$_4$ and evaporated where by red solid was obtained. The crude material from both batches were combined and purified by column chromatography on silica gel using 2.5-3% ethyl acetate in petroleum ether as eluant, and recrystallised from methanol to give the title compound (15.7 g, 70%) as a white solid; $^1$H NMR (400 MHz, CD$_3$OD) δ 1.42 (t, 3H, J=7.3 Hz), 3.84 (q, 2H, J=7.3 Hz), 7.6-7.7 (m, 3H), 7.9-8.0 (m, 2H); Mass Spectrum: M+H$^+$ 272.

Methyl 4-{3-[(2-tert-butyl-1,1-dioxido-3-oxo-5-phenyl-2,3-dihydroisothiazol-4-yl)amino]propoxy}benzoate The title compound was prepared as described for Example 5 from 2-tert-butyl-4-[(3-bromopropyl)amino]-5-phenyl-isothiazol-3(2H)-one 1,1-dioxide and methyl 3-hydroxybenzoate at a temperature of 100° C. The residue was purified by flash chromatography using hexane and EtOAc as eluent to give the title compound (0.124 g, 49%).

4-{2-[1,1-Dioxido-3-oxo-5-phenyl-2,3-dihydroisothiazol-4-yl)amino]ethyl}phenyl methanesulfonate A mixture of 4-{2-[(2-tert-butyl-1,1-dioxido-3-oxo-5-phenyl-2,3-dihydroisothiazol-4-yl)amino]ethyl}phenyl methanesulfonate (Example 77) (0.160 g, 0.334 mmol) in TFA (1 ml) was heated in a microwave reactor at 120° C. for 25 mins. The reaction mixture was evaporated to dryness and the residue purified by silica gel column chromatography (Horizons Biotage) using 6-12% MeOH in EtOAc (+1% AcOH) as eluent to give the title compound (0.047 g, 43%) as a solid; $^1$H NMR (500 MHz CD$_3$OD): δ 7.54-7.47 (m, 5H), 7.13 (d, 2H), 6.84 (d, 2H), 3.20-3.14 (m, 5H), 2.56 (t, 2H); $^{13}$C NMR (125 MHz CD$_3$OD): δ 164.2, 148.4, 137.9, 136.7, 131.5, 130.1, 129.1, 128.5, 127.1, 121.9, 108.2, 44.4, 36.2, 34.9; Mass Spectrum: M+H$^+$ 423

Methyl [(2-tert-butyl-1,1-dioxido-3-oxo-5-phenyl-2,3-dihydroisothiazol-4-yl)amino]acetate 2-tert-Butyl-4-chloro-5-phenylisothiazol-3(2H)-one 1,1-dioxide (1.09 g, 3.64 mmol), methyl glycinate hydrochloride (0.68 g, 5.46 mmol) and TEA (10.10 g, 10.92 mmol) were dissolved in a mixture of MeCN (10 mL) and DMF (5 mL) and the reaction mixture was stirred at 65° C. over night. The reaction mixture was evaporated and the residue was diluted with saturated aqueous NaHCO$_3$ and the mixture was extracted with DCM. The organic phases were combined, dried over MgSO$_4$, filtered and evaporated to give the title compound.

[(2-tert-Butyl-1,1-dioxido-3-oxo-5-phenyl-2,3-dihydroisothiazol-4-yl)amino]acetic acid Methyl [(2-tert-butyl-1,1-dioxido-3-oxo-5-phenyl-2,3-dihydroisothiazol-4-yl)amino]acetate (1.28 g, 3.64 mmol) was dispersed in a mixture of dioxane (20 mL), MeOH (20 mL) and water (20 mL). Aqueous LiOH (1M, 0.218 g, 9.10 mmol) was added and the reaction mixture was stirred at rt for 2 h. Aqueous HCl was carefully added to the reaction mixture to give the pH~1 and the resulting mixture was extracted with DCM. The organic phases were combined, dried over Na2SO4, filtered, evaporated and the crude residue was purified by preparative HPLC giving the title compound (0.51 g, 41%). $^1$H-NMR (CD$_3$OD, 500 MHz): δ 7.52-7.48 (m, 2H), 7.46-7.42 (m, 3H), 5.41 (brs, 8H) 1.95 (s, 2H), 1.71 (s, 9H); $^{13}$C-NMR (CD$_3$OD, 125 MHz): δ 178.4, 174.8, 160.8, 136.5, 132.8, 130.4, 129.5, 126.6, 107.4, 62.1, 48.3, 27.9, 22.9.

tert-Butyl [1-(2-cyanoethyl)piperidin-4-yl]carbamate

3-Bromopropionitril (0.74 g, 5.49 mmol) was added to a solution of tert-butyl piperidin-4-ylcarbamate (1.00 g, 4.99 mmol) and TEA (0.56 g, 5.49 mmol) in MeCN (15 mL), and the mixture was heated at 60° C. for 5 h and then evaporated.

The residue was purified by silica gel column chromatography (Horizons Biotage) using a 40:60 and then 15:85-10:90 mixture of heptane and EtOAc as eluant, to give the title compound (0.40 g, 32%). $^1$H NMR (500 MHz, CDCl$_3$): δ 4.44 (br s, 1H), 3.54-3.42 (br m, 1H), 2.88-2.79 (m 2H), 2.69 (t, 2H), 2.51 (t 2H), 2.24-2.16 (m, 2H), 1.99-1.92 (m 2H), 1.47 (s 9H), 1.49-1.41 (m 2H); $^{13}$C NMR (125 MHz, CDCl$_3$): δ 155.4, 119.0, 53.6, 52.2, 47.7, 32.7, 28.6, 16.4.

3-(4-Aminopiperidin-1-yl)propanenitrile

TFA (1.21 g, 10.62 mmol) was added to a solution of tert-butyl [1-(2-cyanoethyl)piperidin-4-yl]carbamate (0.27 g, 1.06 mmol) in DCM (11 mL), and the mixture was stirred at rt for 2 h. The mixture was evaporated and the product was used without any further purification.

2-(4-Phenoxybutyl)-1H-isoindole-1,3(2H)-dione

A mixture of N-(4-bromobutyl)phthalimide) (2.00 g, 7.09 mmol), phenol (0.67 g, 7.09) and K$_2$CO$_3$ (1.96 g, 14.18 mmoml) in dry MeCN (30 ml) was stirred at rt for 66 h. The reaction mixture was then warmed to 50° C. for 20 h before more phenol (0.33 mg, 3.54 mmol) was added and the resulting mixture was warmed at reflux. After 4 h EtOAc was added, the mixture was washed with brine, then 1N NaOH, and brine again before evaporated the organic phase to dryness to give the title compound (1.11 g, 53%) which was used without further purification. $^1$H NMR (500 MHz CDCl$_3$): δ 7-90-7.83 (m, 2H), 7.76-7.70 (m, 2H), 7.28 (t, 2H), 6.93 (t, 1H), 6.89 (d, 2H), 4.01 (t, 2H), 3.79 (t, 2H), 1.96-1.82 (m, 4H); Mass Spectrum: M+H$^+$ 296.

(4-Phenoxybutyl)amine

A mixture of 2-(4-phenoxybutyl)1H-isoindole-1,3(2H)-dione (10.10 g, 3.27 mmol) and 25% hydrazine solution in water (2.88 ml, 13.10 mmol) in EtOH (30 ml) was warmed at reflux. After 1.5 h, EtOAc was added and the mixture was extracted with brine. The combined aqueous phases were then re-extracted with EtOAc and all the organic phases combined. These were then extracted with 1N HCl, the acidic aqueous phases combined, basified with 2N NaOH and re-extracted into EtOAc before evaporating to dryness to give the title compound (0.411 mg, 67%) as an oil. $^1$H NMR (500 MHz CDCl$_3$): δ 7.32-2.26 (m, 2H), 6.95 (t, 1H), 4.00 (t, 2H), 2.80 (t, 2H), 1.90-1.82 (m, 2H), 1.68-1.62 (m, 2H).

tert-Butyl [2-(4-hydroxyphenyl)ethyl]carbamate 4-(2-Aminoethyl)phenol (2.00 g, 14.58 mmol) was dissolved in THF (70 mL) and MeOH (10 mL) and TEA (1.47 g, 14.58 mmol) was added. The mixture was cooled in an ice-bath. Di-tert-butyl dicarbonate (3.18 g, 14.58 mmol) was added. The mixture was stirred for 1 h at 0° C. and left at rt overnight. The solvent was evaporated and column chromatography of the crude product (ISOLUTE SI, (20 g), eluated with Heptane/EtOAc (90:10), Heptane/EtOAc (70:30)) afforded the title compound (3.47 g, 100%). $^1$H NMR (500 MHz, CD$_3$OD): δ 1.43 (s, 9H), 2.66 (t, 2H), 3.20 (t, 2H), 6.72 (d, 2H), 7.02 (d, 2H); Mass Spectrum: M–H$^+$ 236.

4-{2-[(tert-Butoxycarbonyl)amino]ethyl}phenyl methanesulfonate tert-Butyl [2-(4-hydroxyphenyl)ethyl]carbamate (3.45 g, 14.54 mmol) was dissolved in dry DCM (70 mL) and cooled in an ice-water bath. Methanesulfonyl chloride (1.99 g, 17.45 mmol) was added followed by TEA (2.21 g, 21.80 mmol). The reaction mixture was stirred at rt for 2 h. The reaction mixture was washed with saturated aqueous NaHCO$_3$, and the organic phase was dried with MgSO$_4$, filtered and evaporated. Column chromatography of the crude product (ISO-LUTE SI, (20 g), eluated with Heptane/EtOAc (90:10), Heptane/EtOAc (70:30)) afforded the title compound (4.06 g, 88.5%). $^1$H NMR (500 MHz, CD$_3$OD): δ 1.43 (s, 9H), 2.80 (t, 2H), 3.20 (s, 3H), 3.29 (q, 2H), 7.25 (d, 2H), 7.31 (d, 2H).

4-(2-Aminoethyl)phenyl methanesulfonate

4-{2-[(tert-Butoxycarbonyl)amino]ethyl}phenyl methanesulfonate (3.98 g, 12.62 mmol) was dissolved in DCM (12 mL) and TFA (10 mL) and stirred at rt for 4 h. The reaction mixture was concentrated and redissolved in EtOAc, washed with saturated aqueous K$_2$CO$_3$, and the organic phase was dried with Na$_2$SO$_4$, filtered and evaporated affording the title compound (2.71 g, 99.8%). $^1$H NMR (500 MHz, CD$_3$OD): δ 2.79 (t, 2H), 2.89 (t, 2H), 3.21 (s, 3H), 7.26 (d, 2H), 7.32 (d, 2H); $^{13}$C NMR (125 MHz, CD$_3$OD): δ 36.24, 38.34, 42.95, 122.11, 130.19, 139.44, 148.28; Mass Spectrum: M+H$^+$ 216.

tert-Butyl 3-(2-amino-2-oxoethyl)azetidine-1-carboxylate

PyBOP (1.946 g, 3.74 mmol) was added to a solution of [1-(tert-Butoxycarbonyl)azetidin-3-yl]acetic acid (0.805 g, 3.74 mmol) in DMF (10 mL). The mixture was stirred in an ice-bath, ammonia gas was bubbled in for 3 mins and then the mixture was stirred at rt overnight. The reaction mixture was concentrated, water (15 mL) and saturated, aqueous NaHCO$_3$ (5 mL) were added, and the mixture was extracted with EtOAc (20 mLx3). The extracts were combined, washed with water (20 mL) and brine (10mL), dried (Na$_2$SO$_4$) and evaporated. Column chromatography of the residue (ISOLUTE SI, 50 g/150 ml), eluting with EtOAc and heptane (50:50), then EtOAc and then MeOH and EtOAc (1:99, 2:98 and 5:95), gave the title compound (0.461 g, 57.5%) as a white solid. $^1$H NMR (400 MHz, CDCl$_3$): 1.42 (s, 9H), 2.53 (d, 2H), 2.85-2.96 (m, 1H), 3.60 (dd, 2H), 4.09 (t, 2H), 5.78 (s, br, 2H); $^{13}$C NMR (100 MHz, CDCl3): 25.4, 28.3, 39.7, 54.3 (br), 79.4, 156.3, 173.2.

tert-Butyl 3-(2-aminoethyl)azetidine-1-carboxylate tert-Butyl 3-(2-amino-2-oxoethyl)azetidine-1-carboxylate (70 mg, 0.327 mmol) was dissolved in THF (2 mL) and cooled on an ice-bath. Borane dimethyl sulfide complex (0.41 mL, 2M in THF) was added dropwise, whereafter the mixture was refluxed for 6 h. The reaction mixture was allowed to attain rt and a mixture of DIPEA:MeOH (0.6 mL, 1:2) and iodine (166 mg, 0.654 mmol) was added. The mixture was stirred at rt overnight and then evaporated to dryness. Water (5 mL) and EtOAc (5 mL) were added to the residue an the two phases were separated. Saturated, aqueous NaHCO$_3$ (1 mL) was added into the water phase, and it was extracted with EtOAc (5 mLx4). NaOH (1M, ca 1 mL) was added into the water phase and it was extracted with EtOAc (5 mLx2). The extracts were combined, dried (Na$_2$SO$_4$) and evaporated, and the residue was purified by using an ion exchange column (ISOLUTE PRS, 2 g/15 mL), eluting with MeOH and DCM (10:90), then MeOH and then MeOH (saturated with NH$_3$) to give the title compound (35 mg, 53.5%). $^1$H NMR (400 MHz, CDCl$_3$): 1.41 (s, 9H), 1.71 (dt, 2H), 2.49-2.60 (m, 1H), 2.64 (t, 2H), 3.54 (dd, 2H), 3.99 (t, 2H); $^{13}$C NMR (100 MHz, CDCl$_3$): 26.6, 28.3, 38.3, 39.8, 54.3 (br), 79.1, 156.3.

tert-Butyl [2-(4-bromophenyl)ethyl]carbamate

[2-(4-Bromophenyl)ethyl]amine (2.20 g, 11.00 mmol) was dissolved in dry THF (77 mL) and TEA (1.11 g, 11.00 mmol) was added. The mixture was cooled in an ice-bath. Di-tert-butyl dicarbonate (2.40 g, 11.00 mmol) was added. The mixture was stirred for 1 h at 0° C. and left at rt overnight. The solvent was evaporated and column chromatography of the crude product (ISOLUTE SI (20 g), Heptane/EtOAc (90:10)) afforded the title compound (3.18 g, 96.3%). $^1$H NMR (500 MHz, CD$_3$OD): δ 1.42 (s, 9H), 2.73 (t, 2H), 3.25 (t, 2H), 7.14 (d, 2H), 7.43 (d, 2H).

tert-Butyl [2-(4-cyanophenyl)ethyl]carbamate tert-Butyl [2-(4-bromophenyl)ethyl]carbamate (0.52 g, 1.73 mmol) was dissolved in dry DMF (17 mL) under nitrogen atmosphere. Zinc cyanide (0.41 g, 3.46 mmol) and tetrakis(triphenylphosphine)palladium (0.16 g, 0.14 mmol) was added. The reaction mixture was heated in a microwave reactor at 150° C. for 20 mins. The procedure was repeated two more times with equal amount of starting material and the resulting three mixtures were combined. The mixture was diluted with EtOAc, washed with saturated aqueous NaHCO$_3$ and water, dried with Na$_2$SO$_4$, filtered and evaporated. The crude product was purified using Biotage Horizon HPFC system (40+M column, isocratic run DCM/MeOH (99.5:0.5, 960 mL), gradient run DCM/MeOH (99.5:0.5-92:8, 240 mL), isocratic run DCM/MeOH (92:8, 720 mL)) affording the title compound (1.14 g, 88.9%). $^1$H NMR (500 MHz, CDCl$_3$): δ 1.44 (s, 9H), 2.88 (t, 2H), 3.40 (q, 2H), 4.58 (bs, 1H), 7.32 (d, 2H), 7.61 (d, 2H); Mass Spectrum: M+H$^+$ 247.

4-(2-Aminoethyl)benzonitrile tert-Butyl [2-(4-cyanophenyl)ethyl]carbamate (1.14 g, 4.62 mmol) was dissolved in DCM (6 mL) and TFA (5 mL) was added. The mixture was concentrated and dissolved in EtOAc, and the organic phase was washed with saturated aqueous K$_2$CO$_3$. The organic layer was dried with Na$_2$SO$_4$, filtered and evaporated affording the title compound (0.50 g, 74.3%). $^1$H NMR (500 MHz, CDCl$_3$): δ 1.21 (bs, 2H), 2.81 (t, 2H), 2.99 (t, 2H), 7.31 (d, 2H), 7.58 (d, 2H); $^{13}$C NMR (125 MHz, CDCl$_3$): δ 40.38, 43.31, 110.33, 119.23, 129.86, 132.48, 145.93.

tert-Butyl 3-hydroxypyrrolidine-1-carboxylate tert-Butyl 3-oxopyrrolidine-1-carboxylate (3.00 g, 16.20 mmol) was dissolved in dry MeOH (60 mL) and cooled in an ice-water bath. Sodium borohydride (0.61 g, 16.20 mmol) was added carefully and the reaction mixture was stirred at 0° C. for 15 mins. The reaction mixture was diluted with water and pH was set to −9 with HCl (1% aqueous solution). The aqueous layer was extracted with EtOAc and the organic layers were combined, dried with MgSO$_4$, filtered and evaporated to give the title compound (3.00 g, 98.9%). $^1$H NMR (500 MHz, CDCl$_3$): δ 1.42 (s, 9H), 1.85-1.96 (m, 2H), 3.26-3.33 (m, 2H), 3.38-3.47 (m, 3H), 4.38-4.40 (m, 1H); $^{13}$C NMR (125 MHz, CDCl$_3$): δ 28.72, 33.95, 43.99, 54.38, 70.60, 79.57, 155.07.

tert-Butyl 3-[(methylsulfonyl)oxy]pyrrolidine-1-carboxylate tert-Butyl 3-hydroxypyrrolidine-1-carboxylate (3.00 g, 16.02 mmol) was dissolved in dry DCM (50 mL) and cooled in an ice-water bath. Methanesulfonyl chloride (2.38 g, 20.83 mmol) was added followed by TEA (2.43 g, 24.03 mmol) and the reaction mixture was stirred at 0° C. for 3.5 h. The reaction mixture was washed with water (250 mL) and dried with MgSO$_4$, filtered and evaporated. The crude product was purified using Biotage Horizon HPFC system (40+M column, isocratic run heptane/EtOAc (50:50)) affording the title compound (2.70 g, 63.5%). $^1$H NMR (500 MHz, CDCl$_3$): δ 1.38 (s, 9H), 2.07 (bs, 1H), 2.18 (bs, 1H), 2.97 (s, 3H), 3.35-3.61 (m, 4H), 5.16-5.18 (m, 1H); $^{13}$C NMR (125 MHz, CDCl$_3$): δ 28.59, 31.84, 32.76, 38.80, 43.61, 52.16, 80.12, 154.30.

tert-Butyl 3-(acetylthio)pyrrolidine-1-carboxylate

Potassium carbonate (4.42 g, 31.96 mmol) was suspended in dry MeOH (20 mL) and thioacetic acid (2.28 g, 29.96 mmol) was added. The mixture was stirred vigorously for 10 mins, concentrated and diluted in dry DMF (30 mL). tert-Butyl 3-[(methylsulfonyl)oxy]pyrrolidine-1-carboxylate (2.65 g, 9.99 mmol) dissolved in dry DMF (20 mL) was added and the reaction mixture was heated to 60° C. for 3.5 h. The reaction mixture was diluted with water (350 mL) and extracted with EtOAc (2×150 mL) The organic phases were dried with MgSO$_4$, filtered and evaporated. The crude product was purified using Biotage Horizon HPFC system (25+M column, isocratic run heptane/EtOAc (60:40)) affording the title compound (0.592 g, 24.2%) (the product is a mixture of cis and trans isomers). $^1$H NMR (500 MHz, CDCl$_3$): δ 1.41 (d, 18H), 1.66 (d, 1H), 1.74-1.86 (m, 2H), 2.20-2.26 (m, 2H), 2.29 (s, 3H), 3.10-3.26 (m, 2H), 3.30-3.43 (m, 4H), 3.46-3.54 (m, 1H), 3.66-3.74 (m, 2H); $^{13}$C NMR (125 MHz, CDCl$_3$): δ 28.68, 30.82, 31.25, 32.34, 36.16, 41.09, 44.88, 51.60, 55.37, 79.67, 154.43; Mass Spectrum: M+H$^+$ 241.

tert-Butyl 3-mercaptopyrrolidine-1-carboxylate tert-Butyl 3-(acetylthio)pyrrolidine-1-carboxylate (200 mg, 0.81 mmol) was dissolved in MeOH (10 mL) and sodium methanethiolate (57 mg, 0.81 mmol) was added. The reaction mixture was stirred at rt for 30 mins. HCl (1M solution) was added and the aqueous layer extracted with DCM. The organic layer was washed with brine, dried (Na$_2$SO$_4$), filtered and evaporated affording the title compound (0.163 g, 98.4%). $^1$H NMR (500 MHz, CDCl$_3$): δ 1.44 (s, 9H), 1.68 (d, 1H), 1.75-1.84 (m, 1H), 2.22-2.28 (m, 1H), 3.13-3.23 (m, 1H), 3.30-3.40 (m, 2H), 3.47-3.57 (m, 1H), 3.67-3.74 (m, 1H).

[3-(Pyridin-2-yloxy)propyl]amine

3-Aminopropan-1-ol (0.28 ml, 3.64 mmol) was added to a mixture of NaH 60% dispersion in mineral oil (16 mg, 4.11 mmol) in dry THF (8 ml) at rt. The resulting mixture was heated at reflux for 35 mins and cooled to rt before 2-bromopyridine (0.50 g, 3.16 mmol) was added. The mixture was then refluxed for 2 h 20 mins and stirred at rt for another 17 h before more NaH (127 mg, 3.16 mmol) was added and the mixture heated at reflux for 3 h. The mixture was evaporated to dryness, water was added, and the mixture was acidified to pH5 with 1N HCl and washed with DCM. The aqueous phase was then basified to pH4 and extracted again with DCM. The organic extracts were combined and evaporated to give the title compound (0.206 g, 43%) as an oil. $^1$H NMR (500 MHz CDCl$_3$): 8.17-8.12 (m, 1H), 7.58-7.53 (m, 1H), 6.67-6.63 (m, 1H), 6.72 (d, 1H), 4.39 (t, 2H), 2.88 (t, 2H), 1.93 (quintet, 2H). $^{13}$C NMR (125 MHz CDCl$_3$): 164.1, 147.1, 138.7, 116.8, 111.3, 63.8, 39.5, 33.3.

tert-Butyl [1-(5-methylpyridin-2-yl)piperidin-4-yl)carbamate

A solution of 2-bromo-5-methylpyridine (1.00 g, 5.8 mmol), tert-butyl piperidine-4-ylcarbamate (1.28 g, 6.39 mmol) and TEA (1.21 ml, 8.72 mmol) in DMSO (5 ml) was heated at 110° C., After 17 h the reaction mixture was heated at 130° C. for 4 h before more TEA (0.40 ml, 2.91 mmol) was added. After 2.5 h, DBU (1.73 ml, 11.63 mmol) was added and the reaction mixture heated at 110° C. for 17 h. The reaction mixture was then allowed to cool to rt and EtOAc was added. The reaction mixture was washed with brine and evaporated to dryness. The residue was purified using the Biotage SPI eluting with 25% EtOAc in pet. ether 40-60° C. to give the title compound (0.233 g, 14%) as a solid. $^1$H NMR (500 MHz, CDCl$_3$): 8.02 (d, 1H), 7.31 (dd, 1H), 6.62 (d, 1H), 4.48 (bs, 1H), 4.16-4.10 (m, 2H), 3.68 (bs, 1H), 2.95 (dt, 2H), 2.20 (s, 3H), 2.08-2.00 (m, 2H), 1.48-1.40 (m, 9H). $^{13}$C NMR (CDCl$_3$): 158.1, 155.4, 147.9, 138.6, 122.3, 107.5, 79.5, 48.4, 45.1, 32.3, 28.7, 17.5. Mass Spectrum: M+H 292.

1-(5-Methylpyridin-2-yl)piperidin-4-amine dihydrochloride

A solution of tert-butyl [1-(5-methylpyridin-2-yl)piperidin-4-yl)carbamate (0.23 g, 0.79 mmol) in HCl in Dioxane (4M, 2 ml), THF (1 ml) and MeOH (1 ml) was stirred at room temperature. After 17 h, the reaction mixture was filtered, and the residue washed with EtOAc and dried to give the title compound (181 mg, 86.8%) as a solid. $^1$H NMR (500 MHz, D$_2$O): 7.80 (d, 1H), 7.60 (s, 1H), 7.15 (d, 1H), 4.10-4.03 (m, 2), 3.53-3.44 (m, 1H), 3.21 (t, 2H), 2.16-2.10 (m, 5H), 1.65 (dq, 2H); $^{13}$C NMR (D$_2$O): 150.8, 146.8, 133.9, 123.9, 112.9, 47.7, 44.7, 28.8; Mass Spectrum: M+H 192 tert-Butyl [1-(6-chloropyridazin-3-yl)piperidin-4-yl] carbamate tert-Butyl piperidin-4-ylcarbamate (2 g, 10 mmol), 3,6-dichloropyridazine (1.79 g, 12 mmol) and TEA (2.1 ml, 15 mmol) was dissolved in dry DMF (30 ml) and the reaction mixture was heated in a microwave reactor at 150° C. for 20 mins. The reaction mixture was diluted with water (300 ml) and extracted with EtOAc (300 ml). The organic phase was dried (Na$_2$SO$_4$), filtrated and evaporated. The residue was purified by silica gel column chromatography using a 98:2 mixture of DCM:MeOH to give the title compound (2.11 g, 68%) as a solid. $^1$H-NMR (CDCl$_3$, 500 MHz): δ 7.19 (d, 1H), 6.91 (d, 1H), 4.48 (bs, 1H), 4.29-4.20 (m, 2H), 3.73 (bs, 1H), 3.14-3.04 (m, 2H), 2.10-2.02 (m, 2H), 1.49-1.38 (m, 2H), 1.45 (s, 9H); $^{13}$C-NMR (CDCl$_3$, 125 MHz): δ 158.9, 155.2, 146.7, 128.9, 115.5, 79.6, 47.9, 44.4, 31.9, 28.5.

1-(6-Chloropyridazin-3-yl)piperidin-4-amine

[1-(6-Chloro-pyridazin-3-yl)-piperidin-4-yl]-carbamic acid tert-butyl ester (0.59 g 1.89 mmol) was dissolved in THF:MeOH 2:1 (45 ml) and HCl in 1,4-dioxan (4M, 3.8 ml, 7.56 mmol) was added. The reaction was stirred at rt for 3 h and then at 60° C. for 2 h. The solvent was evaporated to yield the title compound (0.49 g, 100%) as the hydrochloric salt. $^1$H-NMR (CD$_3$OD, 500 MHz): δ 8.10 (d, 1H), 7.92 (d, 1H), 4.41-4.35 (m 2H), 3.67-3.57 (m, 2H), 3.55-3.46 (m, 2H), 2.32-2.24 (m, 2H), 1.96-1.83 (m, 2H).

tert-Butyl [1-(6-methoxypyridazin-3-yl)piperidin-4-yl]carbamate tert-Butyl [1-(6-chloropyridazin-3-yl)piperidin-4-yl]carbamate (0.50 g, 1.60 mmol) was dissolved in dry MeOH (15 ml) and sodium metal (0.073 g, 3.20 mmol) dissolved in MeOH (5 ml) was added. The reaction mixture was heated at in a microwave reactor at 120° C. for 4 h. The mixture was diluted with water (500 ml) and extracted with EtOAc (200 ml). The organic phase was dried (Na$_2$SO$_4$), filtered and evaporated to yield the title compound (0.37 g, 75%).

1-(6-Methoxypyridazin-3-yl)piperidin-4-amine

[1-(6-Methoxy-pyridazin-3-yl)-piperidin-4-yl]-carbamic acid tert-butyl ester (0.37, 1.2 mmol) was dissolved in THF: MeOH 9:1 (15 ml) and HCl in 1,4-dioxane (4M, 1.2 ml, 4.8 mmol) was added. The reaction mixture was heated to 60° C. with for 3 h. The solvent was evaporated to yield the title compound (0.35 g, 100%) as the dihydrochloric salt. $^1$H-NMR (CD$_3$OD, 500 MHz): δ 8.04 (d, 1H), 7.57 (d, 1H), 4.34-4.26 (m, 2H), 4.00 (s, 3H), 3.62-3.55 (m, 1H), 3.50-3.40 (m, 2H), 2.30-2.23 (m, 2H), 1.90-1.79 (m, 2H); $^{13}$C-NMR (CD$_3$OD, 125 MHz): δ 159.7, 152.1, 129.8, 127.0, 62.1, 55.9, 46.2, 45,9, 45.7, 30.9, 30.3, 30.1.

tert-Butyl (1-pyridazin-3-ylpiperidin-4-yl)carbamate tert-Butyl [1-(6-chloropyridazin-3-yl)piperidin-4-yl]carbamate (0.5 g, 1.60 mmol) was dissolved in MeOH (20 ml) and cooled to 0° C. with an icebath. 10% Pd/C (60 mg) was added carefully. Ammonium formate (0.30 g, 4.80 mmol) was added and the reaction mixture was heated to 40° C. Ammonium formate (0.604 g, 9.59 mmol) was added in portions during the reaction, after 33 h at 40° C. the reaction mixture was filtered through celite and the celite was washed with MeOH (20 ml). The reaction mixture was evaporated and the residue was diluted with EtOAc (100 mL) and washed with water (200 ml). The organic phase was dried (Na$_2$SO$_4$) filtered and evaporated. The residue was purified by silica gel column chromatography using a 98:2 mixture of DCM: MeOH to give the title compound as a solid (0.25 g, 57%). $^1$H NMR (CDCl$_3$, 500 MHz): δ 8.52-8.47 (m, 1H), 7.17-7.11 (m, 1H), 6.91-6.84 (m, 1H), 4.67-4.57 (m, 1H), 4.30-4.21 (m, 2H), 3.75-3.62 (m, 1H), 3.09-2.99 (m, 2H), 2.05-1.96 (m, 2H), 1.46-1.35 (m, 2H), 1.40 (s, 9H); $^{13}$C NMR (CDCl$_3$, 125 MHz): δ 160.0, 155.4, 143.3, 127.5, 112.7, 79.6, 48.2, 44.3, 32.1, 28.6.

1-Pyridazin-3-ylpiperidin-4-amine tert-Butyl (1-pyridazin-3-ylpiperidin-4-yl)carbamate (0.22 g, 0.92 mmol) was dissolved in THF:MeOH 70:30 (15 ml) and HCl in 1,4-dioxane (4M, 1.84 ml, 7.36 mmol) was added and the mixture was refluxed for 1.5 h. The reaction mixture was evaporated to yield the title compound (0.250 g, 100%) as the dihydrochloric salt. (0.250 g, 100%). $^1$H NMR (CD$_3$OD, 500 MHz): δ 8.72-8.67 (m, 1H), 8.14-8.07 (m, 1H), 8.03-7.97 (m, 1H), 4.55-4.45 (m, 2H), 3.62-3.51 (m, 1H), 3.38-3.27 (m, 2H), 2.27-2.18 (m, 2H), 1.82-1.70 (m, 2H)

Tert-Butyl{1-[3-chloro-5-(trifluoromethyl)pyridine-2-yl]piperidin-4-yl}carbamate A mixture of 2,3-dichloro-5-(trifluoromethyl)pyridine (2.0 g, 9.26 mmol), tert-butyl piperidine-4-ylcarbamate (2.2 g, 111.1 mmol) and anhydrous potassium carbamate (3.8 g, 27.78 mmol) in DMF (15 ml) was heated in a microwave reactor at 150° C. for 10 min. The mixture was concentrated, water and EtOAc were added to the residue and the aqueous phase was extracted with EtOAc. The combined organic phases were dried over $Na_2SO_4$ and concentrated. The crude product was purified by flash column chromatography (hexane/EtOAc 90:10) to yield the title compound (2.5 g, 70%). $^1$H NMR (500 MHz, $CDCl_3$): δ 1.47 s, 9H), 1.53-1.60 (m, 2H), 2.07-2.09 (m, 2H), 3.01-3.06 (m, 2H), 3.72 (br.s., 1H), 3.97-4.00 (m, 2H), 4.54 (br.s., 1H), 7.75 (s, 1H), 8.38 (s, 1H); Mass Spectrum: M+H$^+$ 380.

1-[3-Chloro-5-(trifluoromethyl)-pyridin-2-yl]piperidine-4-amine tert-Butyl{1-[3-chloro-5-(trifluoromethyl)pyridine-2-yl]piperidin-4-yl}carbamate (2.5 g, 6.4 mmol) was stirred in a mixture of THF (25 ml), MeOH (5 ml) and HCl in dioxane (4M, 6.5 ml) over night at rt. HCl in dioxane (4M, 4 ml) was added and after 4 h a third portion of HCl in dioxane/4M, 4 ml) was added. Stirring was continued for 48 h at rt. The solvent was evaporated, and the residue was dissolved in EtOAc. The resulting mixture was washed with aqueous saturated $Na_2CO_3$, water and dried over $Na_2SO_4$. Concentration of the organic phase yielded the title compound (2.3 g, 128%), which contained some impurities. $^1$H NMR (500 MHz, $CDCl_3$): δ 1.50-1.54 (m, 2H), 1.88-1.94 (m, 2H), 2.93-3.00 (m, 3H), 4.01-4.04 (m, 2H), 7.74 (s, 1H), 8.38 (s, 1H); Mass Spectrum: M+H$^+$ 280.

2-(Benzyloxy)phenyl methanesulfonate 2-(Benzyloxy)phenol (3.00 g, 14.98 mmol) was dissolved in dry DCM (70 mL) under nitrogen atmosphere and cooled on an ice-water bath. Methanesulfonyl chloride (2.06 g, 17.98 mmol) was added during stirring followed by TEA (2.27 g, 22.47 mmol). The reaction mixture was stirred at rt for 2 h and then washed with aqueous saturated $NaHCO_3$, dried ($MgSO_4$), filtered and evaporated affording the title compound (4.04 g, 96.9%). $^1$H NMR (500 MHz, $CDCl_3$): δ 3.09 (s, 3H), 5.15 (s, 2H), 7.02 (dt, 1H), 7.09 (dd, 1H), 7.27 (dt, 1H), 7.34-7.48 (m, 6H); $^{13}$C NMR (125 MHz, $CDCl_3$): δ 38.72, 71.37, 114.67, 121.79, 125.06, 127.95, 128.50, 128.68, 129.00, 136.20, 138.96, 150.91.

2-Hydroxyphenyl methanesulfonate 2-(Benzyloxy)phenyl methanesulfonate (4.00 g, 14.37 mmol) was dissolved in dry DCM (50 mL) under nitrogen atmosphere. Boron trifluoride diethyl etherate (8.16 g, 57.49 mmol) was added followed by dimethyl sulfide (3.57 g, 57.49 mmol) and the reaction mixture was stirred at rt overnight. The reaction mixture was poured onto ice and the aqueous layer was extracted with DCM. The organic layers were combined, washed with water, dried ($Na_2SO_4$), filtered and evaporated to give the title compound (2.49 g, 92%). $^1$H NMR (500 MHz, $CDCl_3$): δ 3.26 (s, 3H), 6.16 (s, 1H), 6.96 (dt, 1H), 7.09 (dd, 1M), 7.22-7.28 (m, 2H); $^{13}$C NMR (125 MHz, $CDCl_3$): δ 37.74, 119.01, 121.65, 123.71, 129.09, 136.99, 148.43; Mass Spectrum: M–H$^+$ 187.

tert-Butyl [1-(6-chloropyridin-3-yl)piperidin-4-yl]carbamate

Step 1: A solution of 2-chloro-5-fluoropyridine (1.77 g, 13.47 mmol), tert-butyl piperidine-4-ylcarbamate (3.10 g, 15.49 mmol) and TEA (2.05 mL, 14.81 mmol) in DMSO (7 mL) was heated at 100° C. for 17 h, 120° C. for 4 h and 140° C. for 20 h.

Step 2: A solution of 2-chloro-5-fluoropyridine (1.77 g, 13.47 mmol), tert-butyl piperidine-4-ylcarbamate (2.83 g, 14.14 mmol) and TEA (2.05 ml, 14.81 mmol) in DMSO (7 ml) was heated at 140° C. for 17 h. tert-Butyl piperidine-4-ylcarbamate (0.269 g, 1.35 mmol) was added and the reaction mixture was heated at 140° C. for 17 h and then at 155° C. for 8 h and the reaction mixture was cooled to rt.

EtOAc was added to the combined reaction mixtures from step 1 and step 2, and the organic phase was washed with water and brine before evaporating to dryness. The residue was purified using the Biotage Horizon HPFC system eluting with 10-65% EtOAc in petroleum ether (40-60° C.) to give the title compound (1.21 g, 29%) as a solid. $^1$H NMR (500 MHz, $CDCl_3$): 8.02 (d, 1H), 7.21-7.12 (m, 2H), 4.50 (bs, 1H), 3.64 (bs, 1H), 3.64-3.54 (m, 2H), 2.89 (dt, 2H), 2.12-2.04 (m, 2H), 1.60-1.48 (m, 2H), 1.47 (s, 9H); $^{13}$C NMR ($CDCl_3$): 155.3, 146.3, 141.3, 138.1, 126.4, 124.1, 79.8, 48.2, 47.6, 32.2, 28.6; Mass Spectrum: M+H 312

1-(6-Chloropyridin-3-yl)piperidin-4-amine dihydrochloride

A solution of tert-butyl [1-(6-chloropyridin-3-yl)-piperidin-4-yl)carbamate (1.211 g, 3.88 mmol) in HCl in Dioxane (4M, 5 mL), THF (5 mL) and MeOH (4 mL) was stirred at rt for 20 h. The reaction mixture was filtered, the residue washed with EtOAc and dried to give the title compound (1.02 g, 92%) as a solid; $^1$H NMR (500 MHz, $CD_3OD$): 8.36 (d, 1H), 7.97 (dd, 1H), 7.68 (d, 1H), 4.05-3.96 (m, 2H), 3.51-3.41 (m, 1H), 3.18 (dt, 2H), 2.24-2.17 (m, 2H), 1.85 (dq, 2H); $^{13}$C NMR ($CD_3OD$): 145.8, 136.7, 133.3, 130.7, 126.5, 47.1, 28.9; Mass Spectrum: M+H 212.

Carbamic acid, [2-[[[3-(difluoromethoxy)phenyl]methyl]amino]-2-oxoethyl]-, 1,1-dimethylethyl ester N-(tert-Butoxycarbonyl)glycine (1.01 g, 5.78 mmol) was dissolved in dry DMF (12 mL) and DIPEA (2.24 g, 17.33 mmol) was added followed by HOAt (0.87 g, 6.35 mmol) and EDC (1.44 g, 7.51 mmol). The reaction mixture was stirred at rt for 30 mins followed by addition of [3-(difluoromethoxy) benzyl]amine (1.00 g, 5.78 mmol). The mixture was stirred at rt overnight. The reaction mixture was diluted with EtOAc and washed with water. The organic layer was dried with $Na_2SO_4$, filtered and evaporated. The crude product was purified on a Biotage Horizon HPFC system using DCM and MeOH as eluant affording the title compound (1.59 g, 83.3%). $^1$H NMR (500 MHz, $CDCl_3$): δ 1.44 (s, 9H), 3.84 (d, 2H), 4.47 (d, 2H), 5.27 (bs, 1H), 6.52 (t, $J_{C-F}$=73.6 Hz, 1H), 6.75 (bs, 1H), 7.02-7.04 (m, 2H), 7.13 (d, 1H), 7.30-7.34 (m, 1H); Mass Spectrum: M–H$^+$ 329.

$N^1$-[3-(Difluoromethoxy)benzyl]glycinamide

Carbamic acid, [2-[[[3-(difluoromethoxy)phenyl]methyl]amino]-2-oxoethyl]-, 1,1-dimethylethyl ester (1.58 g, 12.62 mmol) was dissolved in DCM (6 mL) and TFA (5 mL) was added. The reaction mixture was stirred at rt for 1 h The mixture was concentrated and diluted with EtOAc and washed with saturated aqueous $K_2CO_3$. The organic layer was dried with $Na_2SO_4$, filtered and evaporated affording the title compound (1.07 g, 97.2%). $^1$H NMR (500 MHz, $CDCl_3$): δ 1.49 (bs, 2H), 3.42 (s, 2H), 4.49 (d, 2H), 6.52 (t, $J_{C-F}$=73.8 Hz, 1H), 7.02-7.06 (m, 2H), 7.15 (d, 1H), 7.33 (t, 1H), 7.72

(bs, 1H); $^{13}$C NMR (125 MHz, CDCl$_3$): δ 42.70, 44.95, 116.13 (t, J$_{C-F}$=259.4 Hz), 118.52, 118.95, 124.84, 130.29, 141.07, 151.70, 173.01; Mass Spectrum: M+H$^+$ 231.

tert-Butyl (1-pyridin-2-ylpiperidin-4-yl)carbamate

A solution of 2-chloropyridine (0.83 ml, 8.81 mmol), tert-butyl piperidine-4-ylcarbamate (1.85 g, 9.24 mmol) and TEA (0.98 mL, 9.69 mmol) in DMSO (5 mL) was heated at 120° C. for 4 h 45 mins and then warmed to 140° C. for 2 days. EtOAc was added and the organic phase was washed with water then brine before evaporating to dryness. The residue was purified on a Biotage Horizion HPFC system eluting with 20% EtOAc in petroleum ether (40-60° C.) to give the title compound (0.65 mg, 27%). $^1$H NMR (500 MHz, CDCl$_3$): 8.19 (s, 1H), 7.48 (dd, 1H), 6.67 (d, 1H), 6.61 (t, 1H), 4.49 (bs, 1H), 4.21 (d, 2H), 3.70 (bs, 1H), 2.99 (t, 2H), 2.05 (d, 2H), 1.59-1.38 (m, 11H). $^{13}$C NMR (CDCl$_3$): 159.5, 155.4, 148.2, 137.7, 113.3, 107.5, 79.6, 48.4, 44.6, 32.3, 28.7; Mass Spectrum: M+H 278.

1-Pyridin-2-ylpiperidin-4-amine dihydrochloride

A solution of tert-butyl (1-pyridin-2-ylpiperidin-4-yl)carbamate (0.64 g, 2.31 mmol) in HCl in Dioxane (4M, 3.5 ml), THF (2.5 ml) and MeOH (2 ml) was stirred at rt for 17 h. The reaction mixture was filtered, the residue washed with EtOAc and dried to give the title compound (0.49 mg, 85%) as a solid. $^1$H NMR (500 MHz, D$_2$O): 7.91 (dd, 1H), 7.78 (d, 1H), 7.22 (d, 1H), 6.88 (t, 1H), 4.12 (d, 2H), 3.56-3.48 (m, 1H), 3.26 (t, 2H), 2.15 (d, 2H), 1.67 (dq, 2H); $^{13}$C NMR (D$_2$O): 152.1, 144.7, 135.9, 113.3, 47.6, 44.7, 28.8; Mass Spectrum: M+H 178 tert-Butyl [1-(5-fluoropyridin-2-yl)piperidin-4-yl]carbamate

Step 1: A solution of 2-chloro-5-fluoropyridine (1.77 g, 13.47 mmol), tert-butyl piperidine-4-ylcarbamate (3.10 g, 15.49 mmol) and TEA (2.05 mL, 14.81 mmol) in DMSO (7 mL) was heated at 100° C. for 17 h, 120° C. for 4 h and 140° C. for 20 h.
Step 2: A solution of 2-chloro-5-fluoropyridine (1.77 g, 13.47 mmol), tert-butyl piperidine-4-ylcarbamate (2.83 g, 14.14 mmol) and TEA (2.05mL, 14.81 mmol) in DMSO (7 mL) was heated at 140° C. for 17 h. tert-Butyl piperidine-4-ylcarbamate (0.269 g, 1.35 mmol) was added and the reaction mixture heated at 140° C. for 17 h and then at 155° C. for 8 h before cooling to rt.

EtOAc was added to the combined reaction mixtures from step 1 and step 2, and the organic phase was washed with water and brine before evaporating to dryness. The residue was purified using the Biotage Horizon HPFC system eluting with 10-65% EtOAc in petroleum ether (40-60° C.) to give the title compound (0.368 g, 9%) as a solid. $^1$H NMR (500 MHz, CDCl$_3$): 8.05 (d, 1H), 7.27-7.20 (m, 1H), 6.64 (dd, 1H), 4.49 (bs, 1H), 4.16-4.04 (m, 2H), 3.68 (bs, 1H), 2.96 (dt, 2H), 2.10-2.00 (m, 2H), 1.56-1.40 (m, 11H); $^{13}$C NMR (CDCl$_3$): 156.6, 155.4, 154.6, 152.6, 134.9, 134.8, 125.3, 125.1, 108.2, 108.1, 79.7, 48.2, 45.5, 32.3, 28.6; Mass Spectrum: M+H 296.

1-(5-Fluoropyridin-2-yl)piperidin-4-amine dihydrochloride

A solution of tert-butyl (1-(5-fluoropyridin-2-yl)piperidin-4-yl)carbamate (0.36 g, 1.22 mmol) in HCl in Dioxane (4M, 2 mL), THF (2 mL) and MeOH (2 mL) was stirred at rt. After 4 h the reaction mixture was filtered, the residue washed with EtOAc and dried to give the title compound (0.31 g, 96%) as a solid. $^1$H NMR (500 MHz, CD$_3$OD): 8.10-8.02 (m, 2H), 7.52 (dd, 1H), 4.34-4.26 (m, 2H), 3.61-3.50 (m, 1H), 3.38 (dt, 2H), 2.28-2.21 (m, 2H), 1.80 (dq, 2H); $^{13}$C NMR (CD$_3$OD): 153.2, 151.2, 151.0, 134.5, 134.3, 123.9, 123.6, 115.0, 114.9, 45.3, 29.1; Mass Spectrum: M+H 196.

tert-Butyl [1-(5-chloropyridin-2-yl)piperidin-4-yl]carbamate

A solution of 2,5-dicholoropyridine (1.00 g, 6.78 mmol), tert-butyl piperidine-4-ylcarbamate (1.42 g, 7.06 mmol) and TEA (1.03 mL, 7.43 mmol) in DMSO (5 mL) was heated at 120° C. for 21 h and then to 140° C. for 41 h. EtOAc was added and the organic phase was washed with water, brine, and evaporated to dryness. The residue was purified using the Biotage Horizon HPFC system eluting with 0-20% EtOAc in DCM to give the title compound (1.16 g, 55%) as a solid. $^1$H NMR (500 MHz, CDCl$_3$): 8.10 (d, 1H), 7.41 (dd, 1H), 6.61 (d, 1H), 4.18 (bs, 1H), 4.20-4.12 (m, 2H), 3.70 (m, 2H), 2.99 (dt, 2H), 2.08-1.98 (m, 2H), 1.58-1.38 (m, 11H); $^{13}$C NMR (CDCl$_3$): 157.8, 155.4, 146.5, 137.4, 120.1, 108.1, 79.7, 48.3, 44.8, 32.2, 28.6; Mass Spectrum: M+H 256.

1-(5-Chloropyridin-2-yl)piperidin-4-amine dihydrochloride

A solution of tert-butyl (1-(5-chloropyridin-2-yl)piperidin-4-yl)carbamate (1.15 g, 3.70 mmol) in HCl in Dioxane (4M, 5 mL) and THF (5 mL) was stirred at rt for 6.5 h. 4M HCl in Dioxane (2 mL) was added and the reaction mixture stirred for another 20 h. The reaction mixture was filtered, the residue was washed with EtOAc and dried to give the title compound (1.06 g, 100%) as a solid. $^1$H NMR (500 MHz, CD$_3$OD): 8.10 (s, 1H), 8.06 (d, 1H), 7.52 (d, 1H), 4.36 (d, 2H), 3.62-3.54 (m, 1H), 3.42 (dt, 2H), 2.18 (d, 2H), 1.82 (dq, 2H); $^{13}$C NMR (CD$_3$OD): 151.4, 144.4, 134.6, 120.0, 114.7, 45.2, 29.1; Mass Spectrum: M+H 212.

tert-Butyl {1-[4-(trifluoromethyl)pyridin-2-yl]piperidin-4-yl}carbamate

A solution of 2-bromo-4-trifluoromethylpyridine (1.00 g, 4.42 mmol), tert-butyl piperidine-4-ylcarbamate (0.93 g, 4.65 mmol) and TEA (0.67 mL, 4.86 mmol) in DMSO (5 L) was heated at 120° C. for 17 h. The reaction mixture was evaporated to dryness, Et$_2$O was added, and the organic phase was washed with water, brine and evaporated to dryness. The residue was purified using the Biotage Horizon HPFC system eluting with 22% EtOAc in petroleum ether (40-60° C.) to give the title compound (1.08 g, 71%) as a solid. $^1$H NMR (500 MHz, CDCl$_3$): 8.30 (d, 1H), 6.82 (s, 1H), 6.77 (d, 1H), 4.49 (bs, 1H), 4.36-4.22 (m, 2H), 3.74 (bs, 1H), 3.06 (td, 2H), 2.10-2.04 (m, 2H), 1.56-1.38 (m, 11H); $^{13}$C NMR (CDCl$_3$): 159.4, 155.4, 149.5, 140.1, 139.9, 124.5, 122.4, 108.1, 102.7, 79.8, 48.3, 44.4, 32.3, 28.6; Mass Spectrum: M+H 346.

1-[4-(Trifluoromethyl)pyridin-2-yl]piperidin-4-amine

A solution of tert-butyl {1-[4-(trifluoromethyl)pyridin-2-yl)piperidin-4-yl)carbamate (1.07 g, 3.09 mmol) in HCl in Dioxane (4M, 5 mL) and THF (5 mL) was stirred at rt for 6.5 h. HCl in Dioxane (4M, 2 mL) was added and the reaction mixture was stirred for another 20 h. The reaction mixture was filtered, the residue washed with EtOAc and dried to give the title compound (0.99 g, 100%) as a solid. $^1$H NMR (500 MHz, CD$_3$OD): 8.19 (d, 1H), 7.82 (s, 1H), 7.22 (d, 1H), 4.64

(d, 2H), 3.66-3.56 (m, 1H), 3.52 (td, 2H), 3.29 (d, 2H), 1.87 (dq, 2H); $^{13}$C NMR (CD$_3$OD): 152.6, 144.8, 144.5, 144.2, 143.9, 138.7, 125.3, 123.1, 120.9, 118.7, 111.2, 108.1, 45.3, 29.0; Mass Spectrum: M+H 246 tert-Butyl [2-(3-bromophenyl)ethyl]carbamate

[2-(3-Bromophenyl)ethyl]amine (2.22 g, 11.09 mmol) was dissolved in dry THF (80 mL) and TEA (1.12 g, 11.09 mmol) was added. The mixture was cooled in an ice-bath. Di-tert-butyl dicarbonate (2.42 g, 11.09 mmol) was added. The reaction mixture was stirred for 1 h at 0° C. and at rt for 2 h. The solvent was evaporated affording the title compound (3.44 g, 103%). $^1$H NMR (500 MHz, CDCl$_3$): δ 1.45 (s, 9H), 2.79 (t, 2H), 3.37 (q, 2H), 4.58 (bs, 1H), 7.12-7.15 (m, 1H), 7.17-7.20 (m, 1H), 7.35-7.38 (m, 2H); $^{13}$C NMR (125 MHz, CDCl$_3$): δ 28.63, 36.11, 41.82, 79.61, 122.83, 127.71, 129.78, 130.35, 132.12, 141.64, 156.05; Mass Spectrum: M-Na$^+$ 323.

tert-Butyl [2-(3-cyanophenyl)ethyl]carbamate tert-Butyl [2-(3-bromophenyl)ethyl]carbamate (0.60 g, 1.99 mmol) was dissolved in dry DMF (18 mL) in a under nitrogen atmosphere. Zinc cyanide (0.47 g, 3.99 mmol) and tetrakis(triphenylphosphine)palladium (0.18 g, 0.16 mmol) was added. The reaction mixture was heated in a microwave reactor at 150° C. for 20 mins. The procedure was repeated two more times with equal amount of starting material and the resulting three mixtures were combined and diluted with EtOAc. The mixture was washed with saturated aqueous NaHCO$_3$ and water, dried with Na$_2$SO$_4$, filtered and evaporated. The crude product was purified using Biotage Horizon HPFC system using Heptane and EtOAc as eluant affording the title compound (0.95 g, 64.3%). $^1$H NMR (500 MHz, CDCl$_3$): δ 1.39 (s, 9H), 2.82 (t, 2H), 3.34 (q, 2H), 4.75 (bs, 1H), 7.37-7.50 (m, 4H); $^{13}$C NMR (125 MHz, CDCl$_3$): δ 28.57, 36.09, 41.63, 79.61, 112.69, 119.05, 129.56, 130.38, 132.57, 133.68, 140.86, 156.06.

3-(2-Aminoethyl)benzonitrile tert-Butyl [2-(3-cyanophenyl)ethyl]carbamate (0.949 g, 3.853 mmol) was dissolved in DCM (5 mL) and TFA (4 mL) and stirred at rt for 2 h. The mixture was concentrated and redissolved in EtOAc. The mixture was washed with saturated aqueous K$_2$CO$_3$, dried over Na$_2$SO$_4$, filtered and evaporated affording the title compound (0.40 g, 71.7%). $^1$H NMR (500 MHz, CDCl$_3$): δ 1.18 (bs, 2H), 2.79 (t, 2H), 3.00 (t, 2H), 7.39-7.47 (m, 2H), 7.50-7.53 (m, 2H); $^{13}$C NMR (125 MHz, CDCl$_3$): δ 39.81, 43.42, 112.74, 119.17, 129.47, 130.24, 132.57, 133.66, 141.67.

4-(Benzyloxy)phenyl methanesulfonate 4-(Benzyloxy)phenol (4.00 g, 19.98 mmol) was dissolved in dry DCM (80 mL) under nitrogen atmosphere and cooled in an ice-water bath. Methanesulfonyl chloride (2.75 g, 23.97 mmol) was added during stirring followed by TEA (3.03 g, 29.96 mmol). The reaction mixture was stirred at rt for 2 h and then washed with saturated aqueous NaHCO$_3$, dried (MgSO$_4$), filtered and evaporated affording the title compound (5.32 g, 95.6%). $^1$H NMR (500 MHz, CDCl$_3$): δ 3.13 (s, 3H), 5.08 (s, 2H), 7.01 (m, 2H), 7.23 (m, 2H), 7.35-7.45 (m, 5H).

4-Hydroxyphenyl methanesulfonate 4-(Benzyloxy)phenyl methanesulfonate (5.31 g, 19.08 mmol) was dissolved in dry DCM (70 mL) under nitrogen atmosphere. Boron trifluoride diethyl etherate (10.83 g, 76.31 mmol) was added followed by dimethyl sulfide (4.74 g, 76.31 mmol) and the reaction mixture was stirred at rt for 3 h. The reaction mixture was poured onto ice and the aqueous layer was extracted with DCM. The organic layers were combined, washed with water, dried over Na$_2$SO$_4$, filtered and evaporated to give the title compound (2.96 g, 82.5%). $^1$H NMR (500 MHz, CDCl$_3$): δ 3.14 (s, 3H), 5.51 (s, 1H), 6.83 (d, 2H), 7.14 (d, 2H); $^{13}$C NMR (125 MHz, CDCl$_3$): δ 37.35, 116.74, 123.49, 142.68, 155.06.

tert-Butyl {1-[3-chloro-5-(trifluoromethyl)pyridin-2-yl]azetidin-3-yl}carbamate 2,3-Dichloro-5-(trifluoromethyl)pyridine (1.50 g, 6.94 mmol), tert-butyl azetidin-3-ylcarbamate (1.67 g, 9.72 mmol) and K$_2$CO$_3$ (2.88 g, 20.83 mmol) were dissolved in dry DMF (13 mL) under nitrogen atmosphere. The reaction mixture was heated in a microwave reactor at 150° C. for 15 mins. The reaction mixture was filtered and diluted with EtOAc, washed with water, dried over MgSO$_4$, filtered and evaporated. The crude product was purified by column chromatography (ISOLUTE SI (20 g), eluated with DCM, DCM/MeOH (99:1)) affording the title compound (0.85 g, 34.8%). $^1$H NMR (500 MHz, CDCl$_3$): δ 1.48 (s, 9H), 4.10-4.14 (m, 2H), 4.57 (bs, 1H), 4.65 (t, 2H), 5.00 (bs, 1H), 7.61 (s, 1H), 8.28 (s, 1H); $^{13}$C NMR (125 MHz, CDCl$_3$): δ 28.56, 41.67, 60.34, 80.45, 115.51, 117.44 (q, J$_{C-F}$=33.2 Hz), 123.83 (m, J$_{C-F}$=271.4 Hz), 135.06, 143.75, 155.18, 157.35; Mass Spectrum: M−H$^+$ 350.

1-[3-Chloro-5-(trifluoromethyl)pyridin-2-yl]azetidin-3-amine tert-Butyl {1-[3-chloro-5-(trifluoromethyl)pyridin-2-yl]azetidin-3-yl}carbamate (0.85 g, 2.42 mmol) was dissolved in DCM (4 mL) and TFA (3 mL) and stirred at rt for 1 h. The mixture was concentrated and redissolved in EtOAc, washed with saturated aqueous K$_2$CO$_3$. The organic layer was dried with Na$_2$SO$_4$, filtered and evaporated affording the title compound (0.58 g, 95.1%). $^1$H NMR (500 MHz, CDCl$_3$): δ 1.65 (bs, 2H), 3.91-3.98 (m, 3H), 4.57-4.61 (m, 2H), 7.58 (s, 1H), 8.26 (s, 1H); $^{13}$C NMR (125 MHz, CDCl$_3$): δ 43.68, 63.02, 115.38, 116.90 (q, J$_{C-F}$=33.2 Hz), 123.91 (q, J$_{C-F}$=270.9 Hz), 134.95, 143.76, 157.56; Mass Spectrum: M+H$^+$ 252.

Carbamic acid,
[2-oxo-2-[(phenylmethyl)amino]ethyl]-,
1,1-dimethylethyl ester

N-(tert-Butoxycarbonyl)glycine (1.64 g, 9.33 mmol) was dissolved in dry DCM (20 mL) and DIPEA (3.62 g, 27.99 mmol) was added followed by HOAt (1.40 g, 10.27 mmol) and EDC (2.33 g, 12.13 mmol). The reaction mixture was stirred at rt for 30 mins and benzylamine (1.00 g, 9.33 mmol) was added. The mixture was stirred at rt overnight. The reaction mixture was concentrated and diluted with EtOAc, washed with saturated aqueous NaHCO$_3$ and water. The organic layer was dried with Na$_2$SO$_4$, filtered and evaporated. The crude product was purified on a Biotage Horizon HPFC system using DCM and MeOH as eluant affording the title compound (1.26 g, 51%). $^1$H NMR (500 MHz, CDCl$_3$): δ

1.42 (s, 9H), 3.82 (d, 2H), 4.44 (d, 2H), 5.35 (bs, 1H), 6.73 (bs, 1H), 7.25-7.28 (m, 3H), 7.30-7.34 (m, 2H); Mass Spectrum: M+H$^+$ 265.

N$^1$-Benzylglycinamide

Carbamic acid, [2-oxo-2-[(phenylmethyl)amino]ethyl]-, 1,1-dimethylethyl ester (1.25 g, 12.62 mmol) was dissolved in DCM (6 mL) and TFA (5 mL) was added. The reaction mixture was stirred at rt for 2 h. The mixture was concentrated and diluted with EtOAc and washed with saturated aqueous K$_2$CO$_3$. The organic layer was dried with Na$_2$SO$_4$, filtered and evaporated affording the title compound (0.73 g, 94.5%). $^1$H NMR (500 MHz, CDCl$_3$): δ 1.48 (bs, 2H), 3.38 (s, 2H), 4.46 (d, 2H), 7.26-7.35 (m, 5H), 7.64 (bs, 1H); $^{13}$C NMR (125 MHz, CDCl$_3$): δ 43.24, 45.00, 127.65, 127.99, 128.90, 138.66, 172.93; Mass Spectrum: M+H$^+$ 165.

tert-Butyl (4-hydroxycyclohexyl)carbamate

4-Aminocyclohexanol (5.00 g, 43.41 mmol) was dissolved in dry THF (250 mL) and TEA (4.39 g, 43.41 mmol) was added. The mixture was cooled in an ice-bath. Di-tert-butyl dicarbonate (9.47 g, 43.41 mmol) was added and the reaction mixture was stirred at 0° C. for 1 h and left overnight at rt. The solvent was evaporated and column chromatography of the crude product (ISOLUTE SI (20 g) Heptane/EtOAc; 90:10-70:30) afforded the title compound (6.13 g, 65.6%) as a mixture of cis and trans isomeres. $^1$H NMR (500 MHz, CDCl$_3$): δ 1.21-1.37 (m, 4H), 1.45 (d, 9H), 1.53 (s, 9H), 1.57-1.73 (m, 8H), 1.88-1.96 (m, 4H), 3.25-3.31 (m, 1H), 3.40 (bs, 1H), 3.48-3.54 (m, 1H), 3.80-3.84 (m, 1H).

4-[(tert-Butoxycarbonyl)amino]cyclohexyl methanesulfonate tert-Butyl (4-hydroxycyclohexyl)carbamate (2.5 g, 11.61 mmol) and TEA (3.23 ml, 23.22 mmol) was dissolved in DCM (50 ml) and cooled to 0° C. with an icebath. Methansulfonyl chloride (1.17 ml, 15.10 mmol) was added dropwise and the icebath was removed. After stirring at rt for 2 h the reaction mixture was washed with water (200 ml), dried over Na$_2$SO$_4$, filtered and evaporated. The residue was purified by silica gel column chromatography using a 70:30 mixture of heptane:EtOAc to give the title compound (1.8 g, 53%) as 50:50 mixture of cis and trans isomers. $^1$H-NMR (CDCl$_3$, 500 MHz): δ 4.91-4.83 (m, 1H), 4.67-4.56 (m, 1H), 4.53-4.31 (m, 2H), 3.58-3.36 (m, 2H), 3.00 (ds, 6H), 2.17-1.98 (m, 6H), 1.88-1.78 (m, 2H), 1.77-1.50 (m, 6H), 1.43 (ds, 18H), 1.33-1.18 (m, 2H); $^{13}$C-NMR (CDCl$_3$, 125 MHz): δ 155.4, 79.9, 78.1, 48.2, 39.0, 38.9, 31.3, 30.8, 30.0, 28.6, 27.7.

tert-Butyl (4-{[4-(trifluoromethyl)phenyl]thio}cyclohexyl)carbamate

4-[(tert-Butoxycarbonyl)amino]cyclohexyl methanesulfonate (0.7 g, 2.39 mmol), 4-(trifluoromethyl)thiophenol (1.28 g, 7.16 mmol) and K$_2$CO$_3$ (1.32 g, 9.54 mmol) was dissolved in THF (21 ml) and the reaction mixture was heated in a microwave reactor at 130° C. for 30 mins. The reaction mixture was diluted with water (300 ml) and extracted with EtOAc (2×150 ml). The combined organic phases were dried over Na$_2$SO$_4$, filtered and evaporated. The residue was purified by silica gel column chromatography using a 85:15 mixture of heptane:EtOAc to give the title compound (0.386 g, 43%) as a 50:50 mixture of cis and trans isomers. $^1$H-NMR (CDCl$_3$, 500 MHz): δ 7.55-7.50 (m, 4H), 7.45-7.40 (m, 4H), 4.70-4.23 (m, 2H), 3.69-3.36 (m, 3H), 3.16-3.05 (m, 1H), 2.13-2.04 (m, 4H), 1.95-1.64 (m, 9H), 1.54-1.40 (m, 1H), 1.45 (ds, 18H), 1.30-1.15 (m, 2H); $^{13}$C-NMR (CDCl$_3$, 125 MHz): δ 155.4, 141.1, 140.7, 130.5, 129.9, 128.6, 128.5, 128.2, 126.0, 125.9, 125.9, 125.9, 125.4, 123.2, 79.5, 49.1, 47.9, 44.8, 43.8, 33.4, 32.0, 29.2, 29.1, 28.6.

(4-{[4-(Trifluoromethyl)phenyl]thio}cyclohexyl) amine tert-Butyl (4-{[4-(trifluoromethyl)phenyl]thio}cyclohexyl)carbamate (0.38 g, 1.01 mmol) was dissolved in THF:MeOH 8:2 (10 ml) and HCl in 1,4-dioxane (4M, 2 ml) was added. The reaction mixture was stirred at rt for 15 h, and then evaporated. The crude product was diluted with EtOAc (100 ml), washed with a mixture of saturated aqueous Na$_2$CO$_3$ and water (1:2, 100 ml) and water (2×100 ml). The organic layer was dried over Na$_2$SO$_4$, filtrated and evaporated to yield the title compound (0.27 g, 97%) as a 50:50 mixture of cis and trans isomers. $^1$H-NMR (CDCl$_3$, 500 MHz): δ 7.56-7.48 (m, 4H), 7.46-7.39 (m, 4H), 3.59-3.52 (m, 1H), 3.17-3.07 (m, 1H), 2.90-2.79 (m, 1H), 2.78-2.68 (m, 1H), 2.13-2.03 (m, 2H), 1.99-1.14 (m, 18H); $^{13}$C-NMR (CDCl$_3$, 125 MHz): δ 141.6, 141.0, 130.2, 129.7, 125.9, 125.9, 50.0, 48.9, 45.0, 44.0, 36.6, 32.3, 32.1, 30.5, 29.2, 29.0, 28.6.

tert-Butyl {1-[5-(trifluoromethyl)pyridin-2-yl]piperidin-4-yl}carbamate

Mixture of 2-chloro-5-(trifluoromethyl)pyridine (1.00 g, 5.51 mmol), tert-butyl 4-aminopiperidine-1-carboxylate (1.16 g, 5.78 mmol) and TEA (0.84 ml, 6.06 mmol) in DMSO (5 ml) was heated at 120° C. for 18 h. The mixture was evaporated, EtOAc was added and the mixture was washed with water, then brine and evaporated to dryness. The crude product was purified by triturating with MeOH and then EtOAc to give the title compound (1.29 g, 67%) as a solid. $^1$H-NMR (500 MHz CDCl$_3$): 8.39 (s, 1H), 7.62 (dd, 1H), 6.66 (d, 1H), 4.48 (bs, 1H), 4.38-4.28 (m, 2H), 3.75 (bs, 1H), 3.07 (dt, 2H), 2.10-2.02 (m, 2H), 1.58-1.38 (m, 11H); $^{13}$C-NMR (125 MHz CDCl$_3$): 160.3, 155.3, 146.0, 134.8, 125.9, 123.8, 115.3, 115.0, 105.8, 79.8, 48.3, 44.1, 32.3, 28.6; Mass Spectrum M+H$^+$ 346.

1-[5-(trifluoromethyl)pyridin-2-yl]piperidin-4-amine dihydrochloride

A mixture of tert-butyl {1-[5-(trifluoromethyl)pyridin-2-yl]piperidin-4-yl}carbamate (1.27 g, 3.68 mmol) in HCl in Dioxane/THF (4M, 1:1; 10 ml) was stirred at rt. After 6.5 h more HCl in Dioxane (4M, 2 ml) was added and the resulting mixture stirred for a further 18 h. The mixture was filtered and the residue was washed with EtOAc to give the title compound (1.04 g, 89%) as a solid. $^1$H NMR (500 MHz CD$_3$OD): 8.35 (s, 1H), 8.20 (dd, 1H), 7.60 (d, 1H), 4.46 (d, 2H), 3.66-3.56 (m, 1H), 3.48 (td, 2H), 2.28 (d, 2H), 1.90-1.80 (m, 2H); $^{13}$C NMR (125 MHz CD$_3$OD): 153.5, 139.2, 136.3, 126.1, 123.9, 121.8, 120.0, 116.2, 115.9, 115.6, 115.3, 113.9, 45.2, 29.1; Mass Spectrum: M+H$^+$ 246.

tert-Butyl 3-(cyanomethoxy)azetidine-1-carboxylate

NaH (60% dispersion in mineral oil, 276 mg, 6.89 mmol) was added to an ice cold solution of tert-butyl 3-hydroxyazetidine-1-carboxylate (0.92 mg, 5.30 mmol) in THF (8 mL) and stirred for 15 mins. Bromoacetonitrile (0.52 mL, 7.43 mmol) was added dropwise and the reaction mixture allowed to warm to room temperature. After 2.5 h, bromoacetonitrile (0.074 mL, 1.06 mmol) was added and the reaction mixture stirred at rt. After 17 h, NaH (60% dispersion in mineral oil, 0.085 mg, 2.12 mmol) and bromoacetonitrile (0.074 mL, 1.06 mmol) were added. After 2 h the reaction mixture was evaporated to dryness and the crude product purified on a Biotage Horizon HPFC system eluting with 5-90% EtOAc in petroleum ether (40-60° C.) to give the title compound (0.47 g, 42%) as an oil. $^1$H NMR (CDCl$_3$): δ 4.46-4.40 (m, 1H), 4.24 (s, 2H), 4.17 (dd, 2H), 3.92 (dd, 2H), 1.45 (s, 9H); $^{13}$C NMR (CDCl3): δ 156.3, 115.6, 80.2, 69.3, 56.3, 54.6, 28.6.

tert-Butyl 3-(2-aminoethoxy)azetidine-1-carboxylate

A mixture of tert-butyl 3-(cyanomethoxy)azetidine-1-carboxylate (0.46 g, 2.19 mmol) and 10% Pd/C (10%) in EtOH was stirred under H$_2$ gas at 3 atm. After 3 h the reaction mixture was filtered through celite and the filtrate evaporated to dryness to give the title compound (0.41 g, 87%) as an oil. $^1$H NMR (CDCl$_3$): δ 4.27-4.20 (m, 1H), 4.08 (t, 2H), 3.84 (dd, 2H), 3.49 (t, 2H), 2.84 (t, 2H), 1.45 (s, 9H); $^{13}$C NMR (CDCl3): δ 156.6, 79.7, 68.3, 68.2, 56.7, 49.4, 28.6.

2-[4-(Trifluoromethoxy)phenyl]acetamide 4-(Trifluoromethoxy)phenylacetic acid (2 g, 9.085 mmol) was dissolved in DMF (20 ml, dry) and PyBOP (4.728 g, 9.085 mmol) was added. The mixture was stirred in an ice-bath and ammonia gas was bubbled in for 5 mins. The ice-bath was removed and the mixture was stirred at rt overnight and then evaporated in vacuum. Water (50 ml) was added into the residue and it was extracted with EtOAc (20 ml×3). The extracts were combined, washed with saturated aqueous NaHCO$_3$ (15 ml), water (20 ml×3), brine (15 ml), dried (MgSO$_4$) and evaporated. The residue was purified by column chromatography (ISOLUTE SI, 20 g/70 ml), eluting with DCM, then MeOH/DCM (1:99), to give the title compound (1.14 g, 57%) as a white solid. Mass Spectrum: M–H$^+$ 218. $^1$H NMR (400 MHz, CD$_3$OD): δ 3.53 (s, 2H), 7.20 (d, 2H), 7.38 (d, 2H). $^{13}$C NMR (100 MHz, CD$_3$OD): 42.5, 121.9 (q, J=253 Hz), 122.1, 131.8, 136.3, 149.4, 176.2.

2-[4-(Trifluoromethoxy)phenyl]ethanamine

2-[4-(Trifluoromethoxy)phenyl]acetamide (1.13 g, 5.156 mmol) was dissolved in THF (20 ml) and the reaction mixture was cooled in an ice-bath. Borane dimethyl sulfide complex (6.4 ml, 2M in THF) was added dropwise. After the addition, the cooling-bath was removed and the mixture was heated to reflux for 5 h and cooled down to rt. HCl (10%, 4 ml) was added, the mixture was stirred at rt overnight and then evaporated to remove THF. Water (15 ml) and diethyl ether (15 ml) were added into the residue. The two phases were separated and NaHCO$_3$ (sat.) was added into the water phase. It was then extracted with EtOAc (20 ml×3). The extracts were combined and washed with brine, dried (Na$_2$SO$_4$) and evaporated. The residue was purified by column chromatography (ISOLUTE SI, 20 g/70 ml), eluting with MeOH/DCM (1:99, 2:98, 5:95 then 10:90), to give 0.2 g desired product and 0.46 g mixture. The mixture was further purified by re-chromatography (ISOLUTE SI, 20 g/70 ml), eluting with MeOH/EtOAc (2:98, 5:95, 10:90), to give 0.107 g more of the desired product. In total (0.307 g, 29%) of the title compound was obtained. Mass Spectrum: M+H$^+$ 206. $^1$H NMR (400 MHz, CD$_3$OD): δ 2.95 (t, 2H), 3.12 (t, 2H), 7.23 (d, 2H), 7.38 (d, 2H). $^{13}$C NMR (100 MHz, CD$_3$OD): 35.3, 42.5, 122.2 (q, J=250 Hz), 122.6, 131.7, 136.2, 149.7.

Tert-Butyl-(2-{[5-(trifluoromethyl)pyridine-2-yl]oxy}-ethyl)carbamate

Tert-Butyl (2-hydroxyethyl)carbamate (8.88 g, 55.08 mmol) was added to a solution of NaH (55%, 55.08 mmol, washed twice with petroleum ether) in DMF (150 ml) at –10° C. and stirred for 10 mins. 2-Chloro-5-(trifluoromethyl)pyridine (10.0 g, 55.08 mmol) was added and the reaction mixture was stirred at rt for 3 days, heated to 100° C. and cooled to rt. The reaction mixture was evaporated, the residue was washed with isopropylether, and the solution was decanted from insoluble salts and concentrated. The residue was dissolved in EtOAc, washed twice with water, dried over MgSO$_4$ and concentrated. Recrystallisation from isobutylethyl ether gave the title compound (6.2 g, 37%). $^1$H-NMR (500 MHz, CDCl$_3$) δ 1.46 (s, 9H), 3.56 (br.m, 2H), 4.45 (t, 2H), 6.84 (d, 1H), 7.79 (dd, 1H), 8.44 (s, 1H.

2-{[5-Trifluoromethyl)pyridine-2-yl]oxy}ethyl) amine hydrochloride tert-Butyl-(2-{[5-(trifluoromethyl)pyridine-2-yl]oxy}-ethyl)carbamate (6.1 g, 19.92 mmol) in EtOAc (saturated with HCl) was stirred for 2 days. The reaction mixture was concentrated enough for precipitation of the title compound (4.7 g) as the HCl-salt. $^1$H-NMR (300 MHz, CD$_3$OD): δ 3.39 (t, 2H), 4.64 (t, 2H), 7.04 (d, 1H), 7.99 (dd, 1H), 8.5 (s, 1H).

tert-Butyl (1-pyridin-2-ylazetidin-3-yl)carbamate

The title compound was prepared from 2-chloropyridine and tert-butyl azetidin-3-ylcarbamate in a similar manner as described for tert-butyl {1-[3-chloro-5-(trifluoromethyl)pyridin-2-yl]azetidin-3-yl}carbamate. $^1$H NMR (500 MHz CDCl$_3$): δ 1.46 (s, 9H), 3.76-3.80 (m, 2H), 4.31-4.35 (m, 2H), 4.63 (bs, 1H), 5.10 (bs, 1H), 6.29 (d, 1H), 6.61-6.64 (m, 1H), 7.43-7.47 (m, 1H), 8.14-8.16 (m, 1H); $^{13}$C NMR (125 MHz CDCl$_3$): δ 28.58, 41.79, 58.58, 80.22, 106.36, 113.48, 137.37, 148.42, 155.24, 160.66; Mass Spectrum: M+H$^+$ 250.

1-Pyridine-2-ylazetidin-3-amine

The title compound was prepared from tert-butyl (1-pyridin-2-ylazetidin-3-yl)carbamate in a similar manner as described for 1-[3-chloro-5-(trifluoromethyl)pyridin-2-yl]azetidin-3-amine. $^1$H NMR (500 MHz CDCl$_3$): δ 1.96 (bs, 2H), 3.59-3.63 (m, 2H), 3.89-3.95 (m, 1H), 4.22-4.27 (m, 2H), 6.26 (d, 1H), 6.55-6.58 (m, 1H), 7.38-7.43 (m, 1H), 8.11 (s, 1H).

2,6-Dimethylphenyl 4-[(tert-butoxycarbonyl)amino]butanoate 2,6-Dimethylphenol (0.257 g, 2.1 mmol) and 4-[(tert-butoxycarbonyl)amino]butanoic acid (0.427 g, 2.1 mmol) were dissolved in THF (10 ml, dry) and DMAP (0.005 g, 0.04 mmol) was added. After cooling down to 0-2° C., EDC (0.483 g, 2.52 mmol) was added portionwise under nitrogen atmosphere. The ice bath was removed and stirring was continued over night at rt. After 17 h, the mixture was diluted with DCM (50 ml) and extracted with water (20 ml), HCl (2N, 20 ml) and water (20 ml) again. The organic layer was dried (MgSO$_4$) and evaporated. The residue was purified by column chromatography on silica gel, using DCM/MeOH (95:5) as eluent, to give the title compound (0.493 g, 76%) as a colorless solid. $^1$H NMR (400 MHz, CDCl$_3$): δ 1.45 (s 9H), 1.94-2.01 (m, 2H), 2.14 (s, 6H), 2.66 (t, 2H), 3.24-3.29 (m, 2H), 4.66 (bs, 1H), 7.05 (s, 3H); Mass Spectrum: M-tert-Bu+H⁺ 252.1

2,6-Dimethylphenyl 4-aminobutanoate hydrochloride 2,6-Dimethylphenyl 4-[(tert-butoxycarbonyl)amino]butanoate (0.49 g, 1.594 mmol) was dissolved in DCM (20 ml) and HCl (4M in dioxane, 1.2 ml) was added dropwise at 0° C. The mixture was stirred for 30 minutes at 0-2° C. before the ice bath was removed and stirring was continued at rt. The mixture was evaporated in vacuum to give the title compound (0.371 g, 86%) as a white solid. It was used without further purification. ¹H NMR (400 MHz, DMSO-d6): δ 1.88-1.96 (m, 2H), 2.07 (s, 6H), 2.80 (t, 2H), 2.85 (bs, 2H), 7.02-7.11 (m, 3H), 8.10 (bs, 3H).

Phenyl N-(tert-butoxycarbonyl)-β-alaninate

The title compound was prepared from N-(tert-butoxycarbonyl)-β-alanine and phenol in a similar manner as described for 2,6-dimethylphenyl 4-[(tert-butoxycarbonyl)amino]butanoate. Mass Spectrum (M-tert-Bu)+H⁺ 211.09.

Phenyl β-alaninate Hydrochloride

The title compound was prepared from phenyl N-(tert-butoxycarbonyl)-β-alaninate in a similar manner as described for 2,6-dimethylphenyl 4-aminobutanoate hydrochloride. ¹H NMR (400 MHz, CDCl₃): δ 7.36-7.40 (t, 2H), 7.22-7.25 (t, 1H), 7.12-7.14 (d, 2H), 4.82 (s, 3H), 3.27-3.30 (m, 2H), 2.99-3.03 (t, 2H).

4-(Trifluoromethoxy)phenyl N-(tert-butoxycarbonyl)-β-alaninate

The title compound was prepared from N-(tert-butoxycarbonyl)-β-alanine and 4-(trifluoromethoxy)phenol in a similar manner as described for 2,6-dimethylphenyl 4-[(tert-butoxycarbonyl)amino]butanoate. Mass Spectrum (M-tert-Bu)+H⁺ 293.96

4-(Trifluoromethoxy)phenyl β-alaninate

The title compound was prepared from 4-(trifluoromethoxy)phenyl N-(tert-butoxycarbonyl)-β-alaninate in a similar manner as described for 2,6-dimethylphenyl 4-aminobutanoate hydrochloride. Mass Spectrum M+H⁺ 251.10

1-Methylpiperidin-4-yl N-(tert-butoxycarbonyl)-β-alaninate

The title compound was prepared from 1-methylpiperidin-4-ol and N-(tert-butoxycarbonyl)-β-alanine in a similar manner as described for 2,6-dimethylphenyl 4-[(tert-butoxycarbonyl)amino]butanoate. ¹H NMR (400 MHz, CDCl3): δ 4.99 (s, 1H), 4.74-4.79 (m, 1H), 3.32-3.6 (m, 2H), 2.58 (s, 2H), 2.45-2.49 (t, 2H), 2.23 (s, 3H), 2.16-2.19 (m, 2H), 1.83-1.88 (m, 2H), 1.62-1.71 (m, 2H), 1.34 (s, 9H).

1-Methylpiperidin-4-yl β-alaninate hydrochloride

The title compound was prepared from 1-methylpiperidin-4-yl N-(tert-butoxycarbonyl)-β-alaninate in a similar manner as described for 2,6-dimethylphenyl 4-aminobutanoate hydrochloride. Mass Spectrum M+H⁺ 188.17.

Mesitylacetaldehyde

2-Mesitylethanol (0.99 g, 6.0 mmol) was dissolved in DCM (10.0 mL, dry) and cooled to 0° C. 1,1,1-Tris(acetyloxy)-1λ⁵,2-benziodoxol-3(1H)-one (Dess-Martin periodinane) in DCM (15 wt %, 2.80 g, 6.60 mmol) was added dropwise over a period of 20 mins. The ice bath was removed and the reaction mixture was stirred at rt for 4 h. NaOH (2N, 5 mL) was added to the mixture and it was diluted with water (5 mL). The layers were separated and the organic layer was washed with water, dried over Na2SO4, and evaporated. The residue was purified by column chromatography on silica gel using heptane and EtOAc as eluant giving the title compound (0.69 g, 71%). ¹H NMR (CDCl₃, 400 MHz) δ 9.68-9.65 (m, 1H), 6.94-6.90 (m, 2H), 3.75-3.71 (m, 2H), 2.29 (s, 3H), 2.27 (s, 6H).

1-Mesitylpropan-2-ol

Mesitylacetaldehyde (0.68 g, 4.19 mmol) was dissolved in THF (5.0 mL, dry) and MeMgBr in Et₂O (3.0M, 0.75 g, 6.29 mmol)) was added slowly at 0° C. The cooling bath was removed and the reaction mixture was stirred at rt for 4.5 h. The mixture was cooled to 0° C. and excess Grignard reagent was hydrolyzed with HCl (1N). The mixture was diluted with water and extracted with Et₂O. The organic layer was dried over Na₂SO₄, evaporated and the residue was purified by column chromatography on silica gel using MTBE, heptane and DCM as eluant giving the title compound (0.51 g, 61%). ¹H NMR (CDCl₃, 500 MHz) δ 6.88-6.85 (m, 2H), 4.08-3.99 (m, 1H), 2.87-2.72 (m, 2H), 2.32 (s, 6H), 2.26 (s, 3H), 1.29 (d, 3H).

Example 1

2-tert-Butyl-5-phenyl-4-[(4-phenylbutyl)amino] isothiazol-3(2H)-one 1,1-dioxide

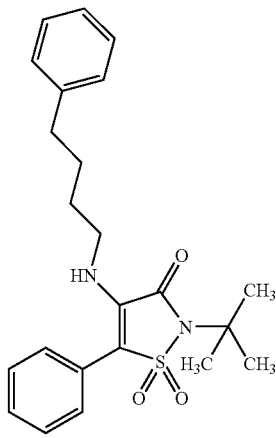

A solution of 2-tert-butyl-4-chloro-5-phenylisothiazol-3 (2H)-one 1,1-dioxide (0.150 g, 0.50 mmol), TEA (0.076 g, 0.751 mmol) and 4-phenylbutylamine (0.097 g, 0.65 mmol) in MeCN (3 mL) was heated in a microwave reactor at 120° C. for 10 mins. The mixture was evaporated and the residue was purified by silica gel column chromatography using a 85:15 mixture of heptane and EtOAc as eluant, to give the title compound (0.19 g, 92%) as a solid; ¹H NMR (500 MHz, CDCl₃): δ 7.52-7.47 (m, 2H), 7.45-7.40 (m, 3H), 7.31-7.26 (m 2H), 7.22-7.17 (m, 1H), 7.08 (d, 2H), 5.26 (t, 1H), 2.88-2.81 (m, 2H), 2.49-7.43 (m, 2H), 1.75 (s 9H), 1.48-1.36 (m 4H); ¹³C NMR (125 MHz, CDCl₃) δ 159.9, 141.8, 135.3, 131.9, 129.8, 128.8, 128.6, 128.5, 126.2, 125.3, 107.0, 61.7, 44.1, 35.5, 29.2, 28.4, 27.9; Mass Spectrum: M−H⁺ 413.

Example 2

2-Cyclopentyl-5-phenyl-4-[(4-phenylbutyl)amino]isothiazol-3(2H)-one 1,1-dioxide

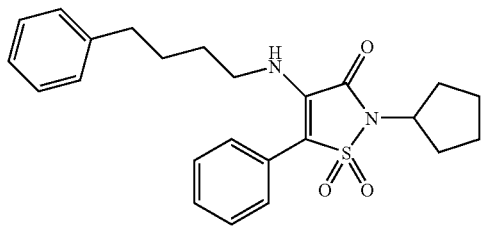

2-tert-Butyl-5-phenyl-4-[(4-phenylbutyl)amino]isothiazol-3(2H)-one 1,1-dioxide (Example 1) (0.150 g, 0.364 mmol) was dissolved in TFA (3 mL) and heated in a microwave reactor at 120° C. for 20 mins. TFA was removed in vacuo and the residue was coevaporated with DCM two times. The residue was dissolved in MeCN (3 mL) and it was mixed with bromocyclopentan (0.162 g, 1.09 mmol) and TEA (0.110 g, 1.09 mmol) and the mixture was heated in a microwave reactor at 120° C. for 20 mins, at 160° C. for 85 mins and at 170° C. for 20 mins. The residue was purified by column chromatography (Horizons Biotage) using a 90:10 mixture of hexane and EtOAc as eluant, to give the title compound (0.055 g, 36%); $^1$H NMR (500 MHz, CDCl$_3$): δ 7.53-7.48 (m, 2H), 7.46-7.41 (m, 3H), 7.31-7.25 (m 2H), 7.22-7.18 (m, 1H), 7.10-7.06 (m, 2H), 5.30-5.24 (br m, 1H), 4.41-4.35 (m, 1H), 2.90-2.83 (m 2H), 2.49-2.43 (m 2H), 2.25-2.17 (m 2H), 2.18-2.09 (m 2H), 1.97-1.87 (m 2H), 1.69-1.60 (m 2H), 1.44-1.36 (m 4H); $^{13}$C NMR (125 MHz, CDCl$_3$): δ 159.0, 141.8, 135.6, 131.8, 129.8, 128.8, 128.6, 128.5, 126.2, 125.3, 106.7, 55.2, 44.2, 35.4, 29.5, 29.2, 28.3, 24.3.

Example 3

5-Phenyl-4-[(4-phenylbutyl)amino]-2-(tetrahydrofuran-2-ylmethyl)isothiazol-3(2H)-one 1,1-dioxide

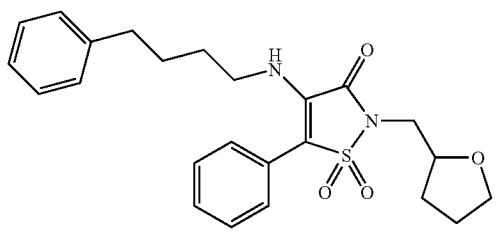

2-tert-Butyl-5-phenyl-4-[(4-phenylbutyl)amino]isothiazol-3(2H)-one 1,1-dioxide (Example 1) (0.150 g, 0.364 mmol) was dissolved in TFA (3 mL) and heated in a microwave reactor at 120° C. for 20 mins. TFA was removed in vacuo and coevaporated with DCM two times. The residue was dissolved in MeCN (3 mL) and mixed with 2-(bromomethyl)tetrahydrofuran (0.312 g, 1.892 mmol), TEA (0.148 g, 1.454 mmol) and K$_2$CO$_3$ (0.251 g, 1.818 mmol) and heated in a microwave reactor at 140° C. for 15 mins and at 160° C. for 80 mins. The residue was purified by column chromatography (Horizons Biotage) using a 75:25 mixture of hexane and EtOAc as eluant, to give the title compound (0.055 g, 36%); $^1$H NMR (500 Mz, CDCl$_3$): δ 7.53-7.49 (m, 2H), 7.46-7.41 (m, 3H), 7.31-7.25 (m 2H), 7.22-7.18 (m, 1H), 7.10-7.06 (m, 2H), 5.30-5.24 (br m, 1H), 4.42-4.36 (m, 1H), 4.00-3.95 (m 1H), 3.86-3.79 (m 2H), 3.72-3.65 (dd 1H), 2.91-2.83 (m 2H), 2.49-2.43 (m 2H), 2.14-2.06 (m 1H), 2.06-1.89 (dm 2H), 1.77-1.68 (m 1H), 1.44-1.36 (m 4H); $^{13}$C NMR (125 MHz, CDCl$_3$): δ 159.7, 141.7, 135.6, 131.9, 129.9, 128.8, 128.6, 128.5, 126.2, 125.1, 107.0, 68.5, 44.2, 35.4, 29.6, 29.2, 28.3, 25.7; Mass Spectrum: M–H$^+$ 425.

Example 4

2-tert-Butyl-4-[(2,3-dihydro-1,4-benzodioxin-2-ylmethyl)amino]-5-phenylisothiazol-3(2H)-one 1,1-dioxide

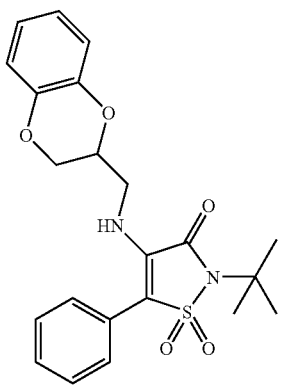

A mixture of 2-tert-butyl-4-chloro-5-phenylisothiazol-3(2H)-one 1,1-dioxide (0.150 g, 0.50 mmol) and (2,3-dihydro-1,4-benzodioxin-2-ylmethyl)amine (0.083 g, 0.50 mmol) and TEA (0.07 mL, 0.50 mmol) in MeCN (2 mL) was heated in a microwave reactor at 100° C. for 45 mins. The reaction mixture was evaporated and the residue was purified by silica gel column chromatography using a 15-25% EtOAc in petroleum ether mixture as eluant, to give the title compound (0.139 g, 65%) as a solid; $^1$H NMR (500 MHz, CDCl$_3$): δ 7.54-7.50 (m, 2H), 7.50-7.45 (m, 3H), 6.92-6.82 (m, 4H), 5.65 (t, 1H), 4.12-4.04 (m, 1H), 3.86 (dd, 1H), 3.68 (dd, 1H), 3.17 (t, 2H), 1.75 (s, 9H); $^{13}$C NMR (125 MHz, CDCl3): δ 159.5, 142.9, 142.3, 135.1, 131.7, 130.2, 129.2, 124.8, 122.2, 122.1, 117.7, 117.5, 108.7, 71.4, 65.3, 61.9, 44.1, 27.9; Mass Spectrum: [M+H]$^+$ 429.

Example 5

2-tert-Butyl-5-phenyl-4-{[3-(pyridin-3-yloxy)propyl]amino}isothiazol-3(2H)-one 1,1-dioxide

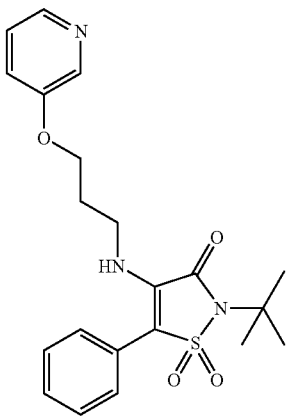

A mixture of 4-[(3-bromopropyl)amino]-2-tert-butyl-5-phenylisothiazol-3(2H)-one 1,1-dioxide (0.120 g, 0.29 mmol), 3-hydroxypyridine (0.028 g, 0.29 mmol) and K$_2$CO$_3$ (0.207 g, 1.49 mmol) in MeCN (2 mL) was heated in a microwave reactor at 140° C. for 30 mins. The solvent was evaporated and the residue was purified by silica gel column chromatography using a 35-85% EtOAc in hexane mixture as eluant, to give the title compound (0.056 g, 45%) as a solid. $^1$H NMR (500 MHz, CDCl$_3$): δ 8.28-8.22 (m, 2H), 7.54-7.50 (m, 2H), 7.50-7.42 (m, 3H), 7.24-7.20 (m, 1H), 7.16-7.12 (m, 1H), 5.68 (t, 1H), 3.92 (t, 2H), 3.14-3.08 (m, 2H), 1.90-1.82 (m, 2H), 1.74 (s, 9H); $^{13}$C NMR (125 MHz, CDCl$_3$): δ 159.8, 154.7, 142.8, 137.9, 135.2, 131.8, 129.9, 128.8, 125.2, 124.1, 121.3, 107.5, 66.3, 61.8, 42.1, 29.0, 27.8; Mass Spectrum: M+H$^+$ 416.

Example 6

2-Butyl-4-(hexylamino)-5-phenylisothiazol-3(2H)-one 1,1-dioxide

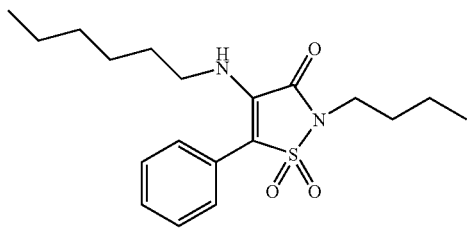

A solution of 2-butyl-4-chloro-5-phenylisothiazol-3(2H)-one 1,1-dioxide (0.110 g, 0.33 mmol) and hexylamine (0.100 g, 0.984 mmol) in DMF (0.5 mL) was heated in a microwave reactor at 140° C. for 25 mins. The residue was purified by preparative HPLC (Ace C8 column, 0.1M NH$_4$OAc/MeCN, gradient) to give the title compound (0.060 g, 47%); $^1$H-NMR (400 MHz, CD$_3$CN): δ 7.49-7.53 (m, 5H), 5.85 (bs, 1H), 3.66 8 (t, 2H), 2.85 (dd, 2H), 1.71-1.80 (m, 2H), 1.37-1.48 (m, 2H), 1.13-1.34 (m, 4H), 0.94-1.09 (m, 7H), 0.82 (t, 3H); Mass Spectrum: M+H 365.

Example 7

N-(3-{3-[(2-Butyl-1,1-dioxido-3-oxo-5-phenyl-2,3-dihydroisothiazol-4-yl)amino]propoxy}phenyl)acetamide

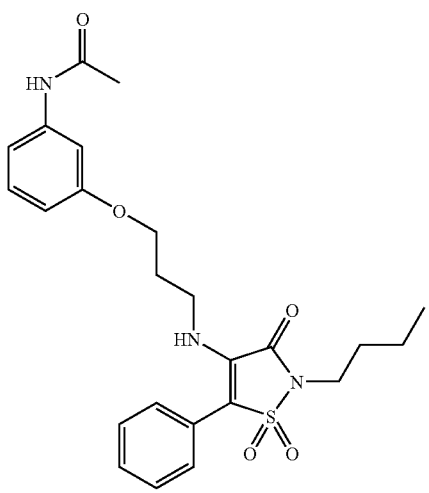

A mixture of 2-butyl-4-chloro-5-phenylisothiazol-3(2H)-one 1,1-dioxide (0.150 g, 0.50 mmol) and 3-(3-aminopropyloxy)acetanilide (0.208 mg, 1.00 mmol) in MeCN (2 mL) was heated in a microwave reactor at 120° C. for 15 mins. The reaction mixture was filtered and the solid residue was washed with EtOAc. The filtrate was evaporated and the residue was purified by silica gel column chromatography using a 50-100% EtOAc in petroleum ether mixture as eluant, to give the title compound (0.148 g, 63%) as a solid; $^1$H NMR (500 MHz, CDCl$_3$): δ 7.58-7.52 (m, 2H), 7.50-7.44 (m, 3H), 7.22 (t, 1H), 7.18 (br s, 1H), 6.96 (dd, 1H), 7.64 (dd, 1H), 5.82 (t, 1H), 3.92 (t, 2H), 3.72 (t, 2H), 3.18-3.06 (m, 2H), 2.20 (s, 3H), 1.88-1.80 (m, 4H), 1.50-1.40 (m, 2H), 0.98 (t, 3H); $^{13}$C NMR (125 MHz, CDCl$_3$): δ 168.4, 159.2, 159.0, 139.6, 135.8, 131.7, 130.0, 129.0, 128.9, 125.0, 112.4, 110.8, 106.1, 66.2, 42.7, 40.4, 30.5, 28.9, 25.2, 20.3, 13.8; Mass Spectrum: [M+H]$^+$ 472.

Example 8

2-Isopropyl-4-[(2-phenoxyethyl)amino]-5-phenyl-isothiazol-3(2H)-one 1,1-dioxide

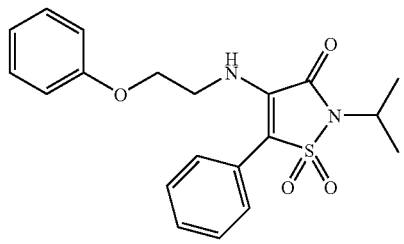

A solution of 4-chloro-2-isopropyl-5-phenylisothiazol-3(2H)-one 1,1-dioxide (0.200 g, 0.700 mmol), TEA (0.106 g, 1.050 mmol) and 2-phenoxyethylamine (0.144 g, 1.050 mmol) in MeCN (3 mL) was heated at in a microwave reactor 120° C. for 5 mins. The residue was purified by silica gel column chromatography (Horizons Biotage) using a 65:35 mixture of heptane and EtOAc as eluant to give the title compound (0.262 g, 97%); $^1$H NMR (500 MHz, CDCl$_3$): δ 7.57-7.54 (m, 2H), 7.49-7.45 (m, 3H), 7.32-7.27 (m, 2H), 7.02-6.97 (m, 1H), 6.86-6.83 (m, 2H), 5.71-5.66 (br m, 1H), 4.46-4.39 (m, 1H), 3.89 (t 2H), 3.27 (q 2H), 1.60 (d 6H); $^{13}$C NMR (125 MHz, CDCl$_3$): δ 158.5, 158.2, 135.6, 131.7, 130.0, 129.8, 129.1, 125.1, 121.8, 114.7, 108.0, 65.8, 47.8, 43.6, 20.4; Mass Spectrum: M−H$^+$ 387.

Example 9

4-({1-[3-Chloro-5-(trifluoromethyl)pyridin-2-yl]piperidin-4-yl}amino)-2-isopropyl-5-phenylisothiazol-3(2H)-one 1,1-dioxide

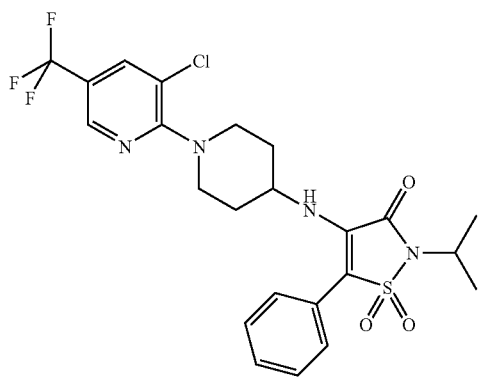

A solution of 4-chloro-2-isopropyl-5-phenylisothiazol-3(2H)-one 1,1-dioxide (0.200 g, 0.700 mmol), TEA (0.106 g, 1.050 mmol) and 1-[3-chloro-5-(trifluoromethyl)pyridin-2-yl]piperidin-4-amine (0.294 g, 1.050 mmol) in MeCN (mL) was heated in a microwave reactor at 120° C. for 30 mins. The residue was purified by silica gel column chromatography (Horizons Biotage) using a 1:1 mixture of heptane and EtOAc as eluant, to give the title compound (0.344 g, 93%); $^1$H NMR (500 MHz, CDCl$_3$): δ 8.34-8.33 (m, 1H), 7.74-7.72 (m, 1H), 7.57-7.54 (m, 2H), 7.49-7.46 (m, 3H), 5.27 (d, 1H), 4.47-4.39 (m, 1H), 3.85-3.78 (m, 2H), 3.24-3.14 (m 1H), 2.55-2.48 (m 2H), 1.82-1.76 (m 2H), 1.60 (d 6H), 1.56-1.48 (m 2H); $^{13}$C NMR (125 MHz, CDCl$_3$): δ 160.0, 158.7, 143.1, 136.2, 134.5, 131.8, 130.2, 129.0, 125.3, 121.3, 120.6, 120.3, 107.1, 66.1, 50.3, 47.9, 47.4, 32.4, 20.4; Mass Spectrum: M–H$^+$ 529.

Example 10

3-{4-[(2-Isopropyl-1,1-dioxido-3-oxo-5-phenyl-2,3-dihydroisothiazol-4-yl)amino]piperidin-1-yl}propanenitrile

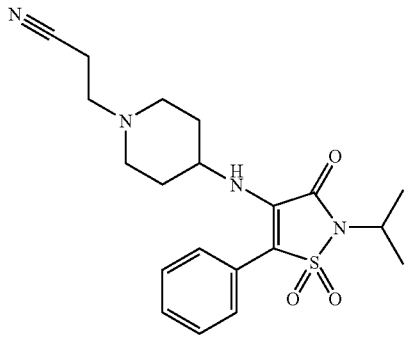

A solution of 4-chloro-2-isopropyl-5-phenylisothiazol-3(2H)-one 1,1-dioxide (0.200 g, 0.700 mmol), TEA (0.283 g, 2.800 mmol) and 3-(4-aminopiperidin-1-yl)propanenitrile (0.161 g, 1.050 mmol) in DMF (3 mL) was heated in a microwave reactor at 120° C. for 10 mins. Water was added and the mixture was extracted with EtOAc. The organic phase was evaporated and the residue was purified by silica gel column chromatography (Horizons Biotage) using a mixture of heptane and EtOAc (20:80) to 100% EtOAc, then a mixture of MeOH and EtOAc (1:99) as eluant, to give the title compound (0.25 g, 89%); $^1$H NMR (500 MHz, CDCl$_3$): δ 7.54-7.51 (m, 2H), 7.49-7.44 (m, 3H), 5.20 (br d 1H), 4.46-4.38 (m, 1H), 3.01-2.91 (br m, 1H), 2.70-2.65 (br m, 2H), 2.55 (t, 2H), 2.41 (t 2H), 1.74-1.63 (m 4H), 1.60 (d 6H) 1.44-1.35 (m 2H); $^{13}$C NMR (125 MHz, CDCl$_3$): δ 158.7, 134.5, 131.8, 130.1, 128.9, 125.3, 118.8, 106.8, 53.3, 51.5, 50.0, 47.8, 32.4, 20.4, 16.4: Mass Spectrum: M–H$^+$ 403.

Example 11

2-Isopropyl-5-phenyl-4-[(4-phenylbutyl)amino]isothiazol-3(2H)-one 1,1-dioxide

A solution of 4-chloro-2-isopropyl-5-phenylisothiazol-3(2H)-one 1,1-dioxide (0.150 g, 0.521 mmol), TEA (0.079 g, 0.782 mmol) and 4-phenylbutylamine (0.117 g, 0.782 mmol) in MeCN (3 mL) was heated in a microwave reactor at 120° C. for 5 mins. The reaction mixture was evaporated and the residue was purified by silica gel column chromatography (Horizons Biotage) using a 75:25 mixture of heptane and EtOAc as eluant, to give the title compound (0.174 g, 84%); $^1$H NMR (500 MHz, CDCl$_3$): δ 7.52-7.48 (m, 2H), 7.45-7.41 (m, 3H), 7.30-7.26 (m, 2H), 7.22-7.17 (m, 1H), 7.10-7.06 (m, 2H), 5.28-5.23 (m, 1H), 4.45-4.38 (m, 1H), 2.89-2.84 (m, 2H), 2.49-2.44 (m, 2H), 1.59 (d, 6H), 1.43-1.38 (m, 4H); $^{13}$C NMR (125 MHz, CDCl$_3$): δ 158.8, 141.8, 135.6, 131.8, 129.8, 128.8, 128.6, 128.5, 126.2, 125.3, 106.8, 47.7, 44.2, 35.4, 29.2, 28.3, 20.4; Mass Spectrum: M–H$^+$ 399.

Example 12

2-tert-Butyl-4-({3-[3-(hydroxymethyl)phenoxy]propyl}amino)-5-phenylisothiazol-3(2H)-one 1,1-dioxide A mixture of 3-[(2-tert-butyl-1,1-dioxido-3-oxo-5-phenyl-2,3-dihydroisothiazol-4-yl)amino]propyl 4-methylbenzenesulfonate (0.120 g, 0.244 mmol), 3-(hydroxymethyl)phenol (0.030 mg, 0.244 mmol) and K$_2$CO$_3$ (0.168 mg, 1.218 mmol) in MeCN (2 ml) was heated in the microwave reactor at 120° C. for 25 mins. The reaction mixture was filtered, evaporated and the residue was purified twice by silica gel column chromatography (Horizons Biotage) using 50% EtOAc in hexane and then 0-10% EtOAc in DCM as eluent to give the title compound (0.049 mg, 45%). $^1$H NMR (500 MHz CDCl$_3$): δ 7.54-7.7.46 (m, 2H), 7.45-7.40 (m, 3H), 7.30-7.24 (m, 1H), 6.96 (d, 1H), 6.91 (s, 1H), 6.78 (d, 1H), 5.73 (t, 1H), 4.69 (s, 2H), 3.92 (t, 2H), 3.11-3.06 (m, 2H), 1.88-1.80 (m, 2H), 1.74 (s, 9H); $^{13}$C NMR (125 MHz CDCl$_3$): δ 159.8, 158.8, 142.9, 135.4, 131.8, 129.9, 129.8, 128.8, 125.3, 119.8, 113.9, 112.9, 107.2, 66.0, 65.4, 61.7, 42.4, 28.9, 27.8; Mass Spectrum M+H$^+$ 445.

Example 13

2-tert-Butyl-4-{[3-(2-methoxyphenoxy)propyl]amino}-5-phenylisothiazol-3(2H)-one 1,1-dioxide The title compound was prepared as described for Example 12 from 2-methoxyphenol and 3-[(2-tert-butyl-1,1-dioxido-3-oxo-5-phenyl-2,3-dihydroisothiazol-4-yl)amino]propyl 4-methylbenzenesulfonate with a reaction time of 15 mins. Purified by silica gel column chromatography (Horizons Biotage) using 15% EtOAc in petroleum ether 40-60° C. as eluent to give the title compound (0.077 mg, 72%). $^1$H NMR (500 MHz CDCl$_3$): δ 7.54-7.50 (m, 2H), 7.43-7.40 (m, 3H), 6.97-6.94 (m, 1H), 6.92-6.88 (m, 2H), 6.81 (dd, 1H), 5.88 (t, 1H), 3.94 (t, 2H), 3.89 (s, 3H, 3.14-3.09 (m, 2H), 1.88-1.84 (m, 2H), 1.75 (s, 9H); $^{13}$C NMR (125 MHz CDCl$_3$): δ 159.8, 149.9, 148.1, 135.6, 131.8, 129.7, 128.8, 125.5, 121.9, 120.9, 113.8, 111.9, 106.9, 67.5, 61.6, 55.9, 42.6, 29.1, 27.9; Mass Spectrum M+H$^+$ 445.

Example 14

2-tert-Butyl-4-({3-[4-(hydroxymethyl)phenoxy]propyl}amino)-5-phenylisothiazol-3(2H)-one 1,1-dioxide The title compound was prepared as described for Example 12 from 4-(hydroxymethyl)phenol and 3-[(2-tert-butyl-1,1-dioxido-3-oxo-5-phenyl-2,3-dihydroisothiazol-4-yl)amino]propyl 4-methylbenzenesulfonate. Purified by silica gel column chromatography (Horizons Biotage) using 0-10% EtOAc in DCM as eluent to give the title compound (0.037 mg, 34%) as a solid. $^1$H NMR (500 MHz CDCl$_3$): δ 7.54-7.48 (m, 2H), 7.46-7.40 (m, 3H), 7.29 (d, 2H), 6.85 (d, 2H), 5.74 (t, 1H), 4.64 (s, 2H), 3.90 (t, 2H), 3.11-3.00 (m, 2H), 1.87-1.82 (m, 2H), 1.75 (s, 9H); $^{13}$C NMR (125 MHz CDCl$_3$): δ 159.8, 158.2, 135.3, 133.8, 131.8, 129.8, 128.9, 128.8, 125.3, 114.7, 107.2, 66.1, 65.2, 61.7, 42.5, 28.9, 27.8, Mass Spectrum M+H$^+$ 445.

Example 15

N-(3-{3-[(2-tert-Butyl-1,1-dioxido-3-oxo-5-phenyl-2,3-dihydroisothiazol-4-yl)amino]propoxy}phenyl)acetamide A mixture of 2-tert-butyl-4-chloro-5-phenylisothiazol-3(2H)-one 1,1-dioxide (0.150 g, 0.500 mmol) and 3-(3-aminopropyloxy)acetanilide (0.208 g, 1.000 mmol) in MeCN (2 ml) was heated in a the microwave reactor at 120° C. for 15 mins. The mixture was evaporated and the residue purified by silica gel column chromatography (Horizons Biotage) using 50-65% EtOAc in hexane as eluent to give the title compound (0.204 mg, 87%). 1H NMR (500 MHz CDCl$_3$): δ 7.56-7.50 (m, 2H), 7.48-7.42 (m, 3H), 7.30-7.24 (m, 1H), 7.24-7.18 (m, 2H), 6.94 (dd, 1H), 6.62 (dd, 1H), 5.69 (t, 1H), 3.88 (t, 2H), 3.12-3.04 (m, 2H), 2.18 (s, 3H), 1.86-1.80 (m, 2H), 1.74 (s, 9H); $^{13}$C NMR (125M CDCl$_3$): δ 168.4, 160.0, 159.4, 139.8, 135.8, 131.8, 129.9, 129.8, 128.8, 125.6, 112.4, 110.9, 106.1, 66.0, 61.8, 42.3, 28.9, 27.8, 25.2; Mass Spectrum M+H$^+$ 472.

Example 16

2-tert-Butyl-4-{[3-(2-fluorophenoxy)propyl]amino}-5-phenylisothiazol-3(2H)-one 1,1-dioxide The title compound was prepared as described for Example 12 from 2-fluorophenol and 3-[(2-tert-butyl-1,1-dioxido-3-oxo-5-phenyl-2,3-dihydroisothiazol-4-yl)amino]propyl 4-methylbenzenesulfonate with a reaction time of 15 mins. The reaction mixture was evaporated and the residue was purified by silica gel column chromatography (Horizons Biotage) using 15% EtOAc in petroleum ether 40-60° C. as eluent then dissolved in EtOAc. The product containing fractions were evaporated and the residue was washed with aqueous K$_2$CO$_3$ (2M) and evaporated to give the title compound (0.063 g, 62%). $^1$H NMR (500 MHz CDCl$_3$): δ 7.54-7.50 (m, 2H), 7.45-7.40 (m, 3H), 7.11-7.03 (m, 2H), 6.94-6.85 (m, 2H), 5.57 (t, 1H), 3.91 (t, 2H), 3.15-3.10 (m, 2H), 1.90-1.82 (m, 2H), 1.74 (s, 9H); $^{13}$C NMR (125 MHz CDCl$_3$): δ 159.8, 153.9, 152.0, 146.8, 146.7, 135.3, 131.8, 129.8, 128.8, 125.2, 124.6, 124.5, 121.9, 121.8, 116.6, 116.5, 115.5, 107.4, 67.2, 61.7, 41.7, 29.2, 27.8. Mass Spectrum M+H$^+$ 433.

Example 17

2-(4-{3-[(2-tert-Butyl-1,1-dioxido-3-oxo-5-phenyl-2,3-dihydroisothiazol-4-yl)amino]propoxy}phenyl)-N,N-dimethylacetamide The title compound was prepared as described for Example 12 from 2-(4-hydroxyphenyl)-N,N-dimethylacetamide and 3-[(2-tert-butyl-1,1-dioxido-3-oxo-5-phenyl-2,3-dihydroisothiazol-4-yl)amino]propyl 4-methylbenzenesulfonate. The reaction mixture was evaporated, purified twice by silica gel column chromatography (Horizons Biotage) using 75-85% EtOAc in petroleum ether 40-60° C. and then 50% DCM in EtOAc as eluent to give the title compound (0.072 g, 59%). $^1$H NMR (500 MHz CDCl$_3$): δ 7.54-7.49 (m, 2H), 7.46-7.42 (m, 3H), 7.18 (d, 2H), 6.82 (d, 2H), 5.76 (t, 1H), 3.87 (t, 2H), 3.66 (s, 2H), 3.08 (m, 2H), 3.01 (s, 3H), 2.98 (s, 3H), 1.83 (m, 2H), 1.74 (s, 9H); $^{13}$C NMR (CDCl$_3$): δ 171.5, 159.8, 157.4, 135.3, 131.8, 130.1, 129.7, 128.8, 127.8, 125.3, 114.8, 107.1, 66.1, 61.7, 42.5, 40.3, 37.9, 35.9, 28.9, 27.8; Mass Spectrum M+H$^+$ 500.

Example 18

2-tert-Butyl-4-{[3-(2-chlorophenoxy)propyl]amino}-5-phenylisothiazol-3(2H)-one 1,1-dioxide The title compound was prepared as described for Example 12 from 2-chlorophenol and 3-[(2-tert-butyl-1,1-dioxido-3-oxo-5-phenyl-2,3-dihydroisothiazol-4-yl)amino]propyl 4-methylbenzenesulfonate with a reaction time of 15 mins. The reaction mixture was evaporated and the crude product was purified by silica gel column chromatography (Horizons Biotage) using 15% EtOAc in petroleum ether 40-60° C. as eluent to give the title compound (0.085 g, 77%). $^1$H NMR (500 MHz CDCl$_3$): δ 7.53-7.50 (m, 2H), 7.44-7.42 (m, 3H), 7.36 (dd, 1H), 7.19 (dt, 1H), 7.6.92 (dt, 1H), 6.83 (dd, 1H), 5.56 (t, 1H), 3.89 (t, 2H), 3.28 (m, 2H), 1.88-1.84 (m, 2H), 1.74 (s, 9H); $^{13}$C NMR (125 MHz CDCl$_3$): δ 159.8, 154.2, 135.3, 131.8, 130.6, 129.8, 128.8, 127.9, 125.2, 123.4, 122.1, 113.7, 107.4, 66.7, 61.7, 41.8, 29.2, 27.8; Mass Spectrum M+H$^+$ 449.

Example 19

2-tert-Butyl-4-{[3-(3-methoxyphenoxy)propyl]amino}-5-phenylisothiazol-3(2H)-one 1,1-dioxide The title compound was prepared as described for Example 12 from 3-methoxyphenol and 3-[(2-tert-butyl-1,1-dioxido-3-oxo-5-phenyl-2,3-dihydroisothiazol-4-yl)amino]propyl 4-methylbenzenesulfonate with a reaction time of 15 mins. The reaction mixture was evaporated and the crude product was purified by silica gel column chromatography (Horizons Biotage) using 15% EtOAc in petroleum ether 40-60° C. as eluent to give the title compound (0.070 g, 65%). $^1$H NMR (500 MHz CDCl$_3$): δ 7.54-7.45 (m, 2H), 7.45 (m, 3H), 7.18 (t, 1H), 6.53 (dd, 1H), 6.48-6.42 (m, 2H), 5.79 (t, 1H), 3.89 (t, 2H), 3.82 (s, 3H), 3.12-3.06 (m, 2H), 1.86-1.82 (m, 2H), 1.75 (s, 9H); $^{13}$C NMR (125 MHz CDCl$_3$): δ 161.1, 159.8, 159.7, 135.3, 131.8, 130.2, 129.7, 128.8, 125.3, 107.2, 107.1, 106.6, 101.2, 66.2, 61.7, 55.5, 42.6, 28.9, 27.8; Mass Spectrum M+H$^+$ 445.

Example 20

(3-{3-[(2-tert-Butyl-1,1-dioxido-3-oxo-5-phenyl-2,3-dihydroisothiazol-4-yl)amino]propoxy}phenyl)acetic acid A mixture of methyl (3-{3-[(2-tert-butyl-1,1-dioxido-3-oxo-5-phenyl-2,3-dihydroisothiazol-4-yl)amino]propoxy}phenyl)acetate (Example 21) (0.087 g, 0.179 mmol) and LiI (0.239 g, 1.788 mmol) in pyridine (2 ml) was heated at 120° C. for 18 h. EtOAc was added and the mixture was washed with 1N HCl, evaporated to dryness and the residue was purified by silica gel column chromatography (Horizons Biotage) using 0-12% MeOH (+1% AcOH) in EtOAc as eluent to give the title compound (0.033 g, 39%). $^1$H NMR (500 MHz CDCl$_3$): δ 7.54-7.46 (m, 2H), 7.45-7.40 (m, 3H), 7.25 (t, 1H), 6.89 (dd, 1H), 6.82-6.75 (m, 2H), 5.73 (t, 1H), 3.87 (t, 2H), 3.63 (s, 2H), 3.10-3.04 (m, 2H), 1.87-1.79 (m, 2H), 1.74 (s, 9H); $^{13}$C NMR (125 MHz CDCl$_3$): δ 176.7, 159.8, 158.7, 135.4, 135.0, 131.8, 129.9, 129.8, 128.8, 125.3, 122.4, 115.7, 113.6, 107.2, 65.9, 61.7, 42.3, 41.2, 29.0, 27.8; Mass Spectrum: M2H$^+$ 472.

Example 21

Methyl (3-{3-[(2-tert-butyl-1,1-dioxido-3-oxo-5-phenyl-2,3-dihydroisothiazol-4-yl)amino]propoxy}phenyl)acetate The title compound was prepared as described for Example 12 from methyl (3-hydroxyphenyl)acetate and 3-[(2-tert-butyl-1,1-dioxido-3-oxo-5-phenyl-2,3-dihydroisothiazol-4-yl)amino]propyl 4-methylbenzenesulfonate. The reaction mixture was evaporated and the residue was purified by silica gel column chromatography (Horizons Biotage) using 20-40% EtOAc in petroleum ether 40-60° C. as eluent. The product containing fractions were evaporated and the residue was dissolved in EtOAc, washed with aqueous $K_2CO_3$ (2M) and evaporated give the title compound (0.097 g, 66%). $^1$H NMR (500 MHz CDCl$_3$): δ 7.55-7.48 (m, 2H), 7.46-7.40 (m, 3H), 7.26 (t, 1H), 6.90 (dd, 1H), 6.82-6.78 (m, 2H), 5.76 (t, 1H), 3.90 (t, 2H), 3.72 (s, 3H), 3.61 (s, 2H), 3.14-3.06 (m, 2H), 1.90-1.80 (m, 2H), 1.75 (s, 9H); $^{13}$C NMR (125 MHz CDCl$_3$): δ 172.1, 159.8, 158.7, 135.7, 135.3, 131.8, 129.9, 129.8, 128.8, 125.3, 122.3, 115.5, 113.4, 107.2, 65.9, 61.7, 52.3, 42.4, 41.4, 29.0, 27.8; Mass Spectrum: M+H$^+$ 487.

Example 22

2-tert-Butyl-5-phenyl-4-{[3-(pyridin-4-yloxy)propyl]amino}isothiazol-3(2H)-one 1,1-dioxide The title compound was prepared as described for Example 12 from 4-hydroxypyridine and 3-[(2-tert-butyl-1,1-dioxido-3-oxo-5-phenyl-2,3-dihydroisothiazol-4-yl)amino]propyl 4-methylbenzenesulfonate with a reaction time of 15 mins. EtOAc was added to the reaction mixture and the mixture was washed with water, brine and evaporated. The residue was purified twice by silica gel column chromatography (Horizons Biotage) using 50-80% EtOAc in hexane then 50% EtOAc in DCM as eluent to give the title compound (0.035 g, 35%). $^1$H NMR (500 MHz CDCl$_3$): δ 8.44 (d, 2H), 7.54-7.48 (m, 2H), 7.48-7.41 (m, 3H), 6.75 (d, 2H), 5.64 (t, 1H), 3.91 (t, 2H), 3.114-3.08 (m, 2H), 1.90-1.82 (m, 2H), 1.74 (s, 9H); $^{13}$C NMR (125 MHz CDCl$_3$): δ 164.5, 159.8, 151.4, 135.2, 131.8, 129.9, 128.9, 125.2, 110.3, 107.6, 65.7, 61.8, 41.9, 28.8, 27.9; Mass Spectrum: M+H$^+$ 416.

Example 23

4-(Benzylamino)-2-tert-butyl-5-phenylisothiazol-3(2H)-one 1,1-dioxide

A mixture of 2-tert-butyl-4-chloro-5-phenylisothiazol-3(2H)-one 1,1-dioxide (0.150 g, 0.500 mmol) and benzylamine (0.110 ml, 1.001 mmol) in DMF (2 ml) was heated in the microwave reactor at 120° C. for 15 mins. EtOAc was added, the mixture was washed with brine and evaporated to dryness. The residue was purified by silica gel column chromatography (Horizons Biotage) using 15-20% EtOAc in petroleum ether 40-60° C. as eluent to give the title compound (0.095 g, 51%) as a solid. $^1$H NMR (500 MHz CDCl$_3$): δ 7.50-7.38 (m, 5H), 7.34-7.25 (m, 3H), 7.06-6.98 (m, 2H), 5.55 (bs, 1H), 4.02 (d, 2H), 1.77 (9H, s); $^{13}$C NMR (125 MHz, CDCl$_3$): δ 159.8, 136.8, 133.0, 131.9, 129.8, 129.0, 128.7, 128.2, 127.6, 124.8, 108.2, 61.6, 48.4, 27.9; Mass Spectrum M+H$^+$ 371.

Example 24

2-tert-Butyl-5-phenyl-4-[(2-phenylethyl)amino]isothiazol-3(2H)-one 1,1-dioxide

A mixture of 2-tert-butyl-4-chloro-5-phenylisothiazol-3(2H)-one 1,1-dioxide (0.150 g, 0.500 mmol) and (2-phenylethyl)amine (0.121 g, 1.001 mmol) in MeCN (2 ml) was heated in a the microwave reactor at 120° C. for 15 nm ins. The reaction mixture was evaporated and the residue was purified by silica gel column chromatography (Horizons Biotage) using 15-20% EtOAc in petroleum ether 40-60° C. to give the title compound (0.124 g, 65%). $^1$H NMR (500 MHz CDCl$_3$): δ 7.58-7.51 (m, 2H), 7.51-7.45 (m, 3H), 7.30-7.18 (m, 3H), 6.87 (d, 2H), 5.35 (t, 1H), 3.14 (q, 2H), 2.62 (t, 2H), 1.73 (s, 9H); $^{13}$C NMR (125 MHz CDCl$_3$): δ 159.8, 137.6, 135.0, 131.8, 129.9, 128.9, 128.7, 127.0, 125.4, 107.5, 61.7, 45.1, 36.0, 27.8; Mass Spectrum M–H$^+$ 384.

Example 25

2-tert-Butyl-5-phenyl-4-{[3-(phenylthio)propyl]amino}isothiazol-3(2H)-one 1,1-dioxide The title compound was prepared as described for Example 12 from 2-tert-butyl-4-[(3-chloropropyl)amino]-5-phenylisothiazol-3(2H)-one 1,1-dioxide and thiophenol at 100° C. for 45 mins. The reaction mixture was filtered, evaporated to dryness and the residue was purified by silica gel column chromatography (Horizons Biotage) using 10-20% EtOAc in hexane as eluent to give the title compound (0.076 g, 65%). $^1$H NMR (500 MHz CDCl$_3$): δ 7.52-7.48 (m, 2H), 7.46-7.38 (m, 3H), 7.32-7.18 (m, 5H), 5.32 (t, 1H), 3.02-2.96 (m, 2H), 2.70 (t, 2H), 1.74 (s, 9H), 1.68-1.60 (m, 2H); $^{13}$C NMR (125 MHz CDCl$_3$): δ 159.8, 135.6, 135.1, 131.8, 129.4, 129.9, 129.3, 128.9, 126.7, 125.1, 107.5, 61.8, 42.8, 31.0, 28.9, 27.9; Mass Spectrum: M+H$^+$ 431.

Example 26

2-tert-Butyl-4-[(3-phenoxypropyl)amino]-5-phenylisothiazol-3(2H)-one 1,1-dioxide The title compound was prepared as described for Example 24 from (3-phenoxypropyl)amine and 2-tert-butyl-4-chloro-5-phenylisothiazol-3(2H)-one 1,1-dioxide. The residue was purified by silica gel column chromatography (Horizons Biotage) using 17-20% EtOAc in hexane as eluent to give the title compound (0.152 g, 73%). $^1$H NMR (500 MHz CDCl$_3$): δ 7.52-7.47 (m, 2H), 7.44-7.38 (m, 3H), 7.32-7.24 (m, 2H), 6.95 (t, 1H), 6.84 (d, 2H), 5.74 (t, 1H), 3.87 (t, 2H), 3.12-3.04 (m, 2H), 1.86-1.78 (m, 2H), 1.72 (s, 9H); $^{13}$C NMR (125 MHz CDCl$_3$): δ 159.8, 158.8, 135.3, 131.8, 129.7, 128.7, 125.3, 121.3, 114.6, 107.2, 65.9, 61.7, 42.5, 29.0, 27.8; Mass Spectrum M+H$^+$ 415.

Example 27

2-tert-Butyl-4-{[3-(3-chlorophenoxy)propyl]amino}-5-phenylisothiazol-3(2H)-one 1,1-dioxide The title compound was prepared as described for Example 12 from 3-chlorophenol and 3-[(2-tert-butyl-1,1-dioxido-3- oxo-5-phenyl-2,3-dihydroisothiazol-4-yl)amino]propyl 4-methylbenzenesulfonate with a reaction time of 15 mins. The reaction mixture was evaporated and purified by silica gel column chromatography (Horizons Biotage) using 15% EtOAc in petroleum ether 40-60° C. as eluent to give the title compound (0.079 g, 72%). $^1$H NMR (500 MHz CDCl$_3$): δ 7.54-7.50 (m, 2H), 7.46-7.40 (m, 3H), 7.20 (t, 1H), 6.95 (d, 1H), 6.84 (s, 1H), 6.75 (dd, 1H), 5.67 (t, 1H), 3.86 (t, 1H), 3.11-3.04 (m, 2H), 1.86-1.80 (m, 2H), 1.75 (s, 9H); $^{13}$C NMR (125 MHz CDCl$_3$): δ 159.8, 159.3, 135.3, 135.1, 131.8, 130.5, 129.8, 128.8, 125.3, 121.5, 115.0, 113.2, 107.4, 66.2, 61.7, 42.4, 28.9, 27.8: Mass Spectrum M+H$^+$ 449.

Example 28

Methyl 3-{3-[(2-tert-butyl-1,1-dioxido-3-oxo-5-phenyl-2,3-dihydroisothiazol-4-yl)amino]propoxy}benzoate The title compound was prepared as described for Example 12 from methyl 3-hydroxybenzoate and 3-[(2-tert-butyl-1,1-dioxido-3-oxo-5-phenyl-2,3-dihydroisothiazol-4-yl)amino]propyl 4-methylbenzenesulfonate with a reaction time of 15 mins. The reaction mixture was evaporated and the residue purified by silica gel column chromatography (Horizons Biotage) using DCM as eluent to give the title compound (0.077 g, 54%). $^1$H NMR (500 MHz CDCl$_3$): δ 7.66 (d, 1H), 7.54-7.48 (m, 3H), 4.47-7.42 (m, 3H), 7.36 (t, 1H), 7.07 (dd, 1H), 5.70 (t, 1H), 3.94-3.90 (m, 5H), 3.13-3.08 (m, 2H), 1.90-1.84 (m, 2H), 1.75 (s, 9H); $^{13}$C NMR (125 MHz CDCl$_3$): δ 167.1, 159.8, 158.5, 135.3, 131.8, 131.7, 129.8, 129.7, 128.8, 125.3, 122.6, 120.2, 114.6, 107.3, 66.2, 61.7, 52.4, 42.3, 28.9, 27.8; Mass Spectrum M+H$^+$ 473.

Example 29

2-Benzyl-5-phenyl-4-[(4-phenylbutyl)amino]isothiazol-3(2H)-one 1,1-dioxide 2-tert-Butyl-5-phenyl-4-[(4-phenylbutyl)amino]isothiazol-3(2H)-one 1,1-dioxide (Example 1) (0.150 g, 0.36 mmol) was dissolved in TFA (3 ml) and heated in a microwave reactor at 120° C. for 20 mins. The reaction mixture was concentrated and the residue was repeatedly dissolved in DCM and evaporated. The crude product was dissolved in dry MeCN (3 ml) and potassium carbonate (0.251 g, 1.82 mmol) and benzylbromide (0.075 g, 0.44 mmol) was added. The reaction mixture was heated at 120° C. for 15 mins and then at 130° C. for 5 mins in a microwave reactor. The reaction mixture was purified by silica gel column chromatography using a 90:10 mixture of hexane and EtOAc as eluant, to give the title compound (0.088 g, 54%). $^1$H NMR (500 MHz, CDCl$_3$): δ 7.55-7.49 (m, 4H), 7.48-7.31 (m, 6H), 7.31-7.25 (m, 2H), 7.23-7.17 (m, 1H), 7.11-7.05 (m, 2H), 5.31-5.25 (m, 1H), 4.85 (s, 2H), 2.90-2.82 (m, 2H), 2.50-2.42 (m, 2H), 1.45-1.33 (m, 4H); $^{13}$C NMR (125 MHz, CDCl$_3$): δ 159.3, 141.7, 135.6, 134.6, 131.8, 130.0, 129.0, 128.9, 128.9, 128.6, 128.5, 128.5, 126.2, 125.1, 107.0, 44.2, 43.8, 35.4, 29.2, 28.3 Mass Spectrum: M−H$^+$ 447.

Example 30

(4-{3-[(2-tert-Butyl-1,1-dioxido-3-oxo-5-phenyl-2,3-dihydroisothiazol-4-yl)amino]propoxy}phenyl)acetic acid The title compound was prepared as described for Example 20 from methyl (4-{3-[(2-tert-butyl-1,1-dioxido-3-oxo-5-phenyl-2,3-dihydroisothiazol-4-yl)amino]propoxy}phenyl)acetate (Example 32). The reaction mixture was evaporated and the residue was purified by silica gel column chromatography (Horizons Biotage) using 5% MeOH (+0.5% AcOH) in EtOAc as eluent to give the title compound (0.05 g, 8%). $^1$H NMR (500 MHz CD$_3$OD): δ 7.52-7.44 (m, 5H), 7.17 (d, 2H), 6.76 (d, 2H), 3.78 (t, 2H), 3.53 (s, 2H), 3.08 (t, 2H), 1.79-1.74 (m, 2H), 1.17 (s, 9H); Mass Spectrum: M+H$^+$ 473.

Example 31

2-tert-Butyl-4-{[3-(3-fluorophenoxy)propyl]amino}-5-phenylisothiazol-3(2H)-one 1,1-dioxide The title compound was prepared as described for Example 12 from 3-fluorophenol and 3-[(2-tert-butyl-1,1-dioxido-3-oxo-5-phenyl-2,3-dihydroisothiazol-4-yl)amino]propyl 4-methylbenzenesulfonate with a reaction time of 15 mins. The reaction mixture was evaporated and the residue was purified by silica gel column chromatography (Horizons Biotage) using 15% EtOAc in hexane as eluent to give the title compound (0.069 g, 65%). $^1$H NMR (500 MHz CDCl$_3$): δ 7.54-7.50 (m, 2H), 7.46-7.42 (m, 3H), 7.26-7.20 (m, 1H), 6.70-6.60 (m, 2H), 6.59-6.55 (m, 1H), 5.69 (t, 1H), 3.86 (t, 1H), 3.12-3.07 (q, 2H), 1.90-1.82 (m, 2H), 1.75 (s, 9H); $^{13}$C NMR (125 MHz CDCl$_3$): δ 164.8, 162.8, 159.9, 159.8, 135.3, 131.8, 130.5, 130.4, 129.8, 128.8, 125.3, 110.4, 108.2, 108.1, 107.3, 102.5, 102.3, 66.3, 61.7, 42.3, 28.9, 27.8; Mass Spectrum: M+H$^+$ 433.

Example 32

Methyl (4-{3-[(2-tert-butyl-1,1-dioxido-3-oxo-5-phenyl-2,3-dihydroisothiazol-4-yl)amino]propoxy}phenyl)acetate The title compound was prepared as described for Example 12 from methyl (4-hydroxyphenyl)acetate and 3-[(2-tert-butyl-1,1-dioxido-3-oxo-5-phenyl-2,3-dihydroisothiazol-4-yl)amino]propyl 4-methylbenzenesulfonate with a reaction time of 30 mins. The reaction mixture was evaporated and the residue was purified by silica gel column chromatography (Horizons Biotage) using 25% EtOAc in hexane as eluent to give the title compound (0.079 g, 75%). $^1$H NMR (500 MHz CDCl$_3$): δ 7.52-7.44 (m, 2H), 7.14-7.38 (m, 3H), 7.17 (d, 2H), 6.78 (d, 2H), 5.72 (t, 1H), 3.85 (t, 2H), 3.68 (s, 3H), 3.56 (s, 2H), 3.10-3.00 (m, 2H), 1.84-1.78 (m, 2H), 1.72 (s, 9H); $^{13}$C NMR (125 MHz CDCl$_3$): δ 172.5, 159.8, 157.7, 135.3, 131.8, 130.7, 130.5, 129.7, 128.8, 126.8, 125.3, 115.7, 114.7, 107.2, 66.1, 61.7, 52.2, 42.4, 40.5, 28.9, 27.8; Mass Spectrum: M+H$^+$ 487.

Example 33

2-tert-Butyl-4-{[3-(4-fluorophenoxy)propyl]amino}-5-phenylisothiazol-3(2H)-one 1,1-dioxide The title compound was prepared as described for Example 5 from 2-tert-butyl-4-[(3-bromopropyl)amino]-5-phenyl-isothiazol-3(2H)-one 1,1-dioxide and 4-fluorophenol using 3 equivalents of K$_2$CO$_3$ and with heating at 80° C. for 15 mins, 100° C. for 1 h and 120° C. for 1 h. The reaction mixture was evaporated to dryness and the residue was purified by silica gel column chromatography (Horizons Biotage) using 12-20% EtOAc in petroleum ether 40-60° C. as eluent to give the title compound (0.007 g, 31%). $^1$H NMR (500 MHz CDCl$_3$): δ 7.54-7.50 (m, 2H), 7.45-7.40 (m, 3H), 7.00-6.96

(m, 2H), 6.82-6.78 (m, 2H), 5.76 (t, 1H), 3.86 (t, 2H), 3.11-3.02 (m, 2H), 1.88-1.80 (m, 2H), 1.75 (s, 9H); 13C NMR (125 MHz CDCl$_3$): δ 159.8, 158., 154.7, 156.7, 135.3, 131.8, 129.7, 128.8, 125.3, 116.2, 160.0, 115.6, 115.5, 107.2, 66.7, 61.7, 42.5, 28.9, 27.8; Mass Spectrum: M+H$^+$ 433.

Example 34

2-Isopropyl-5-phenyl-4-({1-[4-(trifluoromethyl)pyrimidin-2-yl]piperidin-4-yl}amino)isothiazol-3(2H)-one 1,1-dioxide 4-Chloro-2-isopropyl-5-phenylisothiazol-3(2H)-one 1,1-dioxide (0.200 g, 0.70 mmol), 1-(4-trifluoromethyl-pyrimidin-2-yl)-piperidin-4-ylamine (0.190 g, 0.77 mmol) and TEA (0.078 g, 0.77 mmol) was dissolved in dry MeCN (3 ml) and heated in a microwave reactor at 120° C. for 30 mins. The reaction mixture was purified by silica gel column chromatography using a 65:35 mixture of heptane and EtOAc as eluant, to give the title compound (0.280 g, 81%). $^1$H NMR (500 MHz, CDCl$_3$): δ 8.45-8.41 (m, 1H), 7.58-7.52 (m, 2H), 7.49-7.42 (m, 3H), 6.74-6.70 (m, 1H), 5.26-5.19 (m, 1H), 4.59-4.51 (m, 2H), 4.41 (hep, 1H), 3.26-3.16 (m, 1H), 2.58-2.49 (m, 2H), 1.78-1.71 (m, 2H), 1.57 (d, 6H), 1.35-1.24 (m, 2H); $^{13}$C NMR (125 MHz, CDCl$_3$): δ 161.2, 160.3, 158.7, 156.6, 156.3, 134.5, 131.9, 130.2, 129.0, 125.3, 121.8, 119.6, 107.2, 104.9, 50.7, 47.9, 42.4, 32.2, 20.4; Mass Spectrum: M–H$^+$ 496.

Example 35

3-[(2-tert-Butyl-1,1-dioxido-3-oxo-5-phenyl-2,3-dihydroisothiazol-4-yl)amino]propyl 4-hydroxybenzoate The title compound was prepared as described for Example 5 from 2-tert-butyl-4-[(3-bromopropyl)amino]-5-phenylisothiazol-3(2H)-one 1,1-dioxide and 4-hydroxybenzoic acid with a reaction time of 1.5 h. The reaction mixture was acidified with HCl (1N) and extracted with EtOAc. The organic layers were combined and evaporated to dryness. The residue was triturated in MeOH, the solvent was decanted and the residue was purified by silica gel column chromatography (Horizons Biotage) using 50% EtOAc in petroleum ether 40-60° C. as eluent to give the title compound (0.028 g, 21%). $^1$H NMR (500 MHz CD$_3$CN): δ 7.80 (d, 2H), δ 7.62 (bs, 1H), 7.56-7.48 (m, 2H), 7.56-7.42 (m, 3H), 5.93 (t, 1H), 4.09 (t, 2H), 3.08-3.03 (m, 2H), 1.76-1.68 (m, 1H); $^{13}$C NMR (125 MHz CD$_3$CN): δ 166.5, 160.6, 159.8, 135.2, 132.2, 131.8, 129.9, 128.9, 125.0, 122.2, 115.5, 107.4, 62.2, 61.1, 41.1, 28.4, 27.1; Mass Spectrum: M+H$^+$ 459.

Example 36

4-(Benzylamino)-2-isopropyl-5-phenylisothiazol-3 (2H)-one 1,1-dioxide

4-Chloro-2-isopropyl-5-phenylisothiazol-3(2H)-one 1,1-dioxide (0.200 g, 0.70 mmol), benzylamine (0.082 g, 0.77 mmol) and TEA (0.078 g, 0.77 mmol) was dissolved in MeCN (3 ml) and heated at in a microwave reactor 120° C. for 5 mins. The reaction mixture was purified by silica gel column chromatography using a 75:25 mixture of heptane and EtOAc as eluant, to give the title compound (0.145 g, 58%). $^1$H NMR (500 MHz, CDCl$_3$): δ 7.49-7.36 (m, 5H), 7.32-7.26 (m, 3H), 7.05-7.00 (m, 1H), 5.60-5.51 (m, 1H), 4.43 (hep, 1H), 4.08-4.02 (m, 2H), 1.61 (d, 6H); $^{13}$C NMR (125 MHz, CDCl$_3$): δ 158.6, 136.5, 135.2, 131.7, 129.8, 129.0, 128.7, 128.1, 127.5, 124.8, 107.9, 48.3, 47.8, 20.3; Mass Spectrum: M–H$^+$ 357.

Example 37

2-[2-(3-Fluorophenyl)ethyl]-5-phenyl-4-[(4-phenylbutyl)amino]isothiazol-3(2H)-one 1,1-dioxide 2-tert-Butyl-5-phenyl-4-[(4-phenylbutyl)amino]isothiazol-3(2H)-one 1,1-dioxide (Example 1) (0.150 g, 0.36 mmol) was dissolved in TFA (3 ml) and heated in a microwave reactor at 120° C. for 20 mins. The solvent was evaporated and the crude product was reevaporated from DCM (2×5 ml). The crude product, potassium carbonate (0.251 g, 1.82 mmol) and 3-fluorophenethylbromide (0.221 g, 1.09 mmol) was dissolved in dry MeCN (3 ml) and heated at in a microwave reactor 140° C. for 10 mins. The reaction mixture was purified by silica gel column chromatography using a 85:15 mixture of heptane and EtOAc as eluent, to give the title compound (0.113 g, 65%). $^1$H NMR (500 MHz, CDCl$_3$): δ 7.55-7.41 (m, 5H), 7.34-7.25 (m, 3H), 7.23-7.17 (m, 1H), 7.14-7.01 (m, 4H), 7.00-6.93 (m, 1H), 5.28-5.19 (m, 1H), 3.98-3.90 (m, 2H), 3.18-3.10 (m, 2H), 2.91-2.83 (m, 2H), 2.50-2.43 (m, 2H), 1.44-1.36 (m, 4H); $^{13}$C NMR (125 MHz, CDCl$_3$): δ 164.1, 162.2, 159.1, 141.7, 140.3, 140.2, 135.6, 131.8, 130.4, 130.3, 130.0, 128.9, 128.6, 128.5, 126.2, 125.0, 124.8, 116.2, 116.0, 114.1, 113.9, 107.0, 44.2, 41.1, 35.4, 34.4, 29.2, 28.3; Mass Spectrum: M–H$^+$ 479.

Example 38

4-[(cis-4-Hydroxycyclohexyl)amino]-2-isopropyl-5-phenylisothiazol-3(2H)-one 1,1-dioxide The title compound was isolated by separation of the mixture of cis and trans isomers of 4-[(4-hydroxycyclohexyl) amino]-2-isopropyl-5-phenylisothiazol-3(2H)-one 1,1-dioxide (50:50, 130 mg) by HPLC (C8, 0.05M NH4OAc (pH=4.1):MeCN 1:1) giving the title compound (52 mg). $^1$H NMR (500 MHz, CDCl$_3$): δ 7.53-7.48 (m, 2H), 7.45-7.41 (m, 3H), 5.32-5.24 (m, 1H), 4.40 (hep, 1H), 3.78-3.71 (m, 1H), 3.05-2.94 (m, 1H), 1.62-1.40 (m, 6H), 1.58 (d, 6H), 1.32-1.13 (m, 2H); $^{13}$C NMR (125 MHz, CDCl$_3$): δ 158.9, 134.5, 131.9, 129.9, 128.9, 125.5, 106.3, 65.7, 50.5, 47.8, 31.1, 27.4, 20.4; Mass Spectrum: M–H$^+$ 365.

Example 39

2-tert-Butyl-4-[(4-phenoxybutyl)amino]-5-phenylisothiazol-3(2H)-one 1,1-dioxide

The title compound was prepared as described for Example 24 from 1 equivalent of (4-phenoxybutyl)amine, 2-tert-butyl-4-chloro-5-phenylisothiazol-3(2H)-one 1,1-dioxide and 1 equivalent TEA at 100° C. The residue was purified by silica gel column chromatography (Horizons Biotage) using 10-20% EtOAc in hexane as eluent giving the title compound (0.172 g, 80%) as a solid. $^1$H NMR (500 MHz CDCl$_3$): $^1$H NMR (500 MHz CDCl$_3$): δ 7.54-7.50 (m, 2H), 7.44-7.38 (m, 3H), 7.32-7.25 (m, 2H), 6.96 (t, 1H), 6.83 (d, 2H), 5.34 (t, 1H), 3.81 (t, 2H), 2.98-2.90 (m, 2H), 1.75 (s, 9H), 1.64-1.53 (m, 4H); $^{13}$C NMR (125 MHz CDCl$_3$): δ 159.9, 158.9, 135.2, 131.8, 129.8, 129.7, 128.8, 125.3, 121.0, 114.6, 107.2, 67.1, 61.7, 43.9, 27.9, 26.6, 26.4; Mass Spectrum: M+H$^+$ 429.

Example 40

2-tert-Butyl-4-({3-[(1-oxidopyridin-3-yl)oxy]propyl}amino)-5-phenylisothiazol-3(2H)-one 1,1-dioxide 2-tert-Butyl-5-phenyl-4-{[3-(pyridin-3-yloxy)propyl]amino}isothiazol-3(2H)-one 1,1-dioxide (Example 5) (0.202 g, 0.49 mmol) was dissolved in dry DCM (15 ml) and cooled to 0° C. with an icebath. mCPBA (70%) (0.120 g, 0.53 mmol) was added and the icebath was removed and the reaction mixture was allowed to reach rt. After stirring for 2 h the reaction mixture was extracted with saturated aqueous NaHCO$_3$ solution (20 ml) and brine (20 ml). The organic phase was dried (Na$_2$SO$_4$), filtered and evaporated. The residue was purified by silica gel column chromatography using a 10:90 mixture of heptane and EtOAc and then DCM:MeOH 97:3 as eluant, to give the title compound (0.160 g, 76%). $^1$H NMR (500 MHz, CDCl$_3$): δ 7.90-7.83 (m, 2H), 7.51-7.37 (m, 5H), 7.16-7.09 (m, 1H), 6.80-6.74 (m, 1H), 5.68-5.57 (m, 1H), 3.85-3.76 (m, 2H), 3.09-3.02 (m, 2H), 1.85-1.76 (m, 2H), 1.70 (s, 9H); $^{13}$C NMR (125 MHz, CDCl$_3$): δ 159.8, 157.0, 135.1, 133.0, 131.8, 129.9, 128.9, 128.2, 125.7, 125.2, 113.5, 107.6, 67.0, 61.8, 60.6, 41.7, 32.1, 28.8, 27.8, 22.9; Mass Spectrum: M–H$^+$ 432.

Example 41

2-tert-Butyl-4-[(2-phenoxyethyl)amino]-5-phenyl-isothiazol-3(2H)-one 1,1-dioxide The title compound was prepared as described for Example 24 from (2-phenoxyethyl)amine and 2-tert-butyl-4-chloro-5-phenylisothiazol-3(2H)-one 1,1-dioxide. The residue was purified by silica gel column chromatography (Horizons Biotage) using 15-20% EtOAc in petroleum ether 40-60° C. as eluent to give the title compound (0.026 g, 13%). $^1$H NMR (500 MHz CDCl$_3$): δ 7.60-7.51 (m, 2H), 4.72-7.42 (m, 2H), 7.29 (t, 2H), 6.99 (t, 1H), 6.84 (d, 2H), 5.67 (t, 1H), 3.89 (t, 2H), 3.25 (q, 2H), 1.75 (s, 9H); $^{13}$C NMR (125 MHz CDCl$_3$): δ 159.7, 158.3, 135.2, 131.7, 129.5, 129.8, 129.0, 125.2, 121.7, 114.7, 108.1, 65.9, 61.8, 43.5, 27.8; Mass Spectrum M+H$^+$ 401.

Example 42

4-(Benzylamino)-2-cyclopentyl-5-phenylisothiazol-3(2H)-one 1,1-dioxide

The title compound was prepared from 4-(benzylamino)-2-tert-butyl-5-phenylisothiazol-3(2H)-one 1,1-dioxide (Example 23) and bromocyclopentane in a similar way as described for Example 2 and 3. $^1$H NMR (500 MHz, CDCl$_3$): δ 7.48-7.36 (m, 5H), 7.31-7.26 (m, 3H), 7.04-6.99 (m, 2H), 5.61-5.53 (m, 1H), 4.39 (p, 1H), 4.05 (d, 2H), 2.27-2.10 (m, 4H), 1.97-1.87 (m, 2H), 1.7-1.6 (m, 2H); $^{13}$C NMR (125 MHz, CDCl$_3$): δ 158.8, 136.5, 135.2, 131.7, 129.8, 128.9, 128.7, 128.1, 127.4, 124.9, 107.9, 55.2, 48.3, 29.4, 24.1; Mass Spectrum: M–H$^+$ 383.

Example 43

2-tert-Butyl-4-{[3-(4-methoxyphenoxy)propyl]amino}-5-phenylisothiazol-3(2H)-one 1,1-dioxide The title compound was prepared from 4-[(3-bromopropyl)amino]-2-tell-butyl-5-phenylisothiazol-3(2H)-one 1,1-dioxide and 4-methoxyphenol in a similar manner as described for e.g. Example 5 and 33 and 35. $^1$H NMR (500 MHz CDCl$_3$): δ 7.54-7.50 (m, 2H), 7.46-7.42 (m, 3H), 6.86-6.78 (m, 4H), 5.79 (t, 1H), 3.85 (t, 2H), 3.79 (s, 3H), 3.12-3.04 (m, 2H), δ 1.85-1.80 (m, 2H), 1.75 (s, 9H); $^{13}$C NMR (125 MHz CDCl$_3$): δ 159.9, 154.3, 152.7, 135.4, 131.8, 129.7, 128.8, 125.4, 115.5, 114.9, 107.1, 66.8, 61.7, 55.9, 42.6, 29.1, 27.9; Mass Spectrum: M+H$^+$ 445.

Example 44

4-[(4,4-Difluorocyclohexyl)amino]-2-isopropyl-5-phenylisothiazol-3(2H)-one 1,1-dioxide 4-Chloro-2-isopropyl-5-phenylisothiazol-3(2H)-one 1,1-dioxide (0.155 g, 0.54 mmol), 4,4-difluorocyclohexylamine (0.11 g, 0.81 mmol) and TEA (0.082 g, 0.81 mmol) was dissolved in dry MeCN (3 ml) and heated in a microwave reactor at 130° C. for 10 mins. The reaction mixture was purified by silica gel column chromatography using a 85:15 mixture of hexane and EtOAc as eluant, to give the title compound (0.142 g, 68%); $^1$H NMR (500 MHz, CDCl$_3$): δ 7.54-7.49 (m, 2H), 7.49-7.42 (m, 3H), 5.23-5.16 (m, 1H), 4.41 (hep, 1H), 3.10-3.00 (m, 1H), 1.97-1.86 (m, 2H), 1.77-1.68 (m, 2H), 1.57 (d, 6H), 1.49-1.37 (m, 2H), 1.37-1.21 (m, 2H); $^{13}$C NMR (125 MHz, CDCl$_3$): δ 158.6, 134.5, 131.8, 130.3, 129.0, 125.1, 123.9, 122.0, 120.0, 107.3, 49.9, 47.9, 32.1, 31.9, 31.7, 29.0, 28.9, 20.4; Mass Spectrum: M–H$^+$ 385.

Example 45

4-(Benzylamino)-2-butyl-5-phenylisothiazol-3(2H)-one 1,1-dioxide

The title compound was prepared from 2-butyl-4-chloro-5-phenylisothiazol-3(2H)-one 1,1-dioxide and benzylamine in a similar manner as described for e.g. Example 6 and 7. $^1$H NMR (CD$_3$CN) δ 7.47-7.42 (m, 1H), 7.40-7.35 (m, 2H), 7.34-7.29 (m, 2H), 7.23-7.18 (m, 3H), 6.88-6.83 (m, 2H), 6.44-6.35 (m, 1H), 4.16 (d, J=6.6 Hz, 2H), 3.68 (t, J=7.3 Hz, 2H), 1.82-1.71 (m, 2H), 1.49-1.38 (m, 2H), 0.98 (t, J=7.4 Hz, 3H); Mass spectrum: M+H$^+$ 371.

Example 46

2-Butyl-5-phenyl-4-[(2-phenylethyl)amino]isothiazol-3(2H)-one 1,1-dioxide

The title compound was prepared from 2-butyl-4-chloro-5-phenylisothiazol-3(2H)-one 1,1-dioxide and 2-phenylethanamine in a similar manner as described for e.g. Example 6 and 7. $^1$H NMR (500 MHz CDCl$_3$): δ 7.58-7.52 (m, 2H), 7.50-7.42 (m, 2H), 7.30-7.20 (m, 4H), 6.88 (dd, 2H), 5.38 (t, 1H), 3.70 (t, 2H), 3.18 (dt, 2H), 2.62 (t, 2H), 1.88-1.78 (m, 2H), 1.50-1.40 (m, 2H), 0.98 (t, 2H); $^{13}$C NMR (125 MHz CDCl$_3$): δ 159.4, 137.8, 137.5, 131.8, 130.0, 129.0, 128.9, 128.7, 127.1, 125.2, 107.2, 45.1, 40.4, 36.0, 30.4, 20.3, 13.8; Mass-Spectrum M+H$^+$ 385.

Example 47

2-Butyl-4-{[4-(difluoromethoxy)benzyl]amino}-5-phenylisothiazol-3(2H)-one 1,1-dioxide The title compound was prepared from 2-butyl-4-chloro-5-phenylisothiazol-3(2H)-one 1,1-dioxide and 1-[4-(difluoromethoxy)phenyl]methanamine in a similar manner as described for e.g. Example 6 and 7. $^1$H NMR (CD$_3$CN) δ 7.46-7.41 (m, 1H), 7.39-7.33 (m, 2H), 7.29-7.25 (m, 2H), 6.98-6.93 (m, 2H), 6.86-6.81 (m, 2H), 6.72 (t, J=74.4 Hz, 1H), 6.48-6.39 (m, 1H), 4.16 (d, J=6.6 Hz, 2H), 3.67 (t, J=7.2 Hz, 2H), 1.81-1.72 (m, 2H), 1.49-1.38 (m, 2H), 0.98 (t, J=7.3 MHz, 3H); Mass spectrum: M+H$^+$ 437.

Example 48

4-[(trans-4-Hydroxycyclohexyl)amino]-2-isopropyl-5-phenylisothiazol-3(2H)-one 1,1-dioxide The title compound was isolated by separation of a mixture of the cis and trans isomers of 4-[(4-hydroxycyclohexyl)amino]-2-isopropyl-5-phenylisothiazol-3(2H)-one 1,1-dioxide (50:50, 130 mg) by HPLC (C8, 0.05M NH4OAc (pH=4.1):MeCN 1:1) giving the title compound (73 mg). $^1$H NMR (500 MHz, CDCl$_3$): δ 7.52-7.48 (m, 2H), 7.46-7.42 (m, 3H), 5.16-5.08 (m, 1H), 4.39 (hep, 1H), 3.52-3.42 (m 1H), 2.96-2.85 (m, 1H), 1.82-1.70 (m, 4H), 1.57 (d; 6H), 1.16-1.06 (m, 2H), 0.88-0.77 (m, 2H); $^{13}$C NMR (125 MHz, CDCl$_3$): δ 158.8, 134.7, 131.8, 130.1, 128.9, 125.2, 106.5, 69.4, 51.3, 47.8, 33.5, 31.0, 20.4; Mass Spectrum: M–H$^+$ 365.

Example 49

2-tert-Butyl-4-[(3-hydroxypropyl)amino]-5-phenyl-isothiazol-3(2H)-one 1,1-dioxide A mixture of 2-tert-butyl-4-chloro-5-phenylisothiazol-3(2H)-one 1,1-dioxide (0.300 g, 1.001 mmol), 3-hydroxypropyamine (0.08 ml, 1.001 mmol) and TEA (0.14 ml, 1.001 mmol) in MeCN (5 ml) was stirred at rt. After 18 h the mixture was evaporated to dryness and the residue was purified by silica gel column chromatography (Horizons Biotage) eluting with 33-80% EtOAc (+0.5% TEA) in petroleum ether 40-60° C. to give the title compound (0.145 g, 43%). $^1$H NMR (500 MHz, CDCl$_3$): δ 7.55-7.50 (m, 2H), 7.46-7.42 (m, 3H), 5.77 (t, 1H), 3.62 (q, 2H), 3.01 (q, 2H), 1.74 (s, 9H), 1.63 (qt, 2H); Mass Spectrum: M–H$^+$ 337.

Example 50

5-Phenyl-4-[(4-phenylbutyl)amino]-2-(pyridin-3-ylmethyl)isothiazol-3(2H)-one 1,1-dioxide The title compound was prepared from 2-tert-butyl-5-phenyl-4-[(4-phenylbutyl)amino]isothiazol-3(2H)-one 1,1-dioxide (Example 1) and 3-(bromomethyl)pyridine in a similar manner as described for e.g. Example 2 and 3 $^1$H NMR (500 MHz, CDCl$_3$): δ 8.80-8.76 (m, 1H), 8.62-8.58 (m, 1H), 7.89-7.85 (m, 1H), 7.53-7.41 (m, 5H), 7.34-7.24 (m, 3H), 7.22-7.17 (m, 1H), 7.09-7.04 (m, 2H), 5.31-5.25 (m, 1H), 4.84 (s, 2H), 2.90-2.83 (m, 2H), 2.49-2.42 (m, 2H), 1.44-1.35 (m, 4H); $^{13}$C NMR (125 MHz, CDCl$_3$): δ 159.1, 150.3, 149.8, 141.6, 136.7, 135.5, 131.7, 130.3, 130.0, 128.8, 128.5, 128.4, 126.1, 124.7, 123.7, 107.0, 44.1, 41.1, 35.3, 29.0, 28.2; Mass Spectrum: M–H$^+$ 448.

Example 51

2-Butyl-4-[(4-hydroxycyclohexyl)amino]-5-phenyl-isothiazol-3(2H)-one 1,1-dioxide The title compound was prepared from 2-butyl-4-chloro-5-phenylisothiazol-3(2H)-one 1,1-dioxide and 4-aminocyclohexanol in a similar manner as described for e.g. Example 6 and 7 affording a mixture of cis and trans isomeres. $^1$H NMR (500 MHz, CD$_3$CN): δ 0.61-0.72 (m, 2H), 0.95-0.99 (m, 6H), 1.02-1.10 (m, 2H), 1.17-1.27 (m, 2H), 1.38-1.60 (m, 12H), 1.64-1.80 (m, 8H), 2.46 (d, 1H), 2.55 (d, 1H), 2.86-3.05 (m, 2H), 3.29-3.38 (m, 1H), 3.60-3.69 (m, 5H), 5.55-5.66 (m, 2H), 7.47-7.57 (m, 10H).

Example 52

4-{3-[(2-tert-Butyl-1,1-dioxido-3-oxo-5-phenyl-2,3-dihydroisothiazol-4-yl)amino]propoxy}benzoic acid Methyl 4-{3-[(2-tert-Butyl-1,1-dioxido-3-oxo-5-phenyl-2,3-dihydroisothiazol-4-yl)amino]propoxy}benzoate (0.90 g, 0.19 mmol) and LiI (0.382 g, 2.86 mmol) was dissolved in dry pyridine (1 mL) and heated at reflux for 4 h and then left at rt over night. The reaction mixture was purified by flash chromatography using first Hexane and EtOAc and then EtOAc and MeOH as eluant giving the title compound (0.003 g, 3.4%). $^1$H NMR (CD3CN): 7.98 (d, 2H), 7.56-7.48 (m, 5H), 6.90 (d, 2H), 6.02 (t, 1H), 3.90 (t, 2H), 3.12-3.08 (m, 2), 1.82-1.76 (t, 2H), 1.17 (s, 9H); Mass Spectrum: M+H$^+$ 459.

Example 53

2-tert-Butyl-4-{[3-(4-chlorophenoxy)propyl]amino}-5-phenylisothiazol-3(2H)-one 1,1-dioxide The title compound was prepared from 4-[(3-bromopropyl)amino]-2-tert-butyl-5-phenylisothiazol-3(2H)-one 1,1-dioxide and 4-chlorophenol in a similar manner as described for Example 5. $^1$H NMR (500 MHz CDCl$_3$): δ 7.54-7.48 (m, 2H), 7.46-7.40 (m, 3H), 7.26-7.20 (m, 2H), 6.82-6.76 (m, 2H), 5.72 (t, 1H), 3.86 (t, 2H), 3.11-3.06 (m, 2H), 1.88-1.80 (m, 2H), 1.75 (s, 9H); $^{13}$C NMR (125 MHz CDCl$_3$): δ 159.8, 157.1, 135.3, 131.8, 129.8, 129.6, 128.8, 126.2, 125.3, 115.9, 107.3, 66.4, 61.7, 42.4, 28.9, 27.8; Mass Spectrum: M+H$^+$ 449.

Example 54

5-Phenyl-4-[(4-phenylbutyl)amino]-2-(pyridin-4-ylmethyl)isothiazol-3(2H)-one 1,1-dioxide The title compound was prepared from 2-tert-butyl-5-phenyl-4-[(4-phenylbutyl)amino]isothiazol-3(2H)-one 1,1-dioxide (Example 1) and 4-(chloromethyl)pyridine in a similar manner as described for e.g. Example 2 and 3 $^1$H NMR (500 MHz, CDCl$_3$): δ 8.66-8.60 (m, 2H), 7.54-7.38 (m, 7H), 7.31-7.24 (m, 2H), 7.23-7.16 (m, 1H), 7.10-7.04 (m, 2H), 5.34-5.27 (m, 1H), 4.82 (s, 2H), 2.92-2.84 (m, 2H), 2.50-2.42 (m, 2H), 1.45-1.35 (m, 4H); $^{13}$C NMR (125 MHz, CDCl$_3$): δ 159.3, 150.3, 143.4, 141.5, 135.4, 131.7, 130.0, 128.8, 128.5, 128.4, 126.1, 124.7, 123.1, 107.2, 44.1, 42.3, 35.3, 31.5, 29.0, 28.2; Mass Spectrum: M–H$^+$ 448.

Example 55

4-[(1,3-Benzodioxol-5-ylmethyl)amino]-2-butyl-5-phenylisothiazol-3(2H)-one 1,1-dioxide The title compound was prepared from 2-butyl-4-chloro-5-phenylisothiazol-3(2H)-one 1,1-dioxide and 1-(1,3-benzodioxol-5-yl)methanamine in a similar manner as described for e.g. Example 6 and 7. $^1$H NMR (500 MHz, CD$_3$CN): δ

0.97 (t, 3H), 1.39-1.48 (m, 2H), 1.72-1.80 (m, 2H), 3.67 (t, 2H), 4.05 (d, 2H), 5.91 (s, 2H), 6.26-6.34 (m, 2H), 6.64 (d, 1H), 7.32-7.48 (m, 5H).

Example 56

4-(2,3-Dihydro-1H-inden-2-ylamino)-2-(2-methoxyethyl)-5-phenylisothiazol-3(2H)-one 1,1-dioxide The title compound was prepared from 4-chloro-2-(2-methoxyethyl)-5-phenylisothiazol-3(2H)-one 1,1-dioxide and indan-2-amine in a similar manner as described for Example 1. $^1$H NMR (400 MHz, CD$_3$CN): δ 7.65-7.60 (m, 2H), 7.55-7.50 (m, 3H), 7.13-7.11 (m, 4H), 5.90 (d, 1H), 4.06-3.98 (m, 1H), 3.83 (t, 2H), 3.67 (t, 2H), 3.38 (s, 3H), 2.84-2.81 (m, 4H); Mass Spectrum: M+H$^+$ 399.

Example 57

2-Butyl-4-[(2-morpholin-4-ylethyl)amino]-5-phenylisothiazol-3(2H)-one 1,1-dioxide The title compound was prepared from 2-butyl-4-chloro-5-phenylisothiazol-3(2H)-one 1,1-dioxide and 2-morpholin-4-ylethanamine in a similar manner as described for e.g. Example 6 and 7. $^1$H NMR (500 MHz CDCl$_3$): δ 7.58-7.50 (m, 2H), 7.50-7.00 (m, 3H), 6.05 (t, 1H), 3.78-3.65 (m, 6H), 2.92-2.88 (m, 2H), 2.46-2.32 (m, 6H), 1.88-1.80 (m, 2H), 1.50-1.42 (m, 2H), 1.00 (t, 3H); $^{13}$C NMR (125 MHz CDCl$_3$): δ 159.2, 135.9, 131.6, 129.8, 128.9, 125.3, 107.2, 67.1, 56.4, 53.2, 40.3, 40.2, 30.5, 20.3, 13.8; Mass Spectrum: M+H$^+$ 394.

Example 58

2-tert-Butyl-4-{[3-(4-isopropylphenoxy)propyl]amino}-5-phenylisothiazol-3(2H)-one 1,1-dioxide The title compound was prepared from 3-[(2-tert-Butyl-1,1-dioxido-3-oxo-5-phenyl-2,3-dihydroisothiazol-4-yl)amino]propyl 4-methylbenzenesulfonate and 4-isopropylphenol in a similar manner as described for Example 12. $^1$H NMR (500 MHz CDCl$_3$): δ 7.56-7.50 (m, 2H), 7.48-7.42 (m, 3H), 7.16 (d, 2H), 6.80 (d, 2H), 5.78 (t, 1H), 3.88 (t, 2H), 3.10-3.05 (m, 2H), 2.92-2.82 (m, 1H), 1.85-1.80 (m, 2H), 1.75 (s, 9H), 1.24 (d, 6H); $^{13}$C NMR (125 MHz CDCl$_3$): δ 159.8, 156.6, 141.8, 135.4, 131.8, 129.7, 128.8, 127.5, 125.4, 114.4, 107.1, 66.1, 61.7, 42.6, 33.5, 29.0, 27.9, 24.4; Mass Spectrum: M+H$^+$ 457.

Example 59

4-({3-[Benzyl(butyl)amino]propyl}amino)-2-tert-butyl-5-phenylisothiazol-3(2H)-one 1,1-dioxide The title compound was prepared from 4-[(3-bromopropyl)amino]-2-tert-butyl-5-phenylisothiazol-3(2H)-one 1,1-dioxide and N-benzylbutan-1-amine in a similar manner as described for Example 5. $^1$H NMR (500 MHz CDCl$_3$): δ 7.52-7.44 (m, 2H), 7.42-7.38 (m, 3H), 7.33-7.30 (m, 2H), 7.30-7.24 (m, 3H), 6.36 (t, 1H), 3.48 (s, 2H), 2.86-2.78 (m, 2H), 2.40-2.12 (m, 4H), 1.76 (s, 9H), 1.56-1.44 (m, 4H), 1.36-1.24 (m, 2H), 0.91 (t, 3H); $^{13}$C NMR (125 MHz CDCl$_3$): δ 159.8, 139.4, 135.6, 131.8, 129.4, 129.2, 128.9, 128.4, 127.2, 125.7, 106.3, 61.5, 59.2, 54.1, 52.0, 44.3, 29.2, 27.8, 26.3, 20.9, 14.3; Mass Spectrum: M+H$^+$ 484.

Example 60

2-tert-Butyl-4-{[3-(3,5-dipropoxyphenoxy)propyl]amino}-5-phenylisothiazol-3(2H)-one 1,1-dioxide The title compound was prepared from 4-[(3-bromopropyl)amino]-2-tert-butyl-5-phenylisothiazol-3(2H)-one 1,1-dioxide and 3,5-dipropoxyphenol in a similar manner as described for Example 5. $^1$H NMR (500 MHz, CDCl$_3$): δ 7.54-7.50 (m, 2H), 7.46-7.41 (m, 3H), 6.12-6.09 (m, 1H), 6.08-6.06 (m, 2H), 5.89-5.83 (m, 1H), 3.93-3.84 (m, 6H), 3.09-3.03 (m, 2H), 1.87-1.76 (m, 6H), 1.74 (s, 9H), 1.07-1.01 (m, 6H); $^{13}$C NMR (125 MHz, CDCl$_3$): δ 161.2, 160.2, 159.9, 135.4, 131.8, 129.7, 128.8, 125.3, 107.1, 94.8, 94.6, 94.4, 94.0, 69.8, 66.4, 61.6, 42.7, 28.8, 27.8, 22.8, 10.8; Mass Spectrum: M+H$^+$ 531.

Example 61

2-tert-Butyl-4-[(2,2-diphenylethyl)amino]-5-phenylisothiazol-3(2H)-one 1,1-dioxide The title compound was prepared from 2-tert-butyl-4-chloro-5-phenylisothiazol-3(2H)-one 1,1-dioxide and 2,2-diphenylethanamine in a similar manner as described for Example 1. $^1$H NMR (500 MHz CDCl$_3$): δ 7.59-7.54 (m, 2H), 7.48-7.43 (m, 3H), 7.27 (t, 4H), 7.22 (t, 2H), 6.97 (d, 4H), 5.25 (t, 1H), 3.96 (t, 1H), 3.50 (dd, 2H), 1.70 (s, 9H); $^{13}$C NMR (125 MHz CDCl$_3$): δ 159.6, 140.8, 135.0, 131.7, 129.9, 129.0, 128.0, 127.3, 125.3, 108.1, 61.7, 50.7, 48.3, 27.8; Mass Spectrum: M+H$^+$ 461.

Example 62

2-Ethyl-4-{[2-(1H-imidazol-4-yl)ethyl]amino}-5-phenylisothiazol-3(2H)-one 1,1-dioxide The title compound was prepared from 4-chloro-2-ethyl-5-phenylisothiazol-3(2H)-one 1,1-dioxide and 2-(1H-imidazol-4-yl)ethanamine in a similar manner as described for Example 1.

$^1$H NMR (500 MHz, CD$_3$OD): δ 7.54-7.42 (m, 6H), 6.51-6.48 (m, 1H), 3.71 (q, 2H), 3.14 (t, 2H), 2.55 (t, 2H), 1.36 (t, 3H); $^{13}$C NMR (125 MHz, CD$_3$OD): δ 159.9, 137.3, 136.1, 132.9, 132.3, 130.6, 129.7, 126.9, 117.2, 107.2, 44.6, 36.0, 27.8, 14.0; Mass Spectrum: M+H$^+$ 347.

Example 63

2-Butyl-4-[(4-morpholin-4-ylbenzyl)amino]-5-phenylisothiazol-3(2H)-one 1,1-dioxide The title compound was prepared from 2-butyl-4-chloro-5-phenylisothiazol-3(2H)-one 1,1-dioxide and 1-(4-morpholin-4-ylphenyl)methanamine in a similar manner as described for e.g. Example 6 and 7. $^1$H NMR (500 MHz, CDCl$_3$): δ 7.52-7.48 (m, 2H), 7.46-7.40 (m, 3H), 6.94 (d, 2H), 6.81 (d, 2H), 5.47 (t, 1H), 3.95 (d, 2H), 3.87 (t, 4H), 3.72 (t, 2H), 3.15 (t, 4H), 1.88-1.80 (m, 2H), 1.52-1.42 (m, 2H), 0.99 (t, 3H); $^{13}$C NMR (125 MHz, CDCl$_3$): δ 159.2, 151.3, 135.8, 131.8, 129.9, 128.9, 128.8, 127.6, 125.1, 115.9, 108.0, 67.0, 49.4, 48.1, 40.4, 30.5, 20.3, 13.8; Mass Spectrum: M+H$^+$ 456.

Example 64

2-Butyl-4-{[3-(2-methoxyethoxy)propyl]amino}-5-phenylisothiazol-3(2H)-one-1,1-dioxide

The title compound was prepared from 2-butyl-4-chloro-5-phenylisothiazol-3(2H)-one 1,1-dioxide 3-(2-methoxyethoxy)propan-1-amine in a similar manner as described for e.g. Example 6 and 7. $^1$H NMR (500 MHz CDCl$_3$): δ 7.58-7.50 (m, 2H), 7.48-7.42 (m, 3H), 6.04 (t, 1H), 3.70 (t, 2H), 3.58 (s, 4H), 3.46 (t, 2H), 3.40 (s, 3H), 3.04-2.98 (m, 2H), 1.88-1.80 (m, 2H), 1.70-1.66 (m, 2H), 1.50-1.40 (m, 2H), 0.98 (t, 3H); $^{13}$C NMR (125 MHz CDCl$_3$): δ 159.2, 135.9, 131.8, 129.7, 128.8, 125.4, 106.4, 72.1, 70.7, 69.9, 59.3, 43.3, 40.2, 30.5, 28.9, 20.3, 13.8; Mass Spectrum: M+H$^+$ 397.

Example 65

2-Butyl-4-[(3-morpholin-4-ylpropyl)amino]-5-phenylisothiazol-3(2H)-one 1,1-dioxide

The title compound was prepared from 2-butyl-4-chloro-5-phenylisothiazol-3(2H)-one 1,1-dioxide and 3-morpholin-4-ylpropan-1-amine in a similar manner as described for e.g. Example 6 and 7. $^1$H NMR (500 MHz, CDCl$_3$): δ 7.58 (bs, 1H), 7.58-7.52 (m, 2H), 7.48-7.40 (m, 3H), 3.84-3.78 (m, 4H), 3.70 (t, 2H), 2.98-2.92 (m, 2H), 2.50-2.38 (m, 6H), 1.86-1.80 (m, 2H), 1.62-1.52 (m, 2H), 1.50-1.40 (m, 2H), 0.98 (t, 3H); $^{13}$C NMR (125 MHz, CDCl$_3$): δ 159.3, 136.4, 131.8, 129.5, 128.7, 125.7, 105.9, 66.9, 58.3, 54.0, 45.6, 40.2, 30.5, 24.1, 20.3, 13.8; Mass Spectrum: M+H$^+$ 408.

Example 66

2-Butyl-4-[(2-methoxyethyl)amino]-5-phenylisothiazol-3(2H)-one 1,1-dioxide

The title compound was prepared from 2-butyl-4-chloro-5-phenylisothiazol-3(2H)-one 1,1-dioxide and 2-methoxyethanamine in a similar manner as described for e.g. Example 6 and 7. $^1$H NMR (400 MHz, CD$_3$CN): δ 7.55-7.49 (m, 5H), 5.83 (bs, 1H), 3.67 (t, 2H), 3.27 (t, 2H), 3.21 (s, 3H), 3.05-3.00 (m, 2H), 1.80-1.72 (m, 2H), 1.48-1.38 (m, 2H), 0.97 (t, 3H); Mass Spectrum: M+H$^+$ 339.

Example 67

2-(2-Methoxyethyl)-5-phenyl-4-(tetrahydro-2H-pyran-4-ylamino)isothiazol-3(2H)-one 1,1-dioxide

The title compound was prepared from 4-chloro-2-(2-methoxyethyl)-5-phenylisothiazol-3(2H)-one 1,1-dioxide and tetrahydro-2H-pyran-4-amine in a similar manner as described for Example 1. $^1$H NMR (400 MHz, CD$_3$CN): δ 7.58-7.50 (m, 5H), 5.70 (d, 1H), 3.84 (t, 2H), 3.74-3.66 (m, 4H), 3.35 (s, 3H), 3.21-3.10 (m, 1H), 2.86-2.78 (m, 2H), 1.61-1.54 (m, 2H), 1.48-1.36 (m, 2H); Mass Spectrum: M+H$^+$ 367.

Example 68

4-(Hexylamino)-2-(2-methoxyethyl)-5-phenylisothiazol-3(2H)-one 1,1-dioxide

The title compound was prepared from 4-chloro-2-(2-methoxyethyl)-5-phenylisothiazol-3(2H)-one 1,1-dioxide and hexane-1-amine in a similar manner as described for Example 1. $^1$H NMR (400 MHz, CD$_3$CN): δ 7.48-7.56 (m, 5H), 5.83-5.99 (m, 1H), 3.83 (t, 2H), 3.67 (t, 2H), 3.35 (s, 3H), 2.84-2.90 (m, 2H), 1.13-1.32 (m, 4H), 0.92-1.09 (m, 4H), 0.82 (t, 3H); Mass Spectrum: M–H$^+$ 365.

Example 69

4-[(4-Hydroxycyclohexyl)amino]-2-(2-methoxyethyl)-5-phenylisothiazol-3(2H)-one 1,1-dioxide

The title compound was prepared from 4-chloro-2-(2-methoxyethyl)-5-phenylisothiazol-3(2H)-one 1,1-dioxide and 4-aminocyclohesanol in a similar manner as described for Example 1. $^1$H-NMR (CD$_3$CN): δ 7.58-7.48 (m, 5H), 5.66 (d, J=8.5 Hz, 1H), 3.83 (t, J=5.7 Hz, 2H), 3.67 (t, J=5.7 Hz, 2H), 3.65-3.60 (m, 1H), 3.35 (s, 3H), 3.06-2.95 (m, 1H), 2.49 (d, J=3.5 Hz, 1H), 1.62-1.35 (m, 6H), 1.11-0.99 (m, 2H); MS (ESI+) 381.06 (M+1H$^+$).

Example 70

4-[(1,3-Benzodioxol-5-ylmethyl)amino]-2-(2-methoxyethyl)-5-phenylisothiazol-3(2H)-one 1,1-dioxide

The title compound was prepared from 4-chloro-2-(2-methoxyethyl)-5-phenylisothiazol-3(2H)-one 1,1-dioxide and 1-(1,3-benzodioxol-5-yl)methanamine in a similar manner as described for Example 1. $^1$H NMR (400 MHz, CD$_3$CN): δ 7.32-7.49 (m, 5H), 6.64 (d, 1H), 6.31-6.38 (m, 2H), 6.25-6.29 (m, 1H), 5.91 (s, 2H), 4.05 (d, 2H), 3.83 (t, 2H), 3.67 (t, 2H), 3.35 (s, 3H); Mass Spectrum: M–H$^+$ 415.

Example 71

2-Butyl-4-[(4-methoxybenzyl)amino]-5-phenylisothiazol-3(2H)-one 1,1-dioxide

The title compound was prepared from 2-butyl-4-chloro-5-phenylisothiazol-3(2H)-one 1,1-dioxide and 1-(4-methoxyphenyl)methanamine in a similar manner as described for e.g. Example 6 and 7. $^1$H NMR (CD$_3$CN) δ 7.50-7.33 (m, 5H), 6.79-6.74 (m, 4H), 6.34-6.26 (m, 1H), 4.08 (d, J=6.7 Hz, 2H), 3.75 (s, 3H), 3.67 (t, J=7.2 Hz, 2H), 1.81-1.71 (m, 2H), 1.49-1.38 (m, 2H), 0.97 (t, J=7.5 Hz, 3H); Mass spectrum: M–H$^+$ 399.

Example 72

5-Phenyl-4-[(4-phenylbutyl)amino]-2-(pyridin-2-ylmethyl)isothiazol-3(2H)-one 1,1-dioxide

The title compound was prepared from 2-tert-butyl-5-phenyl-4-[(4-phenylbutyl)amino]isothiazol-3(2H)-one 1,1-dioxide (Example 1) and 2-(bromomethyl)pyridine in a similar manner as described for e.g. Example 2 and 3. $^1$H NMR (500 MHz CDCl$_3$): δ 8.65-8.60 (m, 1H), 7.74-7.67 (m, 1H), 7.56-7.51 (m, 2H), 7.50-7.41 (m, 4H), 7.31-7.17 (m, 4H), 7.10-7.05 (m, 2H), 5.35-5.28 (m, 1H), 5.01 (s, 2H), 2.94-2.84 (m, 2H), 2.50-2.42 (m, 2H), 1.45-1.35 (m, 4H); $^{13}$C NMR (125 MHz, CDCl$_3$): δ 159.4, 154.4, 149.7, 141.6, 137.1, 135.5, 131.7, 129.9, 128.8, 128.5, 128.4, 126.1, 124.9, 123.0, 121.9, 107.2, 44.9, 44.1, 35.3, 29.1, 28.2; Mass Spectrum: M–H$^+$ 448.

Example 73

2-tert-Butyl-4-{[3-(3-hydroxyphenoxy)propyl]amino}-5-phenylisothiazol-3(2H)-one 1,1-dioxide

A mixture of 3-[(2-tert-butyl-1,1-dioxido-3-oxo-5-phenyl-2,3-dihydroisothiazol-4-yl)amino]propyl 4-methylbenzenesulfonate (0.045 g, 0.091 mmol), resorcinol (0.020 g, 0.183 mmol) and K₂CO₃ (0.063 g, 0.457 mmol) in MeCN (2 ml) was heated in a microwave reactor at 120° C. for 10 mins. The reaction mixture was evaporated and the residue was purified by silica gel column chromatography (Horizons Biotage) using 0-50% EtOAc in DCM as eluent to give the title compound (0.016 g, 41%) as a solid. $^1$H NMR (500 MHz CDCl₃): δ 7.54-7.48 (m, 2H), 7.46-7.41 (m, 3H), 7.13 (t, 1H), 6.46-6.41 (m, 2H), 6.39-6.36 (m, 1H), 5.75 (t, 1H), 5.14 (s, 1H), 3.86 (t, 2H), 3.11-3.04 (m, 2H), 1.86-1.78 (m, 2H), 1.75 (s, 9H); $^{13}$C NMR (125 MHz CDCl₃): 159.9, 157.1, 135.4, 131.8, 130.4, 129.8, 128.8, 125.3, 108.5, 107.1, 106.9, 102.3, 66.1, 61.8, 42.5, 28.9, 27.8; Mass Spectrum: M+H⁺ 431.

Example 74

3-{3-[(2-tert-Butyl-1,1-dioxido-3-oxo-5-phenyl-2,3-dihydroisothiazol-4-yl)amino]propoxy}benzoic acid The title compound was prepared from 3-[(2-tert-butyl-1,1-dioxido-3-oxo-5-phenyl-2,3-dihydroisothiazol-4-yl)amino]propyl 4-methylbenzenesulfonate and 3-hydroxybenzoic acid in a similar manner as described for Example 12. $^1$H NMR (500 MHz, d8-THF): δ 7.62-7.58 (d, 1H), 7.57-7.51 (m, 2H), 7.49 (s, 1H), 7.46-7.42 (m, 3H), 7.31 (t, 1H), 7.30 (t, 1H), 6.51 (t, 1H), 3.82 (t, 2H), 3.14-3.08 (m, 2H), 1.83-1.78 (m, 2H), 1.70 (s, 9H); $^{13}$C NMR (125 MHz, d8-THF): δ 166.7, 159.8, 158.9, 135.5, 132.5, 131.9, 129.2, 129.1, 128.4, 126.4, 122.1, 119.1, 114.9, 106.9, 65.6, 60.4, 41.3, 29.0, 26.9; Mass Spectrum: M+H⁺ 459.

Example 75

2-tert-Butyl-5-phenyl-4-(piperidin-4-ylamino)isothiazol-3(2H)-one 1,1-dioxide

TFA (1 ml) was added to a solution of tert-butyl 4-[(2-tert-butyl-1,1-dioxido-3-oxo-5-phenyl-2,3-dihydroisothiazol-4-yl)amino]piperidine-1-carboxylate (Example 86) (2.138 g, 4.612 mmol) in DCM (20 ml) and the mixture was stirred at rt for 80 mins. TFA (1 mil) was added and the reaction mixture was stirred for 18 h. The reaction mixture was basified by addition of saturated aqueous NaHCO₃. The organic layer was separated and the aqueous phase was extracted with DCM. The combined organic phases were washed with brine, and evaporated to give the title compound (1.630 g, 97%) as a solid. $^1$H NMR (500 MHz, CDCl₃): δ 7.54-7.50 (m, 2H), 7.50-7.40 (m, 3H), 5.20 (d, 1H), 3.08-2.92 (m, 3H), 2.19 (dt, 2H), 1.74 (s, 9H), 1.72-1.46 (m, 2H), 1.36-1.24 (m, 2H); $^{13}$C NMR (125 MHz, CDCl₃): δ 159.9, 134.0, 131.8, 130.1, 128.9, 125.3, 107.1, 61.8, 50.2, 44.7, 33.1, 27.9; Mass Spectrum: M+H⁺ 364.

Example 76

2-tert-Butyl-4-[(2-hydroxyethyl)amino]-5-phenyl-isothiazol-3(2H)-one 1,1-dioxide The title compound was prepared as described for Example 49 from 2-aminoethanol and 2-tert-butyl-4-chloro-5-phenyl-isothiazol-3(2H)-one 1,1-dioxide. The residue was purified by silica gel column chromatography (Horizons Biotage) using DCM as eluent to give the title compound (1.788 g, 55%) as an oil. $^1$H NMR (500 MHz): δ 7.50-7.44 (m, 5H), 6.81 (t, 1H), 4.69 (t, 1H), 3.29-3.22 (m, 2H), 3.86-2.80 (m, 2H), 1.64 (s, 9H); $^{13}$C NMR (125 MHz DMSO-d₆): 159.9, 136.1, 132.1, 130.0, 129.2, 125.9, 105.4, 61.2, 59.5, 46.6, 27.8; Mass Spectrum: M+H⁺ 325.

Example 77

4-{2-[(2-tert-Butyl-1,1-dioxido-3-oxo-5-phenyl-2,3-dihydroisothiazol-4-yl)amino]ethyl}phenyl methanesulfonate 2-tert-Butyl-4-chloro-5-phenylisothiazol-3(2H)-one 1,1-dioxide (0.175 g, 0.58 mmol) 4-(2-aminoethyl)phenyl methanesulfonate (0.149 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.140 g, 51%). $^1$H NMR (500 MHz, CDCl₃): δ 7.53-7.49 (m, 2H), 7.48-7.43 (m, 3H), 7.14-7.10 (m, 2H), 6.83-6.78 (m, 2H), 5.43-5.36 (m, 1H), 3.15-3.08 (m, 2H), 2.61-2.55 (m, 2H), 1.71 (s, 9H); $^{13}$C NMR (125 MHz, CDCl₃): δ 159.8, 148.2, 137.1, 134.9, 131.9, 130.3, 130.0, 129.0, 125.3, 122.4, 107.7, 61.8, 44.9, 37.6, 35.5, 27.8; Mass Spectrum: M–H⁺ 479.

Example 78

4-{2-[(2-tert-butyl-1,1-dioxido-3-oxo-5-phenyl-2,3-dihydroisothiazol-4-yl)amino]ethyl}benzenesulfonamide 2-tert-Butyl-4-chloro-5-phenylisothiazol-3(2H)-one 1,1-dioxide (0.175 g, 0.58 mmol), 4-(2-aminoethyl)benzenesulfonamide (0.139 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.122 g, 45%). $^1$H NMR (500 MHz, d8-THF): δ 7.70-7.65 (m, 2H), 7.58-7.52 (m, 2H), 7.51-7.45 (m, 3H), 6.90-6.84 (m, 2H), 6.53-6.47 (m, 1H), 6.38-6.34 (m, 1H), 3.19-3.12 (m, 2H), 2.64-2.58 (m, 1H), 1.70 (s, 9H); $^{13}$C NMR (125 MHz, d8-THF): δ 159.7, 143.3, 142.4, 135.2, 132.0, 129.4, 128.8, 128.6, 126.4, 126.3, 107.2, 60.6, 44.7, 35.6, 27.0; Mass Spectrum: M–H⁺ 464.

Example 79

2-tert-Butyl-4-({1-[3-chloro-5-(trifluoromethyl)pyridin-2-yl]piperidin-4-yl}amino)-5-phenylisothiazol-3(2H)-one 1,1-dioxide 2-tert-Butyl-4-chloro-5-phenylisothiazol-3(2H)-one 1,1-dioxide (200 mg, 0.667 mmol) was dissolved in dry DMF (2 mL) under nitrogen atmosphere. 1-[3-Chloro-5-(trifluoromethyl)pyridin-2-yl]piperidin-4-amine (188 mg, 0.674 mmol) was added followed by TEA (68 mg, 0.667 mmol) and the reaction mixture was heated in a microwave reactor at 120° C. for 20 mins. The reaction mixture was diluted with EtOAc, washed with saturated aqueous NaHCO₃-solution, dried over Na₂SO₄, filtered and evaporated. The crude product was purified on a Biotage Horizon HPFC system using Heptane and EtOAc as eluant affording the title compound (284 mg, 77.6%). $^1$H NMR (500 MHz, CDCl₃): δ 1.46-1.54 (m, 2H), 1.73-1.79 (m, 1H), 2.51 (t, 2H), 3.12-3.19 (m, 1H), 3.79-3.82 (m, 2H), 5.28 (d, 1H), 7.44-7.46 (m, 3H), 7.53-7.55 (m, 2H), 7.72 (s, 1H), 8.33 (s, 1H); $^{13}$C NMR (125 MHz, CDCl₃): δ 27.82, 32.36, 47.43, 50.27, 61.80, 107.32, 120.35 (q, J=33.4

Hz), 121.28, 123.48 (q, J=271.3 Hz), 125.36, 128.94, 130.17, 131.85, 134.16, 136.15, 143.10, 159.87, 160.06; Mass Spectrum: M+H+ 543.1.

Example 80 tert-Butyl 3-{2-[(2-tert-butyl-1,1-dioxido-3-oxo-5-phenyl-2,3-dihydroisothiazol-4-yl)amino]ethyl}azetidine-1-carboxylate 2-tert-Butyl-4-chloro-5-phenylisothiazol-3(2H)-one 1,1-dioxide (74 mg, 0.249 mmol) was dissolved in dry DMF (1 mL) nitrogen atmosphere. tert-Butyl 3-(2-aminoethyl)azetidine-1-carboxylate (50 mg, 0.249 mmol) was added followed by TEA (25 mg, 0.247 mmol) and the reaction mixture was heated in a microwave reactor for at 120° C. for 20 mins. The reaction mixture was diluted with EtOAc, washed with saturated aqueous NaHCO$_3$-solution, dried over Na$_2$SO$_4$, filtered and evaporated. The crude product was purified by preparative HPLC affording the title compound (33 mg, 28.8%). $^1$H NMR (500 MHz, CDCl$_3$): δ 1.43 (s, 9H), 1.62 (q, 2H), 1.73 (s, 9H), 2.19-2.27 (m, 1H), 2.83 (q, 2H), 3.23-3.26 (m, 2H), 3.84 (t, 2H), 5.25 (t, 1H), 7.42-7.51 (m, 5H); $^{13}$C NMR (125 MHz, CDCl$_3$): δ 26.24, 27.82, 28.61, 34.35, 41.72, 54.06, 61.82, 79.63, 107.55, 125.15, 128.93, 130.09, 131.79, 135.04, 156.38, 159.81; Mass Spectrum: M−H+ 462.

Example 81

4-{2-[(2-tert-Butyl-1,1-dioxido-3-oxo-5-phenyl-2,3-dihydroisothiazol-4-yl)amino]ethyl}benzonitrile 2-tert-Butyl-4-chloro-5-phenylisothiazol-3(2H)-one 1,1-dioxide (0.175 g, 0.58 mmol), 4-(2-aminoethyl)benzonitrile (0.101 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.039 g, 16%). $^1$H NMR (500 MHz, CDCl$_3$): δ 7.53-7.43 (m, 7H), 6.88-6.84 (m, 2H), 5.39-5.33 (m, 1H), 3.17-3.10 (m, 2H), 2.65-2.60 (m, 2H), 1.71 (s, 9H); $^{13}$C NMR (125 MHz, CDCl$_3$): δ 159.7, 143.2, 134.7, 132.7, 131.8, 130.1, 129.5, 129.1, 125.2, 118.8, 111.1, 108.1, 61.9, 44.5, 41.2, 36.2, 27.8; Mass Spectrum: M−H+ 410.

Example 82

2-ter-Butyl-4-(isopropylamino)-5-phenylisothiazol-3(2H)-one 1,1-dioxide 2-tert-Butyl-4-chloro-5-phenylisothiazol-3(2H)-one 1,1-dioxide (0.175 g, 0.58 mmol), isopropylamine (0.041 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.108 g, 58%). $^1$H NMR (500 MHz, CDCl$_3$): δ 7.52-7.46 (m, 2H), 7.44-7.38 (m, 3H), 5.16-5.04 (m, 1H), 3.34-3.22 (m, 1H), 1.71 (s, 9H), 0.94 (d, 6H); $^{13}$C NMR (125 MHz, CDCl$_3$): δ 160.1, 134.2, 131.7, 129.8, 128.9, 125.6, 106.5, 61.6, 44.8, 27.8, 23.0; Mass Spectrum: M−H+ 323.

Example 83

2-tert-Butyl-5-phenyl-4-{[3-(pyridin-2-yloxy)propyl]amino}isothiazol-3(2H)-one 1,1-dioxide The title compound was prepared as described for Example 24 from 1 equivalent of [3-(pyridin-2-yloxy)propyl]amine, 2-tert-Butyl-4-chloro-5-phenylisothiazol-3(2H)-one 1,1-dioxide and 1 equivalent TEA with a reaction time of 30 mins. The residue was purified by silica gel column chromatography (Horizons Biotage) using 5:1 petroleum ether 40-60° C. in EtOAc as eluent to give the title compound (0.178 g, 65%) as a solid. $^1$H NMR (500 MHz CDCl$_3$): δ 8.17 (dd, 1H), 7.62-7.57 (m, 1H), 7.54-7.48 (m, 2H), 7.45-7.40 (m, 3H), 6.91-6.88 (m, 1H), 6.74 (d, 1H), 6.00 (t, 1H), 4.28 (t, 2H), 3.04 (q, 2H), 1.83 (quintet, 2H), 1.75 (s, 9H); $^{13}$C NMR (125 MHz CDCl$_3$): δ 163.8, 159.9, 147.0, 138.9, 135.5, 131.8, 129.7, 128.8, 125.4, 117.3, 111.5, 106.9, 63.6, 61.6, 42.0, 28.9, 27.9; Mass Spectrum: M+H+ 416.

Example 84

2-tert-Butyl-4-{[1-(5-methylpyridin-2-yl)piperidin-4-yl]amino}-5-phenylisothiazol-3(2H)-one 1,1-dioxide 2-tert-Butyl-4-chloro-5-phenylisothiazol-3(2H)-one 1,1-dioxide (97 mg, 0.324 mmol) was dissolved in dry DMF (1 mL) under nitrogen atmosphere. 1-(5-Methylpyridin-2-yl)piperidin-4-amine dihydrochloride (86 mg, 0.327 mmol) was added followed by TEA (33 g, 0.324 mmol). The reaction mixture was heated in a microwave reactor for at 120° C. for 25 mins. The mixture was diluted with EtOAc and washed with saturated aqueous NaHCO$_3$-solution and water. The organic phase was dried over Na$_2$SO$_4$, filtered and evaporated. The crude product was purified by preparative HPLC affording the title compound (64 mg, 43.5%). $^1$H NMR (500 MHz, CDCl$_3$): δ 1.33-1.41 (m, 2H), 1.71-1.74 (m, 1H), 2.17 (s, 3H), 2.38-2.43 (m, 2H), 3.08-3.15 (m, 1H), 3.95-3.99 (m, 2H), 5.23 (d, 1H), 6.51 (d, 1H), 7.26 (dd, 1H), 7.43-7.45 (m, 3H), 7.53-7.55 (m, 2H), 7.96 (s, 1H); $^{13}$C NMR (125 MHz, CDCl$_3$): δ 17.51, 27.84, 32.05, 44.64, 50.68, 61.78, 107.10, 107.50, 122.63, 125.39, 128.91, 130.11, 131.90, 134.20, 138.65, 147.86, 157.77, 159.91; Mass Spectrum: M+H+ 455.0.

Example 85

2-ter-Butyl-4-{[1-(6-chloropyridazin-3-yl)piperidin-4-yl]amino}-5-phenylisothiazol-3(2H)-one 1,1-dioxide 2-tert-Butyl-4-chloro-5-phenylisothiazol-3(2H)-one 1,1-dioxide (0.450 g, 1.50 mmol), 1-(6-chloropyridazin-3-yl)piperidin-4-amine (0.487 g, 1.95 mmol) and TEA (0.456 g, 4.50 mmol) was dissolved in dry MeCN (15 ml) and heated in a microwave reactor at 120° C. for 30 mins. The reaction mixture was evaporated and the residue was diluted with EtOAc (150 ml) and washed with water (500 ml). The organic phase was dried over MgSO$_4$, filtered and evaporated. The residue was purified by silica gel column chromatography using a 60:40→50:50 mixture of heptane and EtOAc as eluant, to give the title compound (0.191 g, 27%). $^1$H NMR (500 MHz, CDCl$_3$): δ 7.55-7.50 (m, 2H), 7.47-7.43 (m, 3H), 7.15 (d, 1H), 6.81 (d, 1H), 5.20 (d, 1H), 4.11-4.05 (m, 2H), 3.22-3.13 (m, 1H), 2.60-2.52 (m, 2H), 1.80-1.73 (m, 2H), 1.72 (s, 9H), 1.41-1.32 (m, 2H); $^{13}$C NMR (125 MHz, CDCl$_3$): δ 159.5, 158.6, 147, 133.8, 131.6, 130, 128.8, 128.7, 125, 115.4, 107.3, 61.6, 50, 43.8, 31.6, 27.6.

Example 86 tert-Butyl 4-[(2-tert-butyl-1,1-dioxido-3-oxo-5-phenyl-2,3-dihydroisothiazol-4-yl)amino]piperidine-1-carboxylate A mixture of 2-tert-butyl-4-chloro-5-phenylisothiazol-3(2H)-one 1,1-dioxide (2.000 g, 6.672 mmol), tert-butyl-4- aminopiperidine-1-carboxylate (1.336 g, 6.672 mmol) and TEA (0.933 ml, 6.672 mmol) in MeCN (20 ml) was heated in a microwave reactor at 120° C. for 40 mins and 130° C. for 30 mins. tert-Butyl-4-aminopiperidine-1-carboxylate (0.267 mg, 1.334 mmol) and TEA (0.187 ml, 1.334 mmol) was added and the resulting mixture was heated in a microwave reactor for at 120° C. for 20 mins. The reaction mixture was evaporated to dryness and the residue was purified by silica gel column chromatography (Horizons Biotage) eluting with 10% petroleum ether 40-60° C. in DCM then 0-20% EtOAc in DCM to give the title compound (2.228 g, 72%) as a solid. $^1$H NMR (500 MHz, CDCl$_3$): δ 7.54-7.50 (m, 2H), 7.50-7.44 (m, 3H), 5.17 (d, 1H), 3.88 (bs, 2H), 3.08-3.00 (m, 1H), 2.32 (d, 2H), 1.74 (s, 9H), 1.68-1.60 (m, 2H), 1.42 (s, 9H), 1.30-1.17 (m, 2H); $^{13}$C NMR (125 MHz, CDCl$_3$): δ 159.8, 154.7, 134.1, 131.9, 130.2, 128.9, 125.3, 107.3, 80.1, 61.9, 50.4, 42.4, 32.4, 28.6, 27.9; Mass Spectrum M+H$^+$ 464.

Example 87

2-tert-Butyl-4-{[1-(6-methoxypyridazin-3-yl)piperidin-4-yl]amino}-5-phenylisothiazol-3(2H)-one 1,1-dioxide 2-tert-Butyl-4-chloro-5-phenylisothiazol-3(2H)-one 1,1-dioxide (0.300 g, 1.00 mmol), 1-(6-methoxypyridazin-3-yl)piperidin-4-amine dihydrochloride (0.349 g, 1.24 mmol) and TEA (0.405 g, 4.00 mmol) was dissolved in dry DMF (10 ml) and heated in a microwave reactor at 120° C. for 30 mins. The reaction mixture was diluted with water (200 ml) and extracted with EtOAc (200 ml). The organic phase was dried over MgSO$_4$, filtered and evaporated. The residue was purified by silica gel column chromatography using a 55:45 mixture of heptane and EtOAc as eluant, to give the title compound (0.232 g, 49%). $^1$H NMR (500 MHz, CDCl$_3$): δ 7.54-7.49 (m, 2H), 7.46-7.41 (m, 3H), 6.92 (d, 1H), 6.79 (d, 1H), 5.2 (d, 1H), 4.00 (s, 3H), 3.93-3.87 (m, 2H), 3.17-3.08 (m, 1H), 2.53-2.45 (m, 2H), 1.77-1.71 (m, 2H), 1.72 (s, 9H), 1.44-1.35 (m, 2H); $^{13}$C NMR (125 MHz, CDCl$_3$): δ 160.1, 159.6, 157.3, 133.8, 131.6, 129.9, 128.7, 125, 119.4, 119.1, 107, 61.6, 54.3, 50.1, 45.1, 31.6, 27.6; Mass Spectrum: M–H$^+$ 472.

Example 88

2-tert-Butyl-4-{[1-(6-chloropyridin-3-yl)piperidin-4-yl]amino}-5-phenylisothiazol-3(2H)-one 1,1-dioxide 2-tert-Butyl-4-chloro-5-phenylisothiazol-3(2H)-one 1,1-dioxide (0.175 g, 0.58 mmol), 1-(6-chloropyridin-3-yl)piperidin-4-amine dihydrochloride (0.196 g, 0.69 mmol) and TEA (0.23 g, 2.31 mmol) was dissolved in dry DMF (3 ml) and heated in a microwave reactor at 130° C. for 30 mins. The reaction mixture was purified with preparative HPLC giving the title compound (0.022 g, 8%). $^1$H NMR (500 MHz, CDCl$_3$): δ 7.92-7.87 (m, 1H), 7.55-7.48 (m, 2H), 7.48-7.41 (m, 3H), 7.13-7.03 (m, 2H), 5.24-5.18 (m, 1H), 3.45-3.35 (m, 2H), 3.13-3.01 (m, 1H), 2.39-2.29 (m, 2H), 1.82-1.71 (m, 2H), 1.73 (s, 9H), 1.52-1.40 (m, 2H); $^{13}$C NMR (125 MHz, CDCl$_3$): δ 159.8, 145.8, 141.7, 138.0, 134.1, 131.8, 130.2, 129.0, 126.6, 125.3, 124.1, 107.5, 61.9, 49.8, 47.8, 32.0, 27.8; Mass Spectrum: M–H$^+$ 475.

Example 89

4-[(1-Benzylpiperidin-4-yl)amino]-2-tert-butyl-5-phenylisothiazol-3(2H)-one 1,1-dioxide The title compound was prepared as described for Example 24 from 1 equivalent 1-benzylpiperidine-4-amine, 2-tert-butyl-4-chloro-5-phenylisothiazol-3(2H)-one 1,1-dioxide and 1 equivalent TEA with a reaction time of 30 mins. The residue was purified by silica gel column chromatography (Horizons Biotage) using 35% EtOAc in petroleum ether 40-60° C. as eluent to give the title compound (0.132 g, 58%) as a solid. $^1$H NMR (500 MHz CDCl$_3$): δ 7.54-7.7.47 (m, 2H), 7.46-7.42 (m, 3H), 7.31-7.26 (m, 2H), 7.26-7.21 (m, 3H), 5.20 (d, 1H), 3.35 (s, 2H), 2.99-2.90 (m, 1H), 2.67-2.62 (m, 2H), 1.74 (s, 9H), 1.71-1.56 (m, 4H), 1.44-1.33 (m, 2H); $^{13}$C NMR (125 MHz CDCl$_3$): δ 159.9, 138.5, 134.2, 131.8, 129.9, 129.1, 128.8, 128.4, 127.3, 125.4, 106.7, 62.9, 61.7, 51.9, 50.3, 32.6, 27.8; Mass spectrum: M+H$^+$ 454.

Example 90

2-tert-Butyl-4-(ethylamino)-5-phenylisothiazol-3(2H)-one 1,1-dioxide 2-tert-Butyl-4-chloro-5-phenylisothiazol-3(2H)-one 1,1-dioxide (0.175 g, 0.58 mmol), ethylamine hydrochloride (0.056 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.099 g, 55%). $^1$H NMR (500 MHz, CDCl$_3$): δ 7.51-7.46 (m, 2H), 7.43-7.38 (m, 3H), 5.21-5.12 (m, 1H), 2.89-2.80 (m, 2H), 1.72 (s, 9H), 1.01 (t, 3H); $^{13}$C NMR (125 MHz, CDCl$_3$): δ 159.9, 135.2, 131.7, 129.7, 128.7, 125.4, 107.1, 61.7, 39.3, 27.8, 15.0; Mass Spectrum: M–H$^+$ 309.

Example 91

N~2-(2-tert-Butyl-1,1-dioxido-3-oxo-5-phenyl-2,3-dihydroisothiazol-4-yl)-N~1~-[3-(difluoromethoxy)benzyl]glycinamide 2-tert-Butyl-4-chloro-5-phenylisothiazol-3(2H)-one 1,1-dioxide (0.175 g, 0.58 mmol), N-[3-(difluoromethoxy)benzyl]glycinamide (0.159 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.118 g, 41%). $^1$H NMR (500 MHz, CDCl$_3$): δ 7.46-7.35 (m, 5H), 7.35-7.28 (m, 1H), 7.09-7.01 (m, 2H), 6.99-6.94 (m, 1H), 6.50 (t, 1H), 6.02-5.94 (m, 1H), 5.91-5.82 (m, 1H), 4.37-4.31 (m, 2H), 3.53-3.48 (m, 2H), 1.71 (s, 9H); $^{13}$C NMR (125 MHz, CDCl$_3$): δ 167.3, 159.3, 139.9, 134.9, 131.5, 130.5, 130.2, 129.0, 125.1, 124.5, 119.4, 119.0, 116.0, 113.9, 109.9, 62.0, 46.8, 43.4, 27.8; Mass Spectrum: M–H$^+$ 494.

Example 92

2-tert-Butyl-5-phenyl-4-[(1-pyridin-2-ylpiperidin-4-yl)amino]isothiazol-3(2H)-one 1,1-dioxide 2-tert-Butyl-4-chloro-5-phenylisothiazol-3(2H)-one 1,1-dioxide (0.175 g, 0.58 mmol), 1-pyridin-2-ylpiperidin-4-amine dihydrochloride (0.173 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.175 g, 69%). $^1$H NMR (500 MHz, CDCl$_3$): δ 8.08-8.03 (m, 1H), 7.50-7.44 (m, 2H), 7.41-7.32 (m, 4H), 6.55-6.47 (m, 2H), 5.28-5.20 (m, 1H), 4.02-3.93 (m, 2H), 3.11-3.00 (m, 1H), 2.41-2.30 (m, 2H), 1.73-1.60 (m, 2H), 1.67 (s, 9H), 1.36-1.24 (m, 2H); $^{13}$C NMR (125 MHz, CDCl$_3$): δ 159.8, 159.1, 148.0, 137.7, 134.2, 131.9, 130.1, 128.9, 125.4, 113.5, 107.5, 107.0, 61.7, 50.7, 44.1, 41.2, 32.0, 27.8; Mass Spectrum: M–H$^+$ 441.

Example 93

2-tert-Butyl-5-phenyl-4-[(1-pyridazin-3-ylpiperidin-4-yl)amino]isothiazol-3(2H)-one 1,1-dioxide 2-tert-Butyl-4-chloro-5-phenylisothiazol-3(2H)-one 1,1-dioxide (0.240 g, 0.80 mmol), 1-pyridazin-3-ylpiperidin-4-amine (0.257 g, 1.02 mmol) and TEA (0.324 g, 3.2 mmol), was dissolved in dry DMF (10 ml) and heated in a microwave reactor at 120° C. for 30 mins. The reaction mixture was diluted with water (300 ml) and extracted with EtOAc (2×150 ml). The combined organic phases were dried (MgSO$_4$), filtered and evaporated and the residue was purified by silica gel column chromatography using EtOAc as eluant, to give the title compound (0.110 g, 31%). $^1$H NMR (500 MHz, CDCl$_3$): δ 8.55-8.52 (m, 1H), 7.55-7.50 (m, 2H), 7.47-7.42 (m, 3H), 7.19-7.14 (m, 1H), 6.85-6.82 (m, 1H), 5.21 (d, 1H), 4.17-4.11 (m, 2H), 3.22-3.13 (m, 1H), 2.60-2.52 (m, 2H), 1.80-1.73 (m, 2H), 1.72 (s, 9H), 1.42-1.32 (m, 2H); $^{13}$C NMR (125 MHz, CDCl$_3$): δ 159.5, 143.1, 133.8, 131.6, 129.9, 128.7, 127.4, 125, 112.8, 107.2, 61.6, 50.1, 43.6, 31.7, 27.5; Mass Spectrum: M–H$^+$ 442.

Example 94

2-tert-Butyl-4-{[1-(5-fluoropyridin-2-yl)piperidin-4-yl]amino}-5-phenylisothiazol-3(2H)-one 1,1-dioxide 2-tert-Butyl-4-chloro-5-phenylisothiazol-3(2H)-one 1,1-dioxide (0.175 g, 0.58 mmol), 1-(5-fluoropyridin-2-yl)piperidin-4-amine dihydrochloride (0.155 g, 0.58 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.153 g, 58%). $^1$H NMR (500 MHz, CDCl$_3$): δ 8.01-7.95 (m, 1H), 7.56-7.49 (m, 2H), 7.48-7.39 (m, 3H), 7.23-7.16 (m, 1H), 6.56-6.48 (m, 1H), 5.25-5.15 (m, 1H), 3.98-3.86 (m, 2H), 3.17-3.04 (m, 1H), 2.47-2.36 (m, 2H), 1.80-1.64 (m, 2H), 1.72 (s, 9H), 1.43-1.30 (m, 2H); $^{13}$C NMR (125 MHz, CDCl$_3$): δ 159.9, 156.1, 154.7, 152.7, 134.8, 134.6, 134.1, 131.9, 130.1, 128.9, 125.3, 108.3, 107.3, 61.8, 50.5, 45.0, 32.0, 27.8; Mass Spectrum: M–H$^+$ 459.

Example 95

2-tert-Butyl-4-{[3-(3,5-dimethyl-1H-pyrazol-1-yl)propyl]amino}-5-phenylisothiazol-3(2H)-one 1,1-dioxide 2-tert-Butyl-4-chloro-5-phenylisothiazol-3(2H)-one 1,1-dioxide (150 mg, 0.5 mmol), 3-(3,5-dimethyl-pyrazol-1-yl)-propylamine tartrate (167 mg, 0.55 mmol) were mixed in MeCN (3 ml). Triethylamine (0.23 ml, 1.65 mmol) was added and the mixture was heated in a microwave reactor at 120° C. for 15 mins. The reaction mixture was evaporated to dryness and the residue was purified by column chromatography (ISOLUTE SI, 20 g/70 ml), eluting with DCM and then MeOH/DCM (1:99), to give the title compound (195 mg, 94%). $^1$H NMR (400 MHz, CDCl3): δ 1.70 (s, 9H), 1.72-1.79 (m, 2H), 2.05 (s, 3H), 2.18 (s, 3H), 2.81-2.86 (m 2H), 3.79 (t, 2H), 5.71 (bs, 2H), 7.37-7.46 (m, 5H); $^{13}$C NMR (100 MHz, CDCl3): δ 10.8, 13.4, 27.5, 29.2, 41.5, 45.4, 61.3, 105.1, 106.8, 125.0, 128.4, 129.4, 131.4, 135.0, 138.5, 147.3, 159.3; Mass Spectrum: M+H$^+$ 417.

Example 96

2-ter-Butyl-4-{[1-(5-chloropyridin-2-yl)piperidin-4-yl]amino}-5-phenylisothiazol-3(2H)-one 1,1-dioxide 2-tert-Butyl-4-chloro-5-phenylisothiazol-3(2H)-one 1,1-dioxide (0.175 g, 0.58 mmol), 1-(5-chloropyridin-2-yl)piperidin-4-amine dihydrochloride (0.196 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.124 g, 45%). $^1$H NMR (500 MHz, CDCl$_3$): δ 8.06-8.02 (m, 1H), 7.55-7.49 (m, 2H), 7.47-7.41 (m, 3H), 7.39-7.33 (m, 1H), 6.52-6.45 (m, 1H), 5.24-5.14 (m, 1H), 4.02-3.93 (m, 1H), 3.18-3.06 (m, 1H), 2.49-2.39 (m, 2H), 1.78-1.66 (m, 2H), 1.72 (s, 9H), 1.39-1.28 (m, 2H); $^{13}$C NMR (125 MHz, CDCl$_3$): δ 159.8, 157.4, 146.3, 137.5, 134.1, 131.9, 130.2, 128.9, 125.3, 120.5, 108.2, 107.3, 61.9, 50.5, 44.3, 32.0, 27.8; Mass Spectrum: M–H$^+$ 475.

Example 97

2-tert-Butyl-5-phenyl-4-({1-[4-(trifluoromethyl)pyridin-2-yl]piperidin-4-yl}amino)isothiazol-3(2H)-one 1,1-dioxide 2-tert-Butyl-4-chloro-5-phenylisothiazol-3(2H)-one 1,1-dioxide (0.175 g, 0.58 mmol), 1-[4-(trifluoromethyl)pyridin-2-yl]piperidin-4-amine dihydrochloride (0.220 g, 0.69 mmol) and TEA (0.23 g, 2.31 mmol) was dissolved in dry DMF (3 ml) and heated in a microwave reactor at 130° C. for 30 mins. The reaction mixture was purified by preparative HPLC to yield the title compound (0.112 g, 38%). $^1$H NMR (500 MHz, CDCl$_3$): δ 8.28-8.23 (m, 1H), 7.59-7.52 (m, 2H), 7.51-7.44 (m, 3H), 6.79-6.74 (m, 1H), 6.74-6.70 (m, 1H), 5.27-5.17 (m, 1H), 4.17-4.07 (m, 2H), 3.24-3.13 (m, 1H), 2.57-2.48 (m, 2H), 1.83-1.69 (m, 2H), 1.75 (s, 9H), 1.42-1.31 (m, 2H); $^{13}$C NMR (125 MHz, CDCl$_3$): δ 159.8, 149.3, 134.1, 131.9, 130.2, 129.0, 125.3, 108.5, 107.4, 102.9, 61.9, 50.5, 43.9, 32.0, 27.8; Mass Spectrum: M–H$^+$ 509.

Example 98

2-tert-Butyl-4-(tert-butylamino)-5-phenylisothiazol-3(2H)-one 1,1-dioxide

The title compound was prepared as described for Example 24 from tert-butylamine and 2-tert-butyl-4-chloro-5-phenylisothiazol-3(2H)-one 1,1-dioxide at 140° C. for 1.5 h. The residue was purified by silica gel column chromatography (Horizons Biotage) using 0-5% EtOAc in petroleum ether 40-60° C. as eluent to give the title compound (0.029 g, 17%) as a solid. $^1$H NMR (500 MHz CDCl$_3$): δ 0.54-7.50 (m, 2H), 7.48-7.44 (m, 3H), 5.53 (s, 1H), 1.74 (s, 9H), 1.08 (s, 9H); $^{13}$C NMR (125 MHz CDCl$_3$): 160.9, 133.8, 133.5, 130.3, 129.1, 126.8, 106.6, 61.8, 52.2, 30.1, 27.8; Mass Spectrum: M+H$^+$ 337.

Example 99

2-{2-[(2-tert-Butyl-1,1-dioxido-3-oxo-5-phenyl-2,3-dihydroisothiazol-4-yl)amino]ethoxy}phenyl methanesulfonate 2-[(2-tert-Butyl-1,1-dioxido-3-oxo-5-phenyl-2,3-dihydroisothiazol-4-yl)amino]ethyl 4-methylbenzenesulfonate (150 mg, 0.313 mmol) was dissolved in dry MeCN (3 mL)

under nitrogen atmosphere. 2-Hydroxyphenyl methanesulfonate (65 mg, 0.345 mmol) was added followed by potassium carbonate (217 mg, 1.567 mmol). The reaction mixture was heated in a microwave reactor at 120° C. for 15 mins. Potassium carbonate was filtered off and the reaction mixture was evaporated to dryness in a vacuum centrifuge. The crude product was purified by preparative HPLC affording the title compound (94 mg, 58.5%). $^1$H NMR (CDCl$_3$, 500 MHz): δ 1.71 (s, 9H), 3.19 (s, 3H), 3.26 (q, 2H), 3.92 (t, 2H), 5.86 (t, 1H), 6.86 (d, 1H), 6.99 (t, 1H), 7.22 (t, 1H), 7.28 (d, 1H), 7.42-7.45 (m, 3H), 7.49-7.53 (m, 2H); $^{13}$C NMR (CDCl$_3$, 125 MHz): δ 27.82, 38.53, 43.28, 61.78, 67.18, 108.11, 114.66, 122.30, 124.66, 125.15, 128.54, 129.08, 130.04, 131.69, 135.27, 138.61, 150.49, 159.51; Mass Spectrum: M+H$^+$ 494.8.

Example 100 tert-Butyl 3-({2-[(2-tert-butyl-1,1-dioxido-3-oxo-5-phenyl-2,3-dihydroisothiazol-4-yl)amino]ethyl}thio)pyrrolidine-1-carboxylate 2-[(2-tert-Butyl-1,1-dioxido-3-oxo-5-phenyl-2,3-dihydroisothiazol-4-yl)amino]ethyl 4-methylbenzenesulfonate (150 mg, 0.313 mmol) was dissolved in dry MeCN (3 mL) under nitrogen atmosphere. tert-Butyl 3-mercaptopyrrolidine-1-carboxylate (70 mg, 0.345 mmol) was added followed by potassium carbonate (217 mg, 1.567 mmol). The reaction mixture was heated in a microwave reactor at 120° C. for 15 mins. Potassium carbonate was filtered off and the reaction mixture was evaporated to dryness in a vacuum centrifuge. The crude product was purified by preparative HPLC affording the title compound (134 mg, 83.4%). The product is a mixture of cis and trans isomers. $^1$H NMR (CDCl$_3$, 500 MHz): δ 1.47 (s, 9H), 1.73 (s, 10H), 2.05 (s, 1H), 2.46-2.51 (m, 2H), 2.88 (bs, 1H), 3.01-3.13 (m, 3H), 3.29 (s, 1H), 3.41-3.57 (m, 2H), 5.65 (bs, 1H), 7.43-7.46 (m, 3H), 7.49-7.53 (m, 2H); $^{13}$C NMR (CDCl$_3$, 125 MHz): δ 27.83, 28.73, 31.29, 32.33, 32.86, 41.74, 42.41, 43.23, 44.86, 45.09, 52.27, 52.53, 61.86, 79.79, 108.04, 125.15, 129.04, 130.04, 131.65, 134.81, 154.41, 159.66; Mass Spectrum: M+H$^+$ 509.9.

Example 101

Methyl 2-{2-[(2-tert-butyl-1,1-dioxido-3-oxo-5-phenyl-2,3-dihydroisothiazol-4-yl)amino]ethoxy}benzoate 2-[(2-tert-Butyl-1,1-dioxido-3-oxo-5-phenyl-2,3-dihydroisothiazol-4-yl)amino]ethyl 4-methylbenzenesulfonate (150 mg, 0.313 mmol) was dissolved in dry MeCN (3 mL) under nitrogen atmosphere. Methyl salicylate (52 mg, 0.345 mmol) was added followed by potassium carbonate (217 mg, 1.567 mmol). The reaction mixture was heated in a microwave reactor at 120° C. for 20 mins. Potassium carbonate was filtered off and the reaction mixture was evaporated to dryness in a vacuum centrifuge. The crude product was purified by preparative HPLC affording the title compound (9 mg, 6%). $^1$H NMR (CDCl$_3$, 500 MHz): δ 1.74 (s, 9H), 3.27 (q, 2H), 3.97-4.00 (m, 5H), 6.17 (t, 1H), 6.86 (d, 1H), 7.05 (t, 1H), 7.44-7.48 (m, 4H), 7.52-7.56 (m, 2H), 7.85 (dd, 1H); $^{13}$C NMR (CDCl$_3$, 125 MHz): δ 27.85, 43.53, 52.52, 61.69, 67.49, 107.84, 114.40, 121.12, 121.69, 125.42, 129.00, 129.85, 131.69, 132.27, 133.85, 135.56, 158.01, 159.56, 166.79; Mass Spectrum: M+H$^+$ 459.0.

Example 102

2-tert-Butyl-5-phenyl-4-{[2-(pyridin-3-yloxy)ethyl]amino}isothiazol-3(2H)-one 1,1-dioxide 2-[(2-tert-Butyl-1,1-dioxido-3-oxo-5-phenyl-2,3-dihydroisothiazol-4-yl)amino]ethyl 4-methylbenzenesulfonate (150 mg, 0.313 mmol) was dissolved in dry MeCN (3 mL) under nitrogen atmosphere. Pyridin-3-ol (33 mg, 0.345 mmol) was added followed by potassium carbonate (217 mg, 1.567 mmol). The reaction mixture was heated in a microwave reactor at 120° C. for 15 mins. Potassium carbonate was filtered off and the reaction mixture was evaporated to dryness in a vacuum centrifuge. The crude product was purified by preparative HPLC affording the title compound (46 mg, 35.7%). $^1$H NMR (CDCl$_3$, 500 MHz): δ 1.74 (s, 9H), 3.30 (q, 2H), 3.92 (t, 2H), 5.64 (t, 1H), 7.12-7.14 (m, 1H), 7.22-7.24 (m, 1H), 7.46-7.48 (m, 3H), 7.53-7.55 (m, 2H), 8.26-8.28 (m, 2H); $^{13}$C NMR (CDCl$_3$, 125 MHz): δ 27.84, 43.32, 61.90, 66.37, 108.51, 121.55, 124.15, 125.03, 129.09, 130.10, 131.69, 135.11, 137.90, 143.23, 154.51, 159.64; Mass Spectrum: M+H$^+$ 402.1.

Example 103

4-{2-[(2-ter-Butyl-1,1-dioxido-3-oxo-5-phenyl-2,3-dihydroisothiazol-4-yl)amino]ethoxy}phenyl methanesulfonate 2-[(2-tert-Butyl-1,1-dioxido-3-oxo-5-phenyl-2,3-dihydroisothiazol-4-yl)amino]ethyl 4-methylbenzenesulfonate (150 mg, 0.313 mmol) was dissolved in dry MeCN (3 mL) under nitrogen atmosphere. 4-Hydroxyphenyl methanesulfonate (65 mg, 0.345 mmol) was added followed by potassium carbonate (217 mg, 1.567 mmol). The reaction mixture was heated in a microwave reactor at 120° C. for 15 mins. Potassium carbonate was filtered off and the reaction mixture was evaporated to dryness in a vacuum centrifuge. The crude product was purified by preparative HPLC affording the title compound (61 mg, 38.5%). $^1$H NMR (CDCl$_3$, 500 MHz): δ 1.73 (s, 9H), 3.11 (s, 3H), 3.23-3.27 (m, 2H), 3.83-3.86 (m, 2H), 5.65 (bs, 1H), 6.83 (d, 2H), 7.20 (d, 2H), 7.43-7.46 (m, 3H), 7.50-7.54 (m, 2H); $^{13}$C NMR (CDCl$_3$, 125 MHz): δ 27.83, 37.34, 43.30, 61.85, 66.50, 108.27, 115.77, 123.48, 125.07, 129.07, 130.06, 131.68, 135.18, 143.35, 157.21, 159.65; Mass Spectrum: M+NH$_4$+511.8.

Example 104

4-({4-[(2-tert-Butyl-1,1-dioxido-3-oxo-5-phenyl-2,3-dihydroisothiazol-4-yl)amino]piperidin-1-yl}methyl)benzonitrile A mixture of 2-tert-butyl-5-phenyl-4-(piperidin-4-ylamino)isothiazol-3(2H)-one 1,1-dioxide (Example 75) (0.100 g, 0.275 mmol), 4-(bromomethyl)benzonitrile (0.054 g, 0.275 mmol), 1-benzyl-1,3,4,6,7,8-hexahydro-2H-pyrimido[1,2-a]pyrimidine on polystyrene (0.055 g, 0.413 mmol) in DMF (2 ml) was heated in a microwave reactor at 150° C. for 7 mins. The reaction mixture was filtered, evaporated to dryness and the residue was purified by preparative HPLC to give the title compound (0.040 g, 30%); $^1$H NMR (500 MHz CDCl$_3$): δ 7.59 (d, 2H), 7.52-7.49 (m, 2H), 7.48-7.42 (m, 3H), 7.37 (d, 2H), 5.21 (d, 1H), 3.41 (s, 2H), 3.01-2.90 (m, 1H), 2.65-2.56 (m, 2H), 1.74 (s, 9H), 1.69-1.60 (m, 4H), 1.44-1.34 (m, 2H); $^{13}$C NMR (125 MHz CDCl$_3$): δ 159.9, 144.5, 134.2, 132.3, 131.9, 129.9, 129.4, 128.9, 125.4, 119.1, 111.1, 106.9, 62.3, 61.8, 51.9, 50.1, 32.5, 27.8; Mass Spectrum M+H$^+$ 479.

Example 105

2-tert-Butyl-5-phenyl-4-({1-[2-(trifluoromethyl)benzoyl]piperidin-4-yl}amino)isothiazol-3(2H)-one 1,1-dioxide A mixture of 2-tert-butyl-5-phenyl-4-(piperidin-4-ylamino)isothiazol-3(2H)-one 1,1-dioxide (Example 75) (0.100 g, 0.275 mmol), 2-(trifluoromethyl)benzoyl chloride (0.049 ml, 0.330 mmol) and 2-tert-butylimino-2-diethylamino-1,3-dimethyl-perhydro-1,3,2-diazaphosphorine on polystyrene (0.600 g, 1.376 mmol) in DCM (2 ml) was stirred at rt for 17 h. The mixture was filtered, evaporated to dryness and the residue was purified by preparative HPLC to give the title compound (0.053 g, 36%). $^1$H NMR (500 MHz CDCl$_3$): δ 7.68 (t, 1H), 7.61-7.42 (m, 6 h), 7.26 (d, 1H), 7.18 (d, 1H), 5.21 (d, 1H), 4.61-4.46 (m, 1 h), 3.24-3.10 (m, 2H), 2.54-2.38 (m, 2H), 1.88-1.78 (m, 1H), 1.76-1.48 (10H), 1.44-1.32 (m, 1H), 1.26-1.10 (m, 1H); $^{13}$C NMR (125 MHz CDCl$_3$): δ 167.4, 167.3, 159.8, 159.7, 134.8, 133.9, 133.8, 132.5, 132.3, 131.9, 131.7, 130.4, 130.2, 129.5, 129.0, 128.9, 127.3, 127.0, 126.9, 125.3, 125.1, 107.8, 107.5, 61.9, 50.3, 50.1, 45.7, 45.5, 41.2, 40.3, 40.1, 32.5, 32.1, 31.9, 31.8, 27.8; Mass Spectrum: M–H$^+$ 534

Example 106

Methyl 3-({4-[(2-tert-butyl-1,1-dioxido-3-oxo-5-phenyl-2,3-dihydroisothiazol-4-yl)amino]piperidin-1-yl}methyl)benzoate The title compound was prepared as described for Example 104 from methyl 3-(bromomethyl)benzoate and 2-tert-butyl-5-phenyl-4-(piperidin-4-ylamino)isothiazol-3(2H)-one 1,1-dioxide (Example 75) to give the title compound (0.101 g, 48%) as a solid. $^1$H NMR (500 MHz CDCl$_3$): δ 7.95-7.87 (m, 2H), 7.54-7.32 (m, 7H), 5.20 (d, 1H), 3.92 (s, 3H), 3.38 (s, 2H), 3.00-2.80 (m, 1H), 2.66-2.58 (m, 2H), 1.80-1.54 (m, 13H), 1.42-1.30 (m, 2H); $^{13}$C NMR (125 MHz CDCl$_3$): δ 167.4, 159.9, 139.1, 134.3, 133.6, 131.8, 130.4, 130.2, 129.9, 128.8, 128.6, 125.4, 106.8, 62.5, 61.8, 52.3, 51.9, 50.2, 32.5, 27.8; Mass Spectrum: M+H$^+$ 512.

Example 107

2-tert-Butyl-4-({1-[(2-chloropyridin-3-yl)carbonyl]piperidin-4-yl}amino)-5-phenylisothiazol-3(2H)-one 1,1-dioxide The title compound was prepared as described for Example 105 from 2-chloronicotinyl chloride and 2-tert-butyl-5-phenyl-4-(piperidin-4-ylamino)isothiazol-3(2H)-one 1,1-dioxide (Example 75) to give the title compound (0.030 g, 22%). $^1$H NMR (500 MHz CDCl$_3$): δ 8.46-8.42 (m, 1H), 7.62 (d, 1H), 7.58-7.44 (m, 5H), 7.37-7.26 (m, 1H), 7.52 (dd, 1H), 3.30-3.10 (m, 2H), 2.73-2.40 (m, 5H), 1.90-1.80 (m, 1H), 1.74 (s, 9H), 1.68-1.58 (m, 2H), 1.54-1.10 (m, 2H); $^{13}$C NMR (125M CDCl$_3$): δ 165.2, 165.1, 159.7, 159.6, 150.5, 150.3, 147.3, 137.0, 136.9, 133.9, 133.8, 132.3, 132.1, 131.9, 131.7, 1 130.4, 130.2, 129.1, 128.9, 125.3, 125.0, 123.0, 122.9, 108.1, 107.7, 61.9, 50.3, 49.9, 45.7, 44.9, 40.4, 40.2, 32.8, 32.7, 32.0, 31.9, 27.8; Mass Spectrum: M–H$^+$ 503.

Example 108

2-tert-Butyl-4-({1-[(5-methylisoxazol-3-yl)methyl]piperidin-4-yl}amino)-5-phenylisothiazol-3(2H)-one 1,1-dioxide The title compound was prepared as described for Example 104 from 3-(bromomethyl)-5-methylisooxazole and 2-tert-butyl-5-phenyl-4-(piperidin-4-ylamino)isothiazol-3(2H)-one 1,1-dioxide (Example 75) to give the title compound (0.021 g, 17%) as a solid. $^1$H NMR (500 MHz CDCl$_3$): δ 7.52-7.48 (m, 2H), 7.48-7.42 (m, 3H), 5.92 (s, 1H), 5.18 (d, 1H), 3.40 (s, 2H), 2.98-2.88 (m, 1H), 2.70-2.62 (m, 2H), 2.40 (s, 3H), 1.74 (m, 9H), 1.79-1.60 (m, 4H), 1.42-1.32 (m, 2H); $^{13}$C NMR (125 MHz CDCl$_3$): δ 169.7, 161.7, 159.9, 134.2, 131.8, 130.1, 128.9, 125.3, 106.9, 101.8, 61.8, 53.4, 52.0, 50.1, 32.5, 27.8, 12.5; Mass Spectrum M+H$^+$ 459.

Example 109

4-[(1-Benzoylpiperidin-4-yl)amino]-2-ter-butyl-5-phenylisothiazol-3(2H)-one 1,1-dioxide A mixture of 2-tert-butyl-5-phenyl-4-(piperidin-4-ylamino)isothiazol-3(2H)-one 1,1-dioxide (Example 75) (0.150 mg, 0.413 mmol), benzoic acid (0.055 g, 0.454 mmol), EDC (0.087 g, 0.454 mmol), HOBt (0.061 g, 0.454 mmol) and TEA (0.120 ml, 0.825 mmol) in THF (3 ml) was stirred at rt for 3.5 h. The reaction mixture was evaporated and the residue was purified by silica gel column chromatography (Horizons Biotage) using 50% EtOAc in petroleum ether 40-60° C. as eluent to give the title compound (0.136 g, 71%) as a solid. $^1$H NMR (500 MHz CDCl$_3$): δ 7.54-7.50 (m, 2H), 7.50-7.42 (m, 5H), 7.42-7.35 (m, 2H), 7.32-7.29 (m, 1H), 5.21 (d, 1H), 4.48 (bs, 1H), 3.56 (bs, 1H), 3.24-3.12 (m, 1H), 2.58-2.44 (m, 2H), 1.90-1.64 (bs, 2H), 1.74 (s, 9H), 1.48-1.16 (bs, 2H); $^{13}$C NMR (125 MHz CDCl$_3$): δ 170.6, 159.7, 135.7, 133.9, 131.8, 130.2, 130.0, 128.9, 128.7, 126.9, 125.2, 107.7, 61.9, 50.4, 27.8; Mass Spectrum: M+H$^+$ 468.

Example 110

2-tert-Butyl-5-phenyl-4-{[1-(phenylacetyl)piperidin-4-yl]amino}isothiazol-3(2H)-one 1,1-dioxide The title compound was prepared as described for Example 105 from phenylacetic chloride and 2-tert-butyl-5-phenyl-4-(piperidin-4-ylamino)isothiazol-3(2H)-one 1,1-dioxide (Example 75) to give the title compound (0.103 g, 78%). $^1$H NMR (500 MHz CDCl$_3$): δ 7.54-7.47 (m, 2H), 7.47-7.41 (m, 3H), 7.34-7.29 (m, 2H), 7.27-7.23 (m, 1H), 7.18 (d, 2H), 5.12 (d, 1H), 4.43-4.26 (m, 1H), 3.70-3.61 (m, 3H), 3.11-3.02 (m, 1H), 2.55-2.47 (m, 1H), 2.28-2.20 (m, 1H), 1.90-1.65 (m, 11H), 1.54-1.47 (m, 1H), 1.19 (dq, 1H), 0.91 (dq, 1H); $^{13}$C δ NMR (125 MHz CDCl$_3$): 169.5, 159.7, 135.0, 133.9, 131.8, 130.2, 129.0, 128.9, 128.6, 127.2, 125.2, 107.5, 61.9, 50.2, 44.6, 41.3, 41.2, 40.4, 32.6, 32.1, 27.8; Mass Spectrum: M+H$^+$ 482.

Example 111

2-tert-Butyl-4-{[1-(2-chloro-6-methylisonicotinoyl)piperidin-4-yl]amino}-5-phenylisothiazol-3(2H)-one 1,1-dioxide The title compound was prepared as described for Example 105 from 2-chloride-6-methylisonicotinoyl chloride and 2-tert-butyl-5-phenyl-4-(piperidin-4-ylamino)isothiazol-3(2H)-one 1,1-dioxide (Example 75) using DMAP as catalyst and DMF as solvent. EtOAc was added to the reaction mixture, and it was washed with brine, evaporated and the residue was purified by silica gel column chromatography (Horizons Biotage) using 50% EtOAc in petroleum ether 40-60° C. as eluent to give the title compound (0.037 g, 26%). $^1$H NMR (500 MHz CDCl$_3$): δ 7.54-7.50 (m, 2H), 7.50-7.43 (m, 3H), 7.02 (s, 1H), 6.96 (s, 1H), 5.21 (d, 1H), 4.48-4.38 (m, 1H), 3.46-3.36 (m, 1H), 3.24-3.14 (m, 1H), 2.62-2.40 (m, 5H), 1.90-1.80 (m, 1H), 1.74 (s, 9H), 1.70-1.60 (m, 1H), 1.44-1.32 (m, 1H), 1.30-1.18 (m, 1H); $^{13}$C NMR (125 MHz CDCl$_3$): δ 166.7, 160.7, 159.7, 151.3, 146.6, 133.9, 131.8, 130.3, 129.0, 125.2, 119.3, 118.6, 107.9, 61.9, 50.1, 45.8, 41.1, 40.7, 32.9, 31.9, 27.8, 24.5; Mass Spectrum: M+H$^+$ 517.

Example 112

4-({4-[(2-tert-Butyl-1,1-dioxido-3-oxo-5-phenyl-2,3-dihydroisothiazol-4-yl)amino]piperidin-1-yl}carbonyl)benzonitrile The title compound was prepared as described for Example 105 from 4-cyanobenzoyl chloride and 2-tert-butyl-5-phenyl-4-(piperidin-4-ylamino)isothiazol-3(2H)-one 1,1-dioxide (Example 75) using DMF as solvent. The reaction mixture was evaporated and the residue was purified by silica gel column chromatography (Horizons Biotage) using 50% EtOAc in petroleum ether 40-60° C. as eluent. The product containing fractions were evaporated, dissolved in DCM, washed through a cation exchange column and evaporated to give the title compound (0.015 g, 11%). $^1$H NMR (500 MHz CDCl$_3$): δ 7.70 (d, 1H), 7.55-7.50 (m, 2H), 7.49-7.40 (m, 5H), 5.21 (d, 1H), 4.52-4.40 (m, 1H), 3.50-3.36 (m, 1H), 3.24-3.14 (m, 2H), 2.62-2.44 (m, 2H), 1.92-1.78 (m, 1H), 1.74 (s, 9H), 1.67-1.54 (m, 2H), 1.48-1.16 (m, 2H); $^{13}$C NMR (125 MHz CDCl$_3$): δ 168.5, 159.7, 140.1, 133.9, 132.7, 131.8, 130.3, 129.0, 127.7, 125.2, 118.2, 113.9, 107.9, 61.9, 50.1, 46.0, 40.9, 32.9, 32.1, 27.8; M+H$^+$ 493.

Example 113

2-tert-Butyl-4-{[1-(3,4-difluorobenzoyl)piperidin-4-yl]amino}-5-phenylisothiazol-3(2H)-one 1,1-dioxide The title compound was prepared as described for Example 105 from 3,4-difluorobenzoyl chloride and 2-tert-butyl-5-phenyl-4-(piperidin-4-ylamino)isothiazol-3(2H)-one 1,1-dioxide (Example 75) to give the title compound (0.033 g, 24%). $^1$H NMR (500 MHz CDCl$_3$): δ 7.54-7.50 (m, 2H), 7.48-7.42 (m, 3H), 7.22-7.14 (m, 2H), 7.10-7.04 (m, 1H), 5.23 (d, 1H), 4.40 (bs, 1H), 3.58 (bs, 1H), 3.22-3.12 (m, 1H), 2.58-2.46 (m, 2H), 1.80-1.60 (m, 1H), 1.42-1.14 (m, 2H); $^{13}$C NMR (125 MHz CDCl$_3$): δ 168.3, 159.7, 152.6, 152.4, 151.6, 151.4, 150.6, 150.4, 149.6, 149.4, 133.9, 132.5, 131.8, 130.3, 129.0, 125.2, 123.7, 117.9, 117.8, 116.9, 116.8, 107.8, 61.9, 50.2, 46.0, 32.5, 27.8; Mass Spectrum: M−H$^+$ 502.

Example 114

4-{2-[(2-Isopropyl-1,1-dioxido-3-oxo-5-phenyl-2,3-dihydroisothiazol-4-yl)amino]ethyl}phenyl methanesulfonate A mixture of 4-chloro-2-isopropyl-5-phenylisothiazol-3(2H)-one 1,1-dioxide (0.15 g, 0.52 mmol), 4-(2-aminoethyl)phenyl methanesulfonate (0.14 g, 0.63 mmol) and TEA (0.07 g, 0.68 mmol) in MeCN (1.5 ml) was heated in a microwave reactor at 120° C. for 35 mins. 4-(2-Aminoethyl)phenyl methanesulfonate (0.07 g) was added to the mixture, and it was heated in a microwave reactor at 120° C. for 20 mins. The reaction mixture was evaporated and the crude product was purified by flash column chromatography using hexane and EtOAc, 80:20-30:70, as eluant to yield the title compound (0.21 g, 85%). $^1$H NMR (500 MHz, CDCl$_3$): δ 1.57-1.59 (m, 6H), 2.50-2.61 (m, 2H), 3.12-3.16 (m, 5H), 4.39-4.42 (m, 1H), 5.23 (brm, 1H), δ 6.80-6.83 (m, 2H), 7.12-7.15 (m, 2H), 7.48-7.54 (m, 5H); $^{13}$C NMR (125 MHz, CDCl$_3$): δ 14.4, 20.4, 35.5, 37.6, 45.0, 47.8, 107.8, 122.4, 125.2, 129.1, 130.1, 130.3, 131.8, 135.2, 137.0, 148.2, 158.6; Mass Spectrum: M−H$^+$ 463.

Example 115

4-{2-[(2-Isopropyl-1,1-dioxido-3-oxo-5-phenyl-2,3-dihydroisothiazol-4-yl)amino]ethyl}benzenesulfonamide A mixture of 4-chloro-2-isopopyl-5-phenylisothiazol-3(2H)-one 1,1-dioxide (0.16 g, 0.56 mmol), 4-(2-aminoethyl)benzenesulfonamide (0.14 g, 0.67 mmol) and TEA (0.07 g, 0.73 mmol) in MeCN (1.5 ml) was heated in a microwave reactor at 120° C. for 15 mins. The reaction mixture was evaporated and THF was added to the residue. The mixture was filtrated and the eluant was concentrated. The residue was recrystallized from THF and hexane to yield the title compound (0.19 g, 74%). $^1$H NMR (500 MHz, THF): δ 1.53 (d, 6H), 2.62 (t, 2H), 3.16-3.20 (m, 2H), 4.30-4.38 (m, 1H), 6.38 (s, 1H), 6.63 (t, 1H), 6.87 (d, 2H), 7.48-7.51 (m, 3H), 7.56-7.58 (m, 2H), 7.68 (d, 2H); $^{13}$C NMR (125 MHz, THF): δ 19.4, 35.6, 44.7, 47.0, 106.9, 126.3, 126.5, 128.6, 128.8, 129.4, 132.0, 135.6, 142.3, 143.3, 158.5; Mass Spectrum: M+H$^+$ 450.

Example 116

4-{2-[(2-Isopropyl-1,1-dioxido-3-oxo-5-phenyl-2,3-dihydroisothiazol-4-yl)amino]ethyl}benzonitrile A mixture of 4-chloro-2-isopropyl-5-phenylisothiazol-3(2H)-one 1,1-dioxide (0.15 g, 0.52 mmol), 4-(2-aminoethyl)benzonitrile (0.09 g, 0.63 mmol) and TEA (0.07 g, 0.68 mmol) in MeCN (1.5 ml) was heated in a microwave reactor at 120° C. for 35 mins. 4-(2-Aminoethyl)benzonitrile (0.04 g) was added to the reaction mixture, and it was heated in a microwave reactor at 120° C. for 20 mins. The reaction mixture was evaporated and the crude product was purified by flash column chromatography using hexane and EtOAc, 80:20-50:50, as eluant, to yield the title compound (0.14 g, 67%). $^1$H NMR (500 MHz, CDCl$_3$): δ 1.57 (d, 6H), 2.63 (t, 2H), 3.15-3.19 (m, 2H), 4.37-4.43 (m, 1H), 5.46 (brm, 1H), 6.86 (d, 2H), 7.45-5.55 (m, 7H); $^{13}$C NMR (125 MHz, CDCl$_3$): δ 20.4, 36.2, 44.5, 47.9, 107.8, 111.0, 118.9, 125.2, 129.1, 129.5, 130.1, 131.8, 132.7, 135.1, 143.1, 158.6; Mass Spectrum: M−H$^+$ 394.

Example 117

3-{2-[(2-Isopropyl-1,1-dioxido-3-oxo-5-phenyl-2,3-dihydroisothiazol-4-yl)amino]ethyl}benzonitrile 4-Chloro-2-isopropyl-5-phenylisothiazol-3(2H)-one 1,1-dioxide (150 mg, 0.525 mmol) was dissolved in dry DMF (1 mL) under nitrogen atmosphere. 3-(2-Aminoethyl)benzonitrile (78 mg, 0.530 mmol) was added followed by TEA (53 mg, 0.525 mmol) and the reaction mixture was heated in a microwave reactor for at 120° C. for 20 mins. The mixture was diluted with EtOAc, washed with saturated aqueous NaHCO$_3$-solution, dried over Na$_2$SO$_4$, filtered and evaporated. The crude product was purified on a Biotage Horizon HPFC system using Heptane and EtOAc as eluent affording the title compound (118 mg, 56.3%). $^1$H NMR (500 MHz, CDCl$_3$): δ 1.59 (d, 6H), 2.60 (t, 2H), 3.17 (q, 2H), 4.37-4.46

(m, 1H), 5.49 (bs, 1H), 6.88 (s, 1H), 7.02 (d, 1H), 7.30-7.34 (m, 1H), 7.47-7.57 (m, 6H); $^{13}$C NMR (125 MHz, CDCl$_3$): δ 20.38, 35.75, 44.70, 47.90, 107.72, 113.00, 118.70, 125.17, 129.19, 129.67, 130.36, 130.77, 131.95, 132.20, 133.23, 135.11, 139.03, 158.60; Mass Spectrum: M+H$^+$ 396.1.

Example 118

4-({1-[3-Chloro-5-(trifluoromethyl)pyridin-2-yl]
azetidin-3-yl}amino)-2-isopropyl-5-phenylisothia-
zol-3(2H)-one 1,1-dioxide 4-Chloro-2-isopropyl-5-phenylisothiazol-3(2H)-one 1,1-dioxide (150 mg, 0.525 mmol) was dissolved in dry DMF (1 mL) under nitrogen atmosphere. 1-[3-Chloro-5-(trifluoromethyl)pyridin-2-yl]azetidin-3-amine (133 mg, 0.530 mmol) was added followed by TEA (53 mg, 0.525 mmol) and the reaction mixture was heated in a microwave reactor for at 120° C. for 20 mins. The mixture was diluted with EtOAc, washed with saturate aqueous NaHCO$_3$, dried with Na$_2$SO$_4$, filtered and evaporated. The crude product was purified on a Biotage Horizon HPFC system using Heptane and EtOAc as eluant affording the title compound (223 g, 84.0%). $^1$H NMR (500 MHz, CDCl$_3$): δ 1.60 (d, 6H), 4.01-4.06 (m, 3H), 4.10-4.15 (m, 2H), 4.40-4.48 (m, 1H), 5.62 (bs, 1H), 7.51 (s, 5H), 7.59 (s, 1H), 8.25 (s, 1H); $^{13}$C NMR (125 MHz, CDCl$_3$): δ 20.38, 44.61, 48.06, 59.87, 109.52, 115.56, 117.98 (q, $J_{C-F}$=33.6 Hz), 124.42, 124.75, 129.29, 130.48, 131.49, 134.49, 135.16, 143.70, 156.92, 158.26; Mass Spectrum: M+H$^+$ 501.1.

Example 119

2-tert-Butyl-4-[(2-{[3-chloro-5-(trifluoromethyl)
pyridin-2-yl]amino}ethyl)amino]-5-phenylisothia-
zol-3(2H)-one 1,1-dioxide 4-[(2-Aminoethyl)amino]-2-tert-butyl-5-phenylisothiazol-3(2H)-one 1,1-dioxide (0.088 g, 0.27 mmol), 2,3-dichloro-5-(trifluoromethyl)pyridine (0.065 g, 0.30 mmol) and TEA (0.055 g, 0.54 mmol) was dissolved in dry DMF (3 ml) and heated in a microwave reactor at 120° C. for 25 mins. The reaction mixture was extracted with EtOAc (75 ml) and the organic phases were washed with water (3×50 ml), dried over MgSO$_4$, filtered and evaporated. The residue was purified by silica gel column chromatography using petroleum ether and EtOAc (85:15) as eluant, to give the title compound (0.052 g, 38%). $^1$H NMR (500 MHz, CDCl$_3$): δ 8.3-8.25 (m, 1H), 7.67-7.62 (m, 2H), 7.49-7.43 (m, 2H), 7.43-7.35 (m, 3H), 6.47-6.41 (m, 1H), 5.47-5.41 (m, 1H), 3.52 (q, 2H), 3.09 (q, 2H), 1.7 (s, 9H); $^{13}$C NMR (125 MHz, CDCl$_3$): δ 159.4, 155.7, 143.7, 143.6, 135.5, 133.2, 133.1, 131.5, 129.4, 128.5, 125, 124.6, 122.4, 116.8, 116.6, 115, 107.1, 61.4, 45.4, 40.9, 27.5; Mass Spectrum: M–H$^+$ 503.

Example 120

2-{2-[(2-Isopropyl-1,1-dioxido-3-oxo-5-phenyl-2,3-
dihydroisothiazol-4-yl)amino]ethoxy}phenyl meth-
anesulfonate 2-[(2-Isopropyl-1,1-dioxido-3-oxo-5-phenyl-2,3-dihydroisothiazol-4-yl)amino]ethyl 4-methylbenzenesulfonate (200 mg, 0.431 mmol) was dissolved in dry MeCN (4 mL) under nitrogen atmosphere. 2-Hydroxyphenyl methanesulfonate (89 mg, 0.474 mmol) was added followed by potassium carbonate (297 mg, 2.152 mmol). The reaction mixture was heated in a microwave reactor for 15 mins at 120° C. Potassium carbonate was filtered off and the reaction mixture was concentrated and redissolved in EtOAc. The mixture was washed with NaHCO$_3$, dried over Na$_2$SO$_4$, filtered and evaporated. The residue was purified on a Horizon TM flash system using Heptane and EtOAc as eluant and TEA as additative and then purified by column chromatography (ISOLUTE SI, (5 g)) using DCM as eluant to afford the title compound (31 mg, 15%). $^1$H NMR (CDCl$_3$, 500 MHz): δ 1.59 (d, 6H), 3.22 (s, 3H), 3.31 (q, 2H), 3.96 (t, 2H), 4.38-4.46 (m, 1H), 5.88 (t, 1H), 6.89 (d, 1H), 7.02 (t, 1H), 7.23-7.30 (m, 2H), 7.46-7.48 (m, 3H), 7.53-7.56 (m, 2H); $^{13}$C NMR (CDCl$_3$, 125 MHz): δ 20.38, 38.57, 43.36, 47.85, 67.23, 108.08, 114.71, 122.38, 124.59, 125.14, 128.55, 129.15, 130.09, 131.63, 135.62, 138.64, 150.55, 158.40; Mass Spectrum: M+H$^+$ 481.1.

Examples 121 to 139 were prepared from 2-tert-butyl-4-chloro-5-phenylisothiazol-3(2H)-one 1,1-dioxide and the appropriate amine in analogy with the descriptions for Examples 1, 4, 15, 23, 24, 49, 76-82, 84-88, 90-97. Starting material is either commercially available or can be prepared as described or in analogy with methods described in the section for synthesis of starting material and intermediates or can be prepared according to methods known to person skilled in the art.

Example 121

2-tert-Butyl-5-phenyl-4-({2-[2-(trifluoromethoxy)
phenyl]ethyl}amino)isothiazol-3(2H)-one 1,1-diox-
ide Commercially available 2-[2-(trifluoromethoxy)phenyl]ethanamine was also used as starting material to give the title compound. $^1$H NMR (500 MHz, CDCl$_3$): δ 7.56-7.50 (m, 2H), 7.49-7.43 (m, 3H), 7.29-7.12 (m, 3H), 6.77-6.73 (m, 1H), 5.40-5.33 (m, 1H), 3.19-3.11 (m, 2H), 2.72-2.65 (m, 2H), 1.74 (s, 9H); $^{13}$C NMR (125 MHz, CDCl$_3$): δ 159.6, 147.8, 134.8, 131.7, 130.9, 130.0, 129.8, 128.8, 128.5, 127.0, 125.1, 120.7, 107.7, 61.6, 43.6, 30.1, 27.7; Mass Spectrum: M–H$^+$ 469.

Example 122

4-[(1-Benzylpyrrolidin-3-yl)amino]-2-tert-butyl-5-
phenylisothiazol-3(2H)-one 1,1-dioxide Commercially available 1-benzylpyrrolidin-3-amine was also used as starting material to give the title compound. $^1$H NMR (500 MHz CDCl$_3$): δ 7.50-7.46 (m, 2H), 7.46-7.40 (m, 3H), 7.35-7.30 (m, 2H), 7.30-7.24 (m, 3H), 5.53 (d, 1H), 3.68-3.60 (m, 1H), 3.52 (dd, 2H), 2.74-2.68 (m, 1H), 2.45 (dd, 1H), 2.30-2.22 (m, 1H), 2.22-2.14 (m, 1H), 1.80-1.64 (m, 10H), 1.60-1.52 (m, 1H); $^{13}$C NMR (125 MHz CDCl$_3$): δ 159.9, 138.5, 134.5, 131.9, 129.8, 128.9, 128.6, 127.4, 125.2, 107.1, 61.7, 60.8, 59.9, 52.7, 52.4, 33.1, 27.8; Mass Spectrum: M+H$^+$ 440.

Example 123

N-Benzyl-W-(2-tert-butyl-1,1-dioxido-3-oxo-5-phe-
nyl-2,3-dihydroisothiazol-4-yl)glycinamide N$^1$-Benzylglycinamide was also used as starting material to give the title compound. $^1$H NMR (500 MHz, CDCl$_3$): δ 7.48-7.22 (m, 10H), 6.04-5.97 (m, 1H), 5.78-5.71 (m, 1H), 4.39 (d, 2H), 3.52 (d, 2H), 1.74 (s, 9H); $^{13}$C NMR (125 MHz, CDCl$_3$): δ 166.9, 159.2, 137.4, 134.9, 131.4, 130.0, 129.0, 128.9, 128.2, 128.1, 124.5, 109.7, 61.8, 46.7, 43.9, 41.0, 27.7; Mass Spectrum: M–H$^+$ 428.

Example 124

2-tert-Butyl-5-phenyl-4-[(2-pyridin-2-ylethyl)amino]isothiazol-3(2H)-one 1,1-dioxide Commercially available 2-pyridin-2-ylethanamine was also used as starting material to give the title compound. $^1$H NMR (500 MHz, CDCl$_3$): δ 8.57-8.50 (m, 1H), 7.61-7.48 (m, 3H), 7.47-7.38 (m, 3H), 7.18-7.10 (m, 1H), 6.95-6.88 (m, 1H), 6.32-6.22 (m, 1H), 3.30-3.21 (m, 2H), 2.84-2.77 (m, 2H), 1.72 (s, 9H); $^{13}$C NMR (125 MHz, CDCl$_3$): δ 159.7, 158.3, 149.5, 136.8, 135.3, 131.6, 129.5, 128.7, 125.4, 123.3, 121.9, 106.8, 61.4, 43.4, 36.7, 27.7; Mass Spectrum: M–H$^+$ 386.

Example 125

2-tert-Butyl-4-{[2-(2-chlorophenyl)ethyl]amino}-5-phenylisothiazol-3(2H)-one 1,1-dioxide Commercially available 2-(2-chlorophenyl)ethanamine was also used as starting material to give the title compound. $^1$H NMR (500 MHz, CDCl$_3$): δ 7.55-7.49 (m, 2H), 7.49-7.43 (m, 3H), 7.34-7.30 (m, 1H), 7.20-7.10 (m, 2H), 6.78-6.74 (m, 1H), 5.42-5.35 (m, 1H), 3.23-3.15 (m, 2H), 2.79-2.71 (m, 2H), 1.74 (s, 9H); $^{13}$C NMR (125 MHz, CDCl$_3$): δ 159.7, 135.3, 134.9, 134.1, 131.6, 130.8, 129.8, 129.8, 128.8, 128.5, 127.1, 125.2, 107.6, 61.6, 43.3, 41.0, 33.7, 27.7; Mass Spectrum: M–H$^+$ 419.

Example 126

2-tert-Butyl-5-phenyl-4-({2-[3-(trifluoromethyl)phenyl]ethyl}amino)isothiazol-3(2H)-one 1,1-dioxide Commercially available 2-[3-(trifluoromethyl)phenyl]ethanamine was also used as starting material to give the title compound. $^1$H NMR (500 MHz, CDCl$_3$): δ 7.55-7.40 (m, 6H), 7.33-7.27 (m, 1H), 6.98-6.93 (m, 1H), 6.91-6.88 (m, 1H), 5.62-5.55 (m, 1H), 3.16-3.10 (m, 2H), 2.62-2.56 (m, 2H), 1.72 (s, 9H); $^{13}$C NMR (125 MHz, CDCl$_3$): δ 159.8, 138.6, 134.9, 132.2, 131.9, 131.2, 130.9, 130.2, 130.0, 129.2, 129.0, 125.4, 125.4, 125.2, 123.8, 123.8, 123.1, 107.5, 61.8, 44.8, 41.1, 36.0, 27.8; Mass Spectrum: M–H$^+$ 453.

Example 127

2-tert-Butyl-5-phenyl-4-[(4-{[4-(trifluoromethyl)phenyl]thio}cyclohexyl)amino]isothiazol-3(2H)-one 1,1-dioxide 4-{[4-(Trifluoromethyl)phenyl]thio}cyclohexanamine was also used as starting material to give the title compound as a mixture of cis and trans isomers. $^1$H NMR (500 MHz, CDCl$_3$): δ 0.87-0.95 (m, 2H), 1.12-1.20 (m, 2H), 1.42-1.92 (m, 30H), 2.00 (s, 2H), 2.88-3.09 (m, 3H), 3.37-3.40 (m, 1H), 5.15 (d, 1H), 5.31 (d, 1H), 7.35-7.38 (m, 4H), 7.42-7.52 (m, 14H); $^{13}$C NMR (125 MHz, CDCl$_3$): δ 27.83, 28.65, 31.43, 33.02, 43.22, 44.30, 50.35, 51.25, 61.79, 106.92, 124.28 (q, J(C—F)=272.2 Hz), 125.26, 125.44, 125.97, 128.84, 128.90, 129.94, 130.13, 130.18, 130.57, 131.85, 131.89, 134.09, 134.19, 140.20, 140.67, 159.96; Mass Spectrum: M–H$^+$ 536.9.

Example 128

2-tert-Butyl-5-phenyl-4-({1-[5-(trifluoromethyl)pyridin-2-yl]piperidin-4-yl}amino)isothiazol-3(2H)-one 1,1-dioxide 1-[5-(Trifluoromethyl)pyridin-2-yl]piperidin-4-amine was also used as starting material to give the title compound. $^1$H NMR (500 MHz, CDCl$_3$): δ 8.38-8.32 (m, 1H), 7.63-7.51 (m, 3H), 7.51-7.43 (m, 3H), 6.62-6.54 (m, 1H), 5.21 (d, 1H), 4.21-4.14 (m, 2H), 3.25-3.15 (m, 1H), 2.60-2.50 (m, 2H), 1.82-1.70 (m, 2H), 1.74 (s, 9H), 1.4-1.29 (m, 2H); $^{13}$C NMR (125 MHz, CDCl$_3$): δ 159.7, 145.6, 134.8, 134.0, 131.8, 130.1, 128.9, 125.2, 107.4, 105.9, 61.8, 50.3, 43.5, 31.9, 27.7; Mass Spectrum: M–H$^+$ 509.

Example 129 tert-Butyl 3-{2-[(2-tert-butyl-1,1-dioxido-3-oxo-5-phenyl-2,3-dihydroisothiazol-4-yl)amino]ethoxy}azetidine-1-carboxylate tert-Butyl 3-(2-aminoethoxy)azetidine-1-carboxylate was also used as starting material to give the title compound. $^1$H NMR (500 MHz, CDCl$_3$): δ 7.53-7.48 (m, 2H), 7.47-7.42 (m, 3H), 5.57-5.51 (m, 1H), 4.16-4.10 (m, 1H), 4.07-4.00 (m, 2H), 3.80-3.74 (m, 2H), 3.31-3.26 (m, 2H), 3.06-3.00 (m, 2H), 1.74 (s, 9H), 1.45 (s, 9H); $^{13}$C NMR (125 MHz, CDCl$_3$): δ 159.6, 156.3, 135.1, 131.6, 129.8, 128.8, 125.0, 107.9, 79.8, 68.2, 66.5, 61.7, 56.4, 43.6, 28.5, 27.7; Mass Spectrum: M–H$^+$ 480.

Example 130

2-tert-Butyl-4-[(2,2-dimethylpropyl)amino]-5-phenylisothiazol-3(2H)-one 1,1-dioxide Commercially available 2,2-dimethylpropan-1-amine was also used as starting material to give the title compound. $^1$H NMR (500 MHz, CDCl$_3$): δ 7.51-7.46 (m, 2H), 7.46-7.41 (m, 3H), 5.34-5.26 (m, 1H), 2.62 (d, 2H), 1.75 (s, 9H), 0.81 (s, 9H); $^{13}$C NMR (125 MHz, CDCl$_3$): δ 159.9, 135.5, 131.8, 129.6, 128.7, 125.3, 106.6, 61.6, 55.3, 31.9, 27.7, 27.0; Mass Spectrum: M–H$^+$ 351.

Example 131

Methyl ({[(2-tert-butyl-1,1-dioxido-3-oxo-5-phenyl-2,3-dihydroisothiazol-4-yl)amino]acetyl}amino)acetate Commercially available methyl glycylglycinate was also used as starting material to give the title compound. $^1$H NMR (500 MHz, CDCl$_3$): δ 7.54-7.48 (m, 2H), 7.48-7.44 (m, 3H), 6.03 (t, 1H), 5.98 (t, 1H), 4.00 (d, 2H), 3.78 (s, 3H), 3.56 (d, 2H), 1.74 (s, 9H); $^{13}$C NMR (125 MHz, CDCl$_3$): δ 170.1, 167.5, 159.3, 134.9, 131.6, 130.2, 129.1, 124.5, 109.9, 61.9, 52.8, 46.7, 41.4, 27.8; Mass Spectrum: M+H$^+$ 410.

Example 132

2-tert-Butyl-4-[(1-methylpiperidin-4-yl)amino]-5-phenylisothiazol-3(2H)-one 1,1-dioxide Commercially available 1-methylpiperidin-4-amine was also used as starting material to give the title compound. $^1$H NMR (500 MHz, CDCl$_3$): δ 7.54-7.50 (m, 2H), 7.50-7.42 (m, 3H), 5.19 (d, 1H), 2.96-2.86 (m, 1H), 2.63-2.58 (m, 2H), 2.15 (s, 3H), 1.74 (s, 9H), 1.68-1.52 (m, 4H), 1.44-1.34 (m, 2H); $^{13}$C NMR (125 MHz, CDCl$_3$): δ 159.9, 134.3, 131.9, 129.9, 128.9, 125.4, 106.8, 61.8, 54.1, 49.8, 46.2, 32.6, 27.8; Mass Spectrum: M+H$^+$ 378.

Example 133

2-tert-Butyl-4-{[(5-methyl-3-phenylisoxazol-4-yl)methyl]amino}-5-phenylisothiazol-3(2H)-one 1,1-dioxide Commercially available 1-(5-methyl-3-phenylisoxazol-4-yl)methanamine was also used as starting material to give the title compound. $^1$H NMR (500 MHz, CDCl$_3$): δ 7.53-7.46 (m, 7H), 7.43-7.38 (m, 3H), 5.08 (t, 1H), 3.86 (d, 2H), 2.32 (s, 3H), 1.71 (s, 9); $^{13}$C NMR (125 MHz, CDCl$_3$): δ 168.6, 162.2, 159.2, 134.5, 131.4, 130.2, 130.1, 129.3, 128.9, 128.7, 128.1, 124.9, 109.6, 109.4, 61.9, 37.8, 27.8, 11.4; Mass Spectrum: M+H$^+$ 452.

Example 134

2-ter-Butyl-5-phenyl-4-{[(1,3,5-trimethyl-1H-pyrazol-4-yl)methyl]amino}isothiazol-3(2H)-one 1,1-dioxide Commercially available 1-(1,3,5-trimethyl-1H-pyrazol-4-yl)methanamine was also used as starting material to give the title compound. $^1$H NMR (500 MHz, CDCl$_3$): δ 7.61-7.56 (m, 2H), 7.49-7.43 (m, 3H), 4.96 (t, 1H), 3.68 (s, 5H), 2.11 (s, 3H), 2.07 (s, 3H), 1.73 (s, 9H); $^{13}$C NMR (125 MHz, CDCl$_3$): δ 159.6, 146.3, 137.9, 134.9, 131.8, 129.8, 128.8, 125.4, 111.8, 107.8, 61.8, 38.8, 36.1, 27.8, 11.8, 9.8; Mass Spectrum: M+H$^+$ 403.

Example 135

2-ter-Butyl-5-phenyl-4-[(2-{[5-(trifluoromethyl)pyridin-2-yl]oxy}ethyl)amino]isothiazol-3(2H)-one 1,1-dioxide 2-{[5-(trifluoromethyl)pyridin-2-yl]oxy}ethanamine was also used as starting material to give the title compound. $^1$H NMR (500 MHz, CDCl$_3$): δ 8.43-8.39 (m, 1H), 7.83-7.78 (m, 1H), 7.54-7.48 (m, 2H), 7.47-7.40 (m, 3H), 6.87-6.81 (m, 1H), 5.93 (brs, 1H), 4.37-4.32 (m, 2H), 3.29-3.23 (m, 2H), 1.73 (s, 9H); $^{13}$C NMR (125 MHz, CDCl$_3$): δ 165.4, 159.7, 145.0, 145.0, 136.4, 136.3, 135.3, 131.7, 129.9, 129.0, 125.1, 123.0, 121.1, 120.8, 111.6, 108.0, 64.7, 61.8, 43.8, 27.8; Mass Spectrum: M+H$^+$ 470.

Example 136

2-tert-Butyl-5-phenyl-4-({2-[4-(trifluoromethoxy)phenyl]ethyl}amino)isothiazol-3(2H)-one 1,1-dioxide 2-[4-(Trifluoromethoxy)phenyl]ethanamine was also used as starting material to give the title compound. $^1$H NMR (500 MHz, CDCl$_3$): δ 7.54-7.49 (m, 2H), 7.49-7.41 (m, 3H), 7.07-7.02 (m, 2H), 6.80-6.75 (m, 2H), 5.48-5.42 (m, 1H), 3.14-3.06 (m, 2H), 2.59-2.52 (m, 2H), 1.71 (s, 9H); $^{13}$C NMR (125 MHz, CDCl$_3$): δ 159.8, 148.2, 136.4, 135.0, 131.9, 130.0, 130.0, 129.0, 125.3, 121.4, 107.6, 61.8, 45.0, 41.1, 35.4, 27.8; Mass Spectrum: M+H$^+$ 469.

Example 137

2-tert-Butyl-5-phenyl-4-[(2,2,2-trifluoroethyl)amino]isothiazol-3(2H)-one 1,1-dioxide Commercially available 2,2,2-trifluoroethanamine was also used as starting material to give the title compound. $^1$H NMR (500 MHz, CDCl$_3$): δ 7.52-7.45 (m, 5H), 5.42-5.36 (m, 1H), 3.52-3.45 (m, 2H), 1.73 (s, 9H); $^{13}$C NMR (125 MHz, CDCl$_3$): δ 158.9, 133.8, 131.3, 130.5, 129.2, 124.5, 123.5, 122.3, 111.0, 61.9, 44.8, 44.5, 44.3, 44.0, 27.5; Mass Spectrum: M+H$^+$ 363.

Example 138

2-tert-Butyl-4-[(2,3-dihydroxypropyl)amino]-5-phenylisothiazol-3(2H)-one 1,1-dioxide Commercially available 3-aminopropane-1,2-diol was also used as starting material to give the title compound. $^1$H NMR (500 MHz, CDCl$_3$): δ 7.51-7.45 (m, 2H), 7.45-7.40 (m, 3H), 5.75 (brs, 1H), 3.65-3.58 (m, 1H), 3.43-3.36 (m, 1H), 3.32-3.24 (m, 1H), 3.02-2.85 (m, 2H), 2.11 (brs, 2H), 1.72 (s, 9H); $^{13}$C NMR (125 MHz, CDCl$_3$): δ 159.8, 135.5, 131.8, 130.0, 129.0, 125.1, 107.7, 70.2, 64.3, 61.9, 46.3, 27.8; Mass Spectrum: M+H$^+$ 355.

Example 139

3-[(2-tert-Butyl-1,1-dioxido-3-oxo-5-phenyl-2,3-dihydroisothiazol-4-yl)amino]propanenitrile $^1$H NMR (500 MHz, CDCl$_3$): δ 7.52-7.42 (m, 5H), 5.63-5.56 (m, 1H), 3.22-3.13 (m, 2H), 2.25-2.17 (m, 2H), 1.71 (s, 9H); $^{13}$C NMR (125 MHz, CDCl$_3$): δ 159.3, 134.5, 131.6, 130.6, 129.3, 124.4, 117.1, 109.4, 62.1, 39.5, 27.8, 18.5; Mass Spectrum: M+H$^+$ 334 Commercially available 3-aminopropanenitrile was also used as starting material to give the title compound.

Examples 140 to 143 were prepared from 2-[(2-tert-butyl-1,1-dioxido-3-oxo-5-phenyl-2,3-dihydroisothiazol-4-yl)amino]ethyl 4-methylbenzenesulfonate and the appropriate phenol or thiophenol in analogy with the descriptions for Example 99 and 101-103. The starting material is either commercially available or can be prepared as described in or in analogy with the methods in the section for synthesis of starting material and intermediates or can be prepared according to methods known to person skilled in the art.

Example 140

2-tert-Butyl-5-phenyl-4-[(2-{[3-(trifluoromethoxy)phenyl]thio}ethyl)amino]isothiazol-3(2H)-one 1,1-dioxide Commercially available 3-(trifluoromethoxy)benzenethiol was also used as starting material to give the title compound. $^1$H NMR (500 MHz, CDCl$_3$): δ 1.73 (s, 9H), 2.84 (t, 2H), 3.10 (q, 2H), 5.59 (bs, 1H), 7.07-7.09 (m, 2H), 7.14 (d, 1H), 7.30 (t, 1H), 7.38-7.46 (m, 5H); $^{13}$C NMR (125 MHz, CDCl$_3$): δ 27.82, 33.62, 42.54, 61.86, 108.39, 119.41, 120.59 (q, J=258.1 Hz), δ 122.37, 124.90, 128.26, 128.99, 130.05, 130.57, 131.53, 134.81, 136.94, 149.74, 159.59; Mass Spectrum: M+NH4$^+$517.7.

Example 141

2-tert-Butyl-4-{[2-(4-chlorophenoxy)ethyl]amino}-5-phenylisothiazol-3(2H)-one 1,1-dioxide Commercially available 4-chlorophenol was also used as starting material to give the title compound. $^1$H NMR (500 MHz CDCl$_3$): δ 7.55-7.50 (m, 2H), 7.50-7.42 (m, 3H), 7.24 (d, 2H), 6.76 (d, 2H), 5.62 (t, 1H), 3.84 (t, 2H), 3.28-3.22 (m, 2H), 1.74 (s, 9H); $^{13}$C NMR (125 MHz CDCl$_3$): 159.6, 156.9, 135.2, 131.7, 130.0, 129.7, 129.0, 126.7, 125.1, 115.9, 108.3, 66.3, 61.9, 43.4, 27.8; Mass Spectrum: M+H$^+$ 435.

Example 142

2-tert-Butyl-5-phenyl-4-({2-[3-(trifluoromethoxy)phenoxy]ethyl}amino)isothiazol-3(2H)-one 1,1-dioxide Commercially available 3-(trifluoromethoxy)phenol was also used as starting material to give the title compound. $^1$H NMR (500 MHz, CDCl$_3$): δ 1.75 (s, 9H), 3.27 (q, 2H), 3.87 (t, 2H), 5.63 (t, 1H), 6.70 (s, 1H), 6.77 (m, 1H), 6.86 (m, 1H), 7.28-7.31 (m, 1H), 7.46-7.48 (m, 3H), 7.53-7.55 (m, 2H); $^{13}$C NMR (125 MHz, CDCl$_3$): δ 27.84, 43.28, 61.88, 66.34, 107.90, 108.41, 113.03, 113.92, 120.64 (q, J=256.2 Hz), 125.06, 129.06, 130.07, 130.61, 131.70, 135.14, 150.36, 159.29, 159.65; Mass Spectrum: M+NH4$^+$501.8.

Example 143

4-{[2-Biphenyl-2-ylthio)ethyl]amino}-2-tert-butyl-5-phenylisothiazol-3(2H)-one 1,1-dioxide Commercially available bisphenyl-2-thiol was also used as starting material to give the title compound. $^1$H NMR (CDCl$_3$, 500 MHz): δ 1.72 (s, 9H), 2.56 (t, 2H), 2.87 (q, 2H), 5.39 (bs, 1H), 7.26-7.44 (m, 14H); $^{13}$C NMR (CDCl$_3$, 125 MHz): δ 27.84, 33.78, 42.49, 61.67, 107.71, 125.02, 127.42, 127.78, 128.34, 128.88, 129.61, 129.84, 130.94, 131.25, 131.57, 132.58, 134.86, 140.70, 144.20, 159.46; Mass Spectrum: M+H$^+$ 492.9.

Examples 144 and 145 were prepared from 2-tert-butyl-5-phenyl-4-(piperidin-4-ylamino)isothiazol-3(2H)-one 1,1-dioxide (Example 75) and the appropriate acyl halide in analogy with the descriptions for Example 105, 111 and 112. The starting material is either commercially available or can be prepared as described in or in analogy with the methods in the section for synthesis of starting material and intermediates or can be prepared according to methods known to person skilled in the art.

Example 144

4-[(1-Acetylpiperidin-4-yl)amino]-2-tert-butyl-5-phenylisothiazol-3(2H)-one 1,1-dioxide Commercially available acetyl chloride was also used as starting material to give the title compound. $^1$H NMR (500 MHz CDCl$_3$): δ 7.55-7.50 (m, 2H), 7.49-7.43 (m, 3H), 5.20 (d, 1H), 4.39-4.33 (d, 1H), 3.63-3.57 (m, 1H), 3.16-3.08 (m, 1H), 2.58 (ddd, 1H), 2.24 (ddd, 1H), 1.86-1.64 (m, 11H), 1.28-1.19 (m, 2H); $^{13}$C NMR (125 MHz CDCl$_3$): δ 169.0, 159.7, 133.9, 131.9, 130.2, 128.9, 125.2, 107.6, 61.9, 50.3, 44.8, 40.1, 32.9, 32.1, 27.8, 21.6; Mass Spectrum: M–H$^+$ 404

Example 145

2-tert-Butyl-4-[(1-isobutyrylpiperidin-4-yl)amino]-5-phenylisothiazol-3(2H)-one 1,1-dioxide Commercially available 2-methylpropanoyl chloride was also used as starting material to give the title compound. $^1$H NMR (500 MHz CDCl$_3$): δ 7.56-7.50 (m, 2H), 7.44-7.40 (m, 3H), 5.18 (d, 1H), 4.42-4.27 (m, 2H), 3.79-3.74 (m, 1H), 3.19-3.09 (m, 1H), 2.69 (sp, 1 h), 2.62-2.52 (m, 1H), 2.30-2.20 (m, 1H), 1.78-1.66 (m, 11H), 1.29-1.17 (m, 2H), 1.12-1.02 (m, 6H); $^{13}$C NMR (125 MHz CDCl$_3$): 175.5, 159.8, 133.9, 131.8, 130.2, 128.9, 125.3, 107.5, 61.9, 50.4, 43.7, 40.3, 33.2, 32.2, 30.2, 27.8, 19.7, 19.5; Mass Spectrum: M–H$^+$ 432.

Example 146

2-tert-Butyl-5-phenyl-4-{[1-(2-phenylethyl)piperidin-4-yl]amino}isothiazol-3(2H)-one 1,1-dioxide The title compound was prepared from 2-tert-butyl-5-phenyl-4-(piperidin-4-ylamino)isothiazol-3(2H)-one 1,1-dioxide (Example 75) and (2-bromoethyl)benzene in a similar manner as described for Example 104. $^1$H NMR (500 MHz CDCl$_3$): δ 7.64-7.50 (m, 2H), 7.48-7.45 (m, 3H), 7.30-7.25 (m, 2H), 7.22-7.17 (m, 1H), 7.16-7.12 (m, 2H), 5.22 (d, 1H), 3.00-2.90 (m, 1H), 2.81-2.74 (m, 2H), 2.73-2.67 (m, 2H), 2.50-2.43 (m, 2H), 1.82-1.60 (m, 13H), 1.46-1.36 (m, 2H); $^{13}$C NMR (125 MHz CDCl$_3$): δ 159.9, 140.2, 134.3, 131.9, 130.0, 128.9, 128.6, 126.3, 125.4, 106.9, 61.8, 60.2, 51.8, 50.2, 33.8, 32.4, 27.9; Mass Spectrum: M+H$^+$ 468

Example 147

2-tert-Butyl-5-phenyl-4-{[2-(pyrrolidin-3-ylthio)ethyl]amino}isothiazol-3(2H)-one 1,1-dioxide The title compound was prepared from Example 100 in analogy with the description of 2-tert-butyl-5-phenyl-4-(piperidin-4-ylamino)isothiazol-3(2H)-one 1,1-dioxide (Example 75). $^1$H NMR (500 MHz, CDCl$_3$): δ 1.68-1.75 (m, 10H), 1.98 (s, 4H), 2.12-2.19 (m, 1H), 2.49 (t, 2H), 2.83-2.86 (m, 1H), 3.06-3.14 (m, 4H), 3.20-3.25 (m, 1H), 3.31-3.35 (m, 1H), 5.71 (t, 1H), 7.44-7.46 (m, 3H), 7.50-7.52 (m, 2H), 8.02 (bs, 2H); $^{13}$C NMR (125 MHz, CDCl$_3$): δ 23.12, 27.82, 31.51, 32.59, 41.96, 43.05, 44.42, 51.25, 61.87, 108.12, 125.11, 129.06, 130.08, 131.65, 134.85, 159.64; Mass Spectrum: M+H$^+$ 410.1.

Example 148

2-tert-Butyl-4-{[(5-methylisoxazol-3-yl)methyl]amino}-5-phenylisothiazol-3(2H)-one 1,1-dioxide The title compound was prepared as described for Example 24 from 1 equivalent of [(5-methylisoxazol-3-yl)methyl]amine, 2-tert-butyl-4-chloro-5-phenylisothiazol-3(2H)-one 1,1-dioxide and 1 equivalent TEA with a reaction time of 45 mins. The mixture was evaporated and purified by silica gel column chromatography (Horizons Biotage) using 35% EtOAc in pentane as eluent to give the title compound (0.070 g, 56%). $^1$H NMR (500 MHz CDCl$_3$): δ 7.52-7.48 (m, 2H), 7.46-7.41 (m, 3H), 5.73 (s, 1H), 5.66 (t, 1H), 5.07 (d, 2H), 2.39 (s, 3H), 1.74 (s, 9H); $^{13}$C NMR (125 MHz CDCl3): δ 170.7, 159.9, 159.4, 134.8, 131.6, 130.1, 128.9, 124.7, 109.3, 100.4, 61.9, 40.4, 27.8, 12.5; Mass Spectrum: M+H$^+$ 376

Example 149

4-{[2-(3,4-Dimethoxyphenyl)ethyl]amino}-2-isopropyl-5-phenylisothiazol-3(2H)-one 1,1-dioxide The title compound was prepared from 2-tert-Butyl-4-chloro-5-phenylisothiazol-3(2H)-one 1,1-dioxide and [2-(3,4-dimethoxyphenyl)ethyl]amine in a similar manner as described for Example 24. $^1$H NMR (500 MHz CDCl$_3$): δ 7.58-7.52 (m, 2H), 7.50-7.46 (m, 3H), 6.76 (d, 1H), 6.46 (dd, 1H), 6.36 (d, 1H), 5.40 (t, 1H), 4.41 (sept, 1H), 3.86 (s, 3H), 3.82 (s, 3H), 3.13 (q, 2H), 2.57 (t, 2H), 1.59 (d, 6H); $^{13}$C NMR (125 MHz, CDCl3): δ 158.7, 149.3, 148.1, 135.4, 131.7, 130.0, 129.9, 128.8, 125.4, 120.8, 111.8, 111.7, 107.2, 56.1, 47.8, 45.3, 35.6, 20.3; Mass Spectrum M+H$^+$ 431

Example 150

4-{[2-(3-Chloro-4-methoxyphenyl)ethyl]amino}-2-isopropyl-5-phenylisothiazol-3(2H)-one 1,1-dioxide The title compound was prepared from 2-tert-Butyl-4-chloro-5-phenylisothiazol-3(2H)-one 1,1-dioxide and [2-(3-chloro-4-methoxyphenyl)ethyl]amine in a similar manner as described for Example 24. $^1$H NMR (500 MHz DMSO-d$_6$): δ 7.55-7.47 (m, 5H), 7.34 (t, 1H), 6.94 (d, 1H), 6.65 (dd, 1H), 6.61 (d, 1H), 4.32 (qt, 1H), 3.78 (s, 3H), 3.03-2.96 (m, 2H), 2.43-2.37 (m, 2H), 1.46 (d, 6H); $^{13}$C NMR (125 MHz DMSO-d$_6$): δ 158.7, 153.7, 136.1, 132.4, 131.9, 130.3, 129.4, 128.8, 126.1, 121.3, 113.3, 105.0, 56.7, 47.3, 45.0, 34.4, 20.5; Mass spectrum M+H$^+$ 435

Example 151

4-{2-[(2-Isobutyl-1,1-dioxido-3-oxo-5-phenyl-2,3-dihydroisothiazol-4-yl)amino]ethyl}phenyl methanesulfonate A mixture of 4-{2-[1,1-dioxido-3-oxo-5-phenyl-2,3-dihydroisothiazol-4-yl)amino]ethyl}phenyl methanesulfonate (0.096 g, 0.227 mmol), 1-bromo-2-methylpropane (0.050 g, 0.364 mmol)) and TEA (0.041 ml, 0.295 mmol) in DMSO was heated in a microwave at 100° C. for 40 mins and at 130° C. for 1 h. The reaction mixture was evaporated to dryness and the residue was purified by silica gel column chromatography (Horizons Biotage) using 15-100% EtOAc in pentane as eluent to give the title compound (0.047 g, 43%) as a solid; $^1$H NMR (500 MHz CDCl$_3$): δ 7.58-7.46 (m, 5H), 7.15 (d, 2H), 6.84 (d, 2H), 5.43 (t, 1H), 3.52 (d, 2H), 3.21-3.15 (m, 2H), 3.14 (s, 3H), 2.64-2.58 (m, 2H), 2.32-2.23 (m, 1H), 1.02 (d, 6H); $^{13}$C NMR (125 MHz CDCl$_3$): δ 159.6, 148.2, 136.9, 135.2, 131.8, 130.3, 130.2, 129.1, 125.2, 122.5, 107.8, 47.9, 44.9, 37.6, 35.5, 27.8, 20.3; Mass Spectrum: M+H$^+$ 479

Example 152

2-Isopropyl-5-phenyl-4-[(1-pyridin-2-ylpiperidin-4-yl)amino]isothiazol-3(2H)-one 1,1-dioxide The title compound was prepared from 4-Chloro-2-isopropyl-5-phenylisothiazol-3(2H)-one 1,1-dioxide and 1-pyridin-2-ylpiperidine-4-amine dihydrochloride in a similar manner as described for Example 24 with TEA as base. $^1$H NMR (500 MHz CDCl$_3$): δ 8.14 (dd, 1H), 7.58-7.53 (m, 2H), 7.48-7.41 (m, 4H), 6.62-6.55 (m, 2H), 5.23 (d, 1H), 4.42 (sept, 1H), 4.10-4.02 (m, 2H), 3.22-3.12 (m, 1H), 2.49-2.41 (m, 2H), 1.80-1.72 (m, 2H), 1.59 (d, 6H), 1.42-1.33 (m, 2H); $^{13}$C NMR (125 MHz CDCl$_3$): 159.2, 158.7, 148.1, 137.7, 134.5, 131.9, 130.2, 128.9, 125.3, 113.6, 107.5, 106.9, 50.8, 47.8, 44.1, 32.1, 20.4; Mass Spectrum: M+H+ 427

Example 153

4-(2-{[2-(4-Fluorobenzyl)-1,1-dioxido-3-oxo-5-phenyl-2,3-dihydroisothiazol-4-yl]amino}ethyl)phenyl methanesulfonate The title compound was prepared from 4-{2-[1,1-dioxido-3-oxo-5-phenyl-2,3-dihydroisothiazol-4-yl)amino] ethyl}phenyl methanesulfonate and 1-(bromomethyl)-4-fluorobenzene in a similar manner as described for Example 151. $^1$H NMR (500 MHz CDCl$_3$): δ 7.56-7.46 (m, 7H), 7.14 (d, 2H), 7.06 (t, 2H), 6.83 (d, 2H), 5.39 (t, 1H), 4.80 (s, 2H), 3.19-3.14 (m, 2H), 3.13 (s, 3H), 2.61 (t, 2 h); $^{13}$C NMR (125 MHz CDCl$_3$): 163.9, 161.9, 159.0, 148.2, 136.8, 135.2, 131.8, 131.1, 131.0, 130.3, 129.2, 124.9, 122.5, 115.9, 115.7, 107.9, 44.9, 43.1, 37.7, 35.5; Mass Spectrum: M+H$^+$531

Example 154

2-Isopropyl-4-(isopropylamino)-5-phenylisothiazol-3(2H)-one 1,1-dioxide

The title compound was prepared from 4-chloro-2-isopropyl-5-phenylisothiazol-3(2H)-one 1,1-dioxide and isopropylamine in a similar manner as described for Example 24. $^1$H NMR (500 MHz CDCl$_3$): δ 7.56-7.51 (m, 2H), 7.48-7.43 (m, 3H), 5.14 (d, 1H), 4.42 (sept, 1H), 3.40-3.30 (m, 1H), 1.60 (d, 6H), 1.00 (d, 6H); $^{13}$C NMR (125 MHz CDCl$_3$): δ 158.9, 134.6, 131.7, 129.9, 128.9, 125.5, 106.3, 47.8, 44.9, 23.0, 20.4; Mass Spectrum: M+H+ 309.

Example 155

2-Isopropyl-5-phenyl-4-[(1-pyridin-2-ylazetidin-3-yl)amino]isothiazol-3(2H)-one 1,1-dioxide The title compound was prepared from 4-chloro-2-isopropyl-5-phenylisothiazol-3(2H)-one 1,1-dioxide and 1-pyridine-2-ylazetidin-3-amine in a similar manner as described for Example 118. $^1$H NMR (500 MHz CDCl$_3$): δ 1.57 (d, 6H), 3.71-3.75 (m, 2H), 3.84 (t, 2H), 4.04-4.10 (m, 1H), 4.37-4.45 (m, 1H), 5.71-5.76 (m, 1H), 6.19 (d, 1H), 6.60-6.64 (m, 1H), 7.40-7.44 (m, 1H), 7.46-7.52 (m, 5H), 8.10-8.12 (m, 1H); $^{13}$C NMR (125 MHz CDCl$_3$): δ 20.36, 44.88, 48.00, 58.15, 106.25, 109.08, 113.90, 124.58, 129.24, 130.35, 131.46, 134.60, 137.46, 148.39, 158.35, 160.10; Mass Spectrum: M+H$^+$ 399.

Example 156

4-{[2-(4-Hydroxy-3,5-dimethoxyphenyl)ethyl]amino}-2-isopropyl-5-phenylisothiazol-3(2H)-one 1,1-dioxide The title compound was prepared from 4-chloro-2-isopropyl-5-phenylisothiazol-3(2H)-one 1,1-dioxide and 4-(2-aminoethyl)-2,6-dimethoxyphenol in a similar manner as described for Example 118. $^1$H NMR (THF-d$_8$, 500 MHz): δ 1.53 (d, 6H), 2.45 (t, 2H), 3.11 (q, 2H), 3.73 (s, 6H), 4.31-4.39

(m, 1H), 6.03 (s, 2H), 6.47 (t, 1H), 7.22 (s, 1H), 7.46-7.50 (m, 3H), 7.55-7.57 (m, 2H); $^{13}$C NMR (125 MHz, THF-d8): δ 19.57, 35.92, 45.47, 46.98, 55.93, 106.13, 106.56, 126.64, 127.87, 128.56, 129.34, 131.86, 135.49, 135.64, 148.12, 158.61; Mass Spectrum: M+H$^+$ 447.

Example 157

4-{[2-(2-Aminopyridin-4-yl)ethyl]amino}-2-isopropyl-5-phenylisothiazol-3(2H)-one 1,1-dioxide The title compound was prepared in two steps. tert-Butyl (4-{2-[(2-isopropyl-1,1-dioxido-3-oxo-5-phenyl-2,3-dihydroisothiazol-4-yl)amino]ethyl}pyridin-2-yl)carbamate was prepared from 4-chloro-2-isopropyl-5-phenylisothiazol-3 (2H)-one 1,1-dioxide and tert-butyl [4-(2-aminoethyl)pyridin-2-yl]carbamate in a similar manner as described for Example 118. Deprotection of tert-butyl (4-{2-[(2-isopropyl-1,1-dioxido-3-oxo-5-phenyl-2,3-dihydroisothiazol-4-yl) amino]ethyl}pyridin-2-yl)carbamate in a similar manner as described for 1-[3-chloro-5-(trifluoromethyl)pyridin-2-yl] azetidin-3-amine gave the title compound.

Example 158

2-Isopropyl-5-phenyl-4-[(2-pyridin-4-ylethyl)amino] isothiazol-3(2H)-one 1,1-dioxide The title compound was prepared from 4-chloro-2-isopropyl-5-phenylisothiazol-3(2H)-one 1,1-dioxide and (2-pyridin-4-ylethyl)amine in a similar manner as described for Example 118. $^1$H NMR (500 MHz CDCl$_3$): δ 1.59 (d, 6H), 2.58 (t, 2H), 3.18 (q, 2H), 4.37-4.45 (m, 1H), 5.44 (t, 1H), 6.71-6.73 (m, 2H), 7.46-7.57 (m, 5H), 8.44-8.46 (m, 2H); $^{13}$C NMR (125 MHz CDCl$_3$): δ 20.37, 35.42, 44.14, 47.90, 107.90, 123.96, 125.15, 129.14, 130.19, 131.83, 135.12, 146.48, 150.27, 158.57; Mass Spectrum: M+H$^+$ 372.

Example 159

2-Isopropyl-5-phenyl-4-[(2-pyridin-3-ylethyl)amino] isothiazol-3(2H)-one 1,1-dioxide The title compound was prepared from 4-chloro-2-isopropyl-5-phenylisothiazol-3(2H)-one 1,1-dioxide and (2-pyridin-3-ylethyl)amine in a similar manner as described for Example 118. $^1$H NMR (500 MHz CDCl$_3$): δ 1.59 (d, 6H), 2.59 (t, 2H), 3.17 (q, 2H), 4.37-4.45 (m, 1H), 5.47 (t, 1H), 7.06-7.09 (m, 1H), 7.14-7.17 (m, 1H), 7.46-7.55 (m, 5H), 8.07 (s, 1H), 8.44-8.46 (m, 1H); $^{13}$C NMR (125 MHz CDCl$_3$): δ 20.38, 33.39, 44.78, 47.88, 107.76, 123.70, 125.15, 129.13, 130.20, 131.84, 133.02, 135.16, 136.13, 148.57, 150.06, 158.61; Mass Spectrum: M+H$^+$ 372.

Example 160

4-[2-({2-[(Methylthio)methyl]-1,1-dioxido-3-oxo-5-phenyl-2,3-dihydroisothiazol-4-yl}amino)ethyl]phenyl methanesulfonate The title compound was prepared from 4-{2-[1,1-dioxido-3-oxo-5-phenyl-2,3-dihydroisothiazol-4-yl)amino] ethyl}phenyl methanesulfonate and 1,1,1-trifluoro-2-iodoethane in a similar manner as described for Example 151; $^1$H NMR (500 MHz CDCl$_3$): δ 7.58-7.48 (m, 5H), 7.16 (d, 1H), 6.85 (d, 2H), 5.41 (t, 1H), 4.77 (s, 2H), 3.21-3.15 (m, 1H), 3.14 (s, 3H), 2.63 (t, 2H), 2.38 (s, 3H); $^{13}$C NMR (125 MHz CDCl$_3$): δ 159.1, 148.2, 136.8, 135.2, 131.8, 130.4, 130.3, 129.2, 124.8, 122.5, 108.2, 45.0, 44.5, 37.7, 35.5, 16.8; Mass Spectrum: M+H+ 483.

Example 161

4-{[2-(3,5-Dimethylisoxazol-4-yl)ethyl]amino}-2-isopropyl-5-phenylisothiazol-3(2H)-one 1,1-dioxide The title compound was prepared from 4-chloro-2-isopropyl-5-phenylisothiazol-3(2H)-one 1,1-dioxide and [2-(3,5-dimethylisoxazol-4-yl)ethyl]amine in a similar manner as described for Example 24. $^1$H NMR (500 MHz, CDCl$_3$): δ 7.54-7.50 (m, 2H), 7.49-7.45 (m, 3H), 5.32 (t, 1H), 4.47 (sept, 1H), 3.04 (q, 2H), 2.33 (t, 2H), 2.14 (s, 3H), 2.01 (s, 3H), 1.59 (d, 6H); $^{13}$C NMR (125 MHz, CDCl$_3$): δ 166.1, 159.4, 158.6, 134.9, 131.4, 130.2, 129.2, 125.1, 109.7, 107.9, 47.9, 43.3, 23.0, 20.4, 11.1, 10.2; Mass Spectrum: M+H+ 390

Example 162

4-{[2-(3,5-Dimethyl-1H-pyrazol-4-yl)ethyl]amino}-2-isopropyl-5-phenylisothiazol-3(2H)-one 1,1-dioxide The title compound was prepared from 4-chloro-2-isopropyl-5-phenylisothiazol-3(2H)-one 1,1-dioxide and [2-(3,5-dimethyl-1H-pyrazol-4-yl)ethyl]amine dihydrochloride in a similar manner as described for Example 24 with TEA as base. $^1$H NMR (500 MHz, CDCl$_3$): δ 7.53-7.48 (m, 2H), 7.47-7.43 (m, 3H), 5.34 (t, 1H), 4.41 (sept, 1H), 3.01 (q, 2H), 2.41 (t, 2H), 2.05 (s, 6H), 1.58 (d, 6H); $^{13}$C NMR (125 MHz CDCl$_3$): δ 158.8, 135.3, 131.5, 129.9, 129.0, 125.3, 111.2, 107.2, 47.8, 43.9, 23.7, 20.4, 10.9; Mass Spectrum: M+H+ 389

Example 163

4-[2-({2-[(5-Methylisoxazol-3-yl)methyl]-1,1-dioxido-3-oxo-5-phenyl-2,3-dihydroisothiazol-4-yl}amino)ethyl]phenyl methanesulfonate The title compound was prepared from 4-{2-[1,1-dioxido-3-oxo-5-phenyl-2,3-dihydroisothiazol-4-yl)amino] ethyl}phenyl methanesulfonate and 3-(bromomethyl)-5-methylisoxaole in a similar manner as described for Example 151; $^1$H NMR (500 MHz CDCl$_3$): δ 7.57-7.46 (m, 5H), 7.13 (d, 2H), 6.82 (d, 2H), 6.16 (s, 1H), 5.43 (t, 1H), 4.87 (s, 2H), 3.22-3.08 (m, 5H), 2.61 (t, 3H), 2.41 (s, 3H); $^{13}$C NMR (125 MHz CDCl$_3$): δ 170.8, 158.9, 158.6, 148.2, 136.8, 135.2, 131.8, 130.4, 130.3, 129.2, 124.7, 122.5, 108.1, 101.8, 45.0, 37.7, 35.5, 35.1; Mass Spectrum: M+H$^+$ 518

Example 164

2,6-Dimethylphenyl 4-[(2-tert-butyl-1,1-dioxido-3-oxo-5-phenyl-2,3-dihydroisothiazol-4-yl)amino] butanoate 2,6-Dimethylphenyl 4-aminobutanoate hydrochloride (80.4 mg, 0.33 mmol) and 2-tert-butyl-4-chloro-5-phenylisothiazol-3(2H)-one 1,1-dioxide (89.9 mg, 0.91 mmol) were dissolved in a mixture of MeCN/DMF (4:1, 5 ml, dry). TEA (0.134 ml) was added and the reaction mixture was stirred at rt for 15 h. Diethyl ether (30 ml) was added and the resulting mixture was extracted with water (2×10 ml). The organic layer was dried (MgSO$_4$), evaporated and the residue was purified by column chromatography on silica, using n-heptane/EtOAc (7:3) as eluent. The obtained product was further purified by re-chromatography, using the same conditions as before, to give the title compound (17 mg, 11%) as colorless oil, which solidified upon standing. $^1$H NMR (400 MHz, CDCl$_3$): δ 1.73 (s, 9H), 1.78-1.85 (m, 2H), 2.06 (s, 6H), 2.38 (t, 2H), 2.96-3.01 (m, 2H), 5.37 (bt, 1H), 7.04 (s, 31), 7.42-7.44 (m, 3H), 7.50-7.52 (m, 2H).

Example 165

2-Mesitylethyl N-(2-tert-butyl-1,1-dioxido-3-oxo-5-phenyl-2,3-dihydroisothiazol-4-yl)glycinate

The title compound was prepared from [(2-tert-butyl-1,1-dioxido-3-oxo-5-phenyl-2,3-dihydroisothiazol-4-yl)amino]acetic acid and methyl glycinate hydrochloride. Mass Spectrum: [M+H]$^+$ 485.21, [M−H]$^−$ 483.28.

Example 166

2-[(2-tert-Butyl-1,1-dioxido-3-oxo-5-phenyl-2,3-dihydroisothiazol-4-yl)amino]ethyl (2,6-dimethylphenyl)acetate

The title compound was prepared from Example 76 and (2,6-dimethylphenyl)acetic acid. Mass Spectrum: [M+H]$^+$ 471.21, [M−H]$^−$ 469.34.

Example 167

Phenyl N-(2-terthutyl-1,1-dioxido-3-oxo-5-phenyl-2,3-dihydroisothiazol-4-yl)-beta-alaninate

The title compound was prepared from 2-tert-butyl-4-chloro-5-phenylisothiazol-3(2H)-one 1,1-dioxide and phenyl β-alaninate hydrochloride in a similar manner as described for Example 164. Mass Spectrum: [M+H]$^+$ 429.11, [M−H]$^−$ 427.14.

Example 168

4-(Trifluoromethoxy)phenyl N-(2-tert-butyl-1,1-dioxido-3-oxo-5-phenyl-2,3-dihydroisothiazol-4-yl)-beta-alaninate

The title compound was prepared from 2-tert-butyl-4-chloro-5-phenylisothiazol-3(2H)-one 1,1-dioxide and 4-(trifluoromethoxy)phenyl β-alaninate in a similar manner as described for Example 164. Mass Spectrum: [M+H]$^+$ 513.12, [M−H]$^−$ 511.16.

Example 169

1-Methylpiperidin-4-yl N-(2-tert-butyl-1,1-dioxido-3-oxo-5-phenyl-2,3-dihydroisothiazol-4-yl)-beta-alaninate

The title compound was prepared from 2-tert-butyl-4-chloro-5-phenylisothiazol-3(2H)-one 1,1-dioxide and 1-methylpiperidin-4-yl β-alaninate hydrochloride in a similar manner as described for Example 164. Mass Spectrum: [M+H]$^+$ 450.12, [M−H]$^−$ 448.23.

Example 170

2-Mesityl-1-methylethyl [(2-tert-butyl-1,1-dioxido-3-oxo-5-phenyl-2,3-Dihydroisothiazol-4-yl)amino]acetate

The title compound was prepared from [(2-tert-butyl-1,1-dioxido-3-oxo-5-phenyl-2,3-dihydroisothiazol-4-yl)amino]acetic acid and 1-mesitylpropan-2-ol. Mass Spectrum: [M+H]$^+$ 499.15, [M−H]$^−$ 497.98.

Example 171

4-Methoxybenzyl N-(2-tert-butyl-1,1-dioxido-3-oxo-5-phenyl-2,3-dihydroisothiazol-4-yl)glycinate

[(2-tert-Butyl-1,1-dioxido-3-oxo-5-phenyl-2,3-dihydroisothiazol-4-yl)amino]acetic acid (100 mg, 0.30 mmol), (4-methoxyphenyl)methanol (204 mg, 1.48 mmol), TEA (123 µL) and DMAP (9 mg, 0.074 mmol) were dissolved in DCM (10 mL). DMF 81 mL) and EDC (113 mg, 0.59 mmol) was added and the solution was stirred at 40° C. over night. Aqueous $K_2CO_3$ (1M, 50 mL) was added and the reaction mixture was extracted with DCM. The organic phases were combined, dried over $MgSO_4$, filtered and evaporated. The residue was purified by preparative HPLC affording the title compound (23 mg, 17%). $^1$H NMR (CDCl$_3$, 400 MHz) δ 1.69 (s, 9H), 3.54 (s, 2H), 3.77 (s, 3H), 4.98 (s, 2H), 5.79 (t, 1H), 6.83 (d, 2H), 7.17 (d, 2H), 7.32-7.40 (m, 5H). $^{13}$C NMR (CDCl$_3$, 100 MHz) δ 27.7, 45.4, 55.5, 61.8, 67.6, 109.6, 114.2, 124.4, 127.0, 128.9, 130.1, 130.7, 131.5, 134.8, 159.2, 160.2, 168.7.

Example 172

4-Methoxyphenyl N-(2-tert-butyl-1,1-dioxido-3-oxo-5-phenyl-2,3-dihydroisothiazol-4-yl)glycinate

The title compound was prepared from [(2-tert-butyl-1,1-dioxido-3-oxo-5-phenyl-2,3-dihydroisothiazol-4-yl)amino]acetic acid and 4-methoxyphenol as described for Example 171 affording the title compound (28 mg, 21%). $^1$H NMR (CDCl$_3$, 400 MHz) δ 1.71 (s, 9H), 3.77 (s, 3H), 3.81 (d, 2H), 5.78 (t, 1H), 6.85 (dd, 4H), 7.44-7.51 (m, 5H). $^{13}$C NMR (CDCl$_3$, 100 MHz) δ 27.8, 45.6, 55.8, 61.9, 110.1, 114.7, 122.0, 124.5, 129.1, 130.2, 131.6, 134.8, 143.6, 157.8, 159.2, 167.8.

Biological Activity

Co-Activator Recruitment Assay

The Ligand Binding Domain (LBD) of human LXRalpha (amino acid 205-447) and LXRbeta (amino acid 216-461) was produced by recombinant techniques in *E coli*. A fragment of the human Steroid Receptor Co-Activator-1 (SRC-1) was produced as a synthetic peptide. An anti-6×His-antibody coupled with Europium (Eu$^{3+}$) was used to recognize the His-tag on the LXR-LBD and Allophycocyanin (APC) coupled to streptavidin was used to recognize the biotinylated SRC-1. Agonist binding to LXRalpha or LXRbeta enhances the affinity of LXR towards SRC-1 and thereby brings Eu$^{3+}$ and APC in close proximity. Eu$^{3+}$ is excited at 337 nm and emitts light at 620 nm. This emission, when in close proximity, excites APC to emit light at 665 nm.

Compounds (10 mM) in DMSO were diluted (1/3) in DMSO in 10 concentrations. This dilution plates were further diluted in buffer {20 mM [Tris(hydroxymethyl)aminomethane] pH 7.5, 0.125% CHAPS {3-[(3-Cholamidopropyl)dimethylammonio]-1-propanesulfonate}, 2 mM DTT (Dithiothreitol) and 0.05% BSA (Bovine Serum Albumin)} in order to reduce DMSO concentration, 0.5 µl to 13.5 µl. To this, 6 µl assay mix was added, giving an maximal assay concentration of 83 µM, and the plates (384-well V-groove plates) were incubated at room temperature for 60 to 80 min. The assay mix has the following final concentrations; LXRalpha mix: 0.06 µg/mL Eu-labelled anti-6×His Ab, 1.15 µg/mL Streptavidin APC, 30 nM SRC-1 peptide and 0.9 µg/mL LXRalpha in buffer and LXRbeta mix; 0.06 µg/1 mL Eu-labelled anti-6×His Ab, 1.15 µg/mL Streptavidin APC, 90 nM SRC-1 peptide and 0.2 µg/mL LXRbeta in buffer. Time-resolved fluorescence readings were done in a Wallac Victor reader at 665 nm followed by reading at 615 nm. The LXR ligand, 22-R Hydroxycholesterol or an internal compound at 50 µM was used as the 100% control.

Transactivation Assay

Expression vectors were prepared by inserting the ligand binding domain cDNA (complementary DNA) of human LXRalpha (amino acid 205-447) and LXRbeta (amino acid 216-461) in frame with, 3' to the yeast GAL4 transcription factor DNA binding domain and the nuclear localization signal from the T-antigen of Polyoma Virus in the eucaryotic expression vector pSG5 (Stratagene). The resulting expression vectors pSGGAL-LXRalpha and pSGGAL-LXRbeta were used in cotransfection experiments together with the pGL3 luciferase reporter plasmid containing a minimal SV40 promoter (Promega) and five copies of the UAS GAL4 recognition site. 2.5 µg pSGGAL-LXRalpha or beta were mixed with 25 µg pGL3 5×UAS and 22.5 µg pBluscript (Stratagene) in 0.95 mL ice cold PBS containing approx. 4-9 milj. U2/OS osteosarcoma cells. After a five minute incubation on ice the cell/DNA mixture was electroporated in 0.4 cm cuvettes at 960 µF, 230 V using a BioRad electroporator and diluted to 0.32 milj cells/mL in complete DMEM [Dulbecco's Modified Eagle Medium w/o phenol red, (Gibco 11880-028) including 10% FBS (Foetal Bovine Serum), 1% PEST (Penicillin Streptomycin), 20 mM Hepes, 2 mM L-Glutamine and 0.36% Glucose Gibco 31966-021] medium. Cells from at least two electroporations were pooled in order to avoid variations between different electroportations. 25 µl diluted, electroporated cells, were seeded into 384-well plates ($0.8 \times 10^4$ cells/well) and the cells were allowed to adhere for 2 h at 37° C., 5% $CO_2$ in a cell culture incubator. Compounds (10 mM) in DMSO were diluted (1/3) in DMSO in 10 concentrations. This dilution plates were further diluted in complete DMEM w/o phenol red (2.5 µl to 97.5 µl) in order to reduce DMSO concentration. 7 µl of this was added to the electroporated cells in 384-well plates and incubation was continued for 48 h in a cell culture incubator, after which cells were lysed by adding 32 µl/well LucLite luciferase substrate. Luciferase activity was measured as Luminescence in the Wallac Victor reader after 15 min. incubation at room temperature. The LXR ligand, Tularik T0901317, or an internal standard, at 1 µM was used as the 100% control.

In vivo Assay

Separation of the desired antiatherogenic and the undesired lipogenic effects of LXR ligands was tested in normal C57 BL6 mice where the test agents are administered for three days (4 doses) in different or fixed oral doses. Gavage was performed once daily about noon, except the last dose that was given at 0700 hours, 3 hours before anaesthesia. 30 Mice were used in each screen and these were divided into five groups with six animals in each. One group was control group and the remaining 4 groups were treated with test agents in fixed or different doses. The test agents were given by gavage once daily for three days in four doses totally.

Blood samples were then obtained under anaesthesia for determination of plasma levels of TG. The liver was removed for determination of liver weight and TG content. 20-50 mg tissue, liver or intestine (first 2-3 cm distal the stomach) was snap-frozen in liquid nitrogen at necropsy for later analysis of any up regulation of LXR target genes, primarily ABCA1, ABCG1, SREBP1c and FAS. The tissues are kept in a −80° C. freezer until analysis.

Stainless steel beads (Cat. No. 69989, QIAGEN) were added to collection micro tubes, one bead per tube, (Cat. No. 19560, QIAGEN), while the tubes were kept on dry ice. Tissues were transferred to the collection micro tubes after which 750 µl QIAzol (Cat. No. 79306, QIAGEN) was added and then the tubes were placed in a Mixer Mill and homogenized for 2×5 minutes at 25 Hz. After homogenization the 96-well plate was centrifuged at 6000×g for one minute at 4° C. in a Sigma 4K-15C centrifuge. 150 µl chloroform was added to all samples, which were shaken vigorously for 15 seconds and incubated at room temperature for 2-3 minutes and centrifuged again at 6000×g for 15 minutes. 200 µl of the upper aqueous phase was transferred to Square-well tubes (Cat. No. 19573, QIAGEN) and one volume of 70% ethanol was added and mixed by pipetting up and down. After a 10 minute incubation on ice 250 µl samples was loaded onto the wells of a 96-well culture cluster plate (Cat. No. 3595, Corning Incorporated)

RNA was purified using an ABI Prism 6700 or ABI Prism 6100 according to the manufacturers-recommendations. RNA was eluted in 150 µl with a concentration of 50-200 ng/µl and 10 µl of this was analyzed by agarose gel electrophoresis (non denaturating 1% TBE gel) to verify RNA quality. cDNA synthesis was performed using the High-Capacity Archive Kit (Cat. No 4322171, Applied Biosystems) according to the manufacturers recommendations, by random primers, in a total reaction volume of 50 µl/sample.

Gene expression mRNA levels were determined by real-time PCR (7500 Real-time PCR system, Applied Biosystems). Taqman universal PCR master mix (Cat. No. 4305719, Applied Biosystems) was used in a 25 µl reaction containing 400 nM of each target primer, 100 nM of each of the control primers (36B4), 200 nM of the target probe, 100 nM of the control probe (36B4) and 2.5-10 ng of sample cDNA. The threshold cycles (Ct) for the endogenous control gene 36B4 and target genes were determined and relative mRNA levels were calculated using the comparative Ct method and expressed as fold induction.

The following primer and probes were used: ABCA1 Forward; 5'-AAGGGTTTCTTTGCTCAGATTGTC-3' (SEQ ID NO:1), ABCA1 Reverse; 5'-TGCCAAAGGGTGGCACA-3' (SEQ ID NO:2), ABCA1 Probe; 5'-FAM-CCAGCT-GTCTTTGTTTGCATTGCCC-TAMRA-3' (SEQ ID NO:3), ABCG1 Forward; 5'-CCATGAATGCCAGCAGCTACT-3' (SEQ ID NO:4), ABCG1 Reverse; 5'-CACTGACACGCA-CACGGACT-3' (SEQ ID NO:5), ABCG1 Probe; 5'-FAM-TGCCGCAATGACGGAGCCC -TAMRA-3' (SEQ ID NO:6), FAS Forward; 5'-GGCATCATTGGGCACTCCTT-3' (SEQ ID NO:7), FAS Reverse; 5'-GCTGCAAGCACAGC-CTCTCT-3' (SEQ ID NO:8), FAS Probe; 5'-FAM-CCATCT-GCATAGCCACAGGCAACCTC-TAMRA-3' (SEQ ID NO:9), SREBP 1c Forward; 5'-GGAGCCATGGATTGCA-CATT-3' (SEQ ID NO:10), SREBPlc Reverse; 5'-CCTGTCT-CACCCCCAGCATA-3' (SEQ ID NO: 11), SREBPlc Probe; 5'-FAN-CAGCTCATCAACAACCAAGACAGTGACT-TCC-TAMRA-3' (SEQ ID NO:12), 36B4 Forward; 5'-GAG-GAATCAGATGAGGATATGGGA-3' (SEQ ID NO:13), 36B4 Reverse; 5'-AAGCAGGCTGACTTGGTTCC-3' (SEQ ID NO:14), 36B4 Probe; 5'-VIC-TCGGTCTCTCGAC-TAATCCCGCCAA-TAMRA-3' (SEQ ID NO:15). From dose-response relationships, selectivity values (relative potencies) were determined to discriminate between the primary intestinal up regulation of LXR target genes and the unwanted plasma and hepatic TG elevations, respectively.

The compounds of formula I have an $EC_{50}$ of less than 50 µmol/l for LXRα and/or β in coactivator recruitment assays and/or reporter gene assays. For example, the compounds of Example 6 and Example 10 have $EC_{50}$'s for LXRα of 0.58 µmol/l and 1.42 µmol/l in the coactivator recruitment assay, respectively, and the compounds of Examples 2 and Example 7 have $EC_{50}$'s for LXRα of 1.36 µmol/l and 0.27 µmol/l in reporter gene assay.

In addition the compounds of the present invention exhibit favourable pharmacological effects in vivo.

The compounds of the present invention also have a promising toxicological profile

The invention claimed is:

1. A compound of general formula (I)

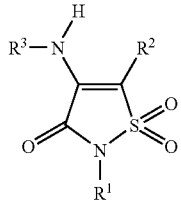

formula (I)

or a pharmaceutically acceptable salt thereof,
wherein:

$R^1$ represents:

X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$; or cycloalkyl or heterocyclyl each optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^a$, $NR^aC(O)R^b$, $C(O)$ $OR^a$, $OC(O)R^b$, $SO_2NR^aR^a$, $NR^aSO_2R^b$, $NR^aC(O)$ $OR^b$, $OC(O)NR^aR^a$ or $NR^aC(O)NR^aR^a$; or phenyl or heteroaryl each optionally substituted by one or more of the following independently selected from: halogen, OH, CN, $NO_2$, $NR^aR^a$, $OR^b$, $SR^b$, $SiR^{13}R^{13}R^{15}$, $S(O)R^b$, $SO_2R^b$, $C(O)R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)NR^aR^a$, $OSO_2R^b$, $NR^aC(O)NR^aR^a$, $SO_2NHC(O)R^b$, or $C_1$-$C_4$alkyl optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)$ $NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)$ $NR^aR^a$ or $NR^aC(O)NR^aR^a$; or cycloalkylY or heterocyclylY wherein cycloalkyl or heterocyclyl each optionally is substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $C(O)NR^aR^b$, $NR^aC(O)R^b$, $C(O)$ $OR^a$, $OC(O)R^b$, $SO_2NR^aR^a$, $NR^aSO_2R^b$, $NR^aC(O)$ $OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)$ $R^b$, $C(O)NR^aR^a$, $NR^aC(O)R^b$, $C(O)OR^a$, $OC(O)R^b$, $SO_2NR^aR^a$, $NR^aSO_2R^b$, $NR^aC(O)OR^b$, $OC(O)$ $NR^aR^a$ or $NR^aC(O)NR^aR^a$; or phenylY or heteroarylY wherein phenyl or heteroaryl each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

R$^2$ represents:

phenyl which is optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R$^3$ resents:

X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$; or MP or Het$^3$P wherein M and Het$^3$ each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het$^3$ each optionally is substituted on the aromatic ring by one or more of the following independently selected from: halogen, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O) R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$; or AP or Het$^5$P wherein A and Het$^5$ each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O) R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$; or E or Het$^4$ each optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)$_b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QZ, Het$^1$, Het$^1$Z, R, RZ, Het$^2$, Het$^2$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O) R$^b$, C(O)OR$^a$, SO$_2$NR$^3$R$^3$, NR$^a$SO$_2$R$^b$, NR$^a$C(O)OR$^b$, OC(O)NR$^a$R$^a$ or NR$^a$C(O)NR$^a$R$^a$, and E or Het$^4$ each optionally is substituted on the aromatic ring by one or more of the following independently selected from: halogen, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QZ, Het$^1$, Het$^1$Z, R, RZ, Het$^2$, Het$^2$Z, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$;

and further wherein:

X represents a straight or branched, saturated or unsaturated alkyl group having 1 to 6 carbon atoms wherein said alkyl group may optionally be interrupted by O, S, SiR$^b$R$^b$, S(O), SO$_2$, C(O), NR$^a$, OC(O), C(O)O, NR$^a$C(O), C(O)NR$^a$, SO$_2$NR$^a$ Or NR$^a$SO$_2$;

Y which binds to the nitrogen in the 2-position of the isothiazol-3(2H)-one 1,1-dioxide and represents a straight or branched, saturated or unsaturated alkylene group having 1 to 3 carbon atoms wherein said alkyl group may optionally be interrupted or ended by one of the following: O, S, SiR$^b$R$^b$, S(O), SO$_2$, C(O), OC(O), C(O)O, NR$^c$C(O), C(O)NR$^c$, NR$^c$ and/or Y is optionally substituted by one or more of the following independently selected from: OH, F, CN, NR$^3$R$^3$, C$_1$-C$_4$alkyl, OR$^b$, SR$^b$, SiR$^b$R$^b$R$^b$, S(O)R$^b$ or SO$_2$R$^b$;

Z binds to E or Het$^4$ and one of the following: Q, Het$^1$, R or Het$^2$, and represents a straight or branched, saturated or unsaturated alkylene group having 1 to 6 carbon atoms wherein said alkylene group may optionally be interrupted or ended by one of the following: O, S, SiR$^b$R$^b$, S(O), SO$_2$, C(O), OC(O), C(O) O, NR$^a$C(O), C(O)NR$^a$, NR$^a$, SO$_2$NR$^a$, NR$^a$SO$_2$, or is one of the following: O, S, SiR$^b$R$^b$, S(O), SO$_2$, C(O), OC(O), C(O)O, NR$^a$C(O), C(O)NR$^a$, NR$^a$, SO$_2$NR$^a$, NR$^a$SO$_2$ and/or Z is optionally substituted by one or more of the following independently selected from: OH, F, CN, NR$^c$R$^c$, C(O)R$^c$, OR$^c$, SR$^c$, SiR$^b$R$^b$R$^b$, S(O)R$^c$, SO$_2$R$^c$, phenyl, phenylC$_1$-C$_3$alkyl, or C$_1$-C$_4$alkyl which is optionally substituted by one or more of the following: F, OH, NR$^a$R$^a$, SR$^b$, SiR$^b$R$^b$R$^b$, S(O)R$^b$, SO$_2$R$^b$, OR$^b$;

M represents a saturated or unsaturated non-aromatic monocarbocyclic ring composed of 3, 4, 5, 6, 7 or 8 carbon atoms or a saturated or unsaturated non-aromatic or partly aromatic bicyclic ring system composed of 8, 9 or 10 carbon atoms;

E represents a saturated or unsaturated non-aromatic monocarbocyclic ring composed of 3, 4, 5, 6, 7 or 8 carbon atoms or a saturated or unsaturated non-aromatic or partly aromatic bicyclic ring system composed of 8, 9 or 10 carbon atoms, and the ring binds, unless otherwise specified, through its non-aromatic part to the amine group bonded to the 4-position on the isothiazol-3(2H)-one 1,1-dioxide;

A represents an aromatic monocyclic ring composed of 6 carbon atoms or an aromatic bicyclic ring system composed of 10 carbon atoms;

P binds to the amine group bonded to the 4-position on the isothiazol-3(2H)-one 1,1-dioxide and represents a straight or branched, saturated or unsaturated alkylene group having 1 to 6 carbon atoms wherein the alkylene group is optionally interrupted or ended by one of the following: O, NR$^a$, S, SiR$^b$R$^b$, S(O), SO$_2$, C(O), OC(O), C(O)O, NR$^a$C(O), C(O)NR$^a$, SO$_2$NR$^a$, NR$^a$SO$_2$ and/or P is optionally substituted by one or more of the following independently selected from: F, OH, CN, NR$^a$R$^a$, C(O)R$^c$, OR$^b$, SR$^b$, SiR$^b$R$^b$R$^b$, S(O)R$^b$, SO$_2$R$^b$, phenyl, phenyl C$_1$-C$_3$alkyl, or C$_1$-C$_4$alkyl which is optionally substituted by one or more of the following independently selected from: F, OH, NR$^a$R$^a$, SR$^b$, SiR$^b$R$^b$R$^b$, S(O)R$^b$, SO$_2$R$^b$ or OR$^b$;

Q represents a saturated or unsaturated non-aromatic monocyclic ring composed of 3, 4, 5, 6, 7 or 8 carbon atoms, which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

R represents a phenyl group which is optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^a$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

T binds to M, Het$^3$, A or Het$^5$ and one of the following: Q, Het$^1$, R or Het$^2$; and represents methylene or is one of the following: O, NR$^a$, S, SiR$^b$R$^b$, S(O), SO$_2$, C(O), OC(O), C(O)O, NR$^a$C(O), C(O)NR$^a$, SO$_2$NR$^a$ or NR$^a$SO$_2$;

Het$^1$ represents a saturated or unsaturated non-aromatic 3, 4, 5, 6, 7, 8, 9 or 10 membered monocyclic ring in which one or more of the atoms in the ring is an element other than carbon independently selected from one or more of nitrogen, oxygen or sulfur, and wherein the ring optionally is substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

Het$^2$ represents an aromatic 5 or 6 membered monocyclic ring in which one or more of the atoms in the ring is an element other than carbon independently selected from one or more of nitrogen, oxygen and sulfur, and which is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, phenylC$_1$alkyl, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, OSO$_2$R$^b$, NR$^a$C(O)NR$^a$R$^a$, SO$_2$NHC(O)R$^b$, or C$_1$-C$_4$alkyl optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, NR$^a$SO$_2$R$^b$, SO$_2$NR$^a$R$^a$, NR$^a$C(O)OR$^b$, OC(O)NR$^a$R$^a$ or NR$^a$C(O)NR$^a$R$^a$;

Het$^3$ represents a saturated or unsaturated non-aromatic 3, 4, 5, 6, 7, 8, 9 or 10 membered monocyclic ring or a saturated or unsaturated non-aromatic or partly aromatic 9 or 10 membered bicyclic ring system in which one or more of the atoms in the monocyclic ring or bicyclic ring system is an element other than carbon independently selected from one or more of nitrogen, oxygen or sulfur;

Het$^4$ represents a saturated or unsaturated non-aromatic 3, 4, 5, 6, 7, 8, 9 or 10 membered monocyclic ring or a saturated or unsaturated non-aromatic or partly aromatic 9 or 10 membered bicyclic ring system in which one or more of the atoms in the monocyclic ring or bicyclic ring system is an element other than carbon independently selected from one or more of nitrogen, oxygen or sulfur, and the ring binds, unless otherwise specified, through its non-aromatic part to in the amine group bonded to the 4-position on the isothiazol-3(2H)-one 1,1-dioxide;

Het$^5$ represents an aromatic 5 or 6 membered monocyclic ring or an aromatic 9 or 10 membered bicyclic ring system in which one or more of the atoms in the monocyclic ring or bicyclic ring system is an element other than carbon independently selected from one or more of nitrogen, oxygen or sulfur;

R$^a$ independently represents H or a straight or branched, saturated or unsaturated C$_1$-C$_4$alkyl chain optionally substituted by one or more F;

205

R$^b$ independently represents a straight or branched, saturated or unsaturated C$_1$-C$_4$alkyl chain optionally substituted by one or more F; and R$^c$ independently represents H or a straight or branched, saturated or unsaturated C$_1$-C$_4$alkyl chain optionally substituted by one or more F.

2. A compound according to claim 1 or a pharmaceutically acceptable salt thereof wherein:

R$^1$ represents:
  X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$ or C(O)R$^b$; or
  cycloalkyl or heterocyclyl each optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$ or C(O)R$^b$; or
  phenyl or heteroaryl each optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$; or
  cycloalkylY or heterocyclylY wherein cycloalkyl or heterocyclyl each optionally is substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$; or
  phenylY or heteroarylY wherein phenyl or heteroaryl each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$; and R$^2$ represents:
  phenyl which is optionally substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, 3. A compound according to claim 2 or a pharmaceutically acceptable salt thereof wherein:

R$^1$ represents:
  X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, C(O)NR$^a$R$^a$, NR$^a$C(O)R$^b$, C(O)OR$^a$, OC(O)R$^b$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$.

206

4. A compound according to claim 3 or a pharmaceutically acceptable salt thereof wherein:

R$^1$ represents:
  X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$ or C(O)R$^b$.

5. A compound according to claim 1 or a pharmaceutically acceptable salt thereof wherein:

R$^3$ represents:
  X which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$, NR$^a$C(O)NR$^a$R$^a$, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$ or NR$^a$C(O)NR$^a$R$^a$.

6. A compound according to claim 1 or a pharmaceutically acceptable salt thereof wherein:

R$^3$ represents:
  MP or Het$^3$P wherein M and Het$^3$ each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$, and wherein M or Het$^3$ each optionally is substituted on the aromatic ring by one or more of the following independently selected from: halogen, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, NR$^a$C(O)NR$^a$R$^a$, OSO$_2$R$^b$, SO$_2$NR$^a$C(O)R$^b$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O)NR$^a$R$^a$; or AP or Het$^5$P wherein A and Het$^5$ each optionally is substituted by one or more of the following independently selected from: halogen, OH, CN, NO$_2$, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, OC(O)NR$^a$R$^a$, NR$^a$C(O)OR$^b$, OSO$_2$R$^b$, SO$_2$NR$^a$C(O)R$^b$, NR$^a$C(O)NR$^a$R$^a$, Q, QT, Het$^1$, Het$^1$T, R, RT, Het$^2$, Het$^2$T, or C$_1$-C$_4$alkyl which is optionally substituted by one or more of the following independently selected from: F, OH, CN, NR$^a$R$^a$, OR$^b$, SR$^b$, SiR$^b$R$^b$R$^b$, S(O)R$^b$, SO$_2$R$^b$, C(O)R$^b$, NR$^a$C(O)R$^b$, C(O)NR$^a$R$^a$, OC(O)R$^b$, C(O)OR$^a$, SO$_2$NR$^a$R$^a$, NR$^a$SO$_2$R$^b$, NR$^a$C(O)OR$^b$, OC(O)NR$^a$R$^a$ or NR$^a$C(O))NR$^a$R$^a$.

7. A compound according to claim 1 or a pharmaceutically acceptable salt thereof wherein:
$R^3$ represents:
E or $Het^4$ each optionally substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QZ, $Het^1$, $Het^1Z$, R, RZ, $Het^2$, $Het^2Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and E or $Het^4$ each optionally is substituted on the aromatic ring by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1Z$, R, RZ, $Het^2$, $Het^2Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

8. A compound according to claim 2 or a pharmaceutically acceptable salt thereof wherein:
$R^3$ represents:
X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$.

9. A compound according to claim 2 or a pharmaceutically acceptable salt thereof wherein:
$R^3$ represents:
MP or $Het^3P$ wherein M and $Het^3$ each optionally is substituted on the non-aromatic ring by one or more of the following independently selected from: F, OH, CN, $NR^aR^a$, $OR^1$, $SR^1$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QT, $Het^1$, Het T, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$, and wherein M or $Het^3$ each optionally is substituted on the aromatic ring by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)$ $OR^b$, $OC(O)NR^aR^a$ or $NR^aC(O)NR^aR^a$; or
AP or $Het^5P$ wherein A and $Het^5$ each optionally is substituted by one or more of the following independently selected from: halogen, OH, CN, $NO_2$, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $OSO_2R^b$, $SO_2NR^aC(O)R^b$, $NR^aC(O)NR^aR^a$, Q, QT, $Het^1$, $Het^1T$, R, RT, $Het^2$, $Het^2T$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

10. A compound according to claim 2 or a pharmaceutically acceptable salt thereof wherein:
$R^3$ represents:
E or $Het^4$ each optionally substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, Q, QZ, $Het^1$, $Het^1Z$, R, RZ, $Het^2$, $Het^2Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)$ $OR^b$, $OC(O)NR^aR^a$ or $NR^aC(O)NR^aR^a$, and E or $Het^4$ each optionally is substituted on the aromatic ring by one or more of the following independently selected from: halogen OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, $Het^1$, $Het^1Z$, R, RZ, $Het^2$, $Het^2Z$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)_b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

11. A compound according to claim 3 or a pharmaceutically acceptable salt thereof wherein:
$R^3$ represents:
X which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$, $NR^aC(O)NR^aR^a$, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$ or $NR^aC(O)NR^aR^a$.

12. A compound according to claim 3 or a pharmaceutically acceptable salt thereof wherein:
$R^3$ represents:
MP or $Het^3P$ wherein M and $Het^3$ each optionally is substituted on the non-aromatic ring by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$ $NR^aSO_2R^b$, $OC(O)NR^aR^a$, $NR^aC(O)OR^b$, $NR^aC(O)NR^aR^a$, Q, QT, $Het^1$, $Het^1T$, R, RT, Het², Het²T, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$, and wherein M or Het³ each optionally is substituted on the aromatic ring by one or more of the following independently selected from: halogen, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, NR$^a$C(O)NR$^a$R$^a$, OSO₂R$^b$, SO₂NR$^a$C(O)R$^b$, Q, QT, Het¹, Het¹T, R, RT, Het², Het²T, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$; or AP or Het⁵P wherein A and Het⁵ each optionally is substituted by one or more of the following independently selected from: halogen, OH, CN, NO₂, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, OSO₂R$^b$, SO₂NR$^a$C(O)R$^b$, NR$^a$C(O)NR$^a$R$^a$, Q, QT, Het¹, Het¹T, R, RT, Het², Het²T, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$.

13. A compound according to claim 3 or a pharmaceutically acceptable salt thereof wherein:

R³ represents:

E or Het⁴ each optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, NR$^a$C(O)NR$^a$R$^a$, Q, QZ, Het¹, Het¹Z, R, RZ, Het², Het²Z, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$, and E or Het⁴ each optionally is substituted on the aromatic ring by one or more of the following independently selected from: halogen, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, NR$^a$C(O)NR$^a$R$^a$, OSO₂R$^b$, SO₂NR$^a$C(O)R$^b$, Q, QZ, Het¹, Het¹Z, R, RZ, Het², Het²Z, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$.

14. A compound according to claim 4 or a pharmaceutically acceptable salt thereof wherein:

R³ represents:

X which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$, NR$^a$C(O)NR$^a$R$^a$, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$ or NR$^a$C(O)NR$^a$R$^a$.

15. A compound according to claim 4 or a pharmaceutically acceptable salt thereof wherein:

R³ represents:

MP or Het³P wherein M and Het³ each optionally is substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, NR$^a$C(O)NR$^a$R$^a$, Q, QT, Het¹, Het¹T, R, RT, Het², Het²T, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$, and wherein M or Het³ each optionally is substituted on the aromatic ring by one or more of the following independently selected from: halogen, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, NR$^a$C(O)NR$^a$R$^a$, OSO₂R$^b$, SO₂NR$^a$C(O)R$^b$, Q, QT, Het¹, Het¹T, R, RT, Het¹, Het²T, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$; or AP or Het⁵P wherein A and Het⁵ each optionally is substituted by one or more of the following independently selected from: halogen, OH, CN, NO₂, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, OSO₂R$^b$, SO₂NR$^a$C(O)R$^b$, NR$^a$C(O)NR$^a$R$^a$, Q, QT, Het¹, Het¹T, R, RT, Het², Het²T, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$.

16. A compound according to claim 4 or a pharmaceutically acceptable salt thereof wherein:

R³ represents:

E or Het⁴ each optionally substituted on the non-aromatic ring by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, OC(O)NR$^a$R$^a$, NR$^a$C(O)OR$^b$, NR$^a$C(O)NR$^a$R$^a$, Q, QZ, Het¹, Het¹Z, R, RZ, Het², Het²Z, or C₁-C₄alkyl which is optionally substituted by one or more of the following independently selected from: F, OH, CN, NR$^a$R$^a$, OR$^b$, SR$^b$, SiR$^b$R$^b$R$^b$, S(O)R$^b$, SO₂R$^b$, C(O)R$^b$, NR$^a$C(O)R$^b$, C(O)NR$^a$R$^a$, OC(O)R$^b$, C(O)OR$^a$, SO₂NR$^a$R$^a$, NR$^a$SO₂R$^b$, NR$^a$C(O)OR$^b$, OC(O)NR$^a$R$^a$ or NR$^a$C(O)NR$^a$R$^a$, and E or Het each optionally is substituted on the aromatic ring by one or more of the following independently selected from: halogen, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $OC(O)NR^aR^a$, $NR^aC(O)OR^b$, $NR^aC(O)NR^aR^a$, $OSO_2R^b$, $SO_2NR^aC(O)R^b$, Q, QZ, Het¹, Het¹Z, R, RZ, Het², Het²Z, or $C_1$-$C_4$alkyl which is optionally substituted by one or more of the following independently selected from: F, OH, CN, $NR^aR^a$, $OR^b$, $SR^b$, $SiR^bR^bR^b$, $S(O)R^b$, $SO_2R^b$, $C(O)R^b$, $NR^aC(O)R^b$, $C(O)NR^aR^a$, $OC(O)R^b$, $C(O)OR^a$, $SO_2NR^aR^a$, $NR^aSO_2R^b$, $NR^aC(O)OR^b$, $OC(O)NR^aR^a$ or $NR^aC(O)NR^aR^a$.

17. A compound according to claim 1 in which:

$R^1$ is selected from ethyl, isopropyl, n-butyl, teributyl, cyclopentyl, hexyl, benzyl, 2-methoxyethyl, pyridin-2-ylmethyl, pyridin-3-ylmethyl, pyridin-4-ylmethyl, tetrahydrofuran-2-ylmethyl, 2-(3-fluorophenyl)ethyl, isobutyl, 4-fluorobenzyl, (5-methylisoxazol-3-yl)methyl or (methylthio)methyl;

$R^2$ is phenyl; and $R^3$ is selected from n-butyl, n-hexyl, benzyl, 3-[3-(hydroxymethyl)phenoxy]propyl, 4-phenylbutyl, 3-(2-methoxyphenoxy)propyl, 3-[4-(hydroxymethyl)phenoxy]propyl, 3-(2-fluorophenoxy)propyl, 3-(2-chlorophenoxy)propyl, 3-(2-methoxyphenoxy)propyl, 3-(pyridin-3-yloxy)propyl, 3-(pyridin-4-yloxy)propyl, 1-[3-chloro-5-(trifluoromethyl)pyridin-2-yl]piperidin-4-yl, 3-(phenylthio)propyl, 3-phenoxypropyl, 3-(3-chlorophenoxy)propyl, 3-(3-fluorophenoxy)propyl, 3-(4-fluorophenoxy)propyl, 1-[4-(trifluoromethyl)pyrimidin-2-yl]piperidin-4-yl, cis-4-hydroxycyclohexyl, 4-phenoxybutyl, 3-[(1-oxidopyridin-3-yl)oxy]propyl, 3-(4-methoxyphenoxy)propyl, 4,4-difluorocyclohexyl, 2-phenoxyethyl, 2-phenylethyl, 4-(difluoromethoxy)benzyl, trans-4-hydroxycyclohexyl, 3-hydroxypropyl, 2,3-dihydro-1,4-benzodioxin-2-ylmethyl, 4-hydroxycyclohexyl, 3-(4-chlorophenoxy)propyl, 1,3-benzodioxol-5-ylmethyl, 2,3-dihydro-1H-inden-2-yl, 2-(morpholin-4-yl)ethyl, 3-(4-isopropylphenoxy)propyl, 3-[benzyl(butyl)amino]propyl, 3-(3,5-dipropoxyphenoxy)propyl, 2,2-diphenylethyl, 2-(1H-imidazol-4-yl)ethyl, 4-morpholin-4-ylbenzyl,3-(2-methoxyethoxy)propyl, 3-morpholin-4-ylpropyl, 2-methoxyethyl, tetrahydro-2H-pyran-4-yl, 4-hydroxycyclohexyl, 4-methoxybenzyl, 3-(3-hydroxyphenoxy)propyl, 3-(3-acetamidophenoxy)propyl, 3-(4-N,N-dimethylaminocarbonylmethylphenoxy)propyl, 3-(3-carboxymethylphenoxy)propyl, 3-(3-methoxycarbonylmethylphenoxy)propyl, 3-(3-methoxycarbonylphenoxy)propyl, 3-(4-carboxymethylphenoxy)propyl, 3-(4-methoxycarbonylmethylphenoxy)propyl, 3-(3-acetylaminophenoxy)propyl, 3-(4-hydroxyphenylcarboxy)propyl, 3-(4-carboxyphenoxy)propyl, 1-(2-nitriloethyl)piperidin-4-yl, isopropyl, ethyl, 2,2-dimethylpropyl, tertbutyl, 2-(2-methoxyethoxy)ethyl, 2-hydroxyethyl, 2,2,2-trifluoroethyl, methyl ethanoylglycinate, 2,3-dihydro-1,4-benzodioxin-6-ylmethyl, 1,3,5-trimethyl-1H-pyrazol-4-ylmethyl, 3-(3,5-dimethyl-1H-pyrazol-1-yl)propyl, 2-(pyrrolidin-3-ylthio)ethyl, 2-[1-(tertbutoxycarbonyl)pyrrolidin-3-yl]ethyl, 2-[1-(tert-butoxycarbonyl)pyrrolidin-3-yl]ethyl, 2-{[1-(tert-butoxycarbonyl)pyrrolidin-3-yl]thio}ethyl, 2-pyridin-2-ylethyl, 2-{[3-chloro-5-(trifluoromethyl)pyridin-2-yl]amino}ethyl, 2-{[5-(trifluoromethyl)pyridin-2-yl]oxy}ethyl, 3-(pyridin-2-yloxy)propyl, 1-(tert-butoxycarbonyl)piperidin-4-yl, 1-acetylpiperidin-4-yl, piperidin-4-yl, 1-methylpiperidin-4-yl, 1-isobutyrylpiperidin-4-yl, 1-pyridin-2-ylpiperidin-4-yl, 1-(5-fluoropyridin-2-yl)piperidin-4-yl, 1-(5-chloropyridin-2-yl)piperidin-4-yl, 1-(5-methylpyridin-2-yl)piperidin-4-yl, 1-[4-(trifluoromethyl)pyridin-2-yl]piperidin-4-yl, 1-[5-(trifluoromethyl)pyridin-2-yl]piperidin-4-yl, 1-(6-chloropyridin-3-yl)piperidin-4-yl, 1-pyridazin-3-ylpiperidin-chlorophenyl)ethyl, 3-(3-carboxyphenoxy)propyl, 3-[3-(2-methoxy-2-oxoethyl)phenoxy]propyl, 3-[4-(2-methoxy-2-oxoethyl)phenoxy]propyl, 3-{4-[2-(dimethylamino)-2-oxoethyl]phenoxy}propyl, 3-[(4-hydroxybenzoyl)oxy]propyl, 2-{2-[(methylsulfonyl)oxy]phenoxy}ethyl, 2-{4-[(methylsulfonyl)oxy]phenoxy}ethyl, 2-[2-(methoxycarbonyl)phenoxy]ethyl, 2-(4-chlorophenoxy)ethyl, 2-[3-(trifluoromethoxy)phenoxy]ethyl, 2-{[3-(trifluoromethoxy)phenyl]thio}ethyl, 2-(benzylamino)-2-oxoethyl or 2-{[3-(difluoromethoxy)benzyl]amino}-2-oxoethyl-4-yl, 1-(6-chloropyridazin-3-yl)piperidin-4-yl, 1-(6-methoxypyridazin-3-yl)piperidin-4-yl, 1-(4-cyanobenzyl)piperidin-4-yl, 1-[2-(trifluoromethyl)benzoyl]piperidin-4-yl, 1-[3-(methoxycarbonyl)benzyl]piperidin-4-yl, 1-benzylpiperidin-4-yl, 1-benzoylpiperidin-4-yl, 1-(phenylacetyl)piperidin-4-yl, 1-(4-cyanobenzoyl)piperidin-4-yl, 1-(3,4-difluorobenzoyl)piperidin-4-yl, 1-(2-phenylethyl)piperidin-4-yl, 1-(2-phenylethyl)piperidin-4-yl, 1-benzylpyrrolidin-3-yl, 4-{[4-(trifluoromethyl)phenyl]thio}cyclohexyl, 1-[(5-methylisoxazol-3-yl)methyl]piperidin-4-yl, 1-(2-chloro-6-methylisonicotinoyl)piperidin-4-yl, 1-[(2-chloropyridin-3-yl)carbonyl]piperidin-4-yl, 2-{4-[(methylsulfonyl)oxy]phenyl}ethyl, 2-[4-(aminosulfonyl)phenyl]ethyl, 2-(4-cyanophenyl)ethyl, 2-(3-cyanophenyl)ethyl, 2-[2-(trifluoromethoxy)phenyl]ethyl, 2-[3-(trifluoromethoxy)phenyl]ethyl, or 3-[(1-methylpiperidin-4-yl)oxy]-3-oxopropyl, 2-(3,4-dimethoxyphenyl)ethyl, 2-(3-chloro-4-methoxyphenyl)ethyl, 2-(4-hydroxy-3,5-dimethoxyphenyl)ethyl, 2-(4-methoxyphenoxy)-2-oxoethyl, 2-[(4-methoxybenzyl)oxy]-2-oxoethyl, 2-(2-mesityletoxy)-2-oxoethyl, 2-(2-mesityl-1-methylethoxy)-2-oxoethyl, 3-oxo-3-phenoxypropyl, 3-oxo-3-[4-(trifluoromethoxy)phenoxy]propyl, 2-{[(2,6-dimethylphenyl)acetyl]oxy}ethyl, 4-(2,6-dimethylphenoxy)-4-oxobutyl, (5-methylisoxazol-3-yl)methyl, 2-(2-aminopyridin-4-yl)ethyl, 2-pyridin-4-ylethyl, 2-pyridin-3-ylethyl, 2-(3,5-dimethylisoxazol-4-yl)ethyl or 2-(3,5-dimethyl-1H-pyrazol-4-yl)ethyl, or 1-pyridin-2-ylazetidin-3-yl.

18. A process for the preparation of a compound according to claim 1, comprising reacting (a) a compound of formula (VI),

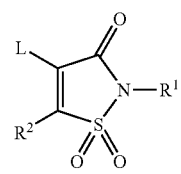

(VI)

wherein $R^1$ and $R^2$ are as defined in claim 1 and L is a leaving group, with a compound of formula (VII),

(VII)

wherein R³ is as defined in claim 1, optionally in the presence of an inert organic solvent, or (b) a compound of formula (X),

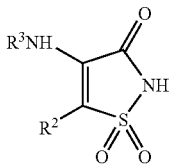
(X)

wherein R² and R³ are as defined in claim 1, either with an alkylating agent or with R¹OH, wherein R¹ is as defined in claim 1, using Mitsunobu conditions.

19. A compound of general formula (V), (VI), (IX), (X), (XII) or (XIII)

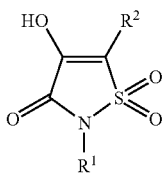
(V)

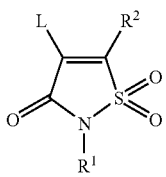
(VI)

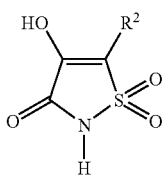
(IX)

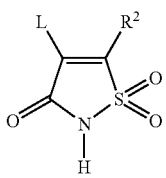
(X)

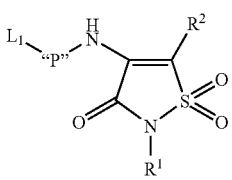
(XII)

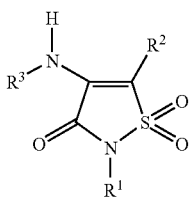
(XIII)

or a pharmaceutically acceptable salt thereof, wherein:
R¹ is defined as in claim 1;
R² is defined as in claim 1;
L is a suitable leaving group;
"P" is defined as for P in claim 1;
L₁ is OH, NH₂, SH or a suitable leaving group; and
R⁵ is Het⁴ or E wherein Het⁴ and E is defined as in claim 1, with the proviso that the following compounds are excluded:
4-hydroxy-5-phenylisothiazol-3(2H)-one 1,1-dioxide,
5-(4-aminophenyl)-4-hydroxy-2-methylisothiazol-3(2H)-one 1,1-dioxide,
4-hydroxy-2-methyl-5-(4-nitrophenyl)isothiazol-3(2H)-one 1,1-dioxide,
4-hydroxy-2-methyl-5-phenylisothiazol-3(2H)-one 1,1-dioxide,
5-(3,4-dichlorophenyl)-4-hydroxyisothiazol-3(2H)-one 1,1-dioxide,
2-benzyl-4-hydroxy-5-phenylisothiazol-3(2H)-one 1,1-dioxide, and
4-hydroxy-2-(4-methylphenyl)-5-phenylisothiazol-3 (2H)-one 1,1-dioxide.

20. A pharmaceutical formulation comprising a compound according to claim 1, or a suitable pharmaceutically acceptable salt thereof, and a pharmaceutically acceptable adjuvant, diluent and/or carrier.

21. A process according to claim 18 wherein the leaving group is Cl, Br, I, p-toluensulfonate, methanesulfonate or trifluoromethanesulfonate.

22. A process according to claim 18 wherein the inert organic solvent is dimethylformamide.

23. A process according to claim 18 wherein the alkylating agent is R¹L, wherein R¹ is defined as in claim 1, and L is a leaving group.

24. A process according to claim 23 wherein L is Cl, Br, I, p-toluensulfonate, methanesulfonate or trifluoromethanesulfonate.

25. A compound according to claim 19 wherein:
L is Cl, Br, I, p-toluensulfonate, methanesulfonate, or trifluoromethanesulfonate; and
L₁ is OH, NH₂, SH or a leaving group chosen from Cl, Br, I, p-toluensulfonate, methanesulfonate, and trifluoromethanesulfonate.

26. A compound chosen from one or more of the following:
2-tert-butyl-4-({3-[3-(hydroxymethy)]phenoxyl}amino)-5-phenylisothiazol-3(2H)-one1,1-dioxide;
2-tert-butyl-5-phenyl-4-[(4-phenylbutyl)amino]isothiazol-3(2H)-one 1,1-dioxide;
2-tert-butyl-4-{[3-(2-methoxyphenoxy)propy]amino}-5-phenylisothiazol-3(2H)-one 1,1-dioxide;
2-tert-butyl-4-( {3-[4-(hydroxymethyl)phenoxy]propyl)}amino)-5-phenylisothiazol -3(2H)-one 1,1-dioxide;
N-(3- {3- [(2-tert-butyl- 1,1-dioxido-3-oxo-5-phenyl-2,3-dihydroisothiazol-4-yl)amino]propoxy}phenyl)acetamide;
2-tert-butyl-4- {[3-(2-fluorophenoxy)propyl]amino}-5-phenyisothiazol-3(2H)-one 1,1-dioxide;
2-isopropyl-5-phenyl-4-[(4-phenylbutyl)amino]isothiazol-3(2H)-one 1,1-dioxide;
2-(4- {3-[(2-tert-butyl-1,1-dioxido-3-oxo-5-phenyl-2,3-dihydroisothiazol-4-yl) amino]propoxy }phenyl)-N,N-dimethylacetamide;
2-tert-butyl-4- {[3-(2-chlorophenoxy)propyl]amino}-5-phenylisothiazol -3(2H)-one 1,1-dioxide;
2-tert-butyl-4- {[3-(3-methoxyphenoxy)propyl]amino}-5-phenylisothiazol-3(2H)-one 1,1-dioxide;

(3-{3-[(2-tert-butyl-1,1-dioxido-3-oxo-5-phenyl-2,3-dihydroisothiazol-4-yl) amino]propoxy}phenyl)acetic acid;

2-tert-butyl-5-phenyl-4-{[3-(pyridin-3-yloxy)propyl]amino}isothiazol-3(2H)-one 1,1-dioxide;

methyl (3-{3-[(2-tert-butyl-1,1-dioxido-3-oxo-5-phenyl-2,3-dihydroisothiazol-4-yl) amino]propoxy}phenyl)acetate;

2-tert-butyl-5-phenyl-4-{[3-(pyridin-4-yloxy)propyl]amino}isothiazol-3(2H)-one 1,1-dioxide;

4-(benzylamino)-2-tert-butyl-5-phenylisothiazol-3 (2H)-one 1,1-dioxide;

4-({1-[3-chloro-5-(trifluoromethyl)pyridin-2-yl]piperidin-4-yl}amino)-2-isopropyl-5-phenylisothiazol-3(2H)-one 1,1-dioxide;

2-tert-butyl-5-phenyl-4-[(2-phenylethyl)amino]isothiazol-3(2H)-one 1,1-dioxide;

2cyclopentyl-5-phenyl4-[(4-phenylbutyl)amino]isothiazol-3(2H)-One 1,1-dioxide;

2-tert-butyl-5-phenyl-4-{[3-(phenylthio)propyl]amino}isothiazol-3(2H)-one 1,1-dioxide;

2-tert-butyl-4[(3-phenoxypropyl)amino]-5-phenylisothiazol-3-(2H)-one 1,1-dioxide;

2-tert-butyl-4-{[3-(3-chlorophenoxy)propyl]amino}-5-phenylisothiazol-3(2H)-one 1,1-dioxide;

methyl 3-{3-[(2-tert-butyl-1,1-dioxido-3-oxo-5-phenyl-2,3-dihydroisothiazol-4-yl)amino]propoxy}benzoate;

2-benzyl-5-phenyl-4-[(4-phenylbutyl)amino]isothiazol-3 (2H)-one 1,1-dioxide;

(4-{3-[(2-tert-butyl-1,1-dioxido-3-oxo-5-phenyl-2,3-dihydroisothiazol-4-yl) amino]propoxy}phenyl)acetic acid;

2-tert-butyl-4-{[3-(3-fluorophenoxy)propyl]amino}-5-phenylisothiazol-3(2H)-one 1,1-dioxide;

methyl (4-{3-[(2-tert-butyl-1,1-dioxido-3-oxo-5-phenyl-2,3-dihydroisothiazol-4-yl) amino]propoxy}phenyl)acetate;

2-tert-butyl-4-{[3-(4-fluorophenoxy)propyl]amino}-5-phenyisothiazol-3(2H)-one 1,1-dioxide;

2-isopropyl-5-phenyl-4-({1-[4-(trifluoromethyl)pyrimidin-2-yl]piperidin-4-yl}amino)isothiazol-3(2H)-one 1,1-dioxide;

N-(3-{3-[(2-butyl-1,1-dioxido-3-oxo-5-phenyl-2,3-dihydroisothiazol-4-yl) amino]propoxy}phenyl)acetamide;

3-[(2-tert-butyl-1,1-dioxido-3-oxo-5-phenyl-2,3-dihydroisothiazol-4-yl)amino]propyl 4-hydroxybenzoate;

4-(benzylamnio)-2-isopropyl-5-phenylisothiazol-3(2H)-one 1,1-dioxide;

2-[2-(3-fluorophenyl)ethyl]-5-phenyl-4-[(4-phenyl butyl)amino]isothiazol-3 (2H)-one 1,1-dioxide;

4-[(cis-4-hydroxycyclohexyl)amino-2-isopropyl-5-phenylisothiazol-3(2H)-one 1,1-dioxide;

2-tert-butyl-4-[(4-phenoxybutyl)amino]-5-phenylisothiazol-3(2H)-one 1,1-dioxide;

2-tert-butyl-4-({3-[(1-oxidopyridin-3-yl)oxy]propyl}amino)-5-phenylisothiazol-3(2H)-one 1,1-dioxide;

2-tert-butyl-4-[(2-phenoxyethyl)amino]-5-phenylisothiazol-3(2H)-one 1,1-dioxide;

4-(benzylamino)-2-cyclopentyl-5-phenylisothiazol-3(2H)-one 1,1-dioxide;

2-tert-buty1-4-{[3-(4-methoxyphenoxy)propyl]aniino}-5-phenylisothiazol-3 (2H)-one 1,1-dioxide;

4-[(4,4-difluorocyclohexyl)amino]-2-isopropyl-5-phenyl-isothiazol-3(2H)-one 1,1-dioxide;

2-isopropyl-4-[(2-phenoxy ethyl)amino]-5-phenyl-isothiazol-3 (2H)-one 1,1-dioxide;

5-pheny1-4-[(4-phenylbutyl)amino]-2-(tetrahydrofuran-2-ylmethyl)isothiazol-3(2H)-one 1,1-dioxide;

4-(benzylamino)-2-butyl-5-phenylisothiazol-3(2H)-one 1,1-dioxide;

2-butyl-4-(hexylamino)-5-phenylisothiazol-3(2H)-one 1,1-dioxide;

2-butyl-5-phenyl-4-[(2-phenylethyl)amino]isothiazol -3(2H)-one 1,1-dioxide;

2-butyl-4-{[4-(difluoromethoxy)benzyl]amino}-5-phenylisothiazol-3(2H)-one 1,1-dioxide;

4-[(trans-4-hydroxycyclohexyl)amino]-2-isopropyl-5-phenylisothiazol-3(2H)-one 1,1-dioxide;

2-tert-butyl-4-[(3-hydroxypropyl)amino]-5-phenyl-isothiazol-3(2H)-one 1,1-dioxide;

5-phenyl-4-[(4-phenylbutyl)amino]-2-(pyridin-3-ylmethyl)isothiazol-3 (2H)-orie 1,1-dioxide;

2-tert-butyl-4-[(2,3-dihydro-1,4-benzodioxin-2-ylmethyl)amino]-5-phenylisothiazol-3(2H)-one 1,1-dioxide;

2-buty1-4-[(4-hydroxycyclohexyl)amino]-5-phenyl-isothiazol-3(2H)-one 1,1-dioxide;

4-{3-[(2-tert-butyl-1,1-dioxido-3-oxo-5-phenyl-2,3-dihydroisothiazol-4-yl) amino]propoxy}benzoic acid;

3-{4-[(2-isopropyl-1,1-dioxido-3-oxo-5-phenyl-2,3-dihydroisothiazol-4-yl) amino]piperidin-1-yl}propanenitrile;

2-tert-butyl-4-{[3-(4-chlorophenoxy)propyl]amino}-5-pheny lisothiazol -3(2H)-one 1,1-dioxide;

5-phenyl-4-[(4-phenylbutyl)amino]-2-(pyridin-4-ylmethyl) isothiazol-3(2H)-one 1,1-dioxide;

4-[(1,3-benzodioxol-5-ylmethyl)amino]-2-butyl-5-phenylisothiazol-3(2H)-one 1,1-dioxide;

4-(2,3-dihydro-1H-inden-2-ylamino)-2-(2-methoxyethyl)-5-pheny lisothiazol-3(2H)-one 1,1-dioxide;

2-butyl-4-[(2-morpholin-4-ylethyl)amino]-5-phenyl-isothiazol-3(2H)-one 1,1-dioxide;

2-tert-butyl-4-{[3-(4-isopropylphenoxy)propyl]arnino}-5-phenylisothiazol-3(2H)-one 1,1-dioxide;

4-({3-[benzyl(butyl)amino]propyl}amino)-2-tert-butyl-5-phenylisothiazol-3 (2H)-one 1,1-dioxide;

2-ter-butyl-4-{[3-(3,5-dipropoxyphenoxy)propyl]amino}-5-phenylisothiazol-3(2H)-one 1,1-dioxide;

2-tert-butyl-4-[(2,2-diphenylethyl)amino]-5-pheny-isothiazol -3(2H)-one 1,1-dioxide;

2-ethyl-4-{[2-(1H-imidazol-4-yl)ethyl]amino}-5-phenyl-isothiazol-3(2H)-one 1,1-dioxide;

2-butyl-4-[(4-morpholin-4-ylbenzyl)amino]-5-phenyl-isothiazol-3(2H)-one 1,1-dioxide;

2-butyl-4-{[3-(2-methoxyethoxy)propyl]amino}-5-phenylisothiazol-3(2H)-one 1,1-dioxide;

2-butyl-4-[(3-morpholin-4-ylpropyl)amino]-5-phenyl-isothiazol-3(2H)-one 1,1-dioxide;

2-butyl-4-[(2-methoxyethyl)amino]-5-phenyisothiazol-3(2H)-one 1,1-dioxide;

2-(2-methoxyethyl)-5-phenyl-4-(tetrahydro-2H-pyran-4-ylamino)isothiazol-3(2H)-one 1,1-dioxide;

4-(hexylamino)-2-(2-methoxyethyl)-5-phenylisothiazol-3(2H)-one 1,1-dioxide;

4-[(4-hydroxycyclohexyl)amino]-2-(2-methoxyethyl)-5-phenylisothiazol-3(2H)-one 1,1-dioxide;

4-[(1,3-benzodioxol-5-ylmethyl)amino]-2-(2-methoxyethyl)-5-phenylisothiazol-3(2H)-one 1,1-dioxide;

2-butyl-4-[(4-methoxybenzyl)amino]-5-phenylisothiazol-3(2H)-one 1,1-dioxide;

5-phenyl-4-[(4-phenylbutyl)amino]-2-(pyridin-2-ylmethyl)isothiazol-3(2H)-one 1,1-dioxide;

2-tert-butyl-4-{[3-(3-hydroxyphenoxy)propyl]amino}-5-phenylisothiazol-3(2H)-one 1,1-dioxide;

3-{3-[(2-tert-butyl-1,1-dioxido-3-oxo-5-phenyl-2,3-dihydroisothiazol-4-yl)amino]propoxy}benzoic acid;

4-{2-[(2-tert-butyl-1,1-dioxido-3-oxo-5-phenyl-2,3-dihydroisothiazol-4-yl)amino]ethyl}phenyl methanesulfonate;

4-{2-[(2-tert-butyl-1,1-dioxido-3-oxo-5-phenyl-2,3-dihydroisothiazol-4-yl)amino]ethyl}benzenesulfonamide;

2-tert-butyl-4-({1-[3-chloro-5-(trifluoromethyl)pyridin-2-yl]piperidin-4-yl}amino)-5-phenylisothiazol-3(2H)-one 1,1-dioxide;

tert-butyl 3-{2-[(2-tert-butyl-1,1-dioxido-3-oxo-5-phenyl-2,3-dihydroisothiazol-4-yl)amino]ethyl}azetidine-1-carboxylate;

2-{2-[(2-tert-butyl-1,1-dioxido-3-oxo-5-phenyl-2,3-dihydroisothiazol-4-yl)Amino]ethoxy}phenyl methanesulfonate;

4-{2-[(2-tert-butyl-1,1-dioxido-3-oxo-5-phenyl-2,3-dihydroisothiazol-4-yl)amino]ethyl}benzonitrile;

4-({4-[(2-tert-butyl-1,1-dioxido-3-oxo-5-phenyl-2,3-dihydroisothiazol-4-yl)amino]piperidin-1-yl}methyl)benzonitrile;

2-tert-butyl-4-(isopropylamino)-5-phenylisothiazol-3(2H)-one 1,1-dioxide;

4-{2-[(2-isopropyl-1,1-dioxido-3-oxo-5-phenyl-2,3-dihydroisothiazOl-4-yl)amino]ethy}phenyl methanesulfonate;

tert-butyl 3-({2-[(2-tert-butyl-1,1-dioxido-3-oxo-5-phenyl-2,3-dihydroisothiazOl-4-yl)amino]ethyl}thio)pyrrolidine-1-carboxylate;

2-tert-butyl-5-phenyl-4-{[3-(pyridin-2-yloxy)propyl]amino}isothiazol-3(2H)-one 1,1-dioxide;

2-tert-butyl-4-[(2-{[3-chloro-5-(trifluoromethyl)pyridin-2-yl]amino}ethyl)amino]-5-phenylisothiazol-3(2H)-one 1,1-dioxide;

2-tert-butyl-5-phenyl-4-({1-[2-(trifluoromethyl)benzoyl]piperidin-4-yl}amino)isothiazol-3(2H)-one 1,1-dioxide;

2-tert-butyl-4-{[1-(5-methylpyridin-2-yl)piperidin-4-yl]amino}-5-phenylisothiazol-3(2H)-one 1,1-dioxide;

2-tert-butyl-4-{[1-(6-chloropyridazin-3-yl)piperidin-4-yl]amino}-5-phenylisothiazol-3(2H)-one 1,1-dioxide;

tert-butyl 4-[(2-tert-butyl-1,1-dioxido-3-oxo-5-phenyl-2,3-dihydroisothiazol-4-yl)amino]piperidine-1-carboxylate;

methyl 2-{2-[(2-tert-butyl-1,1-dioxido-3-oxo-5-phenyl-2,3-dihydroisothiazol-4-yl)amino]ethoxy}benzoate;

methyl 3-({4-[(2-tert-butyl-1,1-dioxido-3-oxo-5-phenyl-2,3-dihydroisothiazol-4-yl)amino]piperidin-1-yl}methyl)benzoate;

2-tert-butyl-4-{[1-(6-methoxypyridazin-3-yl)piperidin-4-yl]amino}-5-phenylisothiazol-3(2H)-one 1,1-dioxide;

2-tert-butyl-4-({1-[(2-chloropyridm-3-yl)carbonyl]piperidin-4-yl}amino)-5-phenylisothiazol-3(2H)-one 1,1-dioxide;

2-{2-[(2-isopropyl-1,1-dioxido-3-oxo-5-phenyl-2,3-dihydroisothiazol-4-yl)ammo]ethoxy}phenyl methanesulfonate;

2-tert-butyl-4-{[1-(6-chloropyridin-3-yl)piperidin-4-yl]amino}-5-phenylisothiazol-3(2H)-one 1,1-dioxide;

4-[(1benzylpiperidin-4-yl)amino]2-tert-butyl-5-phenylisothiazol-3(2H)-one 1,1-dioxide;

4-{2-[(2-isopropyl-1,1-dioxido-3-oxo-5-phenyl-2,3-dihydroisothiazol-4-yl)amino]ethyl}benzenesulfonamide;

4-{2-[(2-isopropyl-1,1-dioxido-3-oxo-5-phenyl-2,3-dihydroisothiazol-4-yl)amino]ethyl}benzonitrile;

2-tert-butyl-4-(ethyl amino)-5-phenylisothiazol-3(2H)-one 1,1-dioxide;

2-tert-butyl-4-({1-[(5-methylisoxazol-3-yl)methyl]piperidin-4-yl}amino)-5-phenylisothiazol-3(2H)-one 1,1-dioxide;

$N^2$-(2-tert-butyl-1,1-dioxido-3-oxo-5-phenyl-2,3-dihydroisothiazol-4-yl)-$N^1$-[3-(diftluoromethoxy) benzyl]glycinamide;

4-[(1-benzoylpiperidin-4-yl)amino]-2-tert-butyl-5-phenylisothiazol-3(2H)-one 1,1-dioxide;

2-tert-butyl-5-phenyl-4-{[1-(phenylacetyl)piperidin-4-yl]amino}isothiazol-3(2H)-one 1,1-dioxide;

2-tert-butyl-5-phenyl-4-[(1-pyridin-2-ylpiperidin-4-yl)amino]isothiazol-3(2H)-one 1,1-dioxide;

2-tert-butyl-5-phenyl-4-[(1-pyridazin-3-ylpiperidin-4-yl)amino]isothiazol-3(2H)-one 1,1-dioxide;

2-tert-butyl-5-phenyl-4-{[2-(pyridin-3-yloxy)ethyl]amino}isothiazol-3(2H)-one 1,1-dioxide;

2-tert-butyl-4-{[1-(5-fluoropyridin-2-yl)piperidin-4-yl]amino}-5-phenylisothiazol-3(2H)-one 1,1-dioxide;

2-tert-butyl-4-{[3-(3,5-dimethyl-1H-pyrazol-1-yl)propyl]amino}-5-phenylisothiazol-3(2H)-one 1,1-dioxide;

2-tert-butyl-4-{[1-(2-chloro-6-methylisonicotinoyl)piperidin-4-yl]amino}-5-phenylisothiazol-3(2H)-one 1,1-dioxide;

2-tert-butyl-4-{[1-(5-chloropyridin-2-yl)piperidin-4-yl]amino}-5-phenylisothiazol-3(2H)-one 1,1-dioxide;

2-tert-butyl-5-phenyl-4-({1-[4-(trifluoromethyl)pyridin-2-yl]piperidin-4-yl}amino) isothiazol-3(2H)-one 1,1-dioxide;

4-({4-[(2-ter-butyl-1,1-dioxido-3-oxo-5-phenyl-2,3-dihydroisothiazol-4-yl)amino]piperidin-1-yl}carbonyl)benzonitrile;

2-tert-butyl-4-{[1-(3,4-difluorobenzoyl)piperidin-4-yl]amino}-5-phenylisothiazol-3(2H)-one 1,1-dioxide;

4-[(1-acetylpiperidin-4-yl)amino]-2-tert-butyl-5-phenylisothiazol-3(2H)-one 1,1-dioxide;

3-{2-[(2-isopropyl-1,1-dioxido-3-oxo-5-phenyl-2,3-dihydroisothiazol-4-yl)amino]ethyl}benzonitrile;

2-tert-butyl-5-phenyl-4-({2-[2-(trifluoromethoxy)phenyl]ethyl}amino)isothiazol-3(2H)-one 1,1-dioxide;

4-{2-[(2-tert-buty 1-1,1-dioxido-3-oxo-5-phenyl-2,3-dihydroisothiazol-4-yl)amino]ethoxy}phenyl methanesulfonate;

4-[(1-benzylpyrrolidin-3-yl)amino]-2-tert-butyl-5-phenylisothiazol-3(2H)-one 1,1-dioxide;

4-({1-[3-chloro-5-(trifluoromethyl)pyridin-2-yl]azetidin-3-yl}amino)-2-isopropyl-5-phenylisothiazol-3(2H)-one 1,1-dioxide;

$N^1$-benzyl-$N^2$-(2-tert-butyl-1,1-dioxido-3-oxo-5-phenyl-2,3-dihydroisothiazol-4-yl-glycinamide;

2-tert-butyl-4-[(1-isobutyiylpiperidin-4-yl)amino]-5-phenylisothiazol-3(2H)-one 1,1-dioxide;

2-tert-butyl-5-phenyl-4-[(2-pyridin-2-ylethyl)anino]isothiazol-3(2H)-one 1,1-dioxide;

2-tert-butyl-4-{[2-(2-chlorophenyl)ethyl]amino}-5-phenylisothiazol-3(2H)-one 1,1-dioxide;

2-tert-butyl-5-phenyl-4-{[1-(2-phenylethyl)piperidin-4-yl]amino}isothiazol-3(2H)-one 1,1-dioxide;

2-tert-butyl-5-phenyl-4-({2-[3-(trifluoromethyl)phenyl]ethyl}amino)isothiazol-3(2H)-one 1,1-dioxide;

2-tert-butyl-5-phenyl-4-[(4-{[4-(trifluoromethyl)phenyl]thio}cyclohexyl)amino]isothiazol-3(2H)-one 1,1-dioxide;

2-tert-butyl-5-phenyl-4-[(2- {[3-(trifluoromethoxy)phenyl]thio}ethyl)amino]isothiazol-3(2H)-one 1,1-dioxide;
2-tert-butyl-4- {[2-(4-chlorophenoxy)ethyl]amino}-5-phenylisothiazol-3(2H)-one 1,1-dioxide;
2-tert-butyl-5-phenyl-4-( {1-[5-(trifluoromethyl)pyridin-2-yl]pipendin-4-yl}amino)isothiazol-3(2H)-one 1,1-dioxide; 2-tert-butyl-5-phenyl-4-( {2-[3-(trifluoromethoxy)phenoxy]ethyl }amino)isothiazol -3(2H)-one 1,1-dioxide;
tert-butyl 3- {2-[(2-tert-butyl- 1,1-dioxido-3-oxo-5-phenyl-2,3-dihydroisothiazol-4-yl) amino]ethoxy }azetidine- 1-carboxylate;
2-tert-butyl-4-[(2,2-dimethylpropy)amino]-5-phenylisothiazo1-3(2H)-one 1,1-dioxide;
2-tert-butyl-4-(tert-butylanuno)-5-phenylisothiazol-3(2H)-one 1,1-dioxide;
methyl( {[(2-tert-butyl-1,1-dioxido-3-oxo-5-phenyl-2,3-dihydroisothiazol-4-yl)amino]acetyl }amino)acetate;
2-tert-butyl-5-pheny1-4-(piperidin-4-ylamino)isothiazol-3(2H)-one 1,1-dioxide;
2-tert-butyl-4-[(1-methylpiperidin-4-yl)amino]-5-phenylisothiazol-3(2H)-one 1,1-dioxide;
2-tert-butyl-4- [(2-hydroxyethyl)amino]-5-phenylisothiazol-3(2H)-one 1,1-dioxide;
4- {[2-(biphenyl-2-ylthio)ethyl]amino}-2-tert-butyl-5-phenylisothiazol-3(2H)-one 1,1-dioxide;
2-tert-butyl-5-phenyl-4- {[2-(pyrrolidin-3-ylthio)ethyl] amino}isothiazol-3(2H)-one 1,1-dioxide;
2-tert-butyl-4- {[(5-methyl-3-phenylisoxazol-4-yl)methyl]amino }-5-phenylisothiazol-3(2H)-one 1,1-dioxide;
2-tert-butyl-5-phenyl-4- {[(1,3,5-trimethyl-1H-pyrazol-4-yl)methyl]amino}isothiazol-3(2H)-one 1,1-dioxide;
2-tert-butyl-5-phenyl-4-[(2- {[5-(trifluoromethyl)pyridin-2-yl]oxy }ethyl)amino]isothiazol-3(2H)-one 1,1-dioxide;
2-tert-butyl-5-phenyl-4-( {2- [4-(trifluoromethoxy)phenyl]ethyl }amino)isothiazol -3 (2H)-one 1,1-dioxide;
2-tert-butyl-5-pheny 1-4-[(2,2,2-trifluoroethyl)amino]isothiazol-3 (2H)-one 1,1-dioxide;
2-tert-butyl-4- [(2,3-dihydroxypropyl)amino]-5-phenyisothiazol-3 (2H)-one 1,1-dioxide;
3-[(2-tert-butyl- 1,1-dioxido-3-oxo-5-phenyl-2,3-dihydroisothiazol-4-yl) amino]propanenitrile;
4- {[2-(3,4-dimethoxyphenyl)ethyl]amino}-2-isopropyl-5-phenylisothiazol-3 (2H)-one 1,1-dioxide;
4- {[2-(3-chloro-4-methoxyphenyl)ethyl]amino}-2-isopropyl-5-phenylisothiazol-3(2H)-one 1,1-dioxide;
4- {2-[(2-isobutyl- 1,1-dioxido-3-oxo-5-phenyl-2,3-dihydroisothiazol-4-yl) Amino]ethyl }phenyl methanesulfonate;
2-isopropyl-5-phenyl-4-[( 1-pyridin-2-ylpiperidin-4-yl)amino]isothiazol-3(2H)-one 1,1-dioxide;
4-(2-{[2-(4-fluorobenzyl)-1,1-dioxido-3-oxo-5-phenyl-2,3-dihydroisothiazol-4-yl]amino}ethyl)phenyl methanesulfonate;
2-isopropyl-4-(isopropylamino)-5-phenylisothiazol-3(2H)-one 1,1-dioxide;
2-isopropyl-5-phenyl-4-[(1-pyridin-2-ylazetidin-3-yl)amino]isothiazol-3(2H)-one 1,1-dioxide;
2-tert-butyl-4- {[(5-methylisoxazol-3-yl)methyl]amino}-5-phenylisothiazol-3(2H)-one 1,1-dioxide;
4- {[2-(4-hydroxy-3,5-dimethoxyphenyl)ethyl]amino}-2-isopropyl-5-phenylisothiazol-3 (2H)-one 1,1-dioxide;
4- {[2-(2-aminopyridin-4-yl)ethyl]amino}-2-isopropyl-5-phenylisothiazol-3(2H)-one 1,1-dioxide;
2-isopropyl-5-phenyl -4-[(2-pyridin-4-ylethyl)amino]isothiazol-3(2H)-one 1,1-dioxide;
2-isopropyl-5-phenyl-4-[(2-pyridin-3-ylethyl)amino]isothiazol-3(2H)-one 1,1-dioxide;
4- {[2-(3,5-dimethylisoxazol-4-yl)ethyl]amino}-2-isopropyl-5-phenylisothiazol-3(2H)-one 1,1-dioxide;
4-[2-( {2-[(5-methylisoxazol-3-yl)methyl]-1,1-dioxido-3-oxo-5-phenyl-2,3-dihydroisothiazol -4-yl }amino) ethyl]phenyl methanesulfonate;
4- {[2-(3,5-dimethyl- 1H-pyrazol-4-yl)ethyl]amino}-2-isopropyl-5-phenylisothiazol-3(2H)-one 1,1-dioxide;
4-[2-( {2-[(methylthio)methyl]- 1,1-dioxido-3-oxo-5-phenyl-2,3-dihydroisothiazol-4-yl}amino)ethyl]phenyl methanesulfonate;
2,6-Dimethyiphenyl 4-[(2-tert-butyl- 1,1-dioxido-3-oxo-5-phenyl-2,3-dihydroisothiazol-4-yl) amino]butanoate;
2-Mesitylethyl N-(2-tert-butyl- 1,1-dioxido-3-oxo-5-phenyl-2,3-dihydroisothiazol-4-yl) glycinate;
2-[(2-tert-butyl- 1,1-dioxido-3-oxo-5-phenyl-2,3-dihydroisothiazol-4-yl)amino]ethyl (2,6-dimethylphenyl) acetate;
Phenyl N-(2-tert-butyl- 1,1-dioxido-3-oxo-5-phenyl-2,3-dihydroisothiazol-4-yl)-beta-alaninate;
4-(Trifluoromethoxy)phenyl N-(2-tert-butyl- 1,1-dioxido-3-oxo-5-phenyl-2,3-dihydroisothiazol -4-yl)-beta-alaninate;
1-Methylpiperidin-4-yl N-(2-tert-butyl- 1,1-dioxido-3-oxo-5-phenyl-2,3-dihydroisothiazol -4-yl)-beta-alaninate;
2-Mesityl-1-methylethyl [(2-tert-butyl- 1,1-dioxido-3-oxo-5-phenyl-2,3-dihydroisothiazol-4-yl)amino]acetate;
4-Methoxybenzyl N-(2-tert-butyl- 1,1-dioxido-3-oxo-5-phenyl-2,3-dihydroisothiazol-4-yl) glycinate; and
4-Methoxyphenyl N-(2-tert-butyl- 1,1-dioxido-3-oxo-5-phenyl -2,3-dihydroisothiazol-4-yl) glycinate;
or a pharmaceutically acceptable salt thereof.

* * * * *